(12) United States Patent
Cochran et al.

(10) Patent No.: US 6,497,882 B1
(45) Date of Patent: Dec. 24, 2002

(54) RECOMBINANT SWINEPOX VIRUS

(75) Inventors: Mark D. Cochran, Carlsbad; David E. Junker, San Diego, both of CA (US)

(73) Assignee: Syntro Corporation, San Diego, CA (US)

( * ) Notice: Subject to any disclaimer, the term of this patent is extended or adjusted under 35 U.S.C. 154(b) by 0 days.

(21) Appl. No.: 08/472,679

(22) Filed: Jun. 7, 1995

Related U.S. Application Data

(63) Continuation-in-part of application No. 08/375,992, filed on Jan. 19, 1995, now Pat. No. 6,328,975, which is a continuation-in-part of application No. PCT/US94/08277, filed on Jul. 22, 1994, and a continuation-in-part of application No. 08/097,554, filed on Jul. 22, 1993, now Pat. No. 5,869,312, and a continuation-in-part of application No. 07/820,154, filed on Jan. 13, 1992, now Pat. No. 5,382,425.

(51) Int. Cl.[7] ..................... A61K 39/12; A61K 39/275; C12N 7/01; C12N 15/863
(52) U.S. Cl. ................ 424/199.1; 424/93.2; 435/235.1; 435/320.1
(58) Field of Search .......................... 435/235.1, 320.2, 435/172.3; 424/199.1, 232.1, 43.2; 935/65, 22, 32

(56) References Cited

U.S. PATENT DOCUMENTS 6,217,882 B1    4/2001    Moyer et al.

FOREIGN PATENT DOCUMENTS

| EP | 0284416 | 9/1988 | ........... C12N/15/00 |
| WO | 8903429 | 4/1989 | ........... C12P/21/00 |
| WO | 93/14194 | * 7/1993 | ........... C12N/7/00 |
| WO | WO8912684 | 12/1999 | ........... C12N/15/00 |

OTHER PUBLICATIONS

R. A. Bhat, et al. (1989), "Efficient Expression of Small RNA Polymerase III Genses From a Noval Simina 40 Vector and Their Effect on Viral Gene Expression", Nucleic Acids Research 17: 1159–1176.
J.J. Esposito, et al. (1988), "Successful Oral Rabies Vaccination of Raccoons with Raccoon Poxvirus Recombinats Expressing Rabies Virus Glycprotein", Virology 165: 313–316.
S. Joshi, et al. (1991), "Inhibition of Human Immunodeficiency Virus Type 1 Multiplication by Antisense and Sense RNA Expression", Journal of Virology; 65: 5524–5530.
C. Flexner, et al. (1990), "Attenuation and Immunogenicity in Primates of Vaccinia Virus Recombinats Expressing Human Interleukin–2", Vaccines 8: 17–21.
L. Kasza (1981) Diseases of Swine, 254–260, Ed. A.D. Leman, et al., The Iowa State University Press.
R.F. Massung and R.W. Moyer, (1991) "The Molecular Biology of Swinepox Virus; A Caharacterization of the Viral DNA", Virology 180: 347–354.
R.F. Massung and R.W. Moyer, (1991) "The Molecular Biology of Swinepox Virus; The Infectious Cycle", Virology 180: 355–365.
J. Taylor, et al. (1991) "Efficacy Studies on a Canarypox–rabies Recombinant Virus", Vaccine 9:190–193.
W.M. Schnitzlein and D.N. Tripathy (1991), "Identification and Nucleotide Sequence of the Thymidine Kinase Gene of Swinepox Virus", Virology 181: 727–732.
M. Wachsman, et al. (1989) "Antigen–presenting Capacity of Epidermal Cells Infected with Vaccinia Virus Recombinants Containing the Herpes Simplex Virus Glcoprotein D, and Protective Immunity", Journal of General Virology 70: 2513–2520.
P.P Williams, et al. (1989) "Immunoligival Responses of Cross–bred and In–bred Miniature Pigs to Swine Poxvirus", Veterinary Immunology and Immunopathology 23: 149–159.
J.A. Feller, et al. (1991) "Isolation and Molecular Characterization of the Swinepox Virus Thymidine Kinase Gene", Virology 183: 578–585.
M. Riviere, et al. (1992) "Protection of Mice and Swine from Pseudorabies Virus Conferred by Vaccinia Virus-–Based Recombinants", Journal of Virology 66:3423–3434 (Exhibit 1).
R.F. Massung, et al. (1993) "DNA Sequence Analysis of Conserved and Unique Regions of Swinepox Virus: Identification of Genetic Elements Supporting Phenotypic Observations Including a Novel G Protein–Coupled Receptor Homologue", Virology 197: 511–528 (Exhibit 2).
T. Tuboly, et al. (1993) "Potential Viral Vectors For the Stimulation of Mucosal Antibody Responses Against Enteric Viral Antigens in Pigs", Research in Veterinary Science 54: 345–350 (Exhibit 3).
P.L. Foley, et al. (1991) "Swinepox Virus as a Vector for the Delivery of Immunogens", Annals New York Academy of Sciences 646: 220–222 (Exhibit 4).
M.L. van der Leek, et al. (1994) Evaluation of Swinepox Virus as a Vaccine Vector in Pigs Using an Ajeszky's (Pseudorabies) Virus Gene Insert Coding For Glycoproteins gp50 and gp63, The Veterinary Record 134: 13–18 (Exhibit 5).
Massung, R.F. et al. Virology, vol. 197, p. 511–528, 1993.*

* cited by examiner

Primary Examiner—Mary E. Mosher

(57) ABSTRACT

This invention provides a recombinant swinepox virus comprising a foreign DNA sequence inserted into the swinepox virus genomic DNA, wherein the foreign DNA sequence is inserted within a HindIII K fragment of the swinepox virus genomic DNA and is capable of being expressed in a swinepox virus infected host cell.

The invention further provides homology vectors, vaccines and methods of immunization.

35 Claims, 114 Drawing Sheets

Figure 1B:
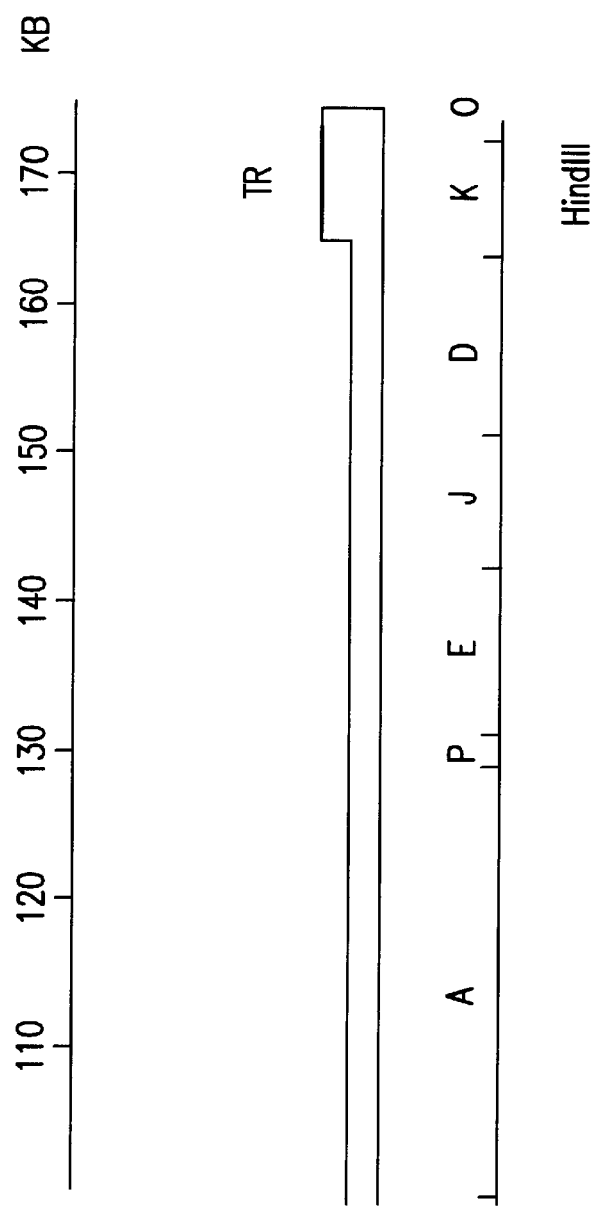

FIGURE 1A
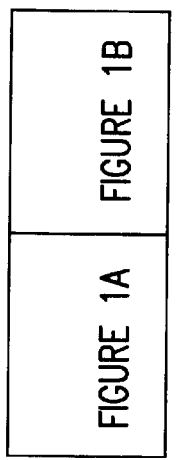
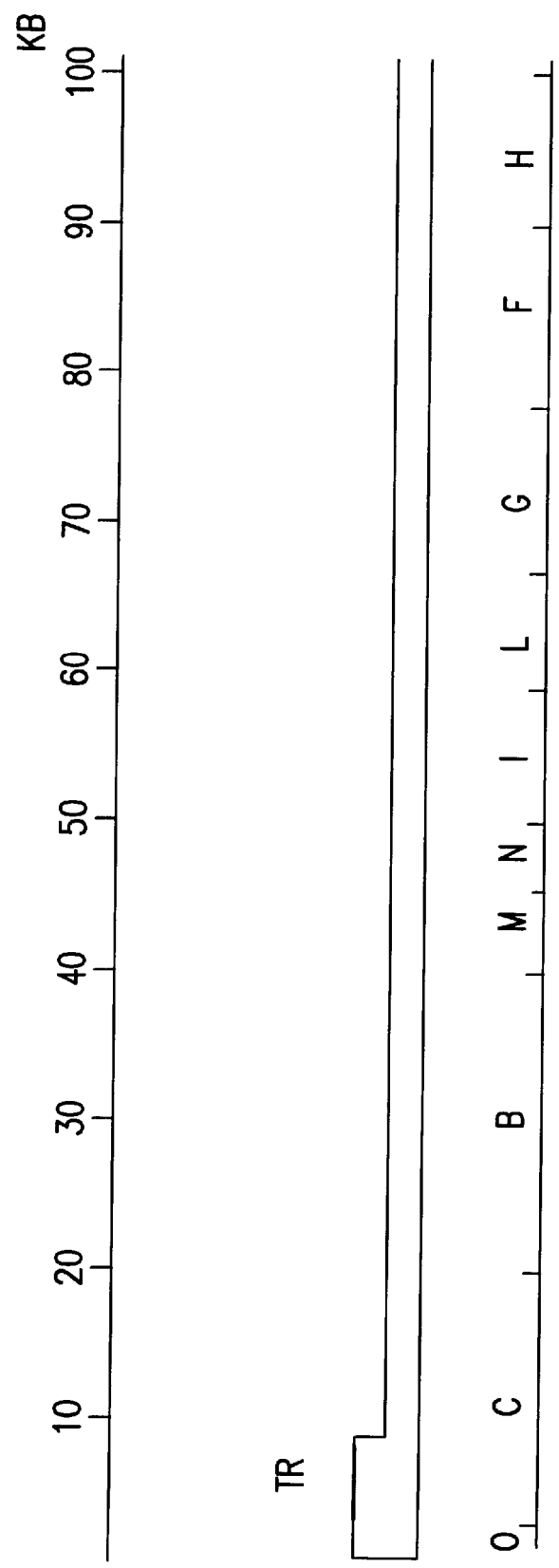

FIGURE 2A

| FIGURE 2A |
|---|
| FIGURE 2B |

```
AATGTATCCAGAGTTGTTGAATGCCTTATCGTACCTAATATTAATATAGAGTTATTAACT
GAATAAGTATATATAAATGATTGTTTTTATAATGTTTGTTATCGCATTTAGTTTTGCTGT
ATGGTTATCATATACATTTTTAAGGCCGTATATGATAAATGAAAATATATAAGCACTTAT
TTTTGTTAGTATAATAACACAATGCCGTCGTATATGTATCCGAAGAACGCAAGAAAAGTA
ATTTCAAAGATTATATCATTACAACTTGATATTAAAAAACTTCCTAAAAAATATATAAAT
ACCATGTTAGAATTTGGTCTACATGGAAATCTACCAGCTTGTATGTATAAAGATGCCGTA
              MetProSer..........
TCATATGATATAAATAATATAAGATTTTTACCTTATAATTGTGTTATGGTTAAAGATTTA
ATAAATGTTATAAAATCATCATCTGTAATAGATACTAGATTACATCAATCTGTATTAAAA
CATCGTAGAGCGTTAATAGATTACGGCGATCAAGACATTATCACTTTAATGATCATTAAT
AAGTTACTATCGATAGATGATATATCCTATATATTAGATAAAAAAAATAATTCATGTAAC
                        ...........IleHisVal
```

FIGURE 2B

```
GAGATATTAAATCATGTAAATGCTCGATATGTTCCGACTCTATAACACATCATATATATG
    AspIleLysSer...............
AAACAACATCATGTATAAATTATAAATCTACCGATAATGATCTTATGATAGTATTGTTCA
ATCTAACTAGATATTTAATGCATGGATGATACATCCTAATCTTATAAGCGTAAAAGGAT
GGGGTCCCCTTATTGGATTATTAACGGGTGATATAGGTATTAATTTAAAACTATATTCCA
CCATGAATATAAATGGGCTACGGTATGGAGATATTACGTTATCTTCATACGATATGAGTA
ATAAATTAGTCTCTATTATTAATACACCCATATATGAGTTAATACCGTTTACTACATGTT
GTTCACTCAATGAATATTATTCAAAAATTGTGATTTTAATAAATGTTATTTTAGAATATA
TGATATCTATTATATTATATAGAATATTGATCGTAAAAAGATTTAATAACATTAAAGAAT
TTATTTCAAAAGTCGTAAATACTGTACTAGAATCATCAGGCATATATTTTTGTCAGATGC
GTGTACATGAACAAATTGAATTGGAAATAGATGAGCTCATTATTAATGGATCTATGCCTG
TACAGCTTATGCATTTACTTCTAAAGGTAGCTACCATAATATTAGAGGAAATCAAAGAAA
                                                ....... LysGluI
TATAACGTATTTTTTCTTTTAAATAAATAAAAATACTTTTTTTTTTAAACAAGGGGTGCT
le---
ACCTTGTCTAATTGTATCTTGTATTTTGGATCTGATGCAAGATTATTAAATAATCGTATG
AAAAAGTAGTAGATATAGTTTATATCGTTACTGGACATGATATTATGTTTAGTTAATTCT
TCTTTGGCATGAATTCTACACGTCGGANAAGGTAATGTATCTATAATGGTATAAAGCTT
```

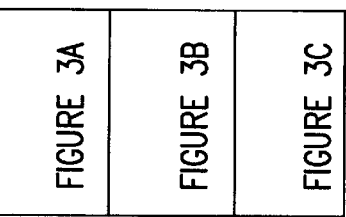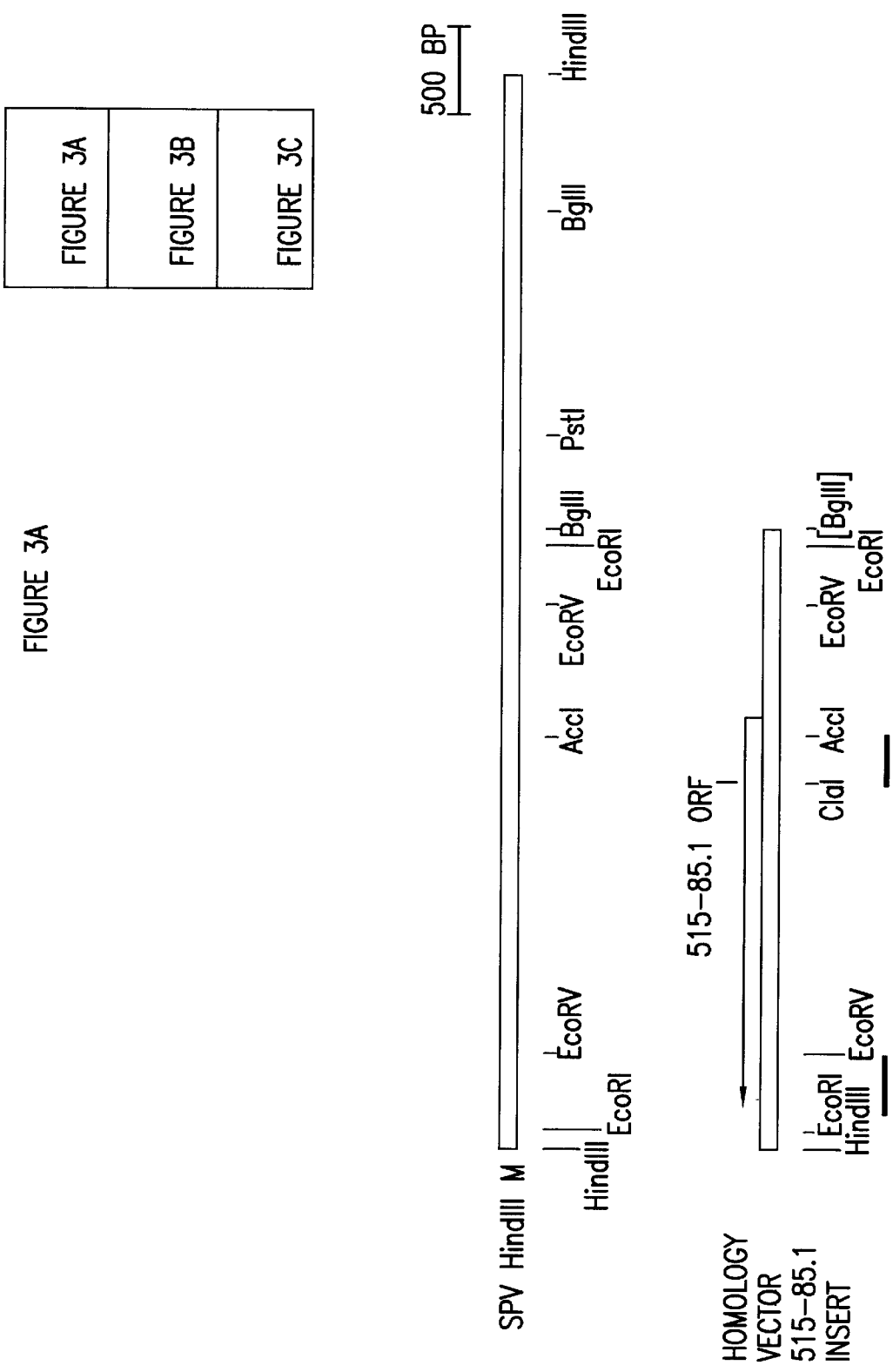
FIGURE 3A

FIGURE 3B

```
                    10         20         30         40         50         60        70
                     *          *          *          *          *          *         *
(A) VV        MFMYPEFARKALSKLISKKLNIEKVSSKHQLVLLDYGLHGLLPKSLYLEAINSDILNVRFFPPEIINVT
orf 01L          :::      :::      ::      : ::     :  ::     :::    ::     ::    ::
(B) SPV       MPSYMYPKNARKVISKIISLQLDIKKLPKKYINTML

FIGURE 3C

```
                   570         580         590         600         610
                    *           *           *           *           *
(C) VV orf O1L     VLNDQYAKIVIFFNTIIEYIIATIYYRLTVLNNYTNVKH

FIGURE 5A
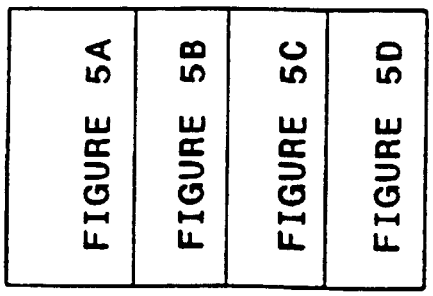
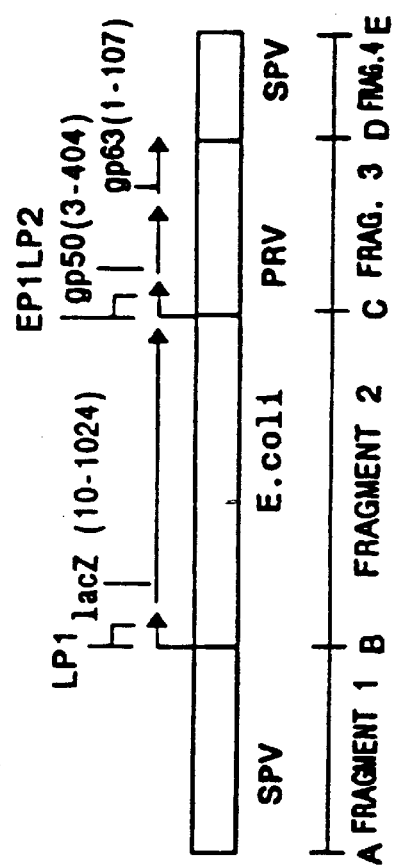

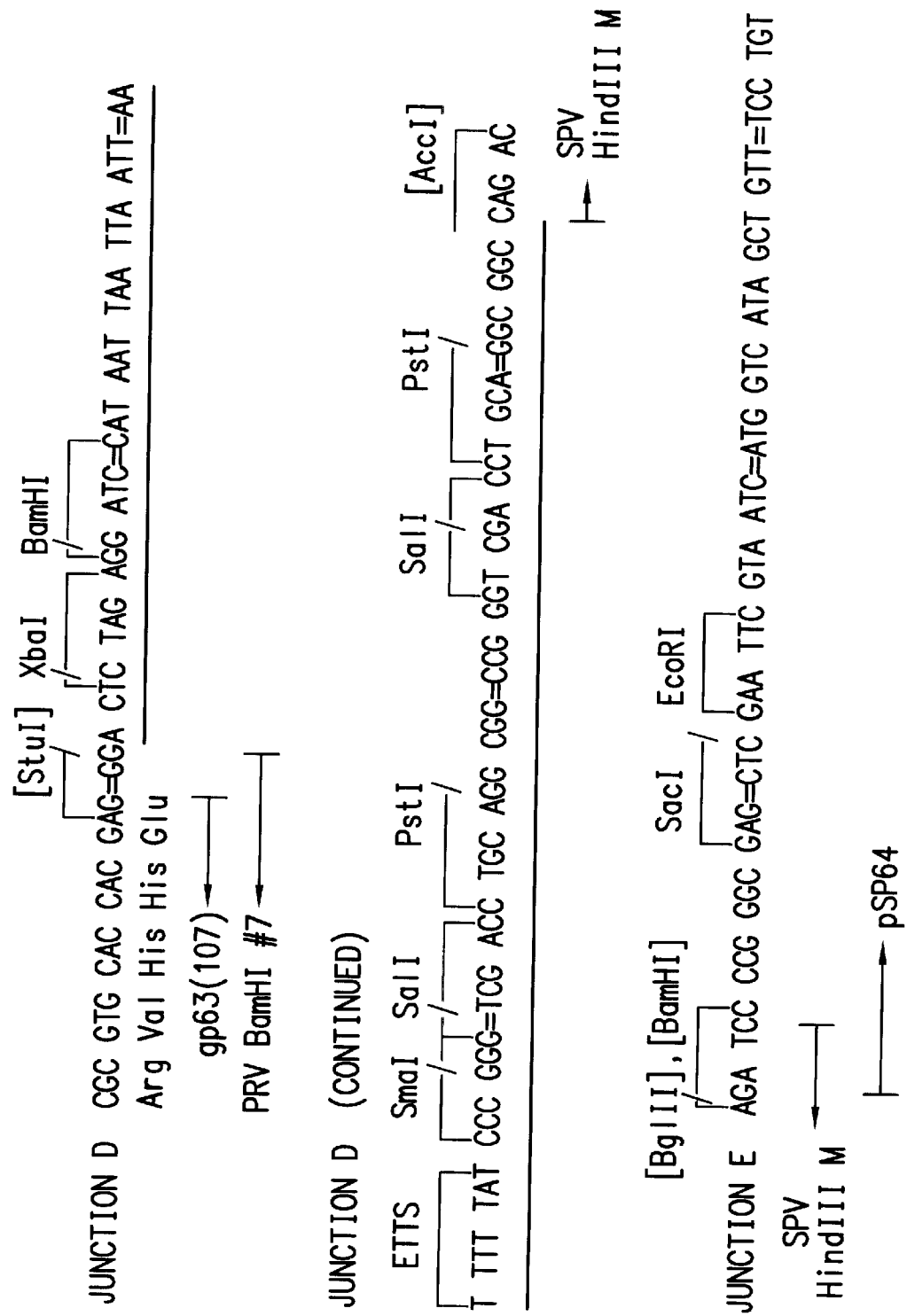

FIGURE 7

ACGGGTAGAACGGTAAGAGAGGCCGCCCCTCAATTGCGAGCCAGACTTCACAACCTCCGT

AvaII

TCTACCGCTTCACCGACAACAGTCCTCAATCATGGACCGCGCCGTTAGCCAAGTTGCGTT
                                           MetAspGly............
AGAGAATGATGAAAGAGAGGCAAAAAATACATGGCGCTTGATATTCCGGATTGCAATCTT
ATTCTTAACAGTAGTGACCTTGGCTATATCTGTAGCCTCCCTTTTATATAGCATGGGGGC
TAGCACACCTAGCGATCTTGTAGGCATACCGACTAGGATTTCCAGGGCAGAAGAAAAGAT
TACATCTACACTTGGTTCCAATCAAGATGTAGTAGATAGGATATATAAGCAAGTGGCCCT
TGAGTCTCCATTGGCATTGTTAAATACTGAGACCACAATTATGAACGCAATAACATCTCT
CTCTTATCAGATTAATGGAGCTGCAAACAACAGCGGGTGGGGGGCACCTATTCATGACCC
AGATTATATAGGGGGGATAGGCAAAGAACTCATTGTAGATGATGCTAGTGATGTCACATC
ATTCTATCCCTCTGCATTTCAAGAACATCTGAATTTTATCCCGGCGCCTACTACAGGATC
AGGTTGCACTCGAATACCCTCATTTGACATGAGTGCTACCCATTACTGCTACACCCATAA
TGTAATATTGTCTGGATGCAGAGATCACTCACACTCACATCAGTATTTAGCACTTGGTGT
GCTCCGGACATCTGCAACAGGGAGGGTATTCTTTTCTACTCTGCGTTCCATCAACCTGGA
CGACACCCAAAATCGGAAGTCTTGCAGTGTGAGTGCAACTCCCCTGGGTTGTGATATGCT
GTGCTCGAAAGCCACGGAGACAGAGGAAGAAGATTATAACTCAGCTGTCCCTACGCGGAT
GGTACATGGGAGGTTAGGGTTCGACGGCCAATATCACGAAAAGGACCTAGATGTCACAAC
ATTATTCGGGGACTGGGTGGCCAACTACCCAGGAGTAGGGGGTGGATCTTTTATTGACAG
CCGCGTGTGGTTCTCAGTCTACGGAGGGTTAAAACCCAATACACCCAGTGACACTGTACA
GGAAGGGAAATATGTGATATACAAGCGATACAATGACACATGCCCAGATGAGCAAGACTA
CCAGATTCGAATGGCCAAGTCTTCGTATAAGCCTGGACGGTTTGGTGGGAAACGCATACA
GCAGGCTATCTTATCTATCAAAGTGTCAACATCCTTAGGCGAAGACCCGGTACTGACTGT
ACCGCCCAACACAGTCACACTCATGGGGGCCGAAGGCAGAATTCTCACAGTAGGGACATC
CCATTTCTTGTATCAGCGAGGGTCATCATACTTCTCTCCCGCGTTATTATATCCTATGAC
AGTCAGCAACAAAACAGCCACTCTTCATAGTCCTTATACATTCAATGCCTTCACTCGGCC
AGGTAGTATCCCTTGCCAGGCTTCAGCAAGATGCCCCAACTCATGTGTTACTGGAGTCTA
TACAGATCCATATCCCCTAATCTTCTATAGAAACCACACCTTGCGAGGGGTATTCGGGAC
AATGCTTGATGGTGAACAAGCAAGACTTAACCCTGCGTCTGCAGTATTCGATAGCACATC
CCGCAGTCGCATAACTCGAGTGAGTTCAAGCAGCATCAAAGCAGCATACACAACATCAAC
TTGTTTTAAAGTGGTCAAGACCAATAAGACCTATTGTCTCAGCATTGCTGAAATATCTAA
TACTCTCTTCGGAGAATTCAGAATCGTCCCGTTACTAGTTGAGATCCTCAAAGATGACGG
GGTTAGAGAAGCCAGGTCTGGCTAGTTGAGTCAACTATGAAAGAGTTGGAAAGATGGCAT
............ArgSerGly---

NaeI

TGTATCACCTATCTTCTGCGACATCAAGAATCAAACCGAATGCCGGC

Figure 8B:
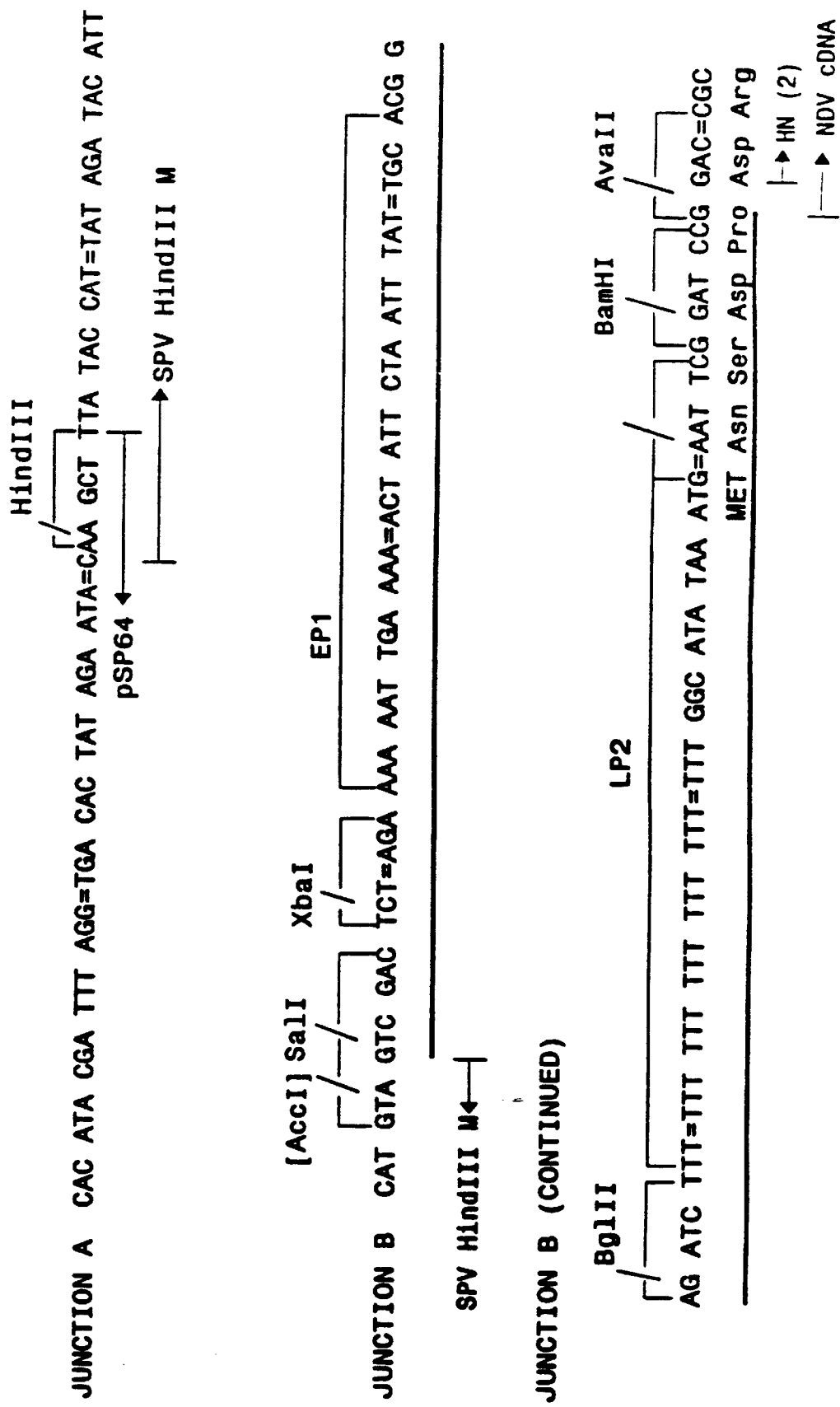
Figure 8D:
Figure 9A:
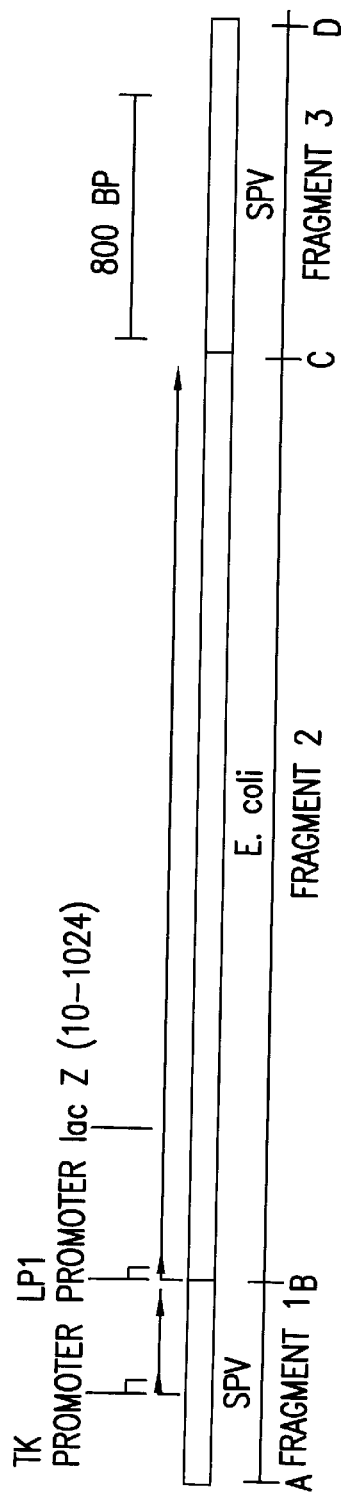
Figure 9B:
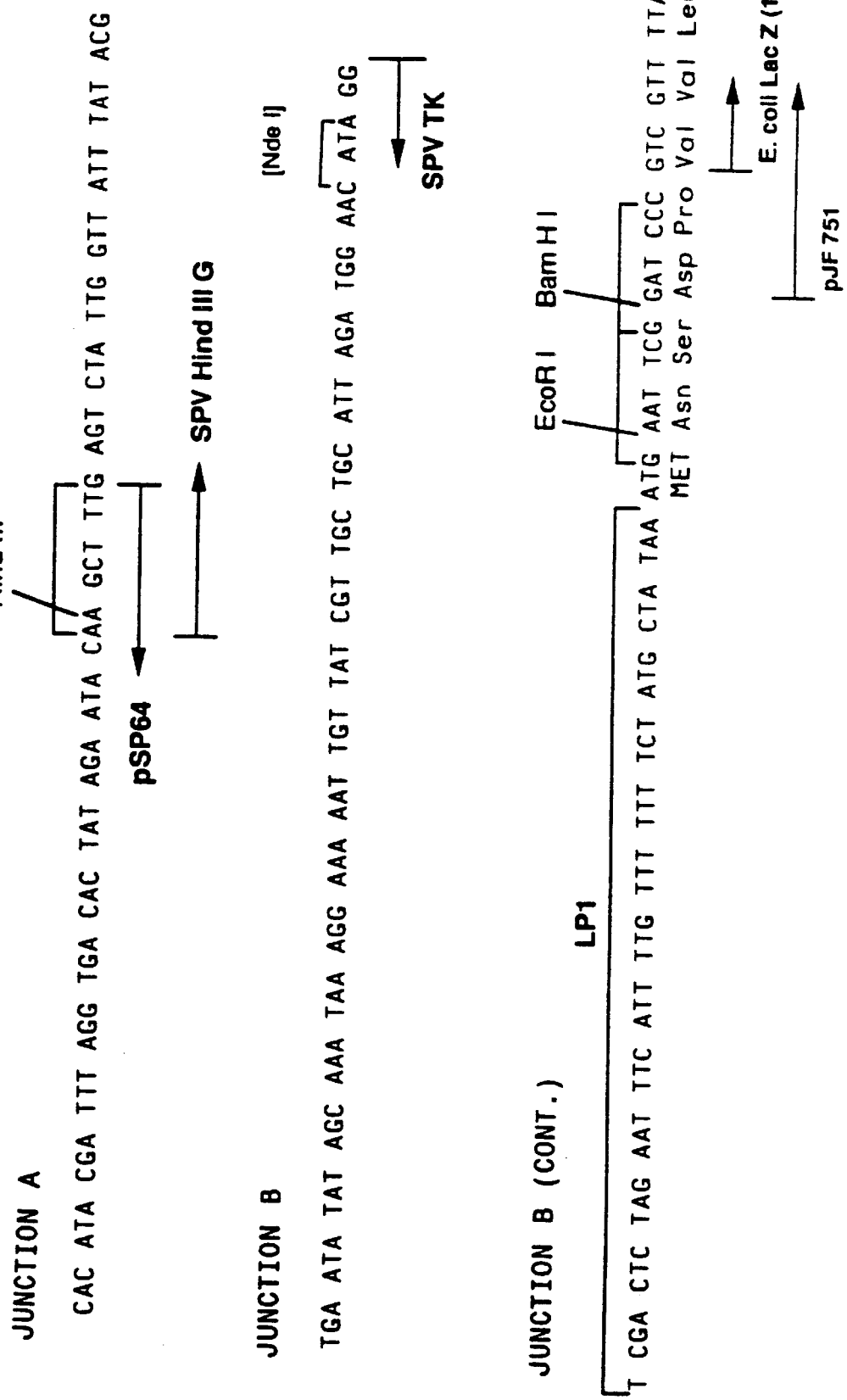
Figure 9C:
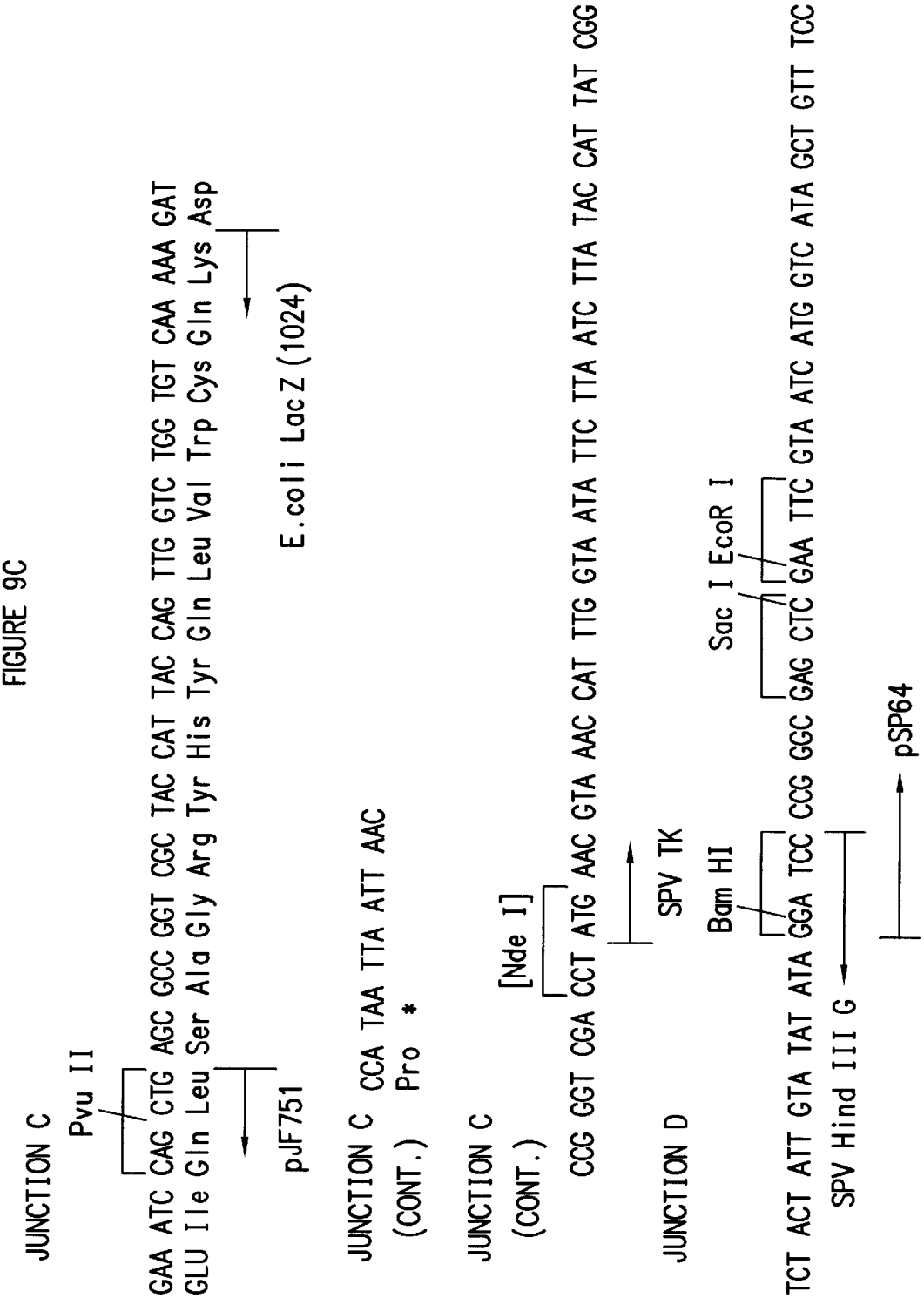

FIGURE 8A
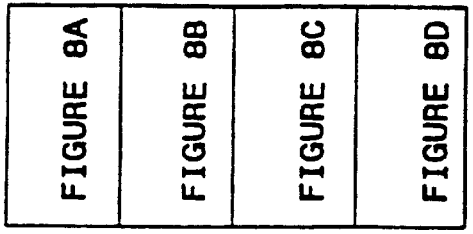
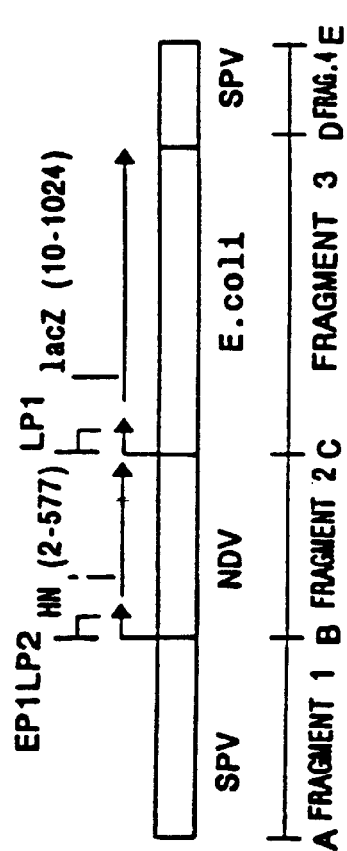

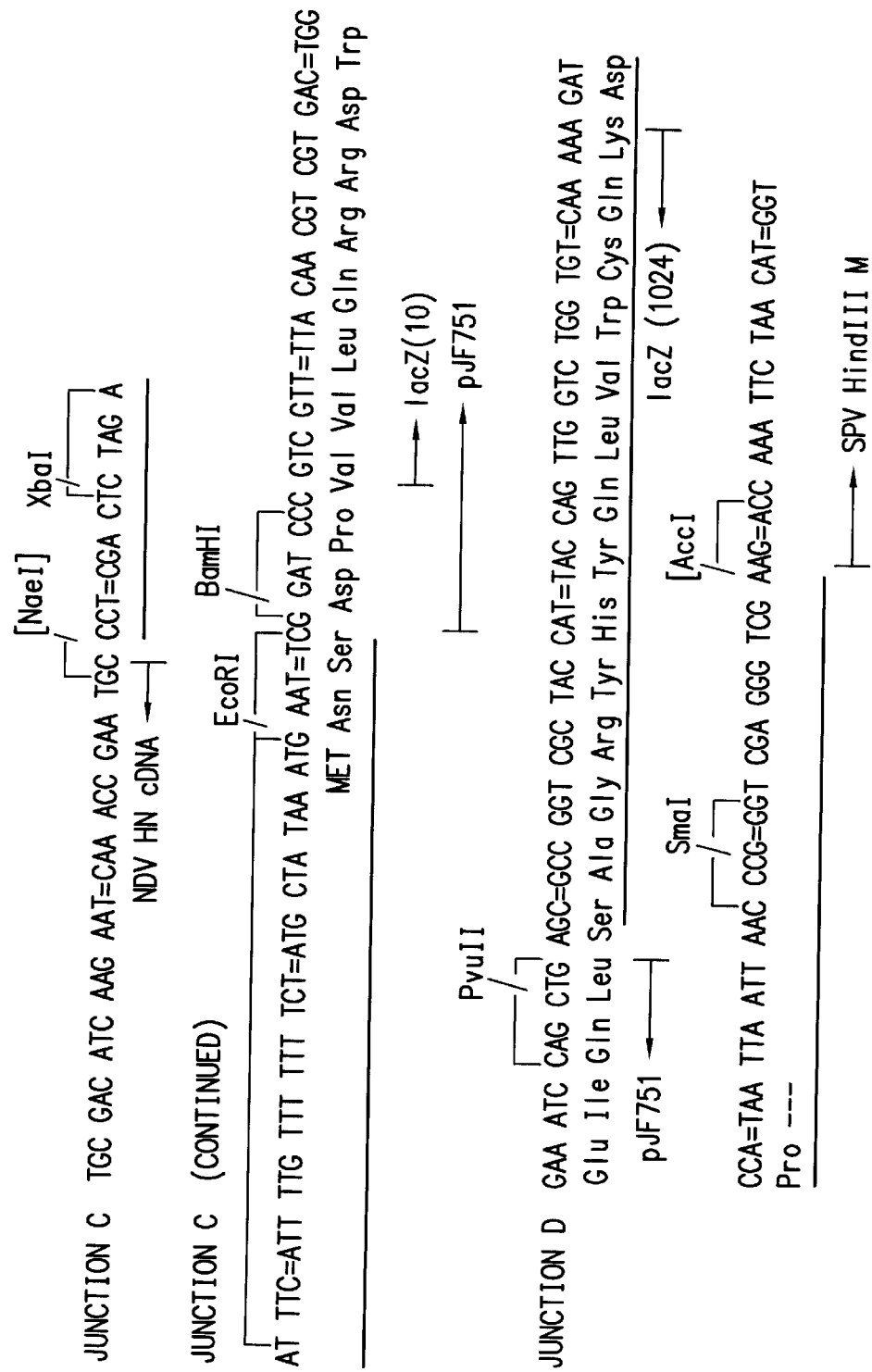

| DNA | ORIGIN | SITES | SIZE |
| --- | --- | --- | --- |
| VECTOR | pSP64 | Bam HI–Hind III | ~2972 BP |
| FRAGMENT 1 | SPV HindIII G | Hind III–Nde I | ~670 BP |
| FRAGMENT 2 | pJF751 | Bam HI–Pvu II | ~3010 BP |
| FRAGMENT 3 | SPV HindIII G | Nde I–Bam HI | ~1069 BP |

| |
| --- |
| FIGURE 9A |
| FIGURE 9B |
| FIGURE 9C |

FIGURE 10B

JUNCTION A

ACA GGA AAC AGC TAT GAC CAT GAT TAC GAA TTC GAG CTC GCC CGG GGA TCT [BamHI/BglII]

← pSP64    SPV HindIII M →

JUNCTION B

AA ATA TAT AAA TAC CAT GTT AGA ATT TGG TCT GCT GCA GGT CGA CTC TAG AAT TTC ATT TTG [AccI]

← SPV HindIII M    LP1 →

JUNCTION B (CONT.)

TTT TTT TCT ATG CTA TAA ATG AAT TCG GAT CCC GTC GTT TTA
                        MET Asn Ser Asp Pro Val Val Leu

LP1 →    EcoRI  BamHI    ← E. coli Lac Z (10)

← pJF 751

FIGURE 10D

JUNCTION D

```
    [Nco I]
  C CAT GCT CTA GAG GAT CCC CGG GCG AGC TCG AAT TCG GAT CCA TAA TTA ATT
       →                                           └─┘
       PRV Bam HI #9                               EcoRI
```

JUNCTION D (CONT.)

```
  AAT TAA TTT TTA TCC CGG GTC GAC CGG GTC GAC CTG CAG CCT ACA TGG AAA TCT ACC
                                                     [Acc I]
                                                        └─┘      ↑
                                                             SPV Hind III M
```

JUNCTION E

```
  TAA TGT ATC TAT AAT GGT ATA AAG CTT GTA TTC TAT AGT GTC ACC TAA ATC
                             └──┬──┘
                             HindIII
                                    ↑                    ↓
                                 pSP64                SPV Hind III M
```

FIGURE 11B

JUNCTION A

ACA GGA AAC AGC TAT GAC CAT GAT TAC GAA TTC GAG CTC GCC CGG GGA TCT [BamHI/BglII]

SPV HindIII M → ← pSP64

JUNCTION B

AA ATA TAT AAA TAC CAT GTT AGA ATT TGG TCT GCT GCA GGT CGA CTC TAG AAT TCA ATT TTG [AccI]

SPV HindIII M → LP1

JUNCTION B (CONT.)

TTT TTT TCT ATG CTA TAA ATG AAT TCG GAT CCC GTC GTT TTA
                                    MET Asn Ser Asp Pro Val Val Leu

LP1    EcoRI  BamHI                              ← E. coli LacZ (10)
                                                 ← pJF 751

FIGURE 11C

JUNCTION C

```
           PvuII
GAA ATC  CAG CTG  AGC GCC GGT CGC TAC CAT TAC CAG TTG GTC TGG TGT CAA AAA GAT
Glu Ile  Gln Leu  Ser Ala Gly Arg Tyr His Tyr Gln Leu Val Trp Cys Gln Lys Asp
         →pJF751                                          E. coli Lac Z (1024)→
```

JUNCTION C (CONT.)

```
                                        SalI   XbaI
CCA TAA TTA ATT AAC CCG GTC GAC TCT AGA AAA AAT TGA AAA ACT ATT CTA ATT TAT TGC AC
Pro •
                          LP2                              EP1
```

JUNCTION C (CONT.)

```
    BglII                                          EcoRI        [NcoI]
GGA GAT CTT TTT TTT TTT GGC ATA TAA ATG AAT TCC GGC ATG GCC TCG CTC GCG
                                       MET Asn Ser Gly Met Ala Ser Leu Ala
                                                            PRV gpC(1)→
```

FIGURE 11D

JUNCTION D

```
     [Nco I]
    ┌───────
   C CAT GCT CTA GAG GAT CCC CGG GCG AGC TCG AAT TCG GAT CCA TAA TTA ATT
                 ↓                                   └──┘
            PRV BamHI #9                             EcoRI
```

JUNCTION D (CONT.)

```
                                                              [Acc I]
                                                              ┌──────
   AAT TAA TTT TTA TCC CGG GTC GAC CGG GTC GAC CTG CAG CCT ACA TGG AAA TCT ACC
                                                                  ↑
                                                            SPV Hind III M
```

JUNCTION E

```
                                     HindIII
                                    ┌────────
   TAA TGT ATC TAT AAT GGT ATA AAG CTT GTA TTC TAT AGT GTC ACC TAA ATC
                                         ↑        ↓
                                        pSP64
                                    ────────────
                                    SPV Hind III M
```

| FIGURE 12A |
|---|
| FIGURE 12B |
| FIGURE 12C |
| FIGURE 12D |

| DNA | ORIGIN | SITES | SIZE |
|---|---|---|---|
| VECTOR | pSP64 | Hind III–Bam HI | ~2972 BP |
| FRAGMENT 1 | SPV HindIII M | Bgl II–Acc I | ~1484 BP |
| FRAGMENT 2 | pJF751 | Bam HI–Pvu II | ~3002 BP |
| FRAGMENT 3 | PRV BamHI 2 & 9 | Nco I–Nco I | ~2378 BP |
| FRAGMENT 4 | SPV HindIII M | Acc I–Hind III | ~2149 BP |

FIGURE 12C

JUNCTION C

```
        Pvu II
GAA ATC CAG CTG AGC GCC GGT CGC TAC CAT TAC CAG TTG GTC TGG TGT CAA AAA GAT
Glu Ile Gln Leu Ser Ala Gly Arg Tyr His Tyr Gln Leu Val Trp Cys Gln Lys Asp
         →                                                                  ←
       pJF 751                                                    E. coli Lac Z (1024)
```

JUNCTION C (CONT.)

```
                           Sal I   Xba I
CCA TAA TTA ATT AAC CCG GTC GAC TCT AGA TTT TTT TTT TTT TTG GCA TAT AAA
Pro *
                                        LP2
```

JUNCTION C (CONT.)

```
 Bgl II                                                  Eco R I          [Nco I]
TAG ATC TGT ATC CTA AAA TTG AAT TGT AAT TAT CGA TAA TAA ATG AAT TCC GGC ATG GCC TCG
                                                        MET Asn Ser Gly Met Ala Ser
              EP2                                                              →
                                                                          PRV gpC (1)
```

FIGURE 12D
JUNCTION D
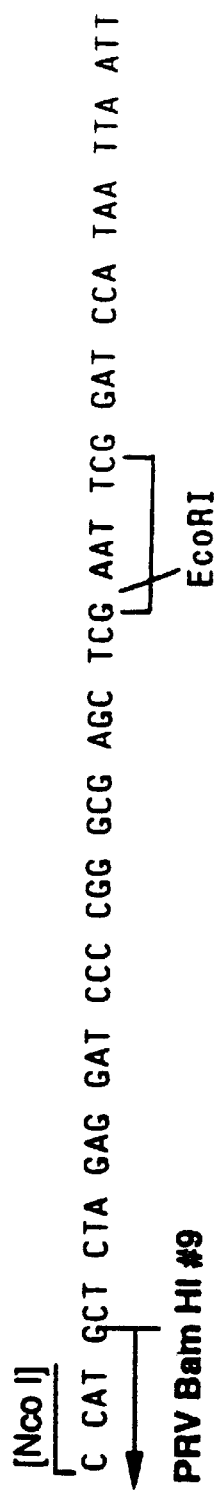
[NcoI]
C CAT GCT CTA GAG GAT CCC CGG GCG AGC TCG AAT TCG GAT CCA TAA TTA ATT
PRV Bam HI #9
EcoRI
JUNCTION D (CONT.)
AAT TAA TTT TTA TCC CGG GTC GAC CGG GTC GAC CTG CAG CCT ACA TGG AAA TCT ACC
[AccI]
SPV Hind III M
JUNCTION E
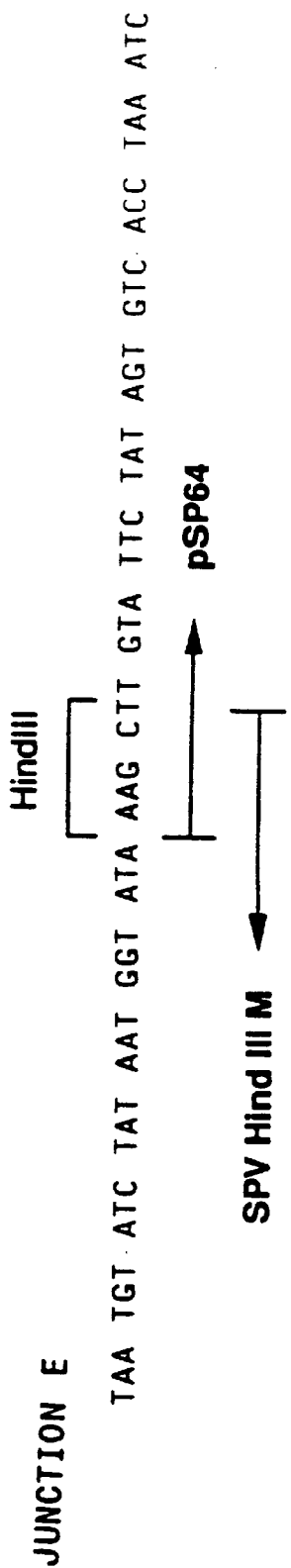
TAA TGT ATC TAT AAT GGT ATA AAG CTT GTA TTC TAT AGT GTC ACC TAA ATC
HindIII
pSP64
SPV Hind III M

FIGURE 16

FIGURE 18B

Junction A

ACA GGA AAC AGC TAT GAC CAT GAT TAC GAA TTC GAG CTC GCC CGG GGA TCT [BamHI/BglII]

← pSP64      SPV HindIII M →

Junction B

```
        NotI            SalI    XbaI
[AccI]                                
GTAT AGC GGC CGC CTG CAG GTC GAC TCT AGA TTT TTT TTT TTT TTT TTG GCA TAT AAA
```
← SPV HindIII M                                    LP2

Junction B Continued

```
BglII
TAG ATC TGT ATC CTA AAA TTG AAT TGT AAT TAT CGA TAA TAA AT
```
EP2

Junction B Continued

[EcoRI, BamHI]
GAAT TTG ATC CAT GAA TCC TAAT
EIV NA PR/56 (55-452) →

FIGURE 18D

Junction D

```
              Pvu II
         ┌────┬────┐
GAA ATC  CAG  CTG  AGC GCC GGT CGC TAC CAT TAC CAG TTG GTC TGG TGT CAA AAA GAT
         └────┴────┘                                                      →
              ↓
            pJF 751                                              E. coli Lac Z (1024)
```

Junction D Continued

```
                      Asc I                      Sal I                      Not I                   [Acc I]
                 ┌────┬────┐                ┌────┬────┐                ┌────┬────┐                ┌────┬────┐
CCA TAA TTA ATT  AAC  CCG  GGT CGA GGC GCG CCG GGT CGA CCT GCA GGC GCG CCG GGC GGC CGC TAT AC
                 └────┴────┘                └────┴────┘                └────┴────┘                └────┴────┘
                                                                                                         ↑
                                                                                                   SPV Hind III M
```

Junction E

```
                                      Hind III
                                 ┌────┬────┐
TAA TGT ATC TAT AAT GGT ATA TTC  AAG  CTT  GTA TTC TAT AGT GTC ACC TAA ATC
                                 └────┴────┘
          ↓                           ↑
    SPV Hind III M                  pSP64
```

| DNA | ORIGIN | SITES | SIZE |
|---|---|---|---|
| VECTOR | pSP64 | Hind III–Bam HI | ~2972 BP |
| FRAGMENT 1 | SPV HindIII M | Bgl II–Acc I | ~1484 BP |
| FRAGMENT 2 | PRV Kpn I C | Sma I–Sac I | ~3500 BP |
| FRAGMENT 3 | pJF751 | Bam HI–Pvu II | ~3010 BP |
| FRAGMENT 4 | SPV HindIII M | Acc I–Hind III | ~2149 BP |

| FIGURE 19A |
| FIGURE 19B |
| FIGURE 19C |
| FIGURE 19D |

FIGURE 19C
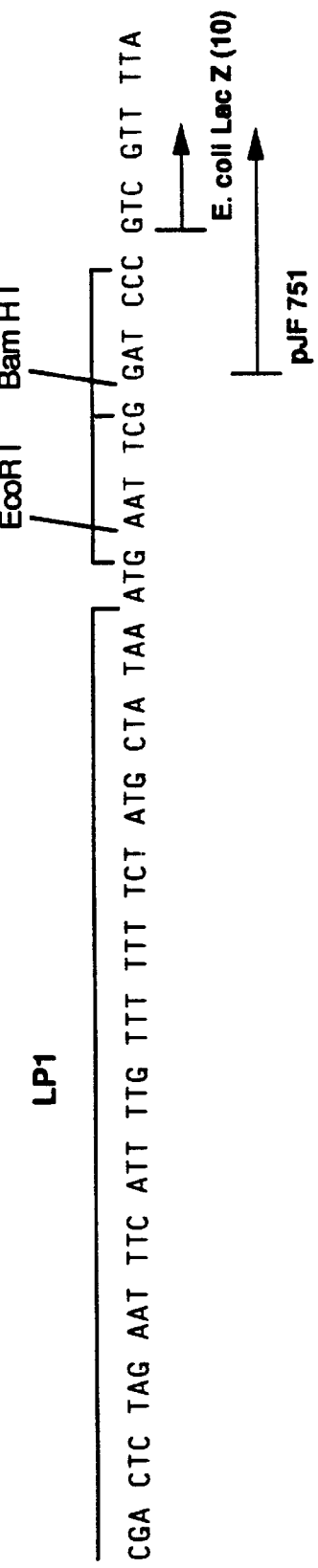

| |
|---|
| FIGURE 21A |
| FIGURE 21B |
| FIGURE 21C |
| FIGURE 21D |
| DNA | Origin | Sites | Size |
|---|---|---|---|
| Vector | pSP64 | Hind III–Bam HI | ~2972 BP |
| Fragment 1 | SPV Hind III M | Bgl II–Acc I | ~1484 BP |
| Fragment 2 | EIVA NA AK/91 | Sal I†–Sal I† | ~1450 BP |
| Fragment 3 | pJF751 | Bam HI–Pvu II | ~3010 BP |
| Fragment 4 | SPV Hind III M | Acc I–Hind III | ~2149 BP |
†Restriction sites introduced by PCR cloning

FIGURE 23C
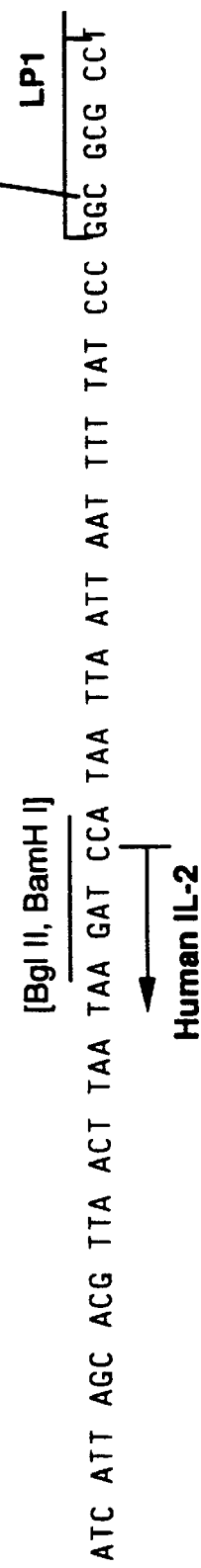
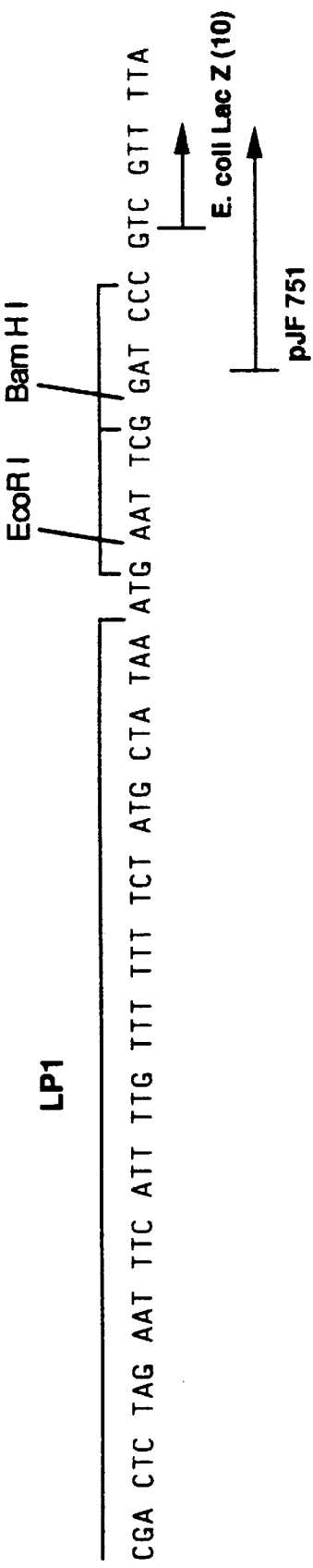

FIGURE 23D

Junction D

Pvu II

GAA ATC CAG CTG AGC GCC GGT CGC TAC CAT TAC CAG TTG GTC TGG TGT CAA AAA GAT

← pJF 751 →  E. coli Lac Z (1024) →

Junction D Continued

Asc I    Sal I    Not I    [Acc I]

CCA TAA TTA ATT AAC CCG GGT CGA GGT CGA CCT GCA GGC GGC CGC TAT AC

← SPV Hind III M →

Junction E

Hind III

TAA TGT ATC TAT AAT GGT ATA AAG CTT GTA TTC TAT AGT GTC ACC TAA ATC

← SPV Hind III M →  ← pSP64 →

| DNA | Origin | Sites | Size |
|---|---|---|---|
| Vector | pSP64 | Hind III–Bam HI | ~2972 BP |
| Fragment 1 | SPV Hind III M | Bgl II–Acc I | ~1484 BP |
| Fragment 2 | EHV-1 BamHI a & I | EcoR I†–Pme I | ~2941 BP |
| Fragment 3 | pJF751 | Bam HI–Pvu II | ~3010 BP |
| Fragment 4 | SPV Hind III M | Acc I–Hind III | ~2149 BP |

† Restriction sites introduced by PCR cloning

| FIGURE 24A |
| FIGURE 24B |
| FIGURE 24C |
| FIGURE 24D |

| DNA | Origin | Sites | Size |
|---|---|---|---|
| Vector | pSP64 | Hind III–Bam HI | ~2972 BP |
| Fragment 1 | SPV Hind III M | Bgl II–Acc I | ~1484 BP |
| Fragment 2 | EHV-1 BamH I "d" | Hind III–Hind III | ~1240 BP |
| Fragment 3 | pJF751 | Bam HI–Pvu II | ~3010 BP |
| Fragment 4 | SPV Hind III M | Acc I–Hind III | ~2149 BP |

| FIGURE 28A |
| FIGURE 28B |
| FIGURE 28C |
| FIGURE 28D |

| DNA | Origin | Sites | Size |
|---|---|---|---|
| Vector | pSP65 | Hind III–Sph I | ~2519 BP |
| Fragment 1 | SPV Hind III M | Sph I–Bgl II† | ~855 BP |
| Fragment 2 | pJF751 | Bam HI–Pvu II | ~3002 BP |
| Fragment 3 | SPV Hind III M | Sal I†–Hind III | ~1113 BP |

†Restriction sites introduced by PCR cloning

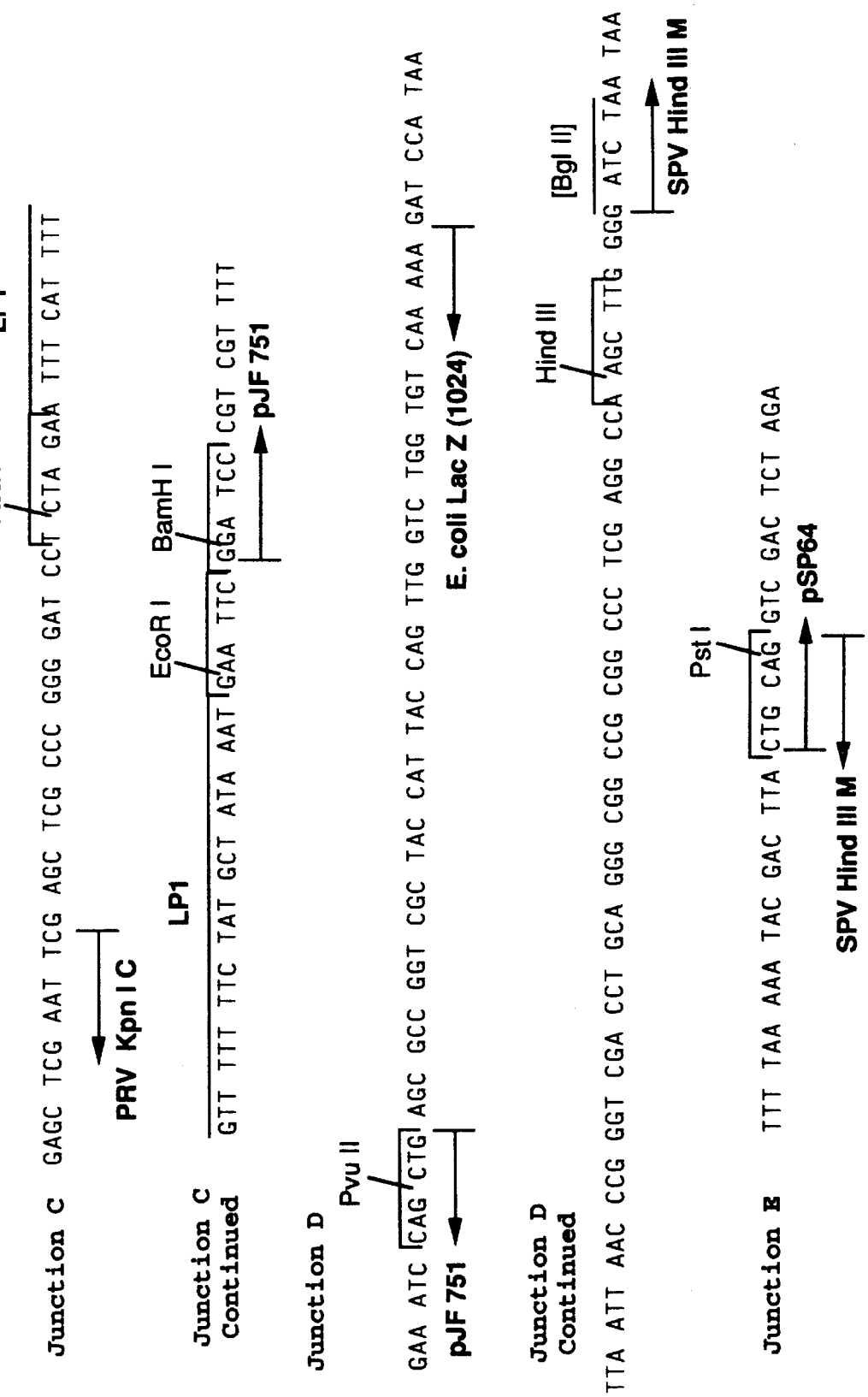

| DNA | Origin | Sites | Size |
|---|---|---|---|
| Vector | pSP64 | Hind III–BamH I | ~2972 BP |
| Fragment 1 | SPV Hind III M | Bgl II–Acc I | ~1484 BP |
| Fragment 2 | PRV BamHI #7 | EcoR I–Stu I | ~1552 BP |
| Fragment 3 | SPV Hind III M | Acc I–Nde I | ~48 BP |
| Fragment 4 | PRV Kpn I C | Sma I–EcoR I | ~3500 BP |
| Fragment 5 | pJF751 | Bam HI–Pvu II | ~3010 BP |
| Fragment 6 | SPV Hind III M | Nde I–Hind III | ~1560 BP |

| DNA | Origin | Sites | Size |
|---|---|---|---|
| Vector | pSP64 | Hind III–BamH I | ~2972 BP |
| Fragment 1 | SPV Hind III M | Bgl II–Acc I | ~1484 BP |
| Fragment 2 | PRV BamHI #7 | EcoR I–Stu I | ~1552 BP |
| Fragment 3 | SPV Hind III M | Acc I–Nde I | ~48 BP |
| Fragment 4 | pJF751 | Bam HI–Pvu II | ~3010 BP |
| Fragment 5 | PRV Bam H I #2&9 | Nco I–Nco I | ~2378 BP |
| Fragment 6 | SPV Hind III M | Nde I–Hind III | ~1560 BP |

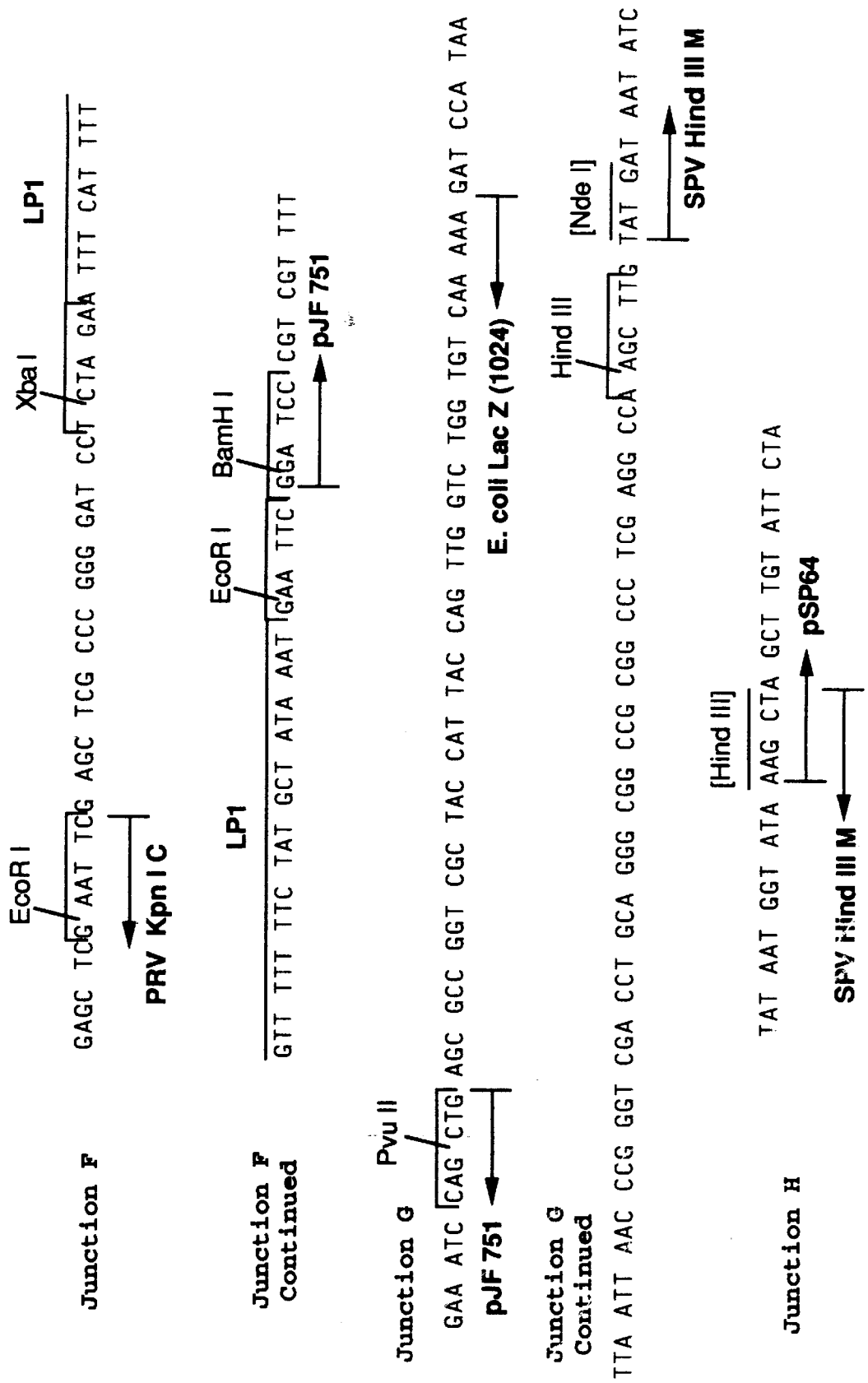

SEQUENCE LISTING (1) GENERAL INFORMATION:

(iii) NUMBER OF SEQUENCES: 267

(2) INFORMATION FOR SEQ ID NO: 1:

(i) SEQUENCE CHARACTERISTICS:
      (A) LENGTH: 599 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Swinepox virus
      (B) STRAIN: Kasza
      (C) INDIVIDUAL ISOLATE: S-SPV-001

(vii) IMMEDIATE SOURCE:
      (B) CLONE: 515-85.1

(viii) POSITION IN GENOME:
      (B) MAP POSITION: []23.2
      (C) UNITS: %G (ix) FEATURE:

```
    (A) NAME/KEY: CDS
    (B) LOCATION: 202..597
    (D) OTHER INFORMATION: /partial
        /codon_start= 202
        /function= "Potential eukaryotic transcriptional
        regulatory protein"
        /standard_name= "515-85.1 ORF"

(xi) SEQUENCE DESCRIPTION: SEQ ID NO: 1:
```

AATGTATCCA GAGTTGTTGA ATGCCTTATC GTACCTAATA TTAATATAGA GTTATTAACT    60

GAATAAGTAT ATATAAATGA TTGTTTTTAT AATGTTTGTT ATCGCATTTA GTTTGCTGT    120

ATGGTTATCA TATACATTTT TAAGGCCGTA TATGATAAAT GAAAATATAT AAGCACTTAT   180

```
TTTTGTTAGT ATAATAACAC A ATG CCG TCG TAT ATG TAT CCG AAG AAC GCA     231
                       Met Pro Ser Tyr Met Tyr Pro Lys Asn Ala
                        1               5                  10

AGA AAA GTA ATT TCA AAG ATT ATA TCA TTA CAA CTT GAT ATT AAA AAA     279
Arg Lys Val Ile Ser Lys Ile Ile Ser Leu Gln Leu Asp Ile Lys Lys
            15                  20                  25

CTT CCT AAA AAA TAT ATA AAT ACC ATG TTA GAA TTT GGT CTA CAT GGA     327
Leu Pro Lys Lys Tyr Ile Asn Thr Met Leu Glu Phe Gly Leu His Gly
        30                  35                  40

AAT CTA CCA GCT TGT ATG TAT AAA GAT GCC GTA TCA TAT GAT ATA AAT     375
Asn Leu Pro Ala Cys Met Tyr Lys Asp Ala Val Ser Tyr Asp Ile Asn
    45                  50                  55

AAT ATA AGA TTT TTA CCT TAT AAT TGT GTT ATG GTT AAA GAT TTA ATA     423
Asn Ile Arg Phe Leu Pro Tyr Asn Cys Val Met Val Lys Asp Leu Ile
60                  65                  70

AAT GTT ATA AAA TCA TCA TCT GTA ATA GAT ACT AGA TTA CAT CAA TCT     471
Asn Val Ile Lys Ser Ser Ser Val Ile Asp Thr Arg Leu His Gln Ser
75                  80                  85                  90

GTA TTA AAA CAT CGT AGA GCG TTA ATA GAT TAC GGC GAT CAA GAC ATT     519
Val Leu Lys His Arg Arg Ala Leu Ile Asp Tyr Gly Asp Gln Asp Ile
            95                  100                 105

ATC ACT TTA ATG ATC ATT AAT AAG TTA CTA TCG ATA GAT GAT ATA TCC     567
Ile Thr Leu Met Ile Ile Asn Lys Leu Leu Ser Ile Asp Asp Ile Ser
        110                 115                 120

TAT ATA TTA GAT AAA AAA ATA ATT CAT GTA AC                          599
Tyr Ile Leu Asp Lys Lys Ile Ile His Val
    125                 130

(2) INFORMATION FOR SEQ ID NO: 2:

(i) SEQUENCE CHARACTERISTICS:
        (A) LENGTH: 132 amino acids
        (B) TYPE: amino acid
        (D) TOPOLOGY: linear (ii) MOLECULE TYPE: protein (xi) SEQUENCE DESCRIPTION: SEQ ID NO: 2:

Met Pro Ser Tyr Met Tyr Pro Lys Asn Ala Arg Lys Val Ile Ser Lys
 1               5                  10                  15

Ile Ile Ser Leu Gln Leu Asp Ile Lys Lys Leu Pro Lys Lys Tyr Ile
            20                  25                  30

Asn Thr Met Leu Glu Phe Gly Leu His Gly Asn Leu Pro Ala Cys Met
        35                  40                  45

Tyr Lys Asp Ala Val Ser Tyr Asp Ile Asn Asn Ile Arg Phe Leu Pro
    50                  55                  60

Tyr Asn Cys Val Met Val Lys Asp Leu Ile Asn Val Ile Lys Ser Ser
65                  70                  75                  80
```

-continued

```
Ser Val Ile Asp Thr Arg Leu His Gln Ser Val Leu Lys His Arg Arg
                85                  90                  95

Ala Leu Ile Asp Tyr Gly Asp Gln Asp Ile Ile Thr Leu Met Ile Ile
                100                 105                 110

Asn Lys Leu Leu Ser Ile Asp Asp Ile Ser Tyr Ile Leu Asp Lys Lys
            115                 120                 125

Ile Ile His Val
    130
```

(2) INFORMATION FOR SEQ ID NO: 3:

(i) SEQUENCE CHARACTERISTICS:
        (A) LENGTH: 899 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (ix) FEATURE:
        (A) NAME/KEY: CDS
        (B) LOCATION: 3..662
        (D) OTHER INFORMATION: /partial
            /codon_start= 3
            /function= "Potential eukaryotic transcriptional
            regulatory protein"
            /standard_name= "515-85.1 ORF"

(ix) FEATURE:
        (A) NAME/KEY: MISC_FEATURE
        (B) LOCATION: 868
        (C) n= any nucleotide (xi) SEQUENCE DESCRIPTION: SEQ ID NO: 3:

```
GA GAT ATT AAA TCA TGT AAA TGC TCG ATA TGT TCC GAC TCT ATA ACA         47
   Asp Ile Lys Ser Cys Lys Cys Ser Ile Cys Ser Asp Ser Ile Thr
   1               5                  10                  15

CAT CAT ATA TAT GAA ACA ACA TCA TGT ATA AAT TAT AAA TCT ACC GAT         95
His His Ile Tyr Glu Thr Thr Ser Cys Ile Asn Tyr Lys Ser Thr Asp
                20                  25                  30

AAT GAT CTT ATG ATA GTA TTG TTC AAT CTA ACT AGA TAT TTA ATG CAT        143
Asn Asp Leu Met Ile Val Leu Phe Asn Leu Thr Arg Tyr Leu Met His
            35                  40                  45

GGG ATG ATA CAT CCT AAT CTT ATA AGC GTA AAA GGA TGG GGT CCC CTT        191
Gly Met Ile His Pro Asn Leu Ile Ser Val Lys Gly Trp Gly Pro Leu
        50                  55                  60

ATT GGA TTA TTA ACG GGT GAT ATA GGT ATT AAT TTA AAA CTA TAT TCC        239
Ile Gly Leu Leu Thr Gly Asp Ile Gly Ile Asn Leu Lys Leu Tyr Ser
    65                  70                  75

ACC ATG AAT ATA AAT GGG CTA CGG TAT GGA GAT ATT ACG TTA TCT TCA        287
Thr Met Asn Ile Asn Gly Leu Arg Tyr Gly Asp Ile Thr Leu Ser Ser
80                  85                  90                  95
```

```
TAC GAT ATG AGT AAT AAA TTA GTC TCT ATT ATT AAT ACA CCC ATA TAT      335
Tyr Asp Met Ser Asn Lys Leu Val Ser Ile Ile Asn Thr Pro Ile Tyr
            100                 105                 110

GAG TTA ATA CCG TTT ACT ACA TGT TGT TCA CTC AAT GAA TAT TAT TCA      383
Glu Leu Ile Pro Phe Thr Thr Cys Cys Ser Leu Asn Glu Tyr Tyr Ser
                115                 120                 125

AAA ATT GTG ATT TTA ATA AAT GTT ATT TTA GAA TAT ATG ATA TCT ATT      431
Lys Ile Val Ile Leu Ile Asn Val Ile Leu Glu Tyr Met Ile Ser Ile
            130                 135                 140

ATA TTA TAT AGA ATA TTG ATC GTA AAA AGA TTT AAT AAC ATT AAA GAA      479
Ile Leu Tyr Arg Ile Leu Ile Val Lys Arg Phe Asn Asn Ile Lys Glu
                145                 150                 155

TTT ATT TCA AAA GTC GTA AAT ACT GTA CTA GAA TCA TCA GGC ATA TAT      527
Phe Ile Ser Lys Val Val Asn Thr Val Leu Glu Ser Ser Gly Ile Tyr
160                 165                 170                 175

TTT TGT CAG ATG CGT GTA CAT GAA CAA ATT GAA TTG GAA ATA GAT GAG      575
Phe Cys Gln Met Arg Val His Glu Gln Ile Glu Leu Glu Ile Asp Glu
                180                 185                 190

CTC ATT ATT AAT GGA TCT ATG CCT GTA CAG CTT ATG CAT TTA CTT CTA      623
Leu Ile Ile Asn Gly Ser Met Pro Val Gln Leu Met His Leu Leu Leu
                195                 200                 205

AAG GTA GCT ACC ATA ATA TTA GAG GAA ATC AAA GAA ATA TAACGTATTT      672
Lys Val Ala Thr Ile Ile Leu Glu Glu Ile Lys Glu Ile
            210                 215                 220

TTTCTTTTAA ATAAATAAAA ATACTTTTTT TTTTAAACAA GGGGTGCTAC CTTGTCTAAT    732

TGTATCTTGT ATTTTGGATC TGATGCAAGA TTATTAAATA ATCGTATGAA AAAGTAGTAG    792

ATATAGTTTA TATCGTTACT GGACATGATA TTATGTTTAG TTAATTCTTC TTTGGCATGA    852

ATTCTACACG TCGGANAAGG TAATGTATCT ATAATGGTAT AAAGCTT                  899
```

(2) INFORMATION FOR SEQ ID NO: 4:

(i) SEQUENCE CHARACTERISTICS:
        (A) LENGTH: 220 amino acids
        (B) TYPE: amino acid
        (D) TOPOLOGY: linear (ii) MOLECULE TYPE: protein (xi) SEQUENCE DESCRIPTION: SEQ ID NO: 4:

```
Asp Ile Lys Ser Cys Lys Cys Ser Ile Cys Ser Asp Ser Ile Thr His
1               5                   10                  15

His Ile Tyr Glu Thr Thr Ser Cys Ile Asn Tyr Lys Ser Thr Asp Asn
            20                  25                  30

Asp Leu Met Ile Val Leu Phe Asn Leu Thr Arg Tyr Leu Met His Gly
        35                  40                  45

Met Ile His Pro Asn Leu Ile Ser Val Lys Gly Trp Gly Pro Leu Ile
    50                  55                  60

Gly Leu Leu Thr Gly Asp Ile Gly Ile Asn Leu Lys Leu Tyr Ser Thr
65              70                  75                  80

Met Asn Ile Asn Gly Leu Arg Tyr Gly Asp Ile Thr Leu Ser Ser Tyr
            85                  90                  95

Asp Met Ser Asn Lys Leu Val Ser Ile Ile Asn Thr Pro Ile Tyr Glu
            100                 105                 110

Leu Ile Pro Phe Thr Thr Cys Cys Ser Leu Asn Glu Tyr Tyr Ser Lys
        115                 120                 125

Ile Val Ile Leu Ile Asn Val Ile Leu Glu Tyr Met Ile Ser Ile Ile
    130                 135                 140
```

```
Leu Tyr Arg Ile Leu Ile Val Lys Arg Phe Asn Asn Ile Lys Glu Phe
145                 150                 155                 160

Ile Ser Lys Val Val Asn Thr Val Leu Glu Ser Ser Gly Ile Tyr Phe
                165                 170                 175

Cys Gln Met Arg Val His Glu Gln Ile Glu Leu Glu Ile Asp Glu Leu
            180                 185                 190

Ile Ile Asn Gly Ser Met Pro Val Gln Leu Met His Leu Leu Leu Lys
        195                 200             205

Val Ala Thr Ile Ile Leu Glu Glu Ile Lys Glu Ile
    210                 215                 220
```

(2) INFORMATION FOR SEQ ID NO: 5:

(i) SEQUENCE CHARACTERISTICS:
        (A) LENGTH: 129 amino acids
        (B) TYPE: amino acid
        (C) STRANDEDNESS: double
        (D) TOPOLOGY: linear (ii) MOLECULE TYPE: peptide (iii) HYPOTHETICAL: YES (iv) ANTI-SENSE: NO (v) FRAGMENT TYPE: N-terminal (vi) ORIGINAL SOURCE:
        (A) ORGANISM: Vaccinia virus
        (B) STRAIN: Copenhagen (viii) POSITION IN GENOME:
        (B) MAP POSITION: []23.2
        (C) UNITS: %G (xi) SEQUENCE DESCRIPTION: SEQ ID NO: 5:

```
Met Phe Met Tyr Pro Glu Phe Ala Arg Lys Ala Leu Ser Lys Leu Ile
1               5                   10                  15

Ser Lys Lys Leu Asn Ile Glu Lys Val Ser Ser Lys His Gln Leu Val
                20                  25                  30

Leu Leu Asp Tyr Gly Leu His Gly Leu Leu Pro Lys Ser Leu Tyr Leu
            35                  40                  45

Glu Ala Ile Asn Ser Asp Ile Leu Asn Val Arg Phe Phe Pro Pro Glu
    50                  55                  60

Ile Ile Asn Val Thr Asp Ile Val Lys Ala Leu Gln Asn Ser Cys Arg
65                  70                  75                  80

Val Asp Glu Tyr Leu Lys Ala Val Ser Leu Tyr His Lys Asn Ser Leu
                85                  90                  95

Met Val Ser Gly Pro Asn Val Val Lys Leu Met Ile Glu Tyr Asn Leu
                100                 105                 110

Leu Thr His Ser Asp Leu Glu Trp Leu Ile Asn Glu Asn Val Val Lys
            115                 120                 125

Ala
```

(2) INFORMATION FOR SEQ ID NO: 6:

(i) SEQUENCE CHARACTERISTICS:
        (A) LENGTH: 132 amino acids
        (B) TYPE: amino acid
        (C) STRANDEDNESS: double
        (D) TOPOLOGY: linear (ii) MOLECULE TYPE: peptide (iii) HYPOTHETICAL: YES (iv) ANTI-SENSE: NO (v) FRAGMENT TYPE: N-terminal (vi) ORIGINAL SOURCE:
               (A) ORGANISM: Swinepox virus
               (B) STRAIN: Kasza (viii) POSITION IN GENOME:
               (B) MAP POSITION: []23.2
               (C) UNITS: %G (xi) SEQUENCE DESCRIPTION: SEQ ID NO: 6:

```
Met Pro Ser Tyr Met Tyr Pro Lys Asn Ala Arg Lys Val Ile Ser Lys
1               5                   10                  15

Ile Ile Ser Leu Gln Leu Asp Ile Lys Lys Leu Pro Lys Lys Tyr Ile
            20                  25                  30

Asn Thr Met Leu Glu Phe Gly Leu His Gly Asn Leu Pro Ala Cys Met
        35                  40                  45

Tyr Lys Asp Ala Val Ser Tyr Asp Ile Asn Asn Ile Arg Phe Leu Pro
    50                  55                  60

Tyr Asn Cys Val Met Val Lys Asp Leu Ile Asn Val Ile Lys Ser Ser
65                  70                  75                  80

Ser Val Ile Asp Thr Arg Leu His Gln Ser Val Leu Lys His Arg Arg
                85                  90                  95

Ala Leu Ile Asp Tyr Gly Asp Gln Asp Ile Ile Thr Leu Met Ile Ile
            100                 105                 110

Asn Lys Leu Leu Ser Ile Asp Asp Ile Ser Tyr Ile Leu Asp Lys Lys
        115                 120                 125

Ile Ile His Val
    130
```

(2) INFORMATION FOR SEQ ID NO: 7:

(i) SEQUENCE CHARACTERISTICS:
(A) LENGTH: 101 amino acids
(B) TYPE: amino acid
(C) STRANDEDNESS: double
(D) TOPOLOGY: linear (ii) MOLECULE TYPE: peptide (iii) HYPOTHETICAL: YES (iv) ANTI-SENSE: NO (v) FRAGMENT TYPE: C-terminal (vi) ORIGINAL SOURCE:
(A) ORGANISM: Vaccinia virus
(B) STRAIN: Copenhagen (viii) POSITION IN GENOME:
(B) MAP POSITION: []23.2
(C) UNITS: %G (xi) SEQUENCE DESCRIPTION: SEQ ID NO: 7:

```
Val Leu Asn Asp Gln Tyr Ala Lys Ile Val Ile Phe Phe Asn Thr Ile
1               5                   10                  15

Ile Glu Tyr Ile Ile Ala Thr Ile Tyr Tyr Arg Leu Thr Val Leu Asn
            20                  25                  30

Asn Tyr Thr Asn Val Lys His Phe Val Ser Lys Val Leu His Thr Val
        35                  40                  45
```

-continued

```
Met Glu Ala Cys Gly Val Leu Phe Ser Tyr Ile Lys Val Asn Asp Lys
    50                  55                  60

Ile Glu His Glu Leu Glu Glu Met Val Asp Lys Gly Thr Val Pro Ser
65                  70                  75                  80

Tyr Leu Tyr His Leu Ser Ile Asn Val Ile Ser Ile Ile Leu Asp Asp
                85                  90                  95

Ile Asn Gly Thr Arg
            100
```

(2) INFORMATION FOR SEQ ID NO: 8:

(i) SEQUENCE CHARACTERISTICS:
(A) LENGTH: 100 amino acids
(B) TYPE: amino acid
(C) STRANDEDNESS: double
(D) TOPOLOGY: linear (ii) MOLECULE TYPE: peptide (iii) HYPOTHETICAL: YES (iv) ANTI-SENSE: NO (v) FRAGMENT TYPE: C-terminal (vi) ORIGINAL SOURCE:
(A) ORGANISM: Swinepox virus
(B) STRAIN: Kasza (viii) POSITION IN GENOME:
(B) MAP POSITION: []23.2
(C) UNITS: %G (xi) SEQUENCE DESCRIPTION: SEQ ID NO: 8:

```
Ser Leu Asn Glu Tyr Tyr Ser Lys Ile Val Ile Leu Ile Asn Val Ile
1               5                   10                  15

Leu Glu Tyr Met Ile Ser Ile Ile Leu Tyr Arg Ile Leu Ile Val Lys
            20                  25                  30

Arg Phe Asn Asn Ile Lys Glu Phe Ile Ser Lys Val Val Asn Thr Val
        35                  40                  45

Leu Glu Ser Ser Gly Ile Tyr Phe Cys Gln Met Arg Val His Glu Gln
    50                  55                  60

Ile Glu Leu Glu Ile Asp Glu Leu Ile Ile Asn Gly Ser Met Pro Val
65                  70                  75                  80

Gln Leu Met His Leu Leu Leu Lys Val Ala Thr Ile Ile Leu Glu Glu
                85                  90                  95

Ile Lys Glu Ile
            100
```

(2) INFORMATION FOR SEQ ID NO: 9:

(i) SEQUENCE CHARACTERISTICS:
(A) LENGTH: 102 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Plasmid (vii) IMMEDIATE SOURCE:

(B) CLONE: 520-17.5 (Junction A)

(x) PUBLICATION INFORMATION:
        (A) AUTHORS: Ferrari, Franco A
            Trach, Kathleen
            Hoch, James A
        (B) TITLE: Sequence Analysis of the spo0B Locus Revels a
            Polycistronic Transcription Unit
        (C) JOURNAL: J. Bacteriol.
        (D) VOLUME: 161
        (E) ISSUE: 2
        (F) PAGES: 556-562
        (G) DATE: Feb.-1985

(xi) SEQUENCE DESCRIPTION: SEQ ID NO: 9:

CACATACGAT TTAGGTGACA CTATAGAATA CAAGCTTTAT ACCATTATAG ATACATTACC     60

TTGTCCGACG TGTAGAATTC ATGCCAAAGA AGAATTAACT AA                      102

(2) INFORMATION FOR SEQ ID NO: 10:

(i) SEQUENCE CHARACTERISTICS:
        (A) LENGTH: 102 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 520-17.5 (Junction B)

(ix) FEATURE:
        (A) NAME/KEY: CDS
        (B) LOCATION: 85..99
        (D) OTHER INFORMATION: /codon_start= 85
            /function= "Translational start of hybrid protein"
            /product= "N-terminal peptide"
            /number= 1
            /standard_name= "Translation of synthetic DNA
            sequence"

(ix) FEATURE:
        (A) NAME/KEY: CDS
        (B) LOCATION: 100..102
        (C) IDENTIFICATION METHOD: experimental
        (D) OTHER INFORMATION: /partial
            /codon_start= 100
            /function= "marker enzyme"
            /product= "Beta-Galactosidase"
            /evidence= EXPERIMENTAL
            /gene= "lacZ"
            /number= 2
            /citation= ([1])

(x) PUBLICATION INFORMATION:
        (A) AUTHORS: Ferrari, Franco A
            Trach, Kathleen
            Hoch, James A
        (B) TITLE: Sequence Analysis of the spo0B Locus Reveals
            a Polycistronic Transcription Unit
        (C) JOURNAL: J. Bacteriol.
        (D) VOLUME: 161
        (E) ISSUE: 2
        (F) PAGES: 556-562
        (G) DATE: Feb.-1985

(xi) SEQUENCE DESCRIPTION: SEQ ID NO: 10:

GTAGTCGACT CTAGAAAAAA TTGAAAAACT ATTCTAATTT ATTGCACGGA GATCTTTTTT     60

```
TTTTTTTTTT TTTTTGGCAT ATAA ATG AAT TCG GAT CCC GTC                    102
                         Met Asn Ser Asp Pro Val
                          1               5
```

(2) INFORMATION FOR SEQ ID NO: 11:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 11:

```
Met Asn Ser Asp Pro
 1               5
```

(2) INFORMATION FOR SEQ ID NO: 12:

(i) SEQUENCE CHARACTERISTICS:
        (A) LENGTH: 1 amino acids
        (B) TYPE: amino acid
        (D) TOPOLOGY: linear (ii) MOLECULE TYPE: peptide (xi) SEQUENCE DESCRIPTION: SEQ ID NO: 12:

```
Val
 1
```

(2) INFORMATION FOR SEQ ID NO: 13:

(i) SEQUENCE CHARACTERISTICS:
        (A) LENGTH: 103 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 520-17.5 (Junction C)

(ix) FEATURE:
        (A) NAME/KEY: CDS
        (B) LOCATION: 1..72
        (C) IDENTIFICATION METHOD: experimental
        (D) OTHER INFORMATION: /partial
            /codon_start= 1
            /function= "marker enzyme"
            /product= "Beta-galactosidase"
            /evidence= EXPERIMENTAL
            /gene= "lacZ"
            /number= 1
            /citation= ([1])

(ix) FEATURE:
        (A) NAME/KEY: CDS
        (B) LOCATION: 73..78
        (C) IDENTIFICATION METHOD: experimental
        (D) OTHER INFORMATION: /codon_start= 73
            /function= "Translational finish of hybrid
            protein"
            /product= "C-terminal peptide"
            /evidence= EXPERIMENTAL
            /number= 2

/standard_name= "Translation of synthetic DNA
              sequence"

(x) PUBLICATION INFORMATION:
        (A) AUTHORS: Ferrari, Franco A
            Trach, Kathleen
            Hoch, James A
        (B) TITLE: Sequence Analysis of the spo0B Locus Reveals
            a Polycistronic Transcription Unit
        (C) JOURNAL: J. Bacteriol.
        (D) VOLUME: 161
        (E) ISSUE: 2
        (F) PAGES: 556-562
        (G) DATE: Feb.-1985

(xi) SEQUENCE DESCRIPTION: SEQ ID NO: 13:

AGC CCG TCA GTA TCG GCG GAA ATC CAG CTG AGC GCC GGT CGC TAC CAT          48
Ser Pro Ser Val Ser Ala Glu Ile Gln Leu Ser Ala Gly Arg Tyr His
1               5                   10                  15

TAC CAG TTG GTC TGG TGT CAA AAA GAT CCA TAATTAATTA ACCCGGGTCG            98
Tyr Gln Leu Val Trp Cys Gln Lys Asp Pro
            20                  25

AAGAC                                                                   103

(2) INFORMATION FOR SEQ ID NO: 14:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO: 14:

Ser Pro Ser Val Ser Ala Glu Ile Gln Leu Ser Ala Gly Arg Tyr His
1               5                   10                  15

Tyr Gln Leu Val Trp Cys Gln Lys
            20

(2) INFORMATION FOR SEQ ID NO: 15:

(i) SEQUENCE CHARACTERISTICS:
        (A) LENGTH: 2 amino acids
        (B) TYPE: amino acid
        (D) TOPOLOGY: linear (ii) MOLECULE TYPE: peptide (xi) SEQUENCE DESCRIPTION: SEQ ID NO: 15:

Asp Pro
1

(2) INFORMATION FOR SEQ ID NO: 16:

(i) SEQUENCE CHARACTERISTICS:
        (A) LENGTH: 48 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:

(B) CLONE: 520-17.5 (Junction D)

(xi) SEQUENCE DESCRIPTION: SEQ ID NO: 16:

AGATCCCCGG GCGAGCTCGA ATTCGTAATC ATGGTCATAG CTGTTTCC                48

(2) INFORMATION FOR SEQ ID NO: 17:

(i) SEQUENCE CHARACTERISTICS:
        (A) LENGTH: 57 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 538-46.26 (Junction A)

(xi) SEQUENCE DESCRIPTION: SEQ ID NO: 17:

CACATACGAT TTAGGTGACA CTATAGAATA CAAGCTTTAT ACCATTATAG ATACATT        57

(2) INFORMATION FOR SEQ ID NO: 18:

(i) SEQUENCE CHARACTERISTICS:
        (A) LENGTH: 102 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 538-46.16 (Junction B)

(ix) FEATURE:
        (A) NAME/KEY: CDS
        (B) LOCATION: 91..102
        (C) IDENTIFICATION METHOD: experimental
        (D) OTHER INFORMATION: /partial
            /codon_start= 91
            /function= "marker enzyme"
            /product= "Beta-Galactosidase"
            /evidence= EXPERIMENTAL
            /gene= "lacZ"
            /number= 2
            /citation= ([1])

(ix) FEATURE:
        (A) NAME/KEY: CDS
        (B) LOCATION: 76..90
        (D) OTHER INFORMATION: /partial
            /codon_start= 76
            /function= "Translational start of hybrid protein"
            /product= "N-terminal peptide"
            /number= 1
            /standard_name= "Translation of synthetic DNA
            sequence"

(x) PUBLICATION INFORMATION:
        (A) AUTHORS: Ferrari, Franco A
            Trach, Kathleen Hoch, James A
(B) TITLE: Sequence Analysis of the spo0B Locus Reveals
    a Polycistronic Transcription Unit
(C) JOURNAL: J. Bacteriol.
(D) VOLUME: 161
(E) ISSUE: 2
(F) PAGES: 556-562
(G) DATE: Feb.-1985

(xi) SEQUENCE DESCRIPTION: SEQ ID NO: 18:

```
AAGCTGGTAG ATTTCCATGT AGGGCCGCCT GCAGGTCGAC TCTAGAATTT CATTTTGTTT      60

TTTTCTATGC TATAA ATG AAT TCG GAT CCC GTC GTT TTA CAA                  102
           Met Asn Ser Asp Pro Val Val Leu Gln
             1               5
```

(2) INFORMATION FOR SEQ ID NO: 19:

(i) SEQUENCE CHARACTERISTICS:
       (A) LENGTH: 5 amino acids
       (B) TYPE: amino acid
       (D) TOPOLOGY: linear (ii) MOLECULE TYPE: peptide (xi) SEQUENCE DESCRIPTION: SEQ ID NO: 19:

```
Met Asn Ser Asp Pro
  1               5
```

(2) INFORMATION FOR SEQ ID NO: 20:

(i) SEQUENCE CHARACTERISTICS:
       (A) LENGTH: 4 amino acids
       (B) TYPE: amino acid
       (D) TOPOLOGY: linear (ii) MOLECULE TYPE: peptide (xi) SEQUENCE DESCRIPTION: SEQ ID NO: 20:

```
Val Val Leu Gln
  1
```

(2) INFORMATION FOR SEQ ID NO: 21:

(i) SEQUENCE CHARACTERISTICS:
       (A) LENGTH: 206 base pairs
       (B) TYPE: nucleic acid
       (C) STRANDEDNESS: double
       (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
         (B) CLONE: 538-46.16 (Junction C)

(ix) FEATURE:
        (A) NAME/KEY: CDS
        (B) LOCATION: 1..63
        (C) IDENTIFICATION METHOD: experimental
        (D) OTHER INFORMATION: /partial
            /codon_start= 1
            /function= "marker enzyme"
            /product= "Beta-galactosidase"
            /evidence= EXPERIMENTAL
            /number= 1
            /citation= ([1])

(ix) FEATURE:
        (A) NAME/KEY: CDS
        (B) LOCATION: 64..69
        (C) IDENTIFICATION METHOD: experimental
        (D) OTHER INFORMATION: /codon_start= 64
            /function= "Translational finish of hybrid
            protein"
            /product= "C-terminal peptide"
            /evidence= EXPERIMENTAL
            /standard_name= "Translation of synthetic DNA
            sequence"

(ix) FEATURE:
        (A) NAME/KEY: CDS
        (B) LOCATION: 177..185
        (C) IDENTIFICATION METHOD: experimental
        (D) OTHER INFORMATION: /codon_start= 177
            /function= "Translational start of hybrid protein"
            /product= "N-terminal peptide"
            /evidence= EXPERIMENTAL
            /standard_name= "Translation of synthetic DNA
            sequence"

(ix) FEATURE:
        (A) NAME/KEY: CDS
        (B) LOCATION: 186..206
        (C) IDENTIFICATION METHOD: experimental
        (D) OTHER INFORMATION: /partial
            /codon_start= 186
            /function= "glycoprotein"
            /product= "PRV gp50"
            /evidence= EXPERIMENTAL
            /gene= "gp50"
            /number= 3
            /citation= ([2])

(x) PUBLICATION INFORMATION:
        (A) AUTHORS: Ferrari, Franco A
            Trach, Kathleen
            Hoch, James A
        (B) TITLE: Sequence Analysis of the spo0B Locus Reveals
            a Polycistronic Transcription Unit
        (C) JOURNAL: J. Bacteriol.
        (D) VOLUME: 161
        (E) ISSUE: 2
        (F) PAGES: 556-562
        (G) DATE: Feb.-1985

(x) PUBLICATION INFORMATION:
        (A) AUTHORS: Petrovskis, Erik A
            Timmins, James G
            Armentrout, Marty A
            Marchioli, Carmine C
            Jr. Yancy, Robert J
            Post, Leonard E
        (B) TITLE: DNA Sequence of the Gene for Pseudorabies
            Virus gp50, a Glycoprotein without N-Linked
            Glycosylation
        (C) JOURNAL: J. Virol.
        (D) VOLUME: 59
        (E) ISSUE: 2
        (F) PAGES: 216-223
        (G) DATE: Aug.-1986

(xi) SEQUENCE DESCRIPTION: SEQ ID NO: 21:

GTA TCG GCG GAA ATC CAG CTG AGC GCC GGT CGC TAC CAT TAC CAG TTG      48
Val Ser Ala Glu Ile Gln Leu Ser Ala Gly Arg Tyr His Tyr Gln Leu
1               5                   10                  15

GTC TGG TGT CAA AAA GAT CCA TAATTAATTA ACCCGGCCGC CTGCAGGTCG         99
Val Trp Cys Gln Lys Asp Pro
                20

ACTCTAGAAA AAATTGAAAA ACTATTCTAA TTTATTGCAC GGAGATCTTT TTTTTTTTTT   159

TTTTTTTTGG CATATAA ATG AAT TCG CTC GCA GCG CTA TTG GCG GCG          206
                   Met Asn Ser Leu Ala Ala Leu Leu Ala Ala (2) INFORMATION FOR SEQ ID NO: 22:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 22:

```
Val Ser Ala Glu Ile Gln Leu Ser Ala Gly Arg Tyr His Tyr Gln Leu
 1               5                  10                  15
Val Trp Cys Gln Lys
            20
```

(2) INFORMATION FOR SEQ ID NO: 23:

(i) SEQUENCE CHARACTERISTICS:
        (A) LENGTH: 2 amino acids
        (B) TYPE: amino acid
        (D) TOPOLOGY: linear (ii) MOLECULE TYPE: peptide (xi) SEQUENCE DESCRIPTION: SEQ ID NO: 23:

```
Asp Pro
 1
```

(2) INFORMATION FOR SEQ ID NO: 24:

(i) SEQUENCE CHARACTERISTICS:
        (A) LENGTH: 3 amino acids
        (B) TYPE: amino acid
        (D) TOPOLOGY: linear (ii) MOLECULE TYPE: peptide (xi) SEQUENCE DESCRIPTION: SEQ ID NO: 24:

```
Met Asn Ser
 1
```

(2) INFORMATION FOR SEQ ID NO: 25:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 25:

```
Leu Ala Ala Leu Leu Ala Ala
 1               5
```

(2) INFORMATION FOR SEQ ID NO: 26:

(i) SEQUENCE CHARACTERISTICS:
        (A) LENGTH: 101 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
            (A) ORGANISM: Plasmid (vii) IMMEDIATE SOURCE:
            (B) CLONE: 538-46.16 (Junction D)

(ix) FEATURE:
            (A) NAME/KEY: CDS
            (B) LOCATION: 1..15
            (D) OTHER INFORMATION: /partial
                /codon_start= 1
                /function= "glycoprotein"
                /product= "PRV gp63"
                /gene= "gp63"
                /number= 1
                /citation= ([1])

(x) PUBLICATION INFORMATION:
            (A) AUTHORS: Petrovskis, Erik A
                Timmins, James G
                Post, Lenoard E
            (B) TITLE: Use of Lambda-gt11 To Isolate Genes for two
                Pseudorabies Virus Glycoproteins with homology to
                Herpes Simplex Virus and Varicella-Zoster Virus
                Glycoproteins
            (C) JOURNAL: J. Virol.
            (D) VOLUME: 60
            (E) ISSUE: 1
            (F) PAGES: 185-193
            (G) DATE: Oct.-1986

(xi) SEQUENCE DESCRIPTION: SEQ ID NO: 26:

```
CGC GTG CAC CAC GAG GGACTCTAGA GGATCCATAA TTAATTAATT AATTTTTATC          55
Arg Val His His Glu
  1               5

CCGGGTCGAC CTGCAGGCGG CCGGGTCGAC CTGCAGGCGG CCAGAC                      101
```

(2) INFORMATION FOR SEQ ID NO: 27:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO: 27:

```
Arg Val His His Glu
  1               5
```

(2) INFORMATION FOR SEQ ID NO: 28:

(i) SEQUENCE CHARACTERISTICS:
            (A) LENGTH: 57 base pairs
            (B) TYPE: nucleic acid
            (C) STRANDEDNESS: double
            (D) TOPOLOGY: circular (ii) MOLECULE TYPE: DNA (genomic)

(iii) HYPOTHETICAL: NO (iv) ANTI-SENSE: NO (vi) ORIGINAL SOURCE:
            (A) ORGANISM: Plasmid (vii) IMMEDIATE SOURCE:
            (B) CLONE: 538-46.16 (Junction E)

(xi) SEQUENCE DESCRIPTION: SEQ ID NO: 28:

```
AGATCCCCGG GCGAGCTCGA ATTCGTAATC ATGGTCATAG CTGTTTCCTG TGTGAAA          57
```

(2) INFORMATION FOR SEQ ID NO: 29:

(i) SEQUENCE CHARACTERISTICS:
        (A) LENGTH: 1907 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Newcastle disease virus
        (B) STRAIN: B1

(vii) IMMEDIATE SOURCE:
        (B) CLONE: 137-23.803 (PSY1142)

(viii) POSITION IN GENOME:
        (B) MAP POSITION: []50%
        (C) UNITS: %G (ix) FEATURE:
        (A) NAME/KEY: CDS
        (B) LOCATION: 92..1822
        (D) OTHER INFORMATION: /codon_start= 92
            /product= "NDV hemagglutinin-Neuraminidase"
            /gene= "HN"
            /number= 1

(xi) SEQUENCE DESCRIPTION: SEQ ID NO: 29:

```
ACGGGTAGAA CGGTAAGAGA GGCCGCCCCT CAATTGCGAG CCAGACTTCA CAACCTCCGT        60

TCTACCGCTT CACCGACAAC AGTCCTCAAT C ATG GAC CGC GCC GTT AGC CAA         112
                                 Met Asp Arg Ala Val Ser Gln
                                  1               5

GTT GCG TTA GAG AAT GAT GAA AGA GAG GCA AAA AAT ACA TGG CGC TTG        160
Val Ala Leu Glu Asn Asp Glu Arg Glu Ala Lys Asn Thr Trp Arg Leu
         10                  15                  20

ATA TTC CGG ATT GCA ATC TTA TTC TTA ACA GTA GTG ACC TTG GCT ATA        208
Ile Phe Arg Ile Ala Ile Leu Phe Leu Thr Val Val Thr Leu Ala Ile
             25                  30                  35

TCT GTA GCC TCC CTT TTA TAT AGC ATG GGG GCT AGC ACA CCT AGC GAT        256
Ser Val Ala Ser Leu Leu Tyr Ser Met Gly Ala Ser Thr Pro Ser Asp
 40                  45                  50                  55

CTT GTA GGC ATA CCG ACT AGG ATT TCC AGG GCA GAA GAA AAG ATT ACA        304
Leu Val Gly Ile Pro Thr Arg Ile Ser Arg Ala Glu Glu Lys Ile Thr
                 60                  65                  70

TCT ACA CTT GGT TCC AAT CAA GAT GTA GTA GAT AGG ATA TAT AAG CAA        352
Ser Thr Leu Gly Ser Asn Gln Asp Val Val Asp Arg Ile Tyr Lys Gln
             75                  80                  85

GTG GCC CTT GAG TCT CCA TTG GCA TTG TTA AAT ACT GAG ACC ACA ATT        400
Val Ala Leu Glu Ser Pro Leu Ala Leu Leu Asn Thr Glu Thr Thr Ile
         90                  95                 100

ATG AAC GCA ATA ACA TCT CTC TCT TAT CAG ATT AAT GGA GCT GCA AAC        448
Met Asn Ala Ile Thr Ser Leu Ser Tyr Gln Ile Asn Gly Ala Ala Asn
105                 110                 115

AAC AGC GGG TGG GGG GCA CCT ATT CAT GAC CCA GAT TAT ATA GGG GGG        496
Asn Ser Gly Trp Gly Ala Pro Ile His Asp Pro Asp Tyr Ile Gly Gly
120                 125                 130                 135

ATA GGC AAA GAA CTC ATT GTA GAT GAT GCT AGT GAT GTC ACA TCA TTC        544
Ile Gly Lys Glu Leu Ile Val Asp Asp Ala Ser Asp Val Thr Ser Phe
                140                 145                 150
```

```
TAT CCC TCT GCA TTT CAA GAA CAT CTG AAT TTT ATC CCG GCG CCT ACT         592
Tyr Pro Ser Ala Phe Gln Glu His Leu Asn Phe Ile Pro Ala Pro Thr
            155                 160                 165

ACA GGA TCA GGT TGC ACT CGA ATA CCC TCA TTT GAC ATG AGT GCT ACC         640
Thr Gly Ser Gly Cys Thr Arg Ile Pro Ser Phe Asp Met Ser Ala Thr
            170                 175                 180

CAT TAC TGC TAC ACC CAT AAT GTA ATA TTG TCT GGA TGC AGA GAT CAC         688
His Tyr Cys Tyr Thr His Asn Val Ile Leu Ser Gly Cys Arg Asp His
            185                 190                 195

TCA CAC TCA CAT CAG TAT TTA GCA CTT GGT GTG CTC CGG ACA TCT GCA         736
Ser His Ser His Gln Tyr Leu Ala Leu Gly Val Leu Arg Thr Ser Ala
200                 205                 210                 215

ACA GGG AGG GTA TTC TTT TCT ACT CTG CGT TCC ATC AAC CTG GAC GAC         784
Thr Gly Arg Val Phe Phe Ser Thr Leu Arg Ser Ile Asn Leu Asp Asp
            220                 225                 230

ACC CAA AAT CGG AAG TCT TGC AGT GTG AGT GCA ACT CCC CTG GGT TGT         832
Thr Gln Asn Arg Lys Ser Cys Ser Val Ser Ala Thr Pro Leu Gly Cys
            235                 240                 245

GAT ATG CTG TGC TCG AAA GCC ACG GAG ACA GAG GAA GAA GAT TAT AAC         880
Asp Met Leu Cys Ser Lys Ala Thr Glu Thr Glu Glu Glu Asp Tyr Asn
            250                 255                 260

TCA GCT GTC CCT ACG CGG ATG GTA CAT GGG AGG TTA GGG TTC GAC GGC         928
Ser Ala Val Pro Thr Arg Met Val His Gly Arg Leu Gly Phe Asp Gly
            265                 270                 275

CAA TAT CAC GAA AAG GAC CTA GAT GTC ACA ACA TTA TTC GGG GAC TGG         976
Gln Tyr His Glu Lys Asp Leu Asp Val Thr Thr Leu Phe Gly Asp Trp
280                 285                 290                 295

GTG GCC AAC TAC CCA GGA GTA GGG GGT GGA TCT TTT ATT GAC AGC CGC        1024
Val Ala Asn Tyr Pro Gly Val Gly Gly Gly Ser Phe Ile Asp Ser Arg
            300                 305                 310

GTG TGG TTC TCA GTC TAC GGA GGG TTA AAA CCC AAT ACA CCC AGT GAC        1072
Val Trp Phe Ser Val Tyr Gly Gly Leu Lys Pro Asn Thr Pro Ser Asp
            315                 320                 325

ACT GTA CAG GAA GGG AAA TAT GTG ATA TAC AAG CGA TAC AAT GAC ACA        1120
Thr Val Gln Glu Gly Lys Tyr Val Ile Tyr Lys Arg Tyr Asn Asp Thr
            330                 335                 340

TGC CCA GAT GAG CAA GAC TAC CAG ATT CGA ATG GCC AAG TCT TCG TAT        1168
Cys Pro Asp Glu Gln Asp Tyr Gln Ile Arg Met Ala Lys Ser Ser Tyr
            345                 350                 355

AAG CCT GGA CGG TTT GGT GGG AAA CGC ATA CAG CAG GCT ATC TTA TCT        1216
Lys Pro Gly Arg Phe Gly Gly Lys Arg Ile Gln Gln Ala Ile Leu Ser
360                 365                 370                 375

ATC AAA GTG TCA ACA TCC TTA GGC GAA GAC CCG GTA CTG ACT GTA CCG        1264
Ile Lys Val Ser Thr Ser Leu Gly Glu Asp Pro Val Leu Thr Val Pro
            380                 385                 390

CCC AAC ACA GTC ACA CTC ATG GGG GCC GAA GGC AGA ATT CTC ACA GTA        1312
Pro Asn Thr Val Thr Leu Met Gly Ala Glu Gly Arg Ile Leu Thr Val
            395                 400                 405

GGG ACA TCC CAT TTC TTG TAT CAG CGA GGG TCA TCA TAC TTC TCT CCC        1360
Gly Thr Ser His Phe Leu Tyr Gln Arg Gly Ser Ser Tyr Phe Ser Pro
            410                 415                 420

GCG TTA TTA TAT CCT ATG ACA GTC AGC AAC AAA ACA GCC ACT CTT CAT        1408
Ala Leu Leu Tyr Pro Met Thr Val Ser Asn Lys Thr Ala Thr Leu His
            425                 430                 435

AGT CCT TAT ACA TTC AAT GCC TTC ACT CGG CCA GGT AGT ATC CCT TGC        1456
Ser Pro Tyr Thr Phe Asn Ala Phe Thr Arg Pro Gly Ser Ile Pro Cys
440                 445                 450                 455

CAG GCT TCA GCA AGA TGC CCC AAC TCA TGT GTT ACT GGA GTC TAT ACA        1504
Gln Ala Ser Ala Arg Cys Pro Asn Ser Cys Val Thr Gly Val Tyr Thr
            460                 465                 470
```

```
GAT CCA TAT CCC CTA ATC TTC TAT AGA AAC CAC ACC TTG CGA GGG GTA    1552
Asp Pro Tyr Pro Leu Ile Phe Tyr Arg Asn His Thr Leu Arg Gly Val
            475                 480                 485

TTC GGG ACA ATG CTT GAT GGT GAA CAA GCA AGA CTT AAC CCT GCG TCT    1600
Phe Gly Thr Met Leu Asp Gly Glu Gln Ala Arg Leu Asn Pro Ala Ser
            490                 495                 500

GCA GTA TTC GAT AGC ACA TCC CGC AGT CGC ATA ACT CGA GTG AGT TCA    1648
Ala Val Phe Asp Ser Thr Ser Arg Ser Arg Ile Thr Arg Val Ser Ser
            505                 510                 515

AGC AGC ATC AAA GCA GCA TAC ACA ACA TCA ACT TGT TTT AAA GTG GTC    1696
Ser Ser Ile Lys Ala Ala Tyr Thr Thr Ser Thr Cys Phe Lys Val Val
520                 525                 530                 535

AAG ACC AAT AAG ACC TAT TGT CTC AGC ATT GCT GAA ATA TCT AAT ACT    1744
Lys Thr Asn Lys Thr Tyr Cys Leu Ser Ile Ala Glu Ile Ser Asn Thr
                540                 545                 550

CTC TTC GGA GAA TTC AGA ATC GTC CCG TTA CTA GTT GAG ATC CTC AAA    1792
Leu Phe Gly Glu Phe Arg Ile Val Pro Leu Leu Val Glu Ile Leu Lys
                555                 560                 565

GAT GAC GGG GTT AGA GAA GCC AGG TCT GGC TAGTTGAGTC AACTATGAAA      1842
Asp Asp Gly Val Arg Glu Ala Arg Ser Gly
            570                 575

GAGTTGGAAA GATGGCATTG TATCACCTAT CTTCTGCGAC ATCAAGAATC AAACCGAATG  1902

CCGGC                                                              1907

(2) INFORMATION FOR SEQ ID NO: 30:

(i) SEQUENCE CHARACTERISTICS:
        (A) LENGTH: 577 amino acids
        (B) TYPE: amino acid
        (D) TOPOLOGY: linear (ii) MOLECULE TYPE: protein (xi) SEQUENCE DESCRIPTION: SEQ ID NO: 30:

Met Asp Arg Ala Val Ser Gln Val Ala Leu Glu Asn Asp Glu Arg Glu
1               5                   10                  15

Ala Lys Asn Thr Trp Arg Leu Ile Phe Arg Ile Ala Ile Leu Phe Leu
                20                  25                  30

Thr Val Val Thr Leu Ala Ile Ser Val Ala Ser Leu Leu Tyr Ser Met
            35                  40                  45

Gly Ala Ser Thr Pro Ser Asp Leu Val Gly Ile Pro Thr Arg Ile Ser
        50                  55                  60

Arg Ala Glu Glu Lys Ile Thr Ser Thr Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Tyr Ile Gly Gly Ile Gly Lys Glu Leu Ile Val Asp Asp
    130                 135                 140

Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Met Ser Ala Thr His Tyr Cys Tyr Thr His Asn Val Ile
```

```
                    180                 185                 190
Leu Ser Gly Cys Arg Asp His Ser His Ser His Gln Tyr Leu Ala Leu
            195                 200                 205

Gly Val Leu Arg Thr Ser Ala Thr Gly Arg Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Ala Thr Glu
                245                 250                 255

Thr Glu Glu Glu Asp Tyr Asn Ser Ala Val Pro Thr Arg Met Val His
            260                 265                 270

Gly Arg Leu Gly Phe Asp Gly Gln Tyr His Glu Lys Asp Leu Asp Val
        275                 280                 285

Thr Thr Leu Phe Gly Asp Trp Val Ala Asn Tyr Pro Gly Val Gly Gly
    290                 295                 300

Gly Ser Phe Ile Asp Ser Arg Val Trp Phe Ser Val Tyr Gly Gly Leu
305                 310                 315                 320

Lys Pro Asn Thr Pro Ser Asp Thr Val Gln Glu Gly Lys Tyr Val Ile
                325                 330                 335

Tyr Lys Arg Tyr Asn Asp Thr Cys Pro Asp Glu Gln Asp Tyr Gln Ile
            340                 345                 350

Arg Met Ala Lys Ser Ser Tyr Lys Pro Gly Arg Phe Gly Gly Lys Arg
        355                 360                 365

Ile Gln Gln Ala Ile Leu Ser Ile Lys Val Ser Thr Ser Leu Gly Glu
    370                 375                 380

Asp Pro Val Leu Thr Val Pro Asn Thr Val Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Ser
            420                 425                 430

Asn Lys Thr Ala Thr Leu His Ser Pro Tyr Thr Phe Asn Ala Phe Thr
        435                 440                 445

Arg Pro Gly Ser Ile Pro Cys Gln Ala Ser Ala Arg Cys Pro Asn Ser
450                 455                 460

Cys Val Thr Gly Val Tyr Thr Asp Pro Tyr Pro Leu Ile Phe Tyr Arg
465                 470                 475                 480

Asn His Thr Leu Arg Gly Val Phe Gly Thr Met Leu Asp Gly Glu Gln
                485                 490                 495

Ala Arg Leu Asn Pro Ala Ser Ala Val Phe Asp Ser Thr Ser Arg Ser
            500                 505                 510

Arg Ile Thr Arg Val Ser Ser Ser Ile Lys Ala Ala Tyr Thr Thr
        515                 520                 525

Ser Thr Cys Phe Lys Val Val Lys Thr Asn Lys Thr Tyr Cys Leu Ser
530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Gly Val Arg Glu Ala Arg Ser
                565                 570                 575

Gly (2) INFORMATION FOR SEQ ID NO: 31:
```

-continued (i) SEQUENCE CHARACTERISTICS:
(A) LENGTH: 57 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Plasmid (vii) IMMEDIATE SOURCE:
(B) CLONE: 538-46.26 (Junction A)

(xi) SEQUENCE DESCRIPTION: SEQ ID NO: 31:

```
CACATACGAT TTAGGTGACA CTATAGAATA CAAGCTTTAT ACCATTATAG ATACATT        57
```

(2) INFORMATION FOR SEQ ID NO: 32:

(i) SEQUENCE CHARACTERISTICS:
(A) LENGTH: 108 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Plasmid (vii) IMMEDIATE SOURCE:
(B) CLONE: 538-46.26 (Junction B)

(ix) FEATURE:
(A) NAME/KEY: exon
(B) LOCATION: 88..102
(D) OTHER INFORMATION: /codon_start= 88
/function= "Translational start of hybrid protein"
/product= "N-terminal peptide"
/number= 1
/standard_name= "Translation of synthetic DNA sequence"

(ix) FEATURE:
(A) NAME/KEY: CDS
(B) LOCATION: 103..108
(C) IDENTIFICATION METHOD: experimental
(D) OTHER INFORMATION: /partial
/codon_start= 103
/product= "NDV Hemagglutinin-Neuraminidase"
/evidence= EXPERIMENTAL
/gene= "HN"
/number= 2

(xi) SEQUENCE DESCRIPTION: SEQ ID NO: 32:

```
CATGTAGTCG ACTCTAGAAA AAATTGAAAA ACTATTCTAA TTTATTGCAC GGAGATCTTT     60

TTTTTTTTTT TTTTTTTTGG CATATAAATG AATTCGGATC CG GAC CGC               108
                                              Asp Arg
                                                1
```

(2) INFORMATION FOR SEQ ID NO: 33:

(i) SEQUENCE CHARACTERISTICS:
(A) LENGTH: 2 amino acids
(B) TYPE: amino acid
(D) TOPOLOGY: linear (ii) MOLECULE TYPE: peptide (xi) SEQUENCE DESCRIPTION: SEQ ID NO: 33:

Asp Arg
1

(2) INFORMATION FOR SEQ ID NO: 34:

(i) SEQUENCE CHARACTERISTICS:
        (A) LENGTH: 108 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 538-46.26 (Junction C)

(ix) FEATURE:
        (A) NAME/KEY: CDS
        (B) LOCATION: 70..84
        (D) OTHER INFORMATION: /codon_start= 70
            /function= "Translational start of hybrid protein"
            /product= "N-terminal peptide"
            /number= 1
            /standard_name= "Translation of synthetic DNA
            sequence"

(ix) FEATURE:
        (A) NAME/KEY: CDS
        (B) LOCATION: 85..108
        (C) IDENTIFICATION METHOD: experimental
        (D) OTHER INFORMATION: /partial
            /codon_start= 85
            /function= "marker enzyme"
            /product= "Beta-galactosidase"
            /evidence= EXPERIMENTAL
            /gene= "lacZ"
            /number= 2
            /citation= ([1])

(x) PUBLICATION INFORMATION:
        (A) AUTHORS: Ferrari, Franco A
            Trach, Kathleen
            Hoch, James A
        (B) TITLE: Sequence Analysis of the spo0B Locus Reveals
            a Polycistronic Transcription Unit
        (C) JOURNAL: J. Bacteriol.
        (D) VOLUME: 161
        (E) ISSUE: 2
        (F) PAGES: 556-562
        (G) DATE: Feb.-1985

(xi) SEQUENCE DESCRIPTION: SEQ ID NO: 34:

TGCGACATCA AGAATCAAAC CGAATGCCCT CGACTCTAGA ATTTCATTTT GTTTTTTTCT      60

ATGCTATAA ATG AAT TCG GAT CCC GTC GTT TTA CAA CGT CGT GAC TGG         108
          Met Asn Ser Asp Pro Val Val Leu Gln Arg Arg Asp Trp
          1               5                   10

(2) INFORMATION FOR SEQ ID NO: 35:

(i) SEQUENCE CHARACTERISTICS:
        (A) LENGTH: 5 amino acids
        (B) TYPE: amino acid
        (D) TOPOLOGY: linear

```
        (ii) MOLECULE TYPE: peptide (xi) SEQUENCE DESCRIPTION: SEQ ID NO: 35:

Met Asn Ser Asp Pro
  1               5

(2) INFORMATION FOR SEQ ID NO: 36:

(i) SEQUENCE CHARACTERISTICS:
             (A) LENGTH: 8 amino acids
             (B) TYPE: amino acid
             (D) TOPOLOGY: linear (ii) MOLECULE TYPE: peptide (xi) SEQUENCE DESCRIPTION: SEQ ID NO: 36:

Val Val Leu Gln Arg Arg Asp Trp
  1               5

(2) INFORMATION FOR SEQ ID NO: 37:

(i) SEQUENCE CHARACTERISTICS:
             (A) LENGTH: 108 base pairs
             (B) TYPE: nucleic acid
             (C) STRANDEDNESS: double
             (D) TOPOLOGY: circular (ii) MOLECULE TYPE: DNA (genomic)

(iii) HYPOTHETICAL: NO (iv) ANTI-SENSE: NO (vi) ORIGINAL SOURCE:
             (A) ORGANISM: Plasmid (vii) IMMEDIATE SOURCE:
             (B) CLONE: 538-46.26

(ix) FEATURE:
             (A) NAME/KEY: CDS
             (B) LOCATION: 1..54
             (C) IDENTIFICATION METHOD: experimental
             (D) OTHER INFORMATION: /partial
                 /codon_start= 1
                 /function= "marker enzyme"
                 /product= "Beta-galactosidase"
                 /evidence= EXPERIMENTAL
                 /gene= "lacZ"
                 /number= 1
                 /citation= ([1])

(ix) FEATURE:
             (A) NAME/KEY: CDS
             (B) LOCATION: 55..63
             (C) IDENTIFICATION METHOD: experimental
             (D) OTHER INFORMATION: /codon_start= 55
                 /function= "Translational finish of hybrid
                 protein"
                 /product= "C-terminal peptide"
                 /evidence= EXPERIMENTAL
                 /number= 2
                 /standard_name= "Translation of synthetic DNA
                 sequence"

(xi) SEQUENCE DESCRIPTION: SEQ ID NO: 37:

GAA ATC CAG CTG AGC GCC GGT CGC TAC CAT TAC CAG TTG GTC TGG TGT        48
Glu Ile Gln Leu Ser Ala Gly Arg Tyr His Tyr Gln Leu Val Trp Cys
  1               5                  10                  15

CAA AAA GAT CCA TAATTAATTA ACCCGGGTCG AGGGTCGAAG ACCAAATTCT           100
Gln Lys Asp Pro
         20
```

AACATGGT                                                              108

(2) INFORMATION FOR SEQ ID NO: 38:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO: 38:

Glu Ile Gln Leu Ser Ala Gly Arg Tyr His Tyr Gln Leu Val Trp Cys
 1               5                  10                  15
Gln Lys (2) INFORMATION FOR SEQ ID NO: 39:

(i) SEQUENCE CHARACTERISTICS:
        (A) LENGTH: 2 amino acids
        (B) TYPE: amino acid
        (D) TOPOLOGY: linear (ii) MOLECULE TYPE: peptide (xi) SEQUENCE DESCRIPTION: SEQ ID NO: 39:

Asp Pro
 1

(2) INFORMATION FOR SEQ ID NO: 40:

(i) SEQUENCE CHARACTERISTICS:
        (A) LENGTH: 57 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 538-46.26 (Junction E)

(xi) SEQUENCE DESCRIPTION: SEQ ID NO: 40:

AGATCCCCGG GCGAGCTCGA ATTCGTAATC ATGGTCATAG CTGTTTCCTG TGTGAAA       57

(2) INFORMATION FOR SEQ ID NO: 41:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudorabies virus
            Synthetic oligonucleotide primer

```
        (xi) SEQUENCE DESCRIPTION: SEQ ID NO: 41:

CGCGAATTCG CTCGCAGCGC TATTGGC                                            27

(2) INFORMATION FOR SEQ ID NO: 42:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Pseudorabies virus
             Synthetic oligonucleotide primer (xi) SEQUENCE DESCRIPTION: SEQ ID NO: 42:

GTAGGAGTGG CTGCTGAAG                                                     19

(2) INFORMATION FOR SEQ ID NO: 43:

(i) SEQUENCE CHARACTERISTICS:
         (A) LENGTH: 70 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Swinepox virus
         (B) STRAIN: Kasza
         (C) INDIVIDUAL ISOLATE: S-SPV-001

(vii) IMMEDIATE SOURCE:
         (B) CLONE: 515-85.1

(viii) POSITION IN GENOME:
         (B) MAP POSITION: []23.2
         (C) UNITS: %G (xi) SEQUENCE DESCRIPTION: SEQ ID NO: 43:

AAAAATTGAA AAACTATTCT AATTTATTGC ACGGAGATCT TTTTTTTTTT TTTTTTTTTG        60

GCATATAAAT                                                               70

(2) INFORMATION FOR SEQ ID NO: 44:

(i) SEQUENCE CHARACTERISTICS:
         (A) LENGTH: 74 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Swinepox virus
         (B) STRAIN: Kasza
         (C) INDIVIDUAL ISOLATE: S-SPV-001
```

(vii) IMMEDIATE SOURCE:
              (B) CLONE: 515-85.1

(viii) POSITION IN GENOME:
              (B) MAP POSITION: [ ]23.2
              (C) UNITS: %G (xi) SEQUENCE DESCRIPTION: SEQ ID NO: 44:

TTTTTTTTTT TTTTTTTTTT GGCATATAAA TAGATCTGTA TCCTAAAATT GAATTGTAAT    60

TATCGATAAT AAAT    74

(2) INFORMATION FOR SEQ ID NO: 45:

(i) SEQUENCE CHARACTERISTICS:
              (A) LENGTH: 37 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Swinepox virus
              (B) STRAIN: Kasza
              (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: [ ]23.2
              (C) UNITS: %G (xi) SEQUENCE DESCRIPTION: SEQ ID NO: 45:

GTATCCTAAA ATTGAATTGT AATTATCGAT AATAAAT    37

(2) INFORMATION FOR SEQ ID NO: 46:

(i) SEQUENCE CHARACTERISTICS:
              (A) LENGTH: 41 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Swinepox virus
              (B) STRAIN: Kasza
              (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: [ ]23.2
              (C) UNITS: %G (xi) SEQUENCE DESCRIPTION: SEQ ID NO: 46:

CGACTCTAGA ATTTCATTTT GTTTTTTTCT ATGCTATAAA T    41

(2) INFORMATION FOR SEQ ID NO: 47:

-continued

```
     (i) SEQUENCE CHARACTERISTICS:
          (A) LENGTH: 60 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Swinepox virus
          (B) STRAIN: Kasza
          (C) INDIVIDUAL ISOLATE: S-SPV-001

(vii) IMMEDIATE SOURCE:
          (B) CLONE: 515-85.1

(viii) POSITION IN GENOME:
          (B) MAP POSITION: []23.2
          (C) UNITS: %G (xi) SEQUENCE DESCRIPTION: SEQ ID NO: 47:

CACATACGAT TTAGGTGACA CTATAGAATA CAAGCTTTGA GTCTATTGGT TATTTATACG     60

(2) INFORMATION FOR SEQ ID NO: 48:

(i) SEQUENCE CHARACTERISTICS:
          (A) LENGTH: 123 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Swinepox virus
          (B) STRAIN: Kasza
          (C) INDIVIDUAL ISOLATE: S-SPV-001

(vii) IMMEDIATE SOURCE:
          (B) CLONE: 515-85.1

(viii) POSITION IN GENOME:
          (B) MAP POSITION: []23.2
          (C) UNITS: %G (ix) FEATURE:
          (A) NAME/KEY: CDS
          (B) LOCATION: 100..123

(xi) SEQUENCE DESCRIPTION: SEQ ID NO: 48:

TGAATATATA GCAAATAAAG GAAAAATTGT TATCGTTGCT GCATTAGATG GAACATAGGT     60

CGACTCTAGA ATTTCATTTT GTTTTTTTCT ATGCTATAA ATG AAT TCG GAT CCC       114
                                           Met Asn Ser Asp Pro
                                             1               5

GTC GTT TTA                                                           123
Val Val Leu (2) INFORMATION FOR SEQ ID NO: 49:

(i) SEQUENCE CHARACTERISTICS:
          (A) LENGTH: 8 amino acids
          (B) TYPE: amino acid
          (D) TOPOLOGY: linear (ii) MOLECULE TYPE: peptide
```

(xi) SEQUENCE DESCRIPTION: SEQ ID NO: 49:

Met Asn Ser Asp Pro Val Val Leu
 1               5

(2) INFORMATION FOR SEQ ID NO: 50:

(i) SEQUENCE CHARACTERISTICS:
        (A) LENGTH: 132 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
(C) INDIVIDUAL ISOLATE: S-SPV-001

(vii) IMMEDIATE SOURCE:
(B) CLONE: 515-85.1

(viii) POSITION IN GENOME:
(B) MAP POSITION: []23.2
(C) UNITS: %G (ix) FEATURE:
(A) NAME/KEY: CDS
(B) LOCATION: 1..63

(xi) SEQUENCE DESCRIPTION: SEQ ID NO: 50:

```
GAA ATC CAG CTG AGC GCC GGT CGC TAC CAT TAC CAG TTG GTC TGG TGT       48
Glu Ile Gln Leu Ser Ala Gly Arg Tyr His Tyr Gln Leu Val Trp Cys
  1               5                  10                  15

CAA AAA GAT CCA TAATTAATTA ACCCGGGTCG ACCTATGAAC GTAAACCATT          100
Gln Lys Asp Pro
             20

TGGTAATATT CTTAATCTTA TACCATTATC GG                                  132
```

(2) INFORMATION FOR SEQ ID NO: 51:

(i) SEQUENCE CHARACTERISTICS:
(A) LENGTH: 20 amino acids
(B) TYPE: amino acid
(D) TOPOLOGY: linear (ii) MOLECULE TYPE: protein (xi) SEQUENCE DESCRIPTION: SEQ ID NO: 51:

```
Glu Ile Gln Leu Ser Ala Gly Arg Tyr His Tyr Gln Leu Val Trp Cys
  1               5                  10                  15

Gln Lys Asp Pro
             20
```

(2) INFORMATION FOR SEQ ID NO: 52:

(i) SEQUENCE CHARACTERISTICS:
(A) LENGTH: 66 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO

```
        (iv) ANTI-SENSE: NO (vi) ORIGINAL SOURCE:
             (A) ORGANISM: Swinepox virus
             (B) STRAIN: Kasza
             (C) INDIVIDUAL ISOLATE: S-SPV-001

(vii) IMMEDIATE SOURCE:
             (B) CLONE: 515-85.1

(viii) POSITION IN GENOME:
             (B) MAP POSITION: []23.2
             (C) UNITS: %G (xi) SEQUENCE DESCRIPTION: SEQ ID NO: 52:

TCTACTATTG TATATATAGG ATCCCCGGGC GAGCTCGAAT TCGTAATCAT GGTCATAGCT        60

GTTTCC                                                                 66

(2) INFORMATION FOR SEQ ID NO: 53:

(i) SEQUENCE CHARACTERISTICS:
             (A) LENGTH: 51 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Swinepox virus
             (B) STRAIN: Kasza
             (C) INDIVIDUAL ISOLATE: S-SPV-001

(vii) IMMEDIATE SOURCE:
             (B) CLONE: 515-85.1

(viii) POSITION IN GENOME:
             (B) MAP POSITION: []23.2
             (C) UNITS: %G (xi) SEQUENCE DESCRIPTION: SEQ ID NO: 53:

ACAGGAAACA GCTATGACCA TGATTACGAA TTCGAGCTCG CCCGGGGATC T                51

(2) INFORMATION FOR SEQ ID NO: 54:

(i) SEQUENCE CHARACTERISTICS:
             (A) LENGTH: 104 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Swinepox virus
             (B) STRAIN: Kasza
             (C) INDIVIDUAL ISOLATE: S-SPV-001

(vii) IMMEDIATE SOURCE:
             (B) CLONE: 515-85.1

(viii) POSITION IN GENOME:
             (B) MAP POSITION: []23.2
             (C) UNITS: %G
```

(ix) FEATURE:
            (A) NAME/KEY: CDS
            (B) LOCATION: 81..104

(xi) SEQUENCE DESCRIPTION: SEQ ID NO: 54:

AAATATATAA ATACCATGTT AGAATTTGGT CTGCTGCAGG TCGACTCTAG AATTTCATTT     60

TGTTTTTTTC TATGCTATAA ATG AAT TCG GAT CCC GTC GTT TTA                104
                     Met Asn Ser Asp Pro Val Val Leu
                      1               5

(2) INFORMATION FOR SEQ ID NO: 55:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 55:

Met Asn Ser Asp Pro Val Val Leu
 1               5

(2) INFORMATION FOR SEQ ID NO: 56:

(i) SEQUENCE CHARACTERISTICS:
        (A) LENGTH: 150 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (ix) FEATURE:
        (A) NAME/KEY: CDS
        (B) LOCATION: 1..63

(ix) FEATURE:
        (A) NAME/KEY: CDS
        (B) LOCATION: 130..150

(xi) SEQUENCE DESCRIPTION: SEQ ID NO: 56:

GAA ATC CAG CTG AGC GCC GGT CGC TAC CAT TAC CAG TTG GTC TGG TGT      48
Glu Ile Gln Leu Ser Ala Gly Arg Tyr His Tyr Gln Leu Val Trp Cys
 1               5                  10                  15

CAA AAA GAT CCA TAATTAATTA ACCCGGTCGA CTCTAGAAAG ATCTGTATCC          100
Gln Lys Asp Pro
            20

TAAAATTGAA TTGTAATTAT CGATAATAA ATG AAT TCC GGC ATG GCC TCG    150
                                      Met Asn Ser Gly Met Ala Ser
                                                       25

(2) INFORMATION FOR SEQ ID NO: 57:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 57:

Glu Ile Gln Leu Ser Ala Gly Arg Tyr His Tyr Gln Leu Val Trp Cys
 1               5                  10                  15

Gln Lys Asp Pro
            20

(2) INFORMATION FOR SEQ ID NO: 58:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 58:

Met Asn Ser Gly Met Ala Ser
 1               5

(2) INFORMATION FOR SEQ ID NO: 59:

(i) SEQUENCE CHARACTERISTICS:
        (A) LENGTH: 109 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO: 59:

CCATGCTCTA GAGGATCCCC GGGCGAGCTC GAATTCGGAT CCATAATTAA TTAATTAATT      60

TTTATCCCGG GTCGACCGGG TCGACCTGCA GCCTACATGG AAATCTACC                109

(2) INFORMATION FOR SEQ ID NO: 60:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:

(A) ORGANISM: Swinepox virus
            (B) STRAIN: Kasza
            (C) INDIVIDUAL ISOLAT

```
AAATATATAA ATACCATGTT AGAATTTGGT CTGCTGCAGG TCGACTCTAG AATTTCATTT         60

TGTTTTTTTC TATGCTATAA ATG AAT TCG GAT CCC GTC GTT TTA                   104
               Met Asn Ser Asp Pro Val Val Leu
                 1               5
```

(2) INFORMATION FOR SEQ ID NO: 63:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 63:

```
Met Asn Ser Asp Pro Val Val Leu
  1               5
```

(2) INFORMATION FOR SEQ ID NO: 64:

(i) SEQUENCE CHARACTERISTICS:
        (A) LENGTH: 182 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
(C) UNITS: %G (ix) FEATURE:
(A) NAME/KEY: CDS
(B) LOCATION: 1..63

(ix) FEATURE:
(A) NAME/KEY: CDS
(B) LOCATION: 156..182

(xi) SEQUENCE DESCRIPTION: SEQ ID NO: 64:

```
GAA ATC CAG CTG AGC GCC GGT CGC TAC CAT TAC CAG TTG GTC TGG TGT       48
Glu Ile Gln Leu Ser Ala Gly Arg Tyr His Tyr Gln Leu Val Trp Cys
  1               5                  10                  15

CAA AAA GAT CCA TAATTAATTA ACCCGGTCGA CTCTAGAAAA AATTGAAAAA          100
Gln Lys Asp Pro
             20

CTATTCTAAT TTATTGCACG GAGATCTTTT TTTTTTTTTT TTTTTTGGCA TATAA ATG     158
                                                             Met

AAT TCC GGC ATG GCC TCG CTC GCG                                      182
Asn Ser Gly Met Ala Ser Leu Ala
             25
```

(2) INFORMATION FOR SEQ ID NO: 65:

(i) SEQUENCE CHARACTERISTICS:
(A) LENGTH: 20 amino acids
(B) TYPE: amino acid (D) TOPOLOGY: linear (ii) MOLECULE TYPE: peptide (xi) SEQUENCE DESCRIPTION: SEQ ID NO: 65:

Glu Ile Gln Leu Ser Ala Gly Arg Tyr His Tyr Gln Leu Val Trp Cys
 1               5                  10                  15

Gln Lys Asp Pro
            20

(2) INFORMATION FOR SEQ ID NO: 66:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 66:

Met Asn Ser Gly Met Ala Ser Leu Ala
 1               5

(2) INFORMATION FOR SEQ ID NO: 67:

(i) SEQUENCE CHARACTERISTICS:
        (A) LENGTH: 109 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO: 67:

CCATGCTCTA GAGGATCCCC GGGCGAGCTC GAATTCGGAT CCATAATTAA TTAATTAATT      60

TTTATCCCGG GTCGACCGGG TCGACCTGCA GCCTACATGG AAATCTACC                 109

(2) INFORMATION FOR SEQ ID NO: 68:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: []23.2
              (C) UNITS: %G (xi) SEQUENCE DESCRIPTION: SEQ ID NO: 68:

TAATGTATCT ATAATGGTAT AAAGCTTGTA TTCTATAGTG TCACCTAAAT C                51

(2) INFORMATION FOR SEQ ID NO: 69:

(i) SEQUENCE CHARACTERISTICS:
              (A) LENGTH: 51 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Swinepox virus
              (B) STRAIN: Kasza
              (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: []23.2
              (C) UNITS: %G (xi) SEQUENCE DESCRIPTION: SEQ ID NO: 69:

ACAGGAAACA GCTATGACCA TGATTACGAA TTCGAGCTCG CCCGGGGATC T                51

(2) INFORMATION FOR SEQ ID NO: 70:

(i) SEQUENCE CHARACTERISTICS:
              (A) LENGTH: 104 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Swinepox virus
              (B) STRAIN: Kasza
              (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: []23.2
              (C) UNITS: %G (ix) FEATURE:
              (A) NAME/KEY: CDS
              (B) LOCATION: 81..104

(xi) SEQUENCE DESCRIPTION: SEQ ID NO: 70:

AAATATATAA ATACCATGTT AGAATTTGGT CTGCTGCAGG TCGACTCTAG AATTTCATTT        60

TGTTTTTTTC TATGCTATAA ATG AAT TCG GAT CCC GTC GTT TTA                  104

```
            Met Asn Ser Asp Pro Val Val Leu
             1               5
```

(2) INFORMATION FOR SEQ ID NO: 71:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 71:

```
Met Asn Ser Asp Pro Val Val Leu
 1               5
```

(2) INFORMATION FOR SEQ ID NO: 72:

(i) SEQUENCE CHARACTERISTICS:
        (A) LENGTH: 180 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (ix) FEATURE:
        (A) NAME/KEY: CDS
        (B) LOCATION: 1..63

(ix) FEATURE:
        (A) NAME/KEY: CDS
        (B) LOCATION: 160..180

(xi) SEQUENCE DESCRIPTION: SEQ ID NO: 72:

```
GAA ATC CAG CTG AGC GCC GGT CGC TAC CAT TAC CAG TTG GTC TGG TGT        48
Glu Ile Gln Leu Ser Ala Gly Arg Tyr His Tyr Gln Leu Val Trp Cys
 1               5                  10                  15

CAA AAA GAT CCA TAATTAATTA ACCCGGTCGA CTCTAGATTT TTTTTTTTT            100
Gln Lys Asp Pro
                20

TTTTTTTGGC ATATAAATAG ATCTGTATCC TAAAATTGAA TTGTAATTAT CGATAATAA     159

ATG AAT TCC GGC ATG GCC TCG                                          180
Met Asn Ser Gly Met Ala Ser
                25
```

(2) INFORMATION FOR SEQ ID NO: 73:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 73:

Glu Ile Gln Leu Ser Ala Gly Arg Tyr His Tyr Gln Leu Val Trp Cys
 1               5                  10                  15

Gln Lys Asp Pro
          20

(2) INFORMATION FOR SEQ ID NO: 74:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 74:

Met Asn Ser Gly Met Ala Ser
 1               5

(2) INFORMATION FOR SEQ ID NO: 75:

(i) SEQUENCE CHARACTERISTICS:
        (A) LENGTH: 109 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO: 75:

CCATGCTCTA GAGGATCCCC GGGCGAGCTC GAATTCGGAT CCATAATTAA TTAATTAATT      60

TTTATCCCGG GTCGACCGGG TCGACCTGCA GCCTACATGG AAATCTACC                 109

(2) INFORMATION FOR SEQ ID NO: 76:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

```
     (viii) POSITION IN GENOME:
           (B) MAP POSITION: []23.2
           (C) UNITS: %G (xi) SEQUENCE DESCRIPTION: SEQ ID NO: 76:

TAATGTATCT ATAATGGTAT AAAGCTTGTA TTCTATAGTG TCACCTAAAT C          51

(2) INFORMATION FOR SEQ ID NO: 77:

(i) SEQUENCE CHARACTERISTICS:
           (A) LENGTH: 51 base pairs
           (B) TYPE: nucleic acid
           (C) STRANDEDNESS: double
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
           (A) ORGANISM: Swinepox virus
           (B) STRAIN: Kasza
           (C) INDIVIDUAL ISOLATE: S-SPV-001

(vii) IMMEDIATE SOURCE:
           (B) CLONE: 515-85.1

(viii) POSITION IN GENOME:
           (B) MAP POSITION: []23.2
           (C) UNITS: %G (xi) SEQUENCE DESCRIPTION: SEQ ID NO: 77:

ACAGGAAACA GCTATGACCA TGATTACGAA TTCGAGCTCG CCCGGGGATC T          51

(2) INFORMATION FOR SEQ ID NO: 78:

(i) SEQUENCE CHARACTERISTICS:
           (A) LENGTH: 117 base pairs
           (B) TYPE: nucleic acid
           (C) STRANDEDNESS: double
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
           (A) ORGANISM: Swinepox virus
           (B) STRAIN: Kasza
           (C) INDIVIDUAL ISOLATE: S-SPV-001

(vii) IMMEDIATE SOURCE:
           (B) CLONE: 515-85.1

(viii) POSITION IN GENOME:
           (B) MAP POSITION: []23.2
           (C) UNITS: %G (ix) FEATURE:
           (A) NAME/KEY: CDS
           (B) LOCATION: 94..117

(xi) SEQUENCE DESCRIPTION: SEQ ID NO: 78:

GGTCTGCTGC AGGTCGACTC TAGAAAAAAT TGAAAAACTA TTCTAATTTA TTGCACGGAG          60

ATCTTTTTTT TTTTTTTTTT TTTTGGCATA TAA ATG AAT TCC GGC TTC AGT AAC         117
                                    Met Asn Ser Gly Phe Ser Asn Ile
                                     1               5           8
```

-continued

```
(2) INFORMATION FOR SEQ ID NO: 79:

(i) SEQUENCE CHARACTERISTICS:
          (A) LENGTH: 8 amino acids
          (B) TYPE: amino acid
          (D) TOPOLOGY: linear (ii) MOLECULE TYPE: peptide (xi) SEQUENCE DESCRIPTION: SEQ ID NO: 79:

Met Asn Ser Gly Phe Ser Asn Ile
  1               5

(2) INFORMATION FOR SEQ ID NO: 80:

(i) SEQUENCE CHARACTERISTICS:
          (A) LENGTH: 126 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Swinepox virus
          (B) STRAIN: Kasza
          (C) INDIVIDUAL ISOLATE: S-SPV-001

(vii) IMMEDIATE SOURCE:
          (B) CLONE: 515-85.1

(viii) POSITION IN GENOME:
          (B) MAP POSITION: []23.2
          (C) UNITS: %G (ix) FEATURE:
          (A) NAME/KEY: CDS
          (B) LOCATION: 103..126

(xi) SEQUENCE DESCRIPTION: SEQ ID NO: 80:

CGCAACATAC CTAACTGCTT CATTTCTGAT CCATAATTAA TTAATTTTTA TCCCGGCGCG     60

CCTCGACTCT AGAATTTCAT TTTGTTTTTT TCTATGCTAT AA ATG AAT TCG GAT       114
                                               Met Asn Ser Asp
                                                 1

CCC GTC GTT TTA                                                      126
Pro Val Val Leu
  5

(2) INFORMATION FOR SEQ ID NO: 81:

(i) SEQUENCE CHARACTERISTICS:
          (A) LENGTH: 8 amino acids
          (B) TYPE: amino acid
          (D) TOPOLOGY: linear (ii) MOLECULE TYPE: peptide (xi) SEQUENCE DESCRIPTION: SEQ ID NO: 81:

Met Asn Ser Asp Pro Val Val Leu
  1               5

(2) INFORMATION FOR SEQ ID NO: 82:

(i) SEQUENCE CHARACTERISTICS:
          (A) LENGTH: 96 base pairs
          (B) TYPE: nucleic acid
          (C) STRANDEDNESS: double
```

```
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (ix) FEATURE:
        (A) NAME/KEY: CDS
        (B) LOCATION: 1..63

(xi) SEQUENCE DESCRIPTION: SEQ ID NO: 82:

GAA ATC CAG CTG AGC GCC GGT CGC TAC CAT TAC CAG TTG GTC TGG TGT        48
Glu Ile Gln Leu Ser Ala Gly Arg Tyr His Tyr Gln Leu Val Trp Cys
 1               5                  10                  15

CAA AAA GAT CCA TAATTAATTA ACCCGGGTCG ACCTGCAGCC TACATG                96
Gln Lys Asp Pro
            20

(2) INFORMATION FOR SEQ ID NO: 83:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 83:

Glu Ile Gln Leu Ser Ala Gly Arg Tyr His Tyr Gln Leu Val Trp Cys
 1               5                  10                  15

Gln Lys Asp Pro
            20

(2) INFORMATION FOR SEQ ID NO: 84:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G
```

```
    (xi) SEQUENCE DESCRIPTION: SEQ ID NO: 84:

TAATGTATCT ATAATGGTAT AAAGCTTGTA TTCTATAGTG TCACCTAAAT C            51

(2) INFORMATION FOR SEQ ID NO: 85:

(i) SEQUENCE CHARACTERISTICS:
         (A) LENGTH: 51 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Swinepox virus
         (B) STRAIN: Kasza
         (C) INDIVIDUAL ISOLATE: S-SPV-001

(vii) IMMEDIATE SOURCE:
         (B) CLONE: 515-85.1

(viii) POSITION IN GENOME:
         (B) MAP POSITION: []23.2
         (C) UNITS: %G (xi) SEQUENCE DESCRIPTION: SEQ ID NO: 85:

ACAGGAAACA GCTATGACCA TGATTACGAA TTCGAGCTCG CCCGGGGATC T            51

(2) INFORMATION FOR SEQ ID NO: 86:

(i) SEQUENCE CHARACTERISTICS:
         (A) LENGTH: 124 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Swinepox virus
         (B) STRAIN: Kasza
         (C) INDIVIDUAL ISOLATE: S-SPV-001

(vii) IMMEDIATE SOURCE:
         (B) CLONE: 515-85.1

(viii) POSITION IN GENOME:
         (B) MAP POSITION: []23.2
         (C) UNITS: %G (ix) FEATURE:
         (A) NAME/KEY: CDS
         (B) LOCATION: 104..124

(xi) SEQUENCE DESCRIPTION: SEQ ID NO: 86:

GTATAGCGGC CGCCTGCAGG TCGACTCTAG ATTTTTTTTT TTTTTTTTTT TGGCATATAA   60

ATAGATCTGT ATCCTAAAAT TGAATTGTAA TTATCGATAA TAA ATG AAT TCG CTA   118
                                                Met Asn Ser Leu Leu
                                                 1               5

GGA ACT                                                             124
Gly Thr (2) INFORMATION FOR SEQ ID NO: 87:
```

-continued

```
     (i) SEQUENCE CHARACTERISTICS:
          (A) LENGTH: 7 amino acids
          (B) TYPE: amino acid
          (D) TOPOLOGY: linear (ii) MOLECULE TYPE: peptide (xi) SEQUENCE DESCRIPTION: SEQ ID NO: 87:

Met Asn Ser Leu Leu Gly Thr
  1               5

(2) INFORMATION FOR SEQ ID NO: 88:

(i) SEQUENCE CHARACTERISTICS:
          (A) LENGTH: 126 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Swinepox virus
          (B) STRAIN: Kasza
          (C) INDIVIDUAL ISOLATE: S-SPV-001

(vii) IMMEDIATE SOURCE:
          (B) CLONE: 515-85.1

(viii) POSITION IN GENOME:
          (B) MAP POSITION: []23.2
          (C) UNITS: %G (ix) FEATURE:
          (A) NAME/KEY: CDS
          (B) LOCATION: 1..12

(ix) FEATURE:
          (A) NAME/KEY: CDS
          (B) LOCATION: 103..126

(xi) SEQUENCE DESCRIPTION: SEQ ID NO: 88:

ATA AAA ATG TGATTAAGTC TGAATGTGGA TCCATAATTA ATTAATTTTT                49
Ile Lys Met
  1

ATCCCGGCGC GCCTCGACTC TAGAATTTCA TTTTGTTTTT TTCTATGCTA TAA ATG        105
                                                           Met

AAT TCG GAT CCC GTC GTT TTA                                           126
Asn Ser Asp Pro Val Val Leu
  5                  10

(2) INFORMATION FOR SEQ ID NO: 89:

(i) SEQUENCE CHARACTERISTICS:
          (A) LENGTH: 3 amino acids
          (B) TYPE: amino acid
          (D) TOPOLOGY: linear (ii) MOLECULE TYPE: peptide (xi) SEQUENCE DESCRIPTION: SEQ ID NO: 89:

Ile Lys Met
  1

(2) INFORMATION FOR SEQ ID NO: 90:
```

```
        (i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO: 90:

Met Asn Ser Asp Pro Val Val Leu
 1               5

(2) INFORMATION FOR SEQ ID NO: 91:

(i) SEQUENCE CHARACTERISTICS:
            (A) LENGTH: 116 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Swinepox virus
            (B) STRAIN: Kasza
            (C) INDIVIDUAL ISOLATE: S-SPV-001

(vii) IMMEDIATE SOURCE:
            (B) CLONE: 515-85.1

(viii) POSITION IN GENOME:
            (B) MAP POSITION: []23.2
            (C) UNITS: %G (ix) FEATURE:
            (A) NAME/KEY: CDS
            (B) LOCATION: 1..63

(xi) SEQUENCE DESCRIPTION: SEQ ID NO: 91:

GAA ATC CAG CTG AGC GCC GGT CGC TAC CAT TAC CAG TTG GTC TGG TGT         48
Glu Ile Gln Leu Ser Ala Gly Arg Tyr His Tyr Gln Leu Val Trp Cys
 1               5                  10                  15

CAA AAA GAT CCA TAATTAATTA ACCCGGGTCG AGGCGCGCCG GGTCGACCTG            100
Gln Lys Asp Pro
            20

CAGGCGGCCG CTATAC                                                      116

(2) INFORMATION FOR SEQ ID NO: 92:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (xi) SEQUENCE DESCRIPTION: SEQ ID NO: 92:

Glu Ile Gln Leu Ser Ala Gly Arg Tyr His Tyr Gln Leu Val Trp Cys
 1               5                  10                  15

Gln Lys Asp Pro
            20

(2) INFORMATION FOR SEQ ID NO: 93:

(i) SEQUENCE CHARACTERISTICS:
            (A) LENGTH: 51 base pairs
            (B) TYPE: nucleic acid
```

```
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO: 93:

TAATGTATCT ATAATGGTAT AAAGCTTGTA TTCTATAGTG TCACCTAAAT C          51

(2) INFORMATION FOR SEQ ID NO: 94:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO: 94:

ACAGGAAACA GCTATGACCA TGATTACGAA TTCGAGCTCG CCCGGGGATC T          51

(2) INFORMATION FOR SEQ ID NO: 95:

(i) SEQUENCE CHARACTERISTICS:
        (A) LENGTH: 124 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1
```

-continued

```
  (viii) POSITION IN GENOME:
          (B) MAP POSITION: []23.2
          (C) UNITS: %G (ix) FEATURE:
          (A) NAME/KEY: CDS
          (B) LOCATION: 104..124

(xi) SEQUENCE DESCRIPTION: SEQ ID NO: 95:

GTATAGCGGC CGCCTGCAGG TCGACTCTAG ATTTTTTTTT TTTTTTTTTT TGGCATATAA      60

ATAGATCTGT ATCCTAAAAT TGAATTGTAA TTATCGATAA TAA ATG AAT TCC CCT      118
                                            Met Asn Ser Pro Ala
                                              1               5

GCC CGG                                                              124
Ala Arg (2) INFORMATION FOR SEQ ID NO: 96:

(i) SEQUENCE CHARACTERISTICS:
          (A) LENGTH: 7 amino acids
          (B) TYPE: amino acid
          (D) TOPOLOGY: linear (ii) MOLECULE TYPE: peptide (xi) SEQUENCE DESCRIPTION: SEQ ID NO: 96:

Met Asn Ser Pro Ala Ala Arg
  1               5

(2) INFORMATION FOR SEQ ID NO: 97:

(i) SEQUENCE CHARACTERISTICS:
          (A) LENGTH: 126 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Swinepox virus
          (B) STRAIN: Kasza
          (C) INDIVIDUAL ISOLATE: S-SPV-001

(vii) IMMEDIATE SOURCE:
          (B) CLONE: 515-85.1

(viii) POSITION IN GENOME:
          (B) MAP POSITION: []23.2
          (C) UNITS: %G (ix) FEATURE:
          (A) NAME/KEY: CDS
          (B) LOCATION: 1..36

(ix) FEATURE:
          (A) NAME/KEY: CDS
          (B) LOCATION: 103..126

(xi) SEQUENCE DESCRIPTION: SEQ ID NO: 97:

CTC CAG GAG CCC GCT CGC CTC GAG CGG GAT CCA TAATTAATTA ATTTTTATCC      53
Leu Gln Glu Pro Ala Arg Leu Glu Arg Asp Pro
  1               5                  10

CGGCGCGCCT CGACTCTAGA ATTTCATTTT GTTTTTTTCT ATGCTATAA ATG AAT        108
                                                      Met Asn

TCG GAT CCC GTC GTT TTA                                              126
```

```
Ser Asp Pro Val Val Leu
     15
```

(2) INFORMATION FOR SEQ ID NO: 98:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 98:

```
Leu Gln Glu Pro Ala Arg Leu Glu Arg Asp Pro
 1               5                  10
```

(2) INFORMATION FOR SEQ ID NO: 99:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 99:

```
Met Asn Ser Asp Pro Val Val Leu
 1               5
```

(2) INFORMATION FOR SEQ ID NO: 100:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (ix) FEATURE:
        (A) NAME/KEY: CDS
        (B) LOCATION: 1..63

(xi) SEQUENCE DESCRIPTION: SEQ ID NO: 100:

```
GAA ATC CAG CTG AGC GCC GGT CGC TAC CAT TAC CAG TTG GTC TGG TGT        48
Glu Ile Gln Leu Ser Ala Gly Arg Tyr His Tyr Gln Leu Val Trp Cys
 1               5                  10                  15

CAA AAA GAT CCA TAATTAATTA ACCCGGGTCG AGGCGCGCCG GGTCGACCTG           100
Gln Lys Asp Pro
             20

CAGGCGGCCG CTATAC                                                    116
```

(2) INFORMATION FOR SEQ ID NO: 101:

```
   (i) SEQUENCE CHARACTERISTICS:
       (A) LENGTH: 20 amino acids
       (B) TYPE: amino acid
       (D) TOPOLOGY: linear (ii) MOLECULE TYPE: peptide (xi) SEQUENCE DESCRIPTION: SEQ ID NO: 101:

Glu Ile Gln Leu Ser Ala Gly Arg Tyr His Tyr Gln Leu Val Trp Cys
 1               5                  10                  15

Gln Lys Asp Pro
            20

(2) INFORMATION FOR SEQ ID NO: 102:

(i) SEQUENCE CHARACTERISTICS:
       (A) LENGTH: 51 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Swinepox virus
       (B) STRAIN: Kasza
       (C) INDIVIDUAL ISOLATE: S-SPV-001

(vii) IMMEDIATE SOURCE:
       (B) CLONE: 515-85.1

(viii) POSITION IN GENOME:
       (B) MAP POSITION: []23.2
       (C) UNITS: %G (xi) SEQUENCE DESCRIPTION: SEQ ID NO: 102:

TAATGTATCT ATAATGGTAT AAAGCTTGTA TTCTATAGTG TCACCTAAAT C          51

(2) INFORMATION FOR SEQ ID NO: 103:

(i) SEQUENCE CHARACTERISTICS:
       (A) LENGTH: 30 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Swinepox virus
       (B) STRAIN: Kasza
       (C) INDIVIDUAL ISOLATE: S-SPV-001

(vii) IMMEDIATE SOURCE:
       (B) CLONE: 515-85.1

(viii) POSITION IN GENOME:
       (B) MAP POSITION: []23.2
       (C) UNITS: %G (xi) SEQUENCE DESCRIPTION: SEQ ID NO: 103:

CCGAATTCCG GCTTCAGTAA CATAGGATCG                                  30

(2) INFORMATION FOR SEQ ID NO: 104:
```

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO: 104:

GTACCCATAC TGGTCGTGGC                                        20

(2) INFORMATION FOR SEQ ID NO: 105:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO: 105:

CCGGAATTCG CTACTTGGAA CTCTGG                                 26

(2) INFORMATION FOR SEQ ID NO: 106:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: []23.2
              (C) UNITS: %G (xi) SEQUENCE DESCRIPTION: SEQ ID NO: 106:

CATTGTCCCG AGACGGACAG                                                            20

(2) INFORMATION FOR SEQ ID NO: 107:

(i) SEQUENCE CHARACTERISTICS:
              (A) LENGTH: 19 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Swinepox virus
              (B) STRAIN: Kasza
              (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: []23.2
              (C) UNITS: %G (xi) SEQUENCE DESCRIPTION: SEQ ID NO: 107:

CGCGATCCAA CTATCGGTG                                                             19

(2) INFORMATION FOR SEQ ID NO: 108:

(i) SEQUENCE CHARACTERISTICS:
              (A) LENGTH: 26 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Swinepox virus
              (B) STRAIN: Kasza
              (C) INDIVIDUAL ISOLATE: S-SPV-001

(vii) IMMEDIATE SOURCE:
              (B) CLONE: 515-85.1

(viii) POSITION IN GENOME:
              (B) MAP POSITION: []23.2
              (C) UNITS: %G (xi) SEQUENCE DESCRIPTION: SEQ ID NO: 108:

GCGGATCCAC ATTCAGACTT AATCAC                                                     26

(2) INFORMATION FOR SEQ ID NO: 109:

(i) SEQUENCE CHARACTERISTICS:
              (A) LENGTH: 30 base pairs (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Swinepox virus
            (B) STRAIN: Kasza
            (C) INDIVIDUAL ISOLATE: S-SPV-001

(vii) IMMEDIATE SOURCE:
            (B) CLONE: 515-85.1

(viii) POSITION IN GENOME:
            (B) MAP POSITION: []23.2
            (C) UNITS: %G (xi) SEQUENCE DESCRIPTION: SEQ ID NO: 109:

ATGAATTCCC CTGCCGCCCG GACCGGCACC                                              30

(2) INFORMATION FOR SEQ ID NO: 110:

(i) SEQUENCE CHARACTERISTICS:
            (A) LENGTH: 30 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Swinepox virus
            (B) STRAIN: Kasza
            (C) INDIVIDUAL ISOLATE: S-SPV-001

(vii) IMMEDIATE SOURCE:
            (B) CLONE: 515-85.1

(viii) POSITION IN GENOME:
            (B) MAP POSITION: []23.2
            (C) UNITS: %G (xi) SEQUENCE DESCRIPTION: SEQ ID NO: 110:

CATGGATCCC GCTCGAGGCG AGCGGGCTCC                                              30

(2) INFORMATION FOR SEQ ID NO: 111:

(i) SEQUENCE CHARACTERISTICS:
            (A) LENGTH: 42 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Swinepox virus
            (B) STRAIN: Kasza
            (C) INDIVIDUAL ISOLATE: S-SPV-001

(vii) IMMEDIATE SOURCE:
            (B) CLONE: 515-85.1

(viii) POSITION IN GENOME:
          (B) MAP POSITION: []23.2
          (C) UNITS: %G (xi) SEQUENCE DESCRIPTION: SEQ ID NO: 111:

CTGGTTCGGC CCAGAATTCT ATGGGTCTCG CGCGGCTCGT GG            42

(2) INFORMATION FOR SEQ ID NO: 112:

(i) SEQUENCE CHARACTERISTICS:
          (A) LENGTH: 42 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Swinepox virus
          (B) STRAIN: Kasza
          (C) INDIVIDUAL ISOLATE: S-SPV-001

(vii) IMMEDIATE SOURCE:
          (B) CLONE: 515-85.1

(viii) POSITION IN GENOME:
          (B) MAP POSITION: []23.2
          (C) UNITS: %G (xi) SEQUENCE DESCRIPTION: SEQ ID NO: 112:

CTCGCTCGCC CAGGATCCCT AGCGGAGGAT GGACTTGAGT CG            42

(2) INFORMATION FOR SEQ ID NO: 113:

(i) SEQUENCE CHARACTERISTICS:
          (A) LENGTH: 3628 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Swinepox virus
          (B) STRAIN: Kasza
          (C) INDIVIDUAL ISOLATE: S-SPV-001

(vii) IMMEDIATE SOURCE:
(B) CLONE: 515-85.1

(viii) POSITION IN GENOME:
(B) MAP POSITION: []23.2
(C) UNITS: %G (ix) FEATURE:
(A) NAME/KEY: CDS
(B) LOCATION: 57..1226

(ix) FEATURE:
(A) NAME/KEY: CDS
(B) LOCATION: 1362..3395

(ix) FEATURE:
(A) NAME/KEY: MISC_FEATURE
(B) LOCATION: (35), (162), (238), (253), (278), (284), (304),
(312), (340), (361), (364), (376), (381), (387), (397), (401), (412), (694), (695), (3598)
(C) n= any nucleotide (xi) SEQUENCE DESCRIPTION: SEQ ID NO: 113:

```
TTGAAGATGA ATGCATAGAG GAAGATGATG TCGANACGTC ATTATTTAAT GTATAAATGG      60
ATAAATTGTA TGCGGCAATA TTCGGCGTTT TTATGACATC TAAAGATGAT GATTTTAATA     120
ACTTTATAGA AGTTGTAAAA TCTGTATTAA CAGATACATC ANCTAATCAT ACAATATCGT     180
CGTCCAATAA TAATACATGG ATATATATAT TTCTAGCGAT ATTATTTGGT GTTATGGNAT     240
TATTAGTTTT TANTTTGTAT GTAGAAGTTC CTAAACCNAC TTANATGGAG GAAGCAGATA     300
ACCNACTCGT TNTAAATAGT ATTAGTGCTA GAGCATTGGN GGCATTTTTT GTATCTAAAA     360
NTANTGATAT GGTCGNTGAA NTAGTTNCCC AAAAATNTCC NCCAAAGAAG ANATCACAAA     420
TAAAACGCAT AGATACACGA ATTCCTATTG ATCTTATTAA TCAACAATTC GTTAAAAGAT     480
TTAAACTAGA AAATTATAAA AATGGAATTT TATCCGTTCT TATCAATAGT TTAGTCGAAA     540
ATAATTACTT TGAACAAGAT GGTAAACTTA ATAGCAGTGA TATTGATGAA TTAGTGCTCA     600
CAGACATAGA GAAAAAGATT TTATCGTTGA TTCCTAGATG TTCTCCTCTT TATATAGATA     660
TCAGTGACGT TAAAGTTCTC GCATCTAGGT TAANNAAAAG TGCTAAATCA TTTACGTTTA     720
ATGATCATGA ATATATTATA CAATCTGATA AAATAGAGGA ATTAATAAAT AGTTTATCTA     780
GAAACCATGA TATTATACTA GATGAAAAAA GTTCTATTAA AGACAGCATA TATATACTAT     840
CTGATGATCT TTTGAATATA CTTCGTGAAA GATTATTTAG ATGTCCACAG GTTAAAGATA     900
ATACTATTTC TAGAACACGT CTATATGATT ATTTTACTAG AGTGTCAAAG AAAGAAGAAG     960
CGAAAATATA CGTTATATTG AAAGATTTAA AGATTGCTGA TATACTCGGT ATCGAAACAG    1020
TAACGATAGG ATCATTTGTA TATACGAAAT ATAGCATGTT GATTAATTCA ATTTCGTCTA    1080
ATGTTGATAG ATATTCAAAA AGGTTCCATG ACTCTTTTTA TGAAGATATT GCGGAATTTA    1140
TAAAGGATAA TGAAAAAATT AATGTATCCA GAGTTGTTGA ATGCCTTATC GTACCTAATA    1200
TTAATATAGA GTTATTAACT GAATAAGTAT ATATAAATGA TTGTTTTTAT AATGTTTGTT    1260
ATCGCATTTA GTTTTGCTGT ATGGTTATCA TATACATTTT TAAGGCCGTA TATGATAAAT    1320
GAAAATATAT AAGCACTTAT TTTTGTTAGT ATAATAACAC AATGCCGTCG TATATGTATC    1380
CGAAGAACGC AAGAAAAGTA ATTTCAAAGA TTATATCATT ACAACTTGAT ATTAAAAAAC    1440
TTCCTAAAAA ATATATAAAT ACCATGTTAG AATTTGGTCT ACATGGAAAT CTACCAGCTT    1500
GTATGTATAA AGATGCCGTA TCATATGATA TAAATAATAT AAGATTTTTA CCTTATAATT    1560
GTGTTATGGT TAAAGATTTA ATAAATGTTA TAAAATCATC ATCTGTAATA GATACTAGAT    1620
TACATCAATC TGTATTAAAA CATCGTAGAG CGTTAATAGA TTACGGCGAT CAAGACATTA    1680
TCACTTTAAT GATCATTAAT AAGTTACTAT CGATAGATGA TATATCCTAT ATATTAGATA    1740
AAAAAATAAT TCATGTAACA AAAATATTAA AAATAGACCC TACAGTAGCC AATTCAAACA    1800
TGAAACTGAA TAAGATAGAG CTTGTAGATG TAATAACATC AATACCTAAG TCTTCCTATA    1860
CATATTTATA TAATAATATG ATCATTGATC TCGATACATT ATTATATTTA TCCGATGCAT    1920
TCCACATACC CCCCACACAT ATATCATTAC GTTCACTTAG AGATATAAAC AGGATTATTG    1980
AATTGCTTAA AAAATATCCG AATAATAATA TTATTGATTA TATATCCGAT AGCATAAAAT    2040
CAAATAGTTC ATTCATTCAC ATACTTCATA TGATAATATC AAATATGTTT CCTGCTATAA    2100
TCCCTAGTGT AAACGATTTT ATATCTACCG TAGTTGATAA AGATCGACTT ATTAATATGT    2160
ATGGGATTAA GTGTGTTGCT ATGTTTTCGT ACGATATAAA CATGATCGAT TTAGAGTCAT    2220
```

-continued

```
TAGATGACTC AGATTACATA TTTATAGAAA AAAATATATC TATATACGAC GTTAAATGTA   2280

GAGATTTTGC GAATATGATT AGAGATAAGG TTAAAAGAGA AAAGAATAGA ATATTAACTA   2340

CGAAATGTGA AGATATTATA AGATATATAA AATTATTCAG TAAAAATAGA ATAAACGATG   2400

AAAATAATAA GGTGGAGGAG GTGTTGATAC ATATTGATAA TGTATCTAAA AATAATAAAT   2460

TATCACTGTC TGATATATCA TCTTTAATGG ATCAATTTCG TTTAAATCCA TGTACCATAA   2520

GAAATATATT ATTATCTTCA GCAACTATAA AATCAAAACT ATTAGCGTTA CGGGCAGTAA   2580

AAAACTGGAA ATGTTATTCA TTGACAAATG TATCAATGTA TAAAAAAATA AAGGGTGTTA   2640

TCGTAATGGA TATGGTTGAT TATATATCTA CTAACATTCT TAAATACCAT AAACAATTAT   2700

ATGATAAAAT GAGTACGTTT GAATATAAAC GAGATATTAA ATCATGTAAA TGCTCGATAT   2760

GTTCCGACTC TATAACACAT CATATATATG AAACAACATC ATGTATAAAT TATAAATCTA   2820

CCGATAATGA TCTTATGATA GTATTGTTCA ATCTAACTAG ATATTTAATG CATGGGATGA   2880

TACATCCTAA TCTTATAAGC GTAAAAGGAT GGGGTCCCCT TATTGGATTA TTAACGGGTG   2940

ATATAGGTAT TAATTTAAAA CTATATTCCA CCATGAATAT AAATGGGCTA CGGTATGGAG   3000

ATATTACGTT ATCTTCATAC GATATGAGTA ATAAATTAGT CTCTATTATT AATACACCCA   3060

TATATGAGTT AATACCGTTT ACTACATGTT GTTCACTCAA TGAATATTAT TCAAAAATTG   3120

TGATTTTAAT AAATGTTATT TTAGAATATA TGATATCTAT TATATTATAT AGAATATTGA   3180

TCGTAAAAAG ATTTAATAAC ATTAAAGAAT TTATTTCAAA AGTCGTAAAT ACTGTACTAG   3240

AATCATCAGG CATATATTTT TGTCAGATGC GTGTACATGA ACAAATTGAA TTGGAAATAG   3300

ATGAGCTCAT TATTAATGGA TCTATGCCTG TACAGCTTAT GCATTTACTT CTAAAGGTAG   3360

CTACCATAAT ATTAGAGGAA ATCAAAGAAA TATAACGTAT TTTTTCTTTT AAATAAATAA   3420

AAATACTTTT TTTTTTAAAC AAGGGGTGCT ACCTTGTCTA ATTGTATCTT GTATTTTGGA   3480

TCTGATGCAA GATTATTAAA TAATCGTATG AAAAAGTAGT AGATATAGTT TATATCGTTA   3540

CTGGACATGA TATTATGTTT AGTTAATTCT TCTTTGGCAT GAATTCTACA CGTCGGANAA   3600

GGTAATGTAT CTATAATGGT ATAAAGCT                                      3628
```

(2) INFORMATION FOR SEQ ID NO: 114:

(i) SEQUENCE CHARACTERISTICS:
(A) LENGTH: 389 amino acids
(B) TYPE: amino acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Swinepox virus
(B) STRAIN: Kasza
(C) INDIVIDUAL ISOLATE: S-SPV-001

(vii) IMMEDIATE SOURCE:
(B) CLONE: 515-85.1

(viii) POSITION IN GENOME:
(B) MAP POSITION: []23.2
(C) UNITS: %G (ix) FEATURE:
(A) NAME/KEY: MISC_FEATURE
(B) LOCATION: (36), (61), (66), (76), (83), (86), (95), (102), (103), (107), (109), (111), (114), (119), (213)

(C) Xaa = any amino acid (xi) SEQUENCE DESCRIPTION: SEQ ID NO: 114:

```
Met Asp Lys Leu Tyr Ala Ala Ile Phe Gly Val Phe Met Thr Ser Lys
1               5                   10                  15

Asp Asp Asp Phe Asn Asn Phe Ile Glu Val Val Lys Ser Val Leu Thr
                20                  25                  30

Asp Thr Ser Xaa Asn His Thr Ile Ser Ser Asn Asn Asn Thr Trp
            35                  40                  45

Ile Tyr Ile Phe Leu Ala Ile Leu Phe Gly Val Met Xaa Leu Leu Val
    50                  55                  60

Phe Xaa Leu Tyr Val Glu Val Pro Lys Pro Thr Xaa Met Glu Glu Ala
65                  70                  75                  80

Asp Asn Xaa Leu Val Xaa Asn Ser Ile Ser Ala Arg Ala Leu Xaa Ala
                85                  90                  95

Phe Phe Val Ser Lys Xaa Xaa Asp Met Val Xaa Glu Xaa Val Xaa Gln
                100                 105                 110

Lys Xaa Pro Pro Lys Lys Xaa Ser Gln Ile Lys Arg Ile Asp Thr Arg
    115                 120                 125

Ile Pro Ile Asp Leu Ile Asn Gln Gln Phe Val Lys Arg Phe Lys Leu
130                 135                 140

Glu Asn Tyr Lys Asn Gly Ile Leu Ser Val Leu Ile Asn Ser Leu Val
145                 150                 155                 160

Glu Asn Asn Tyr Phe Glu Gln Asp Gly Lys Leu Asn Ser Ser Asp Ile
                165                 170                 175

Asp Glu Leu Val Leu Thr Asp Ile Glu Lys Lys Ile Leu Ser Leu Ile
                180                 185                 190

Pro Arg Cys Ser Pro Leu Tyr Ile Asp Ile Ser Asp Val Lys Val Leu
        195                 200                 205

Ala Ser Arg Leu Xaa Lys Ser Ala Lys Ser Phe Thr Phe Asn Asp His
        210                 215                 220

Glu Tyr Ile Ile Gln Ser Asp Lys Ile Glu Glu Leu Ile Asn Ser Leu
225                 230                 235                 240

Ser Arg Asn His Asp Ile Ile Leu Asp Glu Lys Ser Ser Ile Lys Asp
                245                 250                 255

Ser Ile Tyr Ile Leu Ser Asp Asp Leu Leu Asn Ile Leu Arg Glu Arg
        260                 265                 270

Leu Phe Arg Cys Pro Gln Val Lys Asp Asn Thr Ile Ser Arg Thr Arg
        275                 280                 285

Leu Tyr Asp Tyr Phe Thr Arg Val Ser Lys Lys Glu Glu Ala Lys Ile
        290                 295                 300

Tyr Val Ile Leu Lys Asp Leu Lys Ile Ala Asp Ile Leu Gly Ile Glu
305                 310                 315                 320

Thr Val Thr Ile Gly Ser Phe Val Tyr Thr Lys Tyr Ser Met Leu Ile
                325                 330                 335

Asn Ser Ile Ser Ser Asn Val Arg Tyr Ser Lys Arg Phe His Asp
                340                 345                 350

Ser Phe Tyr Glu Asp Ile Ala Glu Phe Ile Lys Asp Asn Glu Lys Ile
        355                 360                 365

Asn Val Ser Arg Val Val Glu Cys Leu Ile Val Pro Asn Ile Asn Ile
        370                 375                 380

Glu Leu Leu Thr Glu
385
```

(2) INFORMATION FOR SEQ ID NO: 115:

(i) SEQUENCE CHARACTERISTICS:
        (A) LENGTH: 677 amino acids
        (B) TYPE: amino acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
        (C) UNITS: %G (xi) SEQUENCE DESCRIPTION: SEQ ID NO: 115:

```
Met Pro Ser Tyr Met Tyr Pro Lys Asn Ala Arg Lys Val Ile Ser Lys
1               5                  10                  15

Ile Ile Ser Leu Gln Leu Asp Ile Lys Lys Leu Pro Lys Lys Tyr Ile
            20                  25                  30

Asn Thr Met Leu Glu Phe Gly Leu His Gly Asn Leu Pro Ala Cys Met
        35                  40                  45

Tyr Lys Asp Ala Val Ser Tyr Asp Ile Asn Asn Ile Arg Phe Leu Pro
50                  55                  60

Tyr Asn Cys Val Met Val Lys Asp Leu Ile Asn Val Ile Lys Ser Ser
65                  70                  75                  80

Ser Val Ile Asp Thr Arg Leu His Gln Ser Val Leu Lys His Arg Arg
                85                  90                  95

Ala Leu Ile Asp Tyr Gly Asp Gln Asp Ile Ile Thr Leu Met Ile Ile
            100                 105                 110

Asn Lys Leu Leu Ser Ile Asp Asp Ile Ser Tyr Ile Leu Asp Lys Lys
        115                 120                 125

Ile Ile His Val Thr Lys Ile Leu Lys Ile Asp Pro Thr Val Ala Asn
    130                 135                 140

Ser Asn Met Lys Leu Asn Lys Ile Glu Leu Val Asp Val Ile Thr Ser
145                 150                 155                 160

Ile Pro Lys Ser Ser Tyr Thr Tyr Leu Tyr Asn Asn Met Ile Ile Asp
                165                 170                 175

Leu Asp Thr Leu Leu Tyr Leu Ser Asp Ala Phe His Ile Pro Pro Thr
            180                 185                 190

His Ile Ser Leu Arg Ser Leu Arg Asp Ile Asn Arg Ile Ile Glu Leu
        195                 200                 205

Leu Lys Lys Tyr Pro Asn Asn Ile Ile Asp Tyr Ile Ser Asp Ser
    210                 215                 220

Ile Lys Ser Asn Ser Ser Phe Ile His Ile Leu His Met Ile Ile Ser
225                 230                 235                 240

Asn Met Phe Pro Ala Ile Ile Pro Ser Val Asn Asp Phe Ile Ser Thr
                245                 250                 255

Val Val Asp Lys Asp Arg Leu Ile Asn Met Tyr Gly Ile Lys Cys Val
            260                 265                 270
```

-continued

```
Ala Met Phe Ser Tyr Asp Ile Asn Met Ile Asp Leu Glu Ser Leu Asp
            275                 280                 285
Asp Ser Asp Tyr Ile Phe Ile Glu Lys Asn Ile Ser Ile Tyr Asp Val
        290                 295                 300
Lys Cys Arg Asp Phe Ala Asn Met Ile Arg Asp Lys Val Lys Arg Glu
305                 310                 315                 320
Lys Asn Arg Ile Leu Thr Thr Lys Cys Glu Asp Ile Ile Arg Tyr Ile
                325                 330                 335
Lys Leu Phe Ser Lys Asn Arg Ile Asn Asp Glu Asn Asn Lys Val Glu
            340                 345                 350
Glu Val Leu Ile His Ile Asp Asn Val Ser Lys Asn Asn Lys Leu Ser
            355                 360                 365
Leu Ser Asp Ile Ser Ser Leu Met Asp Gln Phe Arg Leu Asn Pro Cys
        370                 375                 380
Thr Ile Arg Asn Ile Leu Leu Ser Ser Ala Thr Ile Lys Ser Lys Leu
385                 390                 395                 400
Leu Ala Leu Arg Ala Val Lys Asn Trp Lys Cys Tyr Ser Leu Thr Asn
                405                 410                 415
Val Ser Met Tyr Lys Lys Ile Lys Gly Val Ile Val Met Asp Met Val
            420                 425                 430
Asp Tyr Ile Ser Thr Asn Ile Leu Lys Tyr His Lys Gln Leu Tyr Asp
        435                 440                 445
Lys Met Ser Thr Phe Glu Tyr Lys Arg Asp Ile Lys Ser Cys Lys Cys
            450                 455                 460
Ser Ile Cys Ser Asp Ser Ile Thr His His Ile Tyr Glu Thr Thr Ser
465                 470                 475                 480
Cys Ile Asn Tyr Lys Ser Thr Asp Asn Asp Leu Met Ile Val Leu Phe
                485                 490                 495
Asn Leu Thr Arg Tyr Leu Met His Gly Met Ile His Pro Asn Leu Ile
            500                 505                 510
Ser Val Lys Gly Trp Gly Pro Leu Ile Gly Leu Leu Thr Gly Asp Ile
            515                 520                 525
Gly Ile Asn Leu Lys Leu Tyr Ser Thr Met Asn Ile Asn Gly Leu Arg
            530                 535                 540
Tyr Gly Asp Ile Thr Leu Ser Ser Tyr Asp Met Ser Asn Lys Leu Val
545                 550                 555                 560
Ser Ile Ile Asn Thr Pro Ile Tyr Glu Leu Ile Pro Phe Thr Thr Cys
                565                 570                 575
Cys Ser Leu Asn Glu Tyr Tyr Ser Lys Ile Val Ile Leu Ile Asn Val
            580                 585                 590
Ile Leu Glu Tyr Met Ile Ser Ile Ile Leu Tyr Arg Ile Leu Ile Val
            595                 600                 605
Lys Arg Phe Asn Asn Ile Lys Glu Phe Ile Ser Lys Val Val Asn Thr
            610                 615                 620
Val Leu Glu Ser Ser Gly Ile Tyr Phe Cys Gln Met Arg Val His Glu
625                 630                 635                 640
Gln Ile Glu Leu Glu Ile Asp Glu Leu Ile Ile Asn Gly Ser Met Pro
                645                 650                 655
Val Gln Leu Met His Leu Leu Leu Lys Val Ala Thr Ile Ile Leu Glu
            660                 665                 670
Glu Ile Lys Glu Ile
            675
```

(2) INFORMATION FOR SEQ ID NO: 116:

(i) SEQUENCE CHARACTERISTICS:
       (A) LENGTH: 43 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Infectious bovine rhinotracheitis virus
       (B) STRAIN: Cooper Strain (xi) SEQUENCE DESCRIPTION: SEQ ID NO: 116:

CTGGTTCGGC CCAGAATTCG ATGCAACCCA CCGCGCCGCC CCG          43

(2) INFORMATION FOR SEQ ID NO: 117:

(i) SEQUENCE CHARACTERISTICS:
       (A) LENGTH: 42 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Infectious bovine rhinotracheitis virus
       (B) STRAIN: Cooper Strain (xi) SEQUENCE DESCRIPTION: SEQ ID NO: 117:

CTCGCTCGCC CAGGATCCCT AGCGGAGGAT GGACTTGAGT CG           42

(2) INFORMATION FOR SEQ ID NO: 118:

(i) SEQUENCE CHARACTERISTICS:
       (A) LENGTH: 31 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Equine Influenza A neuraminidase
       (B) STRAIN: Prague/56

(xi) SEQUENCE DESCRIPTION: SEQ ID NO: 118:

GGGATCCATG AATCCTAATC AAAAACTCTT T                       31

(2) INFORMATION FOR SEQ ID NO: 119:

(i) SEQUENCE CHARACTERISTICS:
       (A) LENGTH: 31 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Equine Influenza A neuraminidase
            (B) STRAIN: Prague/56

(xi) SEQUENCE DESCRIPTION: SEQ ID NO: 119:

GGGATCCTTA CGAAAAGTAT TTAATTTGTG C                                          31

(2) INFORMATION FOR SEQ ID NO: 120:

(i) SEQUENCE CHARACTERISTICS:
            (A) LENGTH: 42 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Equine influenza A hemagglutinin (xi) SEQUENCE DESCRIPTION: SEQ ID NO: 120:

GGAGGCCTTC ATGACAGACA ACCATTATTT TGATACTACT GA                              42

(2) INFORMATION FOR SEQ ID NO: 121:

(i) SEQUENCE CHARACTERISTICS:
            (A) LENGTH: 40 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Equine influenza A hemagglutinin (xi) SEQUENCE DESCRIPTION: SEQ ID NO: 121:

GAAGGCCTTC TCAAATGCAA ATGTTGCATC TGATGTTGCC                                 40

(2) INFORMATION FOR SEQ ID NO: 122:

(i) SEQUENCE CHARACTERISTICS:
            (A) LENGTH: 32 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Equine Influenza A hemagglutinin
            (B) STRAIN: Prague/56

(xi) SEQUENCE DESCRIPTION: SEQ ID NO: 122:

GGGATCCATG AACACTCAAA TTCTAATATT AG                                         32

(2) INFORMATION FOR SEQ ID NO: 123:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Equine Influenza A hemagglutinin
        (B) STRAIN: Prague/56

(xi) SEQUENCE DESCRIPTION: SEQ ID NO: 123:

GGGATCCTTA TATACAAATA GTGCACCGCA                              30

(2) INFORMATION FOR SEQ ID NO: 124:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Equine Influenza A neuraminidase (xi) SEQUENCE DESCRIPTION: SEQ ID NO: 124:

GGGTCGACAT GAATCCAAAT CAAAAGATAA                              30

(2) INFORMATION FOR SEQ ID NO: 125:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Equine Influenza A neuraminidase (xi) SEQUENCE DESCRIPTION: SEQ ID NO: 125:

GGGTCGACTT ACATCTTATC GATGTCAAA                               29

(2) INFORMATION FOR SEQ ID NO: 126:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Human (xi) SEQUENCE DESCRIPTION: SEQ ID NO: 126:

CTCGAATTCG AAGTGGGCAA CGTGGATCCT CGC                                    33

(2) INFORMATION FOR SEQ ID NO: 127:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Human (xi) SEQUENCE DESCRIPTION: SEQ ID NO: 127:

CAGTTAGCCT CCCCCATCTC CCCA                                              24

(2) INFORMATION FOR SEQ ID NO: 128:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Equine herpesvirus type 1

(xi) SEQUENCE DESCRIPTION: SEQ ID NO: 128:

CGGAATTCCT CTGGTTGCCG T                                                 21

(2) INFORMATION FOR SEQ ID NO: 129:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Equine herpesvirus type 1

(xi) SEQUENCE DESCRIPTION: SEQ ID NO: 129:

GACGGTGGAT CCGGTAGGCG GT                                                22

(2) INFORMATION FOR SEQ ID NO: 130:

(i) SEQUENCE CHARACTERISTICS:
            (A) LENGTH: 34 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bovine parainfluenza-3 virus (xi) SEQUENCE DESCRIPTION: SEQ ID NO: 130:

TTATGGATCC TGCTGCTGTG TTGAACAACT TTGT                                          34

(2) INFORMATION FOR SEQ ID NO: 131:

(i) SEQUENCE CHARACTERISTICS:
            (A) LENGTH: 38 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bovine parainfluenza-3 virus (xi) SEQUENCE DESCRIPTION: SEQ ID NO: 131:

CCGCGGATCC CATGACCATC ACAACCATAA TCATAGCC                                      38

(2) INFORMATION FOR SEQ ID NO: 132:

(i) SEQUENCE CHARACTERISTICS:
            (A) LENGTH: 43 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bovine parainfluenza-3 virus (xi) SEQUENCE DESCRIPTION: SEQ ID NO: 132:

CGTCGGATCC CTTAGCTGCA GTTTTTTGGA ACTTCTGTTT TGA                                43

(2) INFORMATION FOR SEQ ID NO: 133:

(i) SEQUENCE CHARACTERISTICS:
            (A) LENGTH: 40 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bovine parainfluenza-3 virus (xi) SEQUENCE DESCRIPTION: SEQ ID NO: 133:

CATAGGATCC CATGGAATAT TGGAAACACA CAAACAGCAC                    40

(2) INFORMATION FOR SEQ ID NO: 134:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bovine viral diarrhea virus
        (B) STRAIN: Singer Strain (xi) SEQUENCE DESCRIPTION: SEQ ID NO: 134:

ACGTCGGATC CCTTACCAAA CCACGTCTTA CTCTTGTTTT CC                 42

(2) INFORMATION FOR SEQ ID NO: 135:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bovine viral diarrhea virus
        (B) STRAIN: Singer Strain (xi) SEQUENCE DESCRIPTION: SEQ ID NO: 135:

ACATAGGATC CCATGGGAGA AAACATAACA CAGTGGAACC                    40

(2) INFORMATION FOR SEQ ID NO: 136:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bovine viral diarrhea virus
        (B) STRAIN: Singer Strain (xi) SEQUENCE DESCRIPTION: SEQ ID NO: 136:

CGTGGATCCT CAATTACAAG AGGTATCGTC TAC                           33

(2) INFORMATION FOR SEQ ID NO: 137:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bovine viral diarrhea virus
        (B) STRAIN: Singer Strain (xi) SEQUENCE DESCRIPTION: SEQ ID NO: 137:

CATAGATCTT GTGGTGCTGT CCGACTTCGC A                                   31

(2) INFORMATION FOR SEQ ID NO: 138:

(i) SEQUENCE CHARACTERISTICS:
        (A) LENGTH: 37 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bovine respiratory syncytial virus
        (B) STRAIN: Strain 375

(xi) SEQUENCE DESCRIPTION: SEQ ID NO: 138:

TGCAGGATCC TCATTTACTA AAGGAAAGAT TGTTGAT                              37

(2) INFORMATION FOR SEQ ID NO: 139:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bovine respiratory syncytial virus
        (B) STRAIN: Strain 375

(xi) SEQUENCE DESCRIPTION: SEQ ID NO: 139:

CTCTGGATCC TACAGCCATG AGGATGATCA TCAGC                                35

(2) INFORMATION FOR SEQ ID NO: 140:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO

-continued (iv) ANTI-SENSE: NO (vi) ORIGINAL SOURCE:
            (A) ORGANISM: Bovine respiratory syncytial virus
            (B) STRAIN: Strain 375

(xi) SEQUENCE DESCRIPTION: SEQ ID NO: 140:

CGTCGGATCC CTCACAGTTC CACATCATTG TCTTTGGGAT                  40

(2) INFORMATION FOR SEQ ID NO: 141:

(i) SEQUENCE CHARACTERISTICS:
            (A) LENGTH: 41 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bovine respiratory syncytial virus
            (B) STRAIN: Strain 375

(xi) SEQUENCE DESCRIPTION: SEQ ID NO: 141:

CTTAGGATCC CATGGCTCTT AGCAAGGTCA AACTAAATGA C                41

(2) INFORMATION FOR SEQ ID NO: 142:

(i) SEQUENCE CHARACTERISTICS:
            (A) LENGTH: 41 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bovine respiratory syncytial virus
            (B) STRAIN: Strain 375

(xi) SEQUENCE DESCRIPTION: SEQ ID NO: 142:

CGTTGGATCC CTAGATCTGT GTAGTTGATT GATTTGTGTG A                41

(2) INFORMATION FOR SEQ ID NO: 143:

(i) SEQUENCE CHARACTERISTICS:
            (A) LENGTH: 41 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bovine respiratory syncytial virus
            (B) STRAIN: Strain 375

(xi) SEQUENCE DESCRIPTION: SEQ ID NO: 143:

CTCTGGATCC TCATACCCAT CATCTTAAAT TCAAGACATT A                41

(2) INFORMATION FOR SEQ ID NO: 144:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 144:

```
ACAGGAAACA GCTATGACCA TGATTACGAA TTCGAGCTCG CCCGGGGATC T           51
```

(2) INFORMATION FOR SEQ ID NO: 145:

(i) SEQUENCE CHARACTERISTICS:
        (A) LENGTH: 128 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 145:

```
GTATAGCGGC CGCCTGCAGG TCGACTCTAG ATTTTTTTTT TTTTTTTTTT TGGCATATAA   60
ATAGATCTGT ATCCTAAAAT TGAATTGTAA TTATCGATAA TAAATGAATT TGATCCATGa  120
ATCCTAAT                                                          128
```

(2) INFORMATION FOR SEQ ID NO: 146:

(i) SEQUENCE CHARACTERISTICS:
        (A) LENGTH: 120 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 146:

```
CTTTTCGTAA GGATCAATTC GGATCCATAA TTAATTAATT TTTATCCCGG CGCGCCTCGA   60
CTCTAGAATT TCATTTTGTT TTTTTCTATG CTATAAATGA ATTCGGATCC CGTCGTTTTA  120
```

(2) INFORMATION FOR SEQ ID NO: 147:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 147:

```
GAAATCCAGC TGAGCGCCGG TCGCTACCAT TACCAGTTGG TCTGGTGTCA AAAAGATCCA        60

TAATTAATTA ACCCGGGTCG AGGCGCGCCG GGTCGACCTG CAGGCGGCCG CTATAC          116
```

(2) INFORMATION FOR SEQ ID NO: 148:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 148:

```
TAATGTATCT ATAATGGTAT AAAGCTTGTA TTCTATAGTG TCACCTAAAT C              51
```

(2) INFORMATION FOR SEQ ID NO: 149:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 149:

```
ACAGGAAACA GCTATGACCA TGATTACGAA TTCGAGCTCG CCCGGGGATC T              51
```

(2) INFORMATION FOR SEQ ID NO: 150:

(i) SEQUENCE CHARACTERISTICS:
        (A) LENGTH: 168 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 150:

```
GTATTGCGGC CGCCTGCAGG TCGACTCTAG ATTTTTTTTT TTTTTTTTTT TGGCATATAA       60

ATAGATCTGT ATCCTAAAAT TGAATTGTAA TTATCGATAA TAAATGAATT CACCCGCTGG      120

TGGCGGTCTT TGGCGCGGGC CCCGTGGGCA TCGGCCCGGG CACCACGG                  168
```

(2) INFORMATION FOR SEQ ID NO: 151:

(i) SEQUENCE CHARACTERISTICS:
        (A) LENGTH: 112 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 151:

GAGCTCGAAT TCGGATCCAT AATTAATTAA TTTTTATCCC GGCGCGCCTC GACTCTAGAA      60

TTTCATTTTG TTTTTTTCTA TGCTATAAAT GAATTCGGAT CCCGTCGTTT TA             112

(2) INFORMATION FOR SEQ ID NO: 152:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 152:

GAAATCCAGC TGAGCGCCGG TCGCTACCAT TACCAGTTGG TCTGGTGTCA AAAAGATCCA      60

TAATTAATTA ACCCGGGTCG AGGCGCGCCG GGTCGACCTG CAGGCGGCCG CTATAC         116

(2) INFORMATION FOR SEQ ID NO: 153:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 153:

TAATGTATCT ATAATGGTAT AAAGCTTGTA TTCTATAGTG TCACCTAAAT C               51

(2) INFORMATION FOR SEQ ID NO: 154:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 154:

ACAGGAAACA GCTATGACCA TGATTACGAA TTCGAGCTCG CCCGGGGATC T               51

(2) INFORMATION FOR SEQ ID NO: 155:

(i) SEQUENCE CHARACTERISTICS:
        (A) LENGTH: 104 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 155:

AAATATATAA ATACCATGTT AGAATTTGGT CTGCTGCAGG TCGACTCTAG AATTTCATTT      60

TGTTTTTTTC TATGCTATAA ATGAATTCGG ATCCCGTCGT TTTA      104

(2) INFORMATION FOR SEQ ID NO: 156:

(i) SEQUENCE CHARACTERISTICS:
         (A) LENGTH: 185 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 156:

GAAATCCAGC TGAGCGCCGG TCGCTACCAT TACCAGTTGG TCTGGTGTCA AAAAGATCCA      60

TAATTAATTA ACCCGGTCGA CTCTAGAAAA AATTGAAAAA CTATTCTAAT TTATTGCACG     120

GAGATCTTTT TTTTTTTTTT TTTTTTGGCA TATAAATGAA TTCGGATCCC CGGTGGCTTT     180

GGGGG      185

(2) INFORMATION FOR SEQ ID NO: 157:

(i) SEQUENCE CHARACTERISTICS:
         (A) LENGTH: 66 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 157:

CTCAATGTTA GGGTACCGAG CTCGAATTGG GTCGACCGGG TCGACCTGCA GCCTACATGG      60

AAATCT      66

(2) INFORMATION FOR SEQ ID NO: 158:

(i) SEQUENCE CHARACTERISTICS:
         (A) LENGTH: 51 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 158:

TAATGTATCT ATAATGGTAT AAAGCTTGTA TTCTATAGTG TCACCTAAAT C      51

(2) INFORMATION FOR SEQ ID NO: 159:

(i) SEQUENCE CHARACTERISTICS:
         (A) LENGTH: 51 base pairs (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 159:

ACAGGAAACA GCTATGACCA TGATTACGAA TTCGAGCTCG CCCGGGGATC T            51

(2) INFORMATION FOR SEQ ID NO: 160:

(i) SEQUENCE CHARACTERISTICS:
         (A) LENGTH: 127 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 160:

GTATAGCGGC CGCCTGCAGG TCGACTCTAG ATTTTTTTTT TTTTTTTTTT TGGCATATAA    60

ATAGATCTGT ATCCTAAAAT TGAATTGTAA TTATCGATAA TAAATGAATT TCGACATGAA   120

TCCAAAT                                                            127

(2) INFORMATION FOR SEQ ID NO: 161:

(i) SEQUENCE CHARACTERISTICS:
         (A) LENGTH: 122 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 161:

GATAAGATGT AAGTCGAAAT TCGGATCCAT AATTAATTAA TTTTTATCCC GGCGCGCCTC    60

GACTCTAGAA TTTCATTTTG TTTTTTTCTA TGCTATAAAT GAATTCGGAT CCCGTCGTTT   120

TA                                                                 122

(2) INFORMATION FOR SEQ ID NO: 162:

(i) SEQUENCE CHARACTERISTICS:
         (A) LENGTH: 116 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 162:

GAAATCCAGC TGAGCGCCGG TCGCTACCAT TACCAGTTGG TCTGGTGTCA AAAAGATCCA    60

```
TAATTAATTA ACCCGGGTCG AGGCGCGCCG GGTCGACCTG CAGGCGGCCG CTATAC        116

(2) INFORMATION FOR SEQ ID NO: 163:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 163:

TAATGTATCT ATAATGGTAT AAAGCTTGTA TTCTATAGTG TCACCTAAAT C             51

(2) INFORMATION FOR SEQ ID NO: 164:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 164:

ACAGGAAACA GCTATGACCA TGATTACGAA TTCGAGCTCG CCCGGGGATC T             51

(2) INFORMATION FOR SEQ ID NO: 165:

(i) SEQUENCE CHARACTERISTICS:
        (A) LENGTH: 61 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 165:

GTATAGCGGC CGCCTGCAGG TCGACCTGCA GTGAATAATA AAATGTGTGT TTGTCCGAAA    60
T                                                                    61

(2) INFORMATION FOR SEQ ID NO: 166:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 166:

CTCCATAGAA GACACCGGGA CCATGGATCC CGTCGTTTTA CAACG                    45
```

(2) INFORMATION FOR SEQ ID NO: 167:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 167:

```
TCGGCGGAAA TCCAGCTGAG CGCCGGTCGC TACCATTACC AGTTGGTCTG GTGTCAAAAA      60

GATCTAGAAT AAGCTAGAGG ATCGATCCCC TATGGCGATC ATCAG                     105
```

(2) INFORMATION FOR SEQ ID NO: 168:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 168:

```
CTGCAGGTCG ACCTGCAGGC GGCCGCTATA C                                     31
```

(2) INFORMATION FOR SEQ ID NO: 169:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 169:

```
TAATGTATCT ATAATGGTAT AAAGCTTGTA TTCTATAGTG TCACCTAAAT C                51
```

(2) INFORMATION FOR SEQ ID NO: 170:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 170:

```
ACAGGAAACA GCTATGACCA TGATTACGAA TTCGAGCTCG CCCGGGGATC T                51
```

(2) INFORMATION FOR SEQ ID NO: 171:

(i) SEQUENCE CHARACTERISTICS:
        (A) LENGTH: 193 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 171:

```
GTATAGCGGC CGCCTGCAGG TCGACTCTAG ATTTTTTTTT TTTTTTTTTT TGGCATATAA     60
ATAGATCTGT ATCCTAAAAT TGAATTGTAA TTATCGATAA TAAATGAATT CCGAAGTGGG    120
CAACGTGGAT CCTCGCCCTC GGGCTCCTCG TGGTCCGCAC CGTCGTGGCC AGAAGTGCTC    180
CTACTAGCTC GAG                                                       193
```

(2) INFORMATION FOR SEQ ID NO: 172:

(i) SEQUENCE CHARACTERISTICS:
        (A) LENGTH: 123 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 172:

```
ATCATTAGCA CGTTAACTTA ATAAGATCCA TAATTAATTA ATTTTTATCC CGGCGCGCCT     60
CGACTCTAGA ATTTCATTTT GTTTTTTTCT ATGCTATAAA TGAATTCGGA TCCCGTCGTT    120
TTA                                                                  123
```

(2) INFORMATION FOR SEQ ID NO: 173:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 173:

```
GAAATCCAGC TGAGCGCCGG TCGCTACCAT TACCAGTTGG TCTGGTGTCA AAAAGATCCA     60
TAATTAATTA ACCCGGGTCG AGGCGCGCCG GTCGACCTG CAGGCGGCCG CTATAC         116
```

(2) INFORMATION FOR SEQ ID NO: 174:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 174:

TAATGTATCT ATAATGGTAT AAAGCTTGTA TTCTATAGTG TCACCTAAAT C        51

(2) INFORMATION FOR SEQ ID NO: 175:

(i) SEQUENCE CHARACTERISTICS:
            (A) LENGTH: 51 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 175:

ACAGGAAACA GCTATGACCA TGATTACGAA TTCGAGCTCG CCCGGGGATC T        51

(2) INFORMATION FOR SEQ ID NO: 176:

(i) SEQUENCE CHARACTERISTICS:
            (A) LENGTH: 133 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 176:

GTATAGCGGC CGCCTGCAGG TCGACTCTAG ATTTTTTTTT TTTTTTTTTT TGGCATATAA       60

ATAGATCTGT ATCCTAAAAT TGAATTGTAA TTATCGATAA TAAATGAATT CCTCTGGTTG      120

CCGTTCTGTC GGC                                                        133

(2) INFORMATION FOR SEQ ID NO: 177:

(i) SEQUENCE CHARACTERISTICS:
            (A) LENGTH: 99 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 177:

GAAAATGAAA AAATGGTTTA AACCGGGGGC GCGCCTCGAC TCTAGAATTT CATTTTGTTT       60

TTTTCTATGC TATAAATGAA TTCGGATCCC GTCGTTTTA                             99

(2) INFORMATION FOR SEQ ID NO: 178:

(i) SEQUENCE CHARACTERISTICS:
            (A) LENGTH: 116 base pairs
            (B) TYPE: nucleic acid
            (C) STRANDEDNESS: double (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 178:

GAAATCCAGC TGAGCGCCGG TCGCTACCAT TACCAGTTGG TCTGGTGTCA AAAAGATCCA      60

TAATTAATTA ACCCGGGTCG AGGCGCGCCG GGTCGACCTG CAGGCGGCCG CTATAC         116

(2) INFORMATION FOR SEQ ID NO: 179:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 179:

TAATGTATCT ATAATGGTAT AAAGCTTGTA TTCTATAGTG TCACCTAAAT C               51

(2) INFORMATION FOR SEQ ID NO: 180:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 180:

ACAGGAAACA GCTATGACCA TGATTACGAA TTCGAGCTCG CCCGGGGATC T               51

(2) INFORMATION FOR SEQ ID NO: 181:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 181:

GTATAGCGGC CGCCTGCAGG TCGACTCTAG ATTTTTTTTT TTTTTTTTTT TGGCATATAA      60

ATAGATCTGT ATCCTAAAAT TGAATTGTAA TTATCGATAA TAAATGAATT CGGATCAGCT    120

TATGATGGAT GGACGTTTGG                                                140

(2) INFORMATION FOR SEQ ID NO: 182:

(i) SEQUENCE CHARACTERISTICS:

```
    (A) LENGTH: 123 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 182:
```

GGAGGTGTCC ACGGCCTTAA AGCTGATCCA TAATTAATTA ATTTTTATCC CGGCGCGCCT    60

CGACTCTAGA ATTTCATTTT GTTTTTTTCT ATGCTATAAA TGAATTCGGA TCCCGTCGTT   120

TTA                                                                 123

```
(2) INFORMATION FOR SEQ ID NO: 183:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 183:
```

GAAATCCAGC TGAGCGCCGG TCGCTACCAT TACCAGTTGG TCTGGTGTCA AAAAGATCCA    60

TAATTAATTA ACCCGGGTCG AGGCGCGCCG GGTCGACCTG CAGGCGGCCG CTATAC       116

```
(2) INFORMATION FOR SEQ ID NO: 184:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 184:
```

TAATGTATCT ATAATGGTAT AAAGCTTGTA TTCTATAGTG TCACCTAAAT C             51

```
(2) INFORMATION FOR SEQ ID NO: 185:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 185:
```

GAAGCATGCC CGTTCTTATC AATAGTTTAG TCGAAAATA                           39

(2) INFORMATION FOR SEQ ID NO: 186:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 186:

CATAAGATCT GGCATTGTGT TATTATACTA ACAAAAATAA G                41

(2) INFORMATION FOR SEQ ID NO: 187:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 187:

CCGTAGTCGA CAAAGATCGA CTTATTAATA TGTATGGGAT T                41

(2) INFORMATION FOR SEQ ID NO: 188:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 188:

GCCTGAAGCT TCTAGTACAG TATTTACGAC TTTTGAAAT                   39

(2) INFORMATION FOR SEQ ID NO: 189:

(i) SEQUENCE CHARACTERISTICS:
        (A) LENGTH: 3942 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(ix) FEATURE:
        (A) NAME/KEY: CDS
        (B) LOCATION: 1..369

(ix) FEATURE:
    (A) NAME/KEY: CDS
    (B) LOCATION: 370..597

(ix) FEATURE:
    (A) NAME/KEY: CDS
    (B) LOCATION: 598..1539

(ix) FEATURE:
    (A) NAME/KEY: CDS
    (B) LOCATION: 1675..3708

(ix) FEATURE:
    (A) NAME/KEY: CDS
    (B) LOCATION: complement (3748..3942)

(xi) SEQUENCE DESCRIPTION: SEQ ID NO: 189:

```
TGT TTG TTC ATT AAT AAG ATG GGT GGA GCT ATT ATA GAA TAC AAG ATA          48
Cys Leu Phe Ile Asn Lys Met Gly Gly Ala Ile Ile Glu Tyr Lys Ile
 1               5                  10                  15

CCT GGT TCC AAA TCT ATA ACC AAA TCT ATT TCC GAA GAA CTA GAA AAT          96
Pro Gly Ser Lys Ser Ile Thr Lys Ser Ile Ser Glu Glu Leu Glu Asn
            20                  25                  30

TTA ACA AAG CGA GAT AAA CCA ATA TCT AAA ATT ATA GTT ATT CCT ATT         144
Leu Thr Lys Arg Asp Lys Pro Ile Ser Lys Ile Ile Val Ile Pro Ile
        35                  40                  45

GTA TGT TAC AGA AAT GCA AAT AGT ATA AAG GTT ACA TTT GCA CTA AAA         192
Val Cys Tyr Arg Asn Ala Asn Ser Ile Lys Val Thr Phe Ala Leu Lys
    50                  55                  60

AAG TTT ATC ATA GAT AAG GAG TTT AGT ACA AAT GTA ATA GAC GTA GAT         240
Lys Phe Ile Ile Asp Lys Glu Phe Ser Thr Asn Val Ile Asp Val Asp
65                  70                  75                  80

GGT AAA CAT GAA AAA ATG TCC ATG AAT GAA ACA TGC GAA GAG GAT GTT         288
Gly Lys His Glu Lys Met Ser Met Asn Glu Thr Cys Glu Glu Asp Val
                85                  90                  95

GCT AGA GGA TTG GGA ATT ATA GAT CTT GAA GAT GAA TGC ATA GAG GAA         336
Ala Arg Gly Leu Gly Ile Ile Asp Leu Glu Asp Glu Cys Ile Glu Glu
            100                 105                 110

GAT GAT GTC GAT ACG TCA TTA TTT AAT GTA TAAATG GAT AAA TTG TAT         384
Asp Asp Val Asp Thr Ser Leu Phe Asn Val     Met Asp Lys Leu Tyr
        115                 120                     125

GCG GCA ATA TTC GGC GTT TTT ATG ACA TCT AAA GAT GAT GAT TTT AAT         432
Ala Ala Ile Phe Gly Val Phe Met Thr Ser Lys Asp Asp Asp Phe Asn
        130                 135                 140

AAC TTT ATA GAA GTT GTA AAA TCT GTA TTA ACA GAT ACA TCA TCT AAT         480
Asn Phe Ile Glu Val Val Lys Ser Val Leu Thr Asp Thr Ser Ser Asn
    145                 150                 155

CAT ACA ATA TCG TCG TCC AAT AAT AAT ACA TGG ATA TAT ATA TTT CTA         528
His Thr Ile Ser Ser Ser Asn Asn Asn Thr Trp Ile Tyr Ile Phe Leu
160                 165                 170                 175

GCG ATA TTA TTT GGT GTT ATG GTA TTA TTA GTT TTT ATT TTG TAT TTA         576
Ala Ile Leu Phe Gly Val Met Val Leu Leu Val Phe Ile Leu Tyr Leu
                180                 185                 190

AAA GTT ACT AAA CCA ACT TAAATG GAG GAA GCA GAT AAC CAA CTC GTT         624
Lys Val Thr Lys Pro Thr     Met Glu Glu Ala Asp Asn Gln Leu Val
            195                 200                 205

TTA AAT AGT ATT AGT GCT AGA GCA TTA AAG GCA TTT TTT GTA TCT AAA         672
Leu Asn Ser Ile Ser Ala Arg Ala Leu Lys Ala Phe Phe Val Ser Lys
        210                 215                 220

ATT AAT GAT ATG GTC GAT GAA TTA GTT ACC AAA AAA TAT CCA CCA AAG         720
Ile Asn Asp Met Val Asp Glu Leu Val Thr Lys Lys Tyr Pro Pro Lys
    225                 230                 235
```

```
AAG AAA TCA CAA ATA AAA CTC ATA GAT ACA CGA ATT CCT ATT GAT CTT      768
Lys Lys Ser Gln Ile Lys Leu Ile Asp Thr Arg Ile Pro Ile Asp Leu
240                 245                 250

ATT AAT CAA CAA TTC GTT AAA AGA TTT AAA CTA GAA AAT TAT AAA AAT      816
Ile Asn Gln Gln Phe Val Lys Arg Phe Lys Leu Glu Asn Tyr Lys Asn
255                 260                 265                 270

GGA ATT TTA TCC GTT CTT ATC AAT AGT TTA GTC GAA AAT AAT TAC TTT      864
Gly Ile Leu Ser Val Leu Ile Asn Ser Leu Val Glu Asn Asn Tyr Phe
                275                 280                 285

GAA CAA GAT GGT AAA CTT AAT AGC AGT GAT ATT GAT GAA TTA GTG CTC      912
Glu Gln Asp Gly Lys Leu Asn Ser Ser Asp Ile Asp Glu Leu Val Leu
        290                 295                 300

ACA GAC ATA GAG AAA AAG ATT TTA TCG TTG ATT CCT AGA TGT TCT CCT      960
Thr Asp Ile Glu Lys Lys Ile Leu Ser Leu Ile Pro Arg Cys Ser Pro
                305                 310                 315

CTT TAT ATA GAT ATC AGT GAC GTT AAA GTT CTC GCA TCT AGG TTA AAA     1008
Leu Tyr Ile Asp Ile Ser Asp Val Lys Val Leu Ala Ser Arg Leu Lys
320                 325                 330

AAA AGT GCT AAA TCA TTT ACG TTT AAT GAT CAT GAA TAT ATT ATA CAA     1056
Lys Ser Ala Lys Ser Phe Thr Phe Asn Asp His Glu Tyr Ile Ile Gln
335                 340                 345                 350

TCT GAT AAA ATA GAG GAA TTA ATA AAT AGT TTA TCT AGA AAC CAT GAT     1104
Ser Asp Lys Ile Glu Glu Leu Ile Asn Ser Leu Ser Arg Asn His Asp
                355                 360                 365

ATT ATA CTA GAT GAA AAA AGT TCT ATT AAA GAC AGC ATA TAT ATA CTA     1152
Ile Ile Leu Asp Glu Lys Ser Ser Ile Lys Asp Ser Ile Tyr Ile Leu
        370                 375                 380

TCT GAT GAT CTT TTG AAT ATA CTT CGT GAA AGA TTA TTT AGA TGT CCA     1200
Ser Asp Asp Leu Leu Asn Ile Leu Arg Glu Arg Leu Phe Arg Cys Pro
                385                 390                 395

CAG GTT AAA GAT AAT ACT ATT TCT AGA ACA CGT CTA TAT GAT TAT TTT     1248
Gln Val Lys Asp Asn Thr Ile Ser Arg Thr Arg Leu Tyr Asp Tyr Phe
400                 405                 410

ACT AGA GTG TCA AAG AAA GAA GAA GCG AAA ATA TAC GTT ATA TTG AAA     1296
Thr Arg Val Ser Lys Lys Glu Glu Ala Lys Ile Tyr Val Ile Leu Lys
415                 420                 425                 430

GAT TTA AAG ATT GCT GAT ATA CTC GGT ATC GAA ACA GTA ACG ATA GGA     1344
Asp Leu Lys Ile Ala Asp Ile Leu Gly Ile Glu Thr Val Thr Ile Gly
                435                 440                 445

TCA TTT GTA TAT ACG AAA TAT AGC ATG TTG ATT AAT TCA ATT TCG TCT     1392
Ser Phe Val Tyr Thr Lys Tyr Ser Met Leu Ile Asn Ser Ile Ser Ser
                450                 455                 460

AAT GTT GAT AGA TAT TCA AAA AGG TTC CAT GAC TCT TTT TAT GAA GAT     1440
Asn Val Asp Arg Tyr Ser Lys Arg Phe His Asp Ser Phe Tyr Glu Asp
        465                 470                 475

ATT GCG GAA TTT ATA AAG GAT AAT GAA AAA ATT AAT GTA TCC AGA GTT     1488
Ile Ala Glu Phe Ile Lys Asp Asn Glu Lys Ile Asn Val Ser Arg Val
        480                 485                 490

GTT GAA TGC CTT ATC GTA CCT AAT ATT AAT ATA GAG TTA TTA ACT GAA     1536
Val Glu Cys Leu Ile Val Pro Asn Ile Asn Ile Glu Leu Leu Thr Glu
495                 500                 505                 510

TAAGTATATA TAAATGATTG TTTTTATAAT GTTTGTTATC GCATTTAGTT TTGCTGTA     1596

GTTATCATAT ACATTTTTAA GGCCGTATAT GATAAATGAA AATATATAAG CACTTATT     1656

TGTTAGTATA ATAACACA ATG CCG TCG TAT ATG TAT CCG AAG AAC GCA AGA     1707
                    Met Pro Ser Tyr Met Tyr Pro Lys Asn Ala Arg
                                    515                 520

AAA GTA ATT TCA AAG ATT ATA TCA TTA CAA CTT GAT ATT AAA AAA CTT     1755
Lys Val Ile Ser Lys Ile Ile Ser Leu Gln Leu Asp Ile Lys Lys Leu
            525                 530                 535
```

```
CCT AAA AAA TAT ATA AAT ACC ATG TTA GAA TTT GGT CTA CAT GGA AAT    1803
Pro Lys Lys Tyr Ile Asn Thr Met Leu Glu Phe Gly Leu His Gly Asn
        540                 545                 550

CTA CCA GCT TGT ATG TAT AAA GAT GCC GTA TCA TAT GAT ATA AAT AAT    1851
Leu Pro Ala Cys Met Tyr Lys Asp Ala Val Ser Tyr Asp Ile Asn Asn
        555                 560                 565

ATA AGA TTT TTA CCT TAT AAT TGT GTT ATG GTT AAA GAT TTA ATA AAT    1899
Ile Arg Phe Leu Pro Tyr Asn Cys Val Met Val Lys Asp Leu Ile Asn
570         575                 580                 585

GTT ATA AAA TCA TCA TCT GTA ATA GAT ACT AGA TTA CAT CAA TCT GTA    1947
Val Ile Lys Ser Ser Ser Val Ile Asp Thr Arg Leu His Gln Ser Val
            590                 595                 600

TTA AAA CAT CGT AGA GCG TTA ATA GAT TAC GGC GAT CAA GAC ATT ATC    1995
Leu Lys His Arg Arg Ala Leu Ile Asp Tyr Gly Asp Gln Asp Ile Ile
                605                 610                 615

ACT TTA ATG ATC ATT AAT AAG TTA CTA TCG ATA GAT GAT ATA TCC TAT    2043
Thr Leu Met Ile Ile Asn Lys Leu Leu Ser Ile Asp Asp Ile Ser Tyr
                    620                 625                 630

ATA TTA GAT AAA AAA ATA ATT CAT GTA ACA AAA ATA TTA AAA ATA GAC    2091
Ile Leu Asp Lys Lys Ile Ile His Val Thr Lys Ile Leu Lys Ile Asp
635                 640                 645

CCT ACA GTA GCC AAT TCA AAC ATG AAA CTG AAT AAG ATA GAG CTT GTA    2139
Pro Thr Val Ala Asn Ser Asn Met Lys Leu Asn Lys Ile Glu Leu Val
650                 655                 660                 665

GAT GTA ATA ACA TCA ATA CCT AAG TCT TCC TAT ACA TAT TTA TAT AAT    2187
Asp Val Ile Thr Ser Ile Pro Lys Ser Ser Tyr Thr Tyr Leu Tyr Asn
            670                 675                 680

AAT ATG ATC ATT GAT CTC GAT ACA TTA TTA TAT TTA TCC GAT GCA TTC    2235
Asn Met Ile Ile Asp Leu Asp Thr Leu Leu Tyr Leu Ser Asp Ala Phe
                685                 690                 695

CAC ATA CCC CCA ACA CAT ATA TCA TTA CGT TCA CTT AGA GAT ATA AAC    2283
His Ile Pro Pro Thr His Ile Ser Leu Arg Ser Leu Arg Asp Ile Asn
                    700                 705                 710

AGG ATT ATT GAA TTG CTT AAA AAA TAT CCG AAT AAT AAT ATT ATT GAT    2331
Arg Ile Ile Glu Leu Leu Lys Lys Tyr Pro Asn Asn Asn Ile Ile Asp
715                 720                 725

TAT ATA TCC GAT AGC ATA AAA TCA AAT AGT TCA TTC ATT CAC ATA CTT    2379
Tyr Ile Ser Asp Ser Ile Lys Ser Asn Ser Ser Phe Ile His Ile Leu
730                 735                 740                 745

CAT ATG ATA ATA TCA AAT ATG TTT CCT GCT ATA ATC CCT AGT GTA AAC    2427
His Met Ile Ile Ser Asn Met Phe Pro Ala Ile Ile Pro Ser Val Asn
            750                 755                 760

GAT TTT ATA TCT ACC GTA GTT GAT AAA GAT CGA CTT ATT AAT ATG TAT    2475
Asp Phe Ile Ser Thr Val Val Asp Lys Asp Arg Leu Ile Asn Met Tyr
                765                 770                 775

GGG ATT AAG TGT GTT GCT ATG TTT TCG TAC GAT ATA AAC ATG ATC GAT    2523
Gly Ile Lys Cys Val Ala Met Phe Ser Tyr Asp Ile Asn Met Ile Asp
                    780                 785                 790

TTA GAG TCA TTA GAT GAC TCA GAT TAC ATA TTT ATA GAA AAA AAT ATA    2571
Leu Glu Ser Leu Asp Asp Ser Asp Tyr Ile Phe Ile Glu Lys Asn Ile
795                 800                 805

TCT ATA TAC GAC GTT AAA TGT AGA GAT TTT GCG AAT ATG ATT AGA GAT    2619
Ser Ile Tyr Asp Val Lys Cys Arg Asp Phe Ala Asn Met Ile Arg Asp
810                 815                 820                 825

AAG GTT AAA AGA GAA AAG AAT AGA ATA TTA ACT ACG AAA TGT GAA GAT    2667
Lys Val Lys Arg Glu Lys Asn Arg Ile Leu Thr Thr Lys Cys Glu Asp
            830                 835                 840

ATT ATA AGA TAT ATA AAA TTA TTC AGT AAA AAT AGA ATA AAC GAT GAA    2715
Ile Ile Arg Tyr Ile Lys Leu Phe Ser Lys Asn Arg Ile Asn Asp Glu
```

-continued

```
                845                  850                  855
AAT AAT AAG GTG GAG GAG GTG TTG ATA CAT ATT GAT AAT GTA TCT AAA        2763
Asn Asn Lys Val Glu Glu Val Leu Ile His Ile Asp Asn Val Ser Lys
        860                  865                  870

AAT AAT AAA TTA TCA CTG TCT GAT ATA TCA TCT TTA ATG GAT CAA TTT        2811
Asn Asn Lys Leu Ser Leu Ser Asp Ile Ser Ser Leu Met Asp Gln Phe
    875                  880                  885

CGT TTA AAT CCA TGT ACC ATA AGA AAT ATA TTA TTA TCT TCA GCA ACT        2859
Arg Leu Asn Pro Cys Thr Ile Arg Asn Ile Leu Leu Ser Ser Ala Thr
890                  895                  900                  905

ATA AAA TCA AAA CTA TTA GCG TTA CGG GCA GTA AAA AAC TGG AAA TGT        2907
Ile Lys Ser Lys Leu Leu Ala Leu Arg Ala Val Lys Asn Trp Lys Cys
        910                  915                  920

TAT TCA TTG ACA AAT GTA TCA ATG TAT AAA AAA ATA AAG GGT GTT ATC        2955
Tyr Ser Leu Thr Asn Val Ser Met Tyr Lys Lys Ile Lys Gly Val Ile
    925                  930                  935

GTA ATG GAT ATG GTT GAT TAT ATA TCT ACT AAC ATT CTT AAA TAC CAT        3003
Val Met Asp Met Val Asp Tyr Ile Ser Thr Asn Ile Leu Lys Tyr His
940                  945                  950

AAA CAA TTA TAT GAT AAA ATG AGT ACG TTT GAA TAT AAA CGA GAT ATT        3051
Lys Gln Leu Tyr Asp Lys Met Ser Thr Phe Glu Tyr Lys Arg Asp Ile
    955                  960                  965

AAA TCA TGT AAA TGC TCG ATA TGT TCC GAC TCT ATA ACA CAT CAT ATA        3099
Lys Ser Cys Lys Cys Ser Ile Cys Ser Asp Ser Ile Thr His His Ile
970                  975                  980                  985

TAT GAA ACA ACA TCA TGT ATA AAT TAT AAA TCT ACC GAT AAT GAT CTT        3147
Tyr Glu Thr Thr Ser Cys Ile Asn Tyr Lys Ser Thr Asp Asn Asp Leu
        990                  995                  1000

ATG ATA GTA TTG TTC AAT CTA ACT AGA TAT TTA ATG CAT GGG ATG ATA        3195
Met Ile Val Leu Phe Asn Leu Thr Arg Tyr Leu Met His Gly Met Ile
    1005                 1010                 1015

CAT CCT AAT CTT ATA AGC GTA AAA GGA TGG GGT CCC CTT ATT GGA TTA        3243
His Pro Asn Leu Ile Ser Val Lys Gly Trp Gly Pro Leu Ile Gly Leu
    1020                 1025                 1030

TTA ACG GGT GAT ATA GGT ATT AAT TTA AAA CTA TAT TCC ACC ATG AAT        3291
Leu Thr Gly Asp Ile Gly Ile Asn Leu Lys Leu Tyr Ser Thr Met Asn
    1035                 1040                 1045

ATA AAT GGG CTA CGG TAT GGA GAT ATT ACG TTA TCT TCA TAC GAT ATG        3339
Ile Asn Gly Leu Arg Tyr Gly Asp Ile Thr Leu Ser Ser Tyr Asp Met
1050                 1055                 1060                 1065

AGT AAT AAA TTA GTC TCT ATT ATT AAT ACA CCC ATA TAT GAG TTA ATA        3387
Ser Asn Lys Leu Val Ser Ile Ile Asn Thr Pro Ile Tyr Glu Leu Ile
        1070                 1075                 1080

CCG TTT ACT ACA TGT TGT TCA CTC AAT GAA TAT TAT TCA AAA ATT GTG        3435
Pro Phe Thr Thr Cys Cys Ser Leu Asn Glu Tyr Tyr Ser Lys Ile Val
    1085                 1090                 1095

ATT TTA ATA AAT GTT ATT TTA GAA TAT ATG ATA TCT ATT ATA TTA TAT        3483
Ile Leu Ile Asn Val Ile Leu Glu Tyr Met Ile Ser Ile Ile Leu Tyr
    1100                 1105                 1110

AGA ATA TTG ATC GTA AAA AGA TTT AAT AAC ATT AAA GAA TTT ATT TCA        3531
Arg Ile Leu Ile Val Lys Arg Phe Asn Asn Ile Lys Glu Phe Ile Ser
    1115                 1120                 1125

AAA GTC GTA AAT ACT GTA CTA GAA TCA TCA GGC ATA TAT TTT TGT CAG        3579
Lys Val Val Asn Thr Val Leu Glu Ser Ser Gly Ile Tyr Phe Cys Gln
1130                 1135                 1140                 1145

ATG CGT GTA CAT GAA CAA ATT GAA TTG GAA ATA GAT GAG CTC ATT ATT        3627
Met Arg Val His Glu Gln Ile Glu Leu Glu Ile Asp Glu Leu Ile Ile
            1150                 1155                 1160

AAT GGA TCT ATG CCT GTA CAG CTT ATG CAT TTA CTT CTA AAG GTA GCT        3675
```

```
Asn Gly Ser Met Pro Val Gln Leu Met His Leu Leu Lys Val Ala
        1165                1170                1175
ACC ATA ATA TTA GAG GAA ATC AAA GAA ATA TAACGTATTT TTTCTTTTAA      3725
Thr Ile Ile Leu Glu Glu Ile Lys Glu Ile
        1180                1185

ATAAATAAAA ATACTTTTTT TTTTAAACAA GGGGTGCTAC CTTGTCTAAT TGTATCTTGT  3785

ATTTTGGATC TGATGCAAGA TTATTAAATA ATCGTATGAA AAAGTAGTAG ATATAGTTTA  3845

TATCGTTACT GGACATGATA TTATGTTTAG TTAATTCTTC TTTGGCATGA ATTCTACACG  3905

TCGGACAAGG TAATGTATCT ATAATGGTAT AAAGCTT                            3942
```

(2) INFORMATION FOR SEQ ID NO: 190:

(i) SEQUENCE CHARACTERISTICS:
        (A) LENGTH: 122 amino acids
        (B) TYPE: amino acid
        (D) TOPOLOGY: linear (ii) MOLECULE TYPE: peptide (xi) SEQUENCE DESCRIPTION: SEQ ID NO: 190:

```
Cys Leu Phe Ile Asn Lys Met Gly Gly Ala Ile Ile Glu Tyr Lys Ile
 1               5                  10                  15

Pro Gly Ser Lys Ser Ile Thr Lys Ser Ile Ser Glu Glu Leu Glu Asn
             20                  25                  30

Leu Thr Lys Arg Asp Lys Pro Ile Ser Lys Ile Val Ile Pro Ile
         35                  40                  45

Val Cys Tyr Arg Asn Ala Asn Ser Ile Lys Val Thr Phe Ala Leu Lys
     50                  55                  60

Lys Phe Ile Ile Asp Lys Glu Phe Ser Thr Asn Val Ile Asp Val Asp
 65                  70                  75                  80

Gly Lys His Glu Lys Met Ser Met Asn Glu Thr Cys Glu Glu Asp Val
                 85                  90                  95

Ala Arg Gly Leu Gly Ile Ile Asp Leu Glu Asp Glu Cys Ile Glu Glu
             100                 105                 110

Asp Asp Val Asp Thr Ser Leu Phe Asn Val
             115                 120
```

(2) INFORMATION FOR SEQ ID NO: 191:

(i) SEQUENCE CHARACTERISTICS:
        (A) LENGTH: 75 amino acids
        (B) TYPE: amino acid
        (D) TOPOLOGY: linear (ii) MOLECULE TYPE: protein (xi) SEQUENCE DESCRIPTION: SEQ ID NO: 191:

```
Met Asp Lys Leu Tyr Ala Ala Ile Phe Gly Val Phe Met Thr Ser Lys
 1               5                  10                  15

Asp Asp Asp Phe Asn Asn Phe Ile Glu Val Val Lys Ser Val Leu Thr
             20                  25                  30

Asp Thr Ser Ser Asn His Thr Ile Ser Ser Ser Asn Asn Asn Thr Trp
         35                  40                  45

Ile Tyr Ile Phe Leu Ala Ile Leu Phe Gly Val Met Val Leu Leu Val
     50                  55                  60

Phe Ile Leu Tyr Leu Lys Val Thr Lys Pro Thr
 65                  70                  75
```

(2) INFORMATION FOR SEQ ID NO: 192:

(i) SEQUENCE CHARACTERISTICS:
        (A) LENGTH: 313 amino acids
        (B) TYPE: amino acid
        (D) TOPOLOGY: linear (ii) MOLECULE TYPE: protein (xi) SEQUENCE DESCRIPTION: SEQ ID NO: 192:

```
Met Glu Glu Ala Asp Asn Gln Leu Val Leu Asn Ser Ile Ser Ala Arg
  1               5                  10                  15
Ala Leu Lys Ala Phe Phe Val Ser Lys Ile Asn Asp Met Val Asp Glu
                 20                  25                  30
Leu Val Thr Lys Lys Tyr Pro Pro Lys Lys Ser Gln Ile Lys Leu
             35                  40                  45
Ile Asp Thr Arg Ile Pro Ile Asp Leu Ile Asn Gln Gln Phe Val Lys
 50                  55                  60
Arg Phe Lys Leu Glu Asn Tyr Lys Asn Gly Ile Leu Ser Val Leu Ile
 65                  70                  75                  80
Asn Ser Leu Val Glu Asn Tyr Phe Glu Gln Asp Gly Lys Leu Asn
                 85                  90                  95
Ser Ser Asp Ile Asp Glu Leu Val Leu Thr Asp Ile Glu Lys Lys Ile
                100                 105                 110
Leu Ser Leu Ile Pro Arg Cys Ser Pro Leu Tyr Ile Asp Ile Ser Asp
            115                 120                 125
Val Lys Val Leu Ala Ser Arg Leu Lys Lys Ser Ala Lys Ser Phe Thr
130                 135                 140
Phe Asn Asp His Glu Tyr Ile Ile Gln Ser Asp Lys Ile Glu Glu Leu
145                 150                 155                 160
Ile Asn Ser Leu Ser Arg Asn His Asp Ile Ile Leu Asp Glu Lys Ser
                165                 170                 175
Ser Ile Lys Asp Ser Ile Tyr Ile Leu Ser Asp Asp Leu Leu Asn Ile
            180                 185                 190
Leu Arg Glu Arg Leu Phe Arg Cys Pro Gln Val Lys Asp Asn Thr Ile
            195                 200                 205
Ser Arg Thr Arg Leu Tyr Asp Tyr Phe Thr Arg Val Ser Lys Lys Glu
210                 215                 220
Glu Ala Lys Ile Tyr Val Ile Leu Lys Asp Leu Lys Ile Ala Asp Ile
225                 230                 235                 240
Leu Gly Ile Glu Thr Val Thr Ile Gly Ser Phe Val Tyr Thr Lys Tyr
                245                 250                 255
Ser Met Leu Ile Asn Ser Ile Ser Asn Val Asp Arg Tyr Ser Lys
            260                 265                 270
Arg Phe His Asp Ser Phe Tyr Glu Asp Ile Ala Glu Phe Ile Lys Asp
            275                 280                 285
Asn Glu Lys Ile Asn Val Ser Arg Val Val Glu Cys Leu Ile Val Pro
290                 295                 300
Asn Ile Asn Ile Glu Leu Leu Thr Glu
305                 310
```

(2) INFORMATION FOR SEQ ID NO: 193:

(i) SEQUENCE CHARACTERISTICS:
        (A) LENGTH: 677 amino acids
        (B) TYPE: amino acid
        (D) TOPOLOGY: linear (ii) MOLECULE TYPE: protein (xi) SEQUENCE DESCRIPTION: SEQ ID NO: 193:

```
Met Pro Ser Tyr Met Tyr Pro Lys Asn Ala Arg Lys Val Ile Ser Lys
 1               5                  10                  15

Ile Ile Ser Leu Gln Leu Asp Ile Lys Lys Leu Pro Lys Lys Tyr Ile
            20                  25                  30

Asn Thr Met Leu Glu Phe Gly Leu His Gly Asn Leu Pro Ala Cys Met
        35                  40                  45

Tyr Lys Asp Ala Val Ser Tyr Asp Ile Asn Asn Ile Arg Phe Leu Pro
    50                  55                  60

Tyr Asn Cys Val Met Val Lys Asp Leu Ile Asn Val Ile Lys Ser Ser
 65                  70                  75                  80

Ser Val Ile Asp Thr Arg Leu His Gln Ser Val Leu Lys His Arg Arg
                85                  90                  95

Ala Leu Ile Asp Tyr Gly Asp Gln Asp Ile Ile Thr Leu Met Ile Ile
                100                 105                 110

Asn Lys Leu Leu Ser Ile Asp Asp Ile Ser Tyr Ile Leu Asp Lys Lys
            115                 120                 125

Ile Ile His Val Thr Lys Ile Leu Lys Ile Asp Pro Thr Val Ala Asn
        130                 135                 140

Ser Asn Met Lys Leu Asn Lys Ile Glu Leu Val Asp Val Ile Thr Ser
145                 150                 155                 160

Ile Pro Lys Ser Ser Tyr Thr Tyr Leu Tyr Asn Asn Met Ile Ile Asp
                165                 170                 175

Leu Asp Thr Leu Leu Tyr Leu Ser Asp Ala Phe His Ile Pro Pro Thr
                180                 185                 190

His Ile Ser Leu Arg Ser Leu Arg Asp Ile Asn Arg Ile Ile Glu Leu
            195                 200                 205

Leu Lys Lys Tyr Pro Asn Asn Asn Ile Ile Asp Tyr Ile Ser Asp Ser
        210                 215                 220

Ile Lys Ser Asn Ser Ser Phe Ile His Ile Leu His Met Ile Ile Ser
225                 230                 235                 240

Asn Met Phe Pro Ala Ile Ile Pro Ser Val Asn Asp Phe Ile Ser Thr
                245                 250                 255

Val Val Asp Lys Asp Arg Leu Ile Asn Met Tyr Gly Ile Lys Cys Val
                260                 265                 270

Ala Met Phe Ser Tyr Asp Ile Asn Met Ile Asp Leu Glu Ser Leu Asp
            275                 280                 285

Asp Ser Asp Tyr Ile Phe Ile Glu Lys Asn Ile Ser Ile Tyr Asp Val
        290                 295                 300

Lys Cys Arg Asp Phe Ala Asn Met Ile Arg Asp Lys Val Lys Arg Glu
305                 310                 315                 320

Lys Asn Arg Ile Leu Thr Thr Lys Cys Glu Asp Ile Ile Arg Tyr Ile
                325                 330                 335

Lys Leu Phe Ser Lys Asn Arg Ile Asn Asp Glu Asn Lys Val Glu
            340                 345                 350

Glu Val Leu Ile His Ile Asp Asn Val Ser Lys Asn Lys Leu Ser
        355                 360                 365

Leu Ser Asp Ile Ser Ser Leu Met Asp Gln Phe Arg Leu Asn Pro Cys
370                 375                 380

Thr Ile Arg Asn Ile Leu Leu Ser Ser Ala Thr Ile Lys Ser Lys Leu
385                 390                 395                 400
```

```
Leu Ala Leu Arg Ala Val Lys Asn Trp Lys Cys Tyr Ser Leu Thr Asn
                405                 410                 415

Val Ser Met Tyr Lys Lys Ile Lys Gly Val Ile Val Met Asp Met Val
                420                 425                 430

Asp Tyr Ile Ser Thr Asn Ile Leu Lys Tyr His Lys Gln Leu Tyr Asp
                435                 440                 445

Lys Met Ser Thr Phe Glu Tyr Lys Arg Asp Ile Lys Ser Cys Lys Cys
            450                 455                 460

Ser Ile Cys Ser Asp Ser Ile Thr His His Ile Tyr Glu Thr Thr Ser
465                 470                 475                 480

Cys Ile Asn Tyr Lys Ser Thr Asp Asn Asp Leu Met Ile Val Leu Phe
                485                 490                 495

Asn Leu Thr Arg Tyr Leu Met His Gly Met Ile His Pro Asn Leu Ile
                500                 505                 510

Ser Val Lys Gly Trp Gly Pro Leu Ile Gly Leu Leu Thr Gly Asp Ile
                515                 520                 525

Gly Ile Asn Leu Lys Leu Tyr Ser Thr Met Asn Ile Asn Gly Leu Arg
530                 535                 540

Tyr Gly Asp Ile Thr Leu Ser Ser Tyr Asp Met Ser Asn Lys Leu Val
545                 550                 555                 560

Ser Ile Ile Asn Thr Pro Ile Tyr Glu Leu Ile Pro Phe Thr Thr Cys
                565                 570                 575

Cys Ser Leu Asn Glu Tyr Tyr Ser Lys Ile Val Ile Leu Ile Asn Val
                580                 585                 590

Ile Leu Glu Tyr Met Ile Ser Ile Leu Tyr Arg Ile Leu Ile Val
                595                 600                 605

Lys Arg Phe Asn Asn Ile Lys Glu Phe Ile Ser Lys Val Val Asn Thr
                610                 615                 620

Val Leu Glu Ser Ser Gly Ile Tyr Phe Cys Gln Met Arg Val His Glu
625                 630                 635                 640

Gln Ile Glu Leu Glu Ile Asp Glu Leu Ile Ile Asn Gly Ser Met Pro
                645                 650                 655

Val Gln Leu Met His Leu Leu Leu Lys Val Ala Thr Ile Ile Leu Glu
                660                 665                 670

Glu Ile Lys Glu Ile
            675

(2) INFORMATION FOR SEQ ID NO: 194:

(i) SEQUENCE CHARACTERISTICS:
        (A) LENGTH: 64 amino acids
        (B) TYPE: amino acid
        (D) TOPOLOGY: linear (ii) MOLECULE TYPE: protein (xi) SEQUENCE DESCRIPTION: SEQ ID NO: 194:

Lys Leu Tyr Thr Ile Ile Asp Thr Leu Pro Cys Pro Thr Cys Arg Ile
 1               5                  10                  15

His Ala Lys Glu Glu Leu Thr Lys His Asn Ile Met Ser Ser Asn Asp
                20                  25                  30

Ile Asn Tyr Ile Tyr Tyr Phe Pro Ile Arg Leu Phe Asn Asn Leu Ala
                35                  40                  45

Ser Asp Pro Lys Tyr Lys Ile Gln Leu Asp Lys Val Ala Pro Leu Val
            50                  55                  60
```

(2) INFORMATION FOR SEQ ID NO: 195:

(i) SEQUENCE CHARACTERISTICS:
        (A) LENGTH: 583 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(ix) FEATURE:
        (A) NAME/KEY: CDS
        (B) LOCATION: 2..583

(xi) SEQUENCE DESCRIPTION: SEQ ID NO: 195:

```
A AGC TTA AGA AAG AAT GTA GGG AAC GAA GAA TAT AGA ACC AAA GAT         46
  Ser Leu Arg Lys Asn Val Gly Asn Glu Glu Tyr Arg Thr Lys Asp
  1               5                   10                  15

TTA TTT ACT GCA TTA TGG GTA CCT GAT TTA TTT ATG GAA CGC GTA GAA       94
Leu Phe Thr Ala Leu Trp Val Pro Asp Leu Phe Met Glu Arg Val Glu
                20                  25                  30

AAA GAT GAA GAA TGG TCT CTA ATG TGT CCA TGC GAA TGT CCA GGA TTA      142
Lys Asp Glu Glu Trp Ser Leu Met Cys Pro Cys Glu Cys Pro Gly Leu
            35                  40                  45

TGC GAT GTA TGG GGG AAT GAT TTT AAC AAA TTA TAT ATA GAA TAC GAA      190
Cys Asp Val Trp Gly Asn Asp Phe Asn Lys Leu Tyr Ile Glu Tyr Glu
        50                  55                  60

ACA AAG AAA AAA ATT AAA GCG ATC GCT AAA GCA AGA AGT TTA TGG AAA      238
Thr Lys Lys Lys Ile Lys Ala Ile Ala Lys Ala Arg Ser Leu Trp Lys
    65                  70                  75

TCT ATT ATC GAG GCT CAA ATA GAA CAA GGA ACG CCG TAT ATA CTA TAT      286
Ser Ile Ile Glu Ala Gln Ile Glu Gln Gly Thr Pro Tyr Ile Leu Tyr
80                  85                  90                  95

AAA GAT TCT TGT AAT AAA AAA TCC AAT CAA AGC AAT TTG GGA ACA ATT      334
Lys Asp Ser Cys Asn Lys Lys Ser Asn Gln Ser Asn Leu Gly Thr Ile
                100                 105                 110

AGA TCG AGT AAT CTC TGT ACA GAG ATT ATA CAA TTT AGT AAC GAG GAT      382
Arg Ser Ser Asn Leu Cys Thr Glu Ile Ile Gln Phe Ser Asn Glu Asp
            115                 120                 125

GAA GTT GCT GTA TGT AAT CTA GGA TCT ATT TCG TGG AGT AAA TTT GTT      430
Glu Val Ala Val Cys Asn Leu Gly Ser Ile Ser Trp Ser Lys Phe Val
        130                 135                 140

AAT AAT AAC GTA TTT ATG TTC GAC AAG TTG AGA ATA ATT ACG AAA ATA      478
Asn Asn Asn Val Phe Met Phe Asp Lys Leu Arg Ile Ile Thr Lys Ile
    145                 150                 155

CTA GTT AAA AAT CTA AAT AAA ATA ATA GAT ATC AAT TAT TAT CCA GTG      526
Leu Val Lys Asn Leu Asn Lys Ile Ile Asp Ile Asn Tyr Tyr Pro Val
160                 165                 170                 175

ATA GAA TCG TCT AGA TCT AAT AAG AAA CAT AGA CCC ATA GGT ATC GGG      574
Ile Glu Ser Ser Arg Ser Asn Lys Lys His Arg Pro Ile Gly Ile Gly
                180                 185                 190

GTT CAG GGT                                                          583
Val Gln Gly
```

(2) INFORMATION FOR SEQ ID NO: 196:

(i) SEQUENCE CHARACTERISTICS:
        (A) LENGTH: 194 amino acids
        (B) TYPE: amino acid
        (D) TOPOLOGY: linear (ii) MOLECULE TYPE: protein (xi) SEQUENCE DESCRIPTION: SEQ ID NO: 196:

Ser Leu Arg Lys Asn Val Gly Asn Glu Glu Tyr Arg Thr Lys Asp Leu
 1               5                  10                  15

Phe Thr Ala Leu Trp Val Pro Asp Leu Phe Met Glu Arg Val Glu Lys
            20                  25                  30

Asp Glu Glu Trp Ser Leu Met Cys Pro Cys Glu Cys Pro Gly Leu Cys
        35                  40                  45

Asp Val Trp Gly Asn Asp Phe Asn Lys Leu Tyr Ile Glu Tyr Glu Thr
    50                  55                  60

Lys Lys Lys Ile Lys Ala Ile Ala Lys Ala Arg Ser Leu Trp Lys Ser
65                  70                  75                  80

Ile Ile Glu Ala Gln Ile Glu Gln Gly Thr Pro Tyr Ile Leu Tyr Lys
                85                  90                  95

Asp Ser Cys Asn Lys Lys Ser Asn Gln Ser Asn Leu Gly Thr Ile Arg
            100                 105                 110

Ser Ser Asn Leu Cys Thr Glu Ile Ile Gln Phe Ser Asn Glu Asp Glu
        115                 120                 125

Val Ala Val Cys Asn Leu Gly Ser Ile Ser Trp Ser Lys Phe Val Asn
    130                 135                 140

Asn Asn Val Phe Met Phe Asp Lys Leu Arg Ile Ile Thr Lys Ile Leu
145                 150                 155                 160

Val Lys Asn Leu Asn Lys Ile Ile Asp Ile Asn Tyr Tyr Pro Val Ile
                165                 170                 175

Glu Ser Ser Arg Ser Asn Lys Lys His Arg Pro Ile Gly Ile Gly Val
            180                 185                 190

Gln Gly (2) INFORMATION FOR SEQ ID NO: 197:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 197:

ACAGGAAACA GCTATGACCA TGATTACGAA TTCGAGCTCG CCCGGGGATC T          51

(2) INFORMATION FOR SEQ ID NO: 198:

(i) SEQUENCE CHARACTERISTICS:
        (A) LENGTH: 138 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 198:

GTATAGCGGC CGCCTGCAGG TCGACTCTAG ATTTTTTTTT TTTTTTTTTT TGGCATATAA      60

ATAGATCTGT ATCCTAAAAT TGAATTGTAA TTATCGATAA TAAATGAATT CGATGGCTGT     120

GCCTGCAAGC CCACAGCA                                                  138

(2) INFORMATION FOR SEQ ID NO: 199:

(i) SEQUENCE CHARACTERISTICS:
            (A) LENGTH: 120 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 199:

CTTAGCCCCA AACGCACCTC AGATCCATAA TTAATTAATT TTTATCCCGG CGCGCCTCGA      60

CTCTAGAATT TCATTTTGTT TTTTTCTATG CTATAAATGA ATTCGGATCC CGTCGTTTTA     120

(2) INFORMATION FOR SEQ ID NO: 200:

(i) SEQUENCE CHARACTERISTICS:
            (A) LENGTH: 116 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 200:

GAAATCCAGC TGAGCGCCGG TCGCTACCAT TACCAGTTGG TCTGGTGTCA AAAAGATCCA      60

TAATTAATTA ACCCGGGTCG AGGCGCGCCG GGTCGACCTG CAGGCGGCCG CTATAC        116

(2) INFORMATION FOR SEQ ID NO: 201:

(i) SEQUENCE CHARACTERISTICS:
            (A) LENGTH: 51 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 201:

TAATGTATCT ATAATGGTAT AAAGCTTGTA TTCTATAGTG TCACCTAAAT C               51

(2) INFORMATION FOR SEQ ID NO: 202:

(i) SEQUENCE CHARACTERISTICS:
            (A) LENGTH: 51 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 202:

| ACAGGAAACA GCTATGACCA TGATTACGAA TTCGAGCTCG CCCGGGGATC T | 51 |
|---|---|

(2) INFORMATION FOR SEQ ID NO: 203:

(i) SEQUENCE CHARACTERISTICS:
        (A) LENGTH: 141 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 203:

| GTATAGCGGC CGCCTGCAGG TCGACTCTAG ATTTTTTTTT TTTTTTTTTT TGGCATATAA | 60 |
|---|---|
| ATAGATCTGT ATCCTAAAAT TGAATTGTAA TTATCGATAA TAAATGAATT CCATGTGCTG | 120 |
| CCTCACCCCT GTGCTGGCGC T | 141 |

(2) INFORMATION FOR SEQ ID NO: 204:

(i) SEQUENCE CHARACTERISTICS:
        (A) LENGTH: 120 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 204:

| TCGCCCGCCT CTGACGCCCC GGATCCATAA TTAATTAATT TTTATCCCGG CGCGCCTCGA | 60 |
|---|---|
| CTCTAGAATT TCATTTTGTT TTTTTCTATG CTATAAATGA ATTCGGATCC CGTCGTTTTA | 120 |

(2) INFORMATION FOR SEQ ID NO: 205:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 205:

| GAAATCCAGC TGAGCGCCGG TCGCTACCAT TACCAGTTGG TCTGGTGTCA AAAAGATCCA | 60 |
|---|---|
| TAATTAATTA ACCCGGGTCG AGGCGCGCCG GTCGACCTG CAGGCGGCCG CTATAC | 116 |

(2) INFORMATION FOR SEQ ID NO: 206:

(i) SEQUENCE CHARACTERISTICS:
    (A) LENGTH: 51 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 206:

```
TAATGTATCT ATAATGGTAT AAAGCTTGTA TTCTATAGTG TCACCTAAAT C          51
```

(2) INFORMATION FOR SEQ ID NO: 207:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 207:

```
CAAGGAATGG TGCATGCCCG TTCTTATCAA TAGTTTAGTC GAAAA               45
```

(2) INFORMATION FOR SEQ ID NO: 208:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 208:

```
TATATAAGCA CTTATTTTTG TTAGTATAAT AACACAATGC CAGATCCCGT CGTTTTA    57
```

(2) INFORMATION FOR SEQ ID NO: 209:

(i) SEQUENCE CHARACTERISTICS:
        (A) LENGTH: 249 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 209:

```
TCCAGCTGAG CGCCGGTCGC TACCATTACC AGTTGGTCTG GTGTCAAAAA GATCCATAAT    60
TAATTAACCA GCGGCCGCCT GCAGGTCGAC TCTAGATTTT TTTTTTTTTT TTTTTTGGCA   120
TATAAATAGA TCTGTATCCT AAAATTGAAT TGTAATTATC GATAATAAAT GAATTCGGAT   180
CCATAATTAA TTAATTTTTA TCCCGGCGCG CCGGGTCGAC CTGCAGGCGG CCGCTGGGTC   240
```

```
GACAAAGAT                                                            249

(2) INFORMATION FOR SEQ ID NO: 210:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 210:

CAAAAGTCGT AAATACTGTA CTAGAAGCTT GGCGTAATCA TGGTC                     45

(2) INFORMATION FOR SEQ ID NO: 211:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 211:

CGACGGATCC GAGGTGCGTT TGGGGCTAAG TGC                                  33

(2) INFORMATION FOR SEQ ID NO: 212:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 212:

CCACGGATCC AGCACAACGC GAGTCCCACC ATGGCT                               36

(2) INFORMATION FOR SEQ ID NO: 213:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 213:

CCACGAATTC GATGGCTGTG CCTGCAAGCC CACAG                                35
```

(2) INFORMATION FOR SEQ ID NO: 214:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 214:

CGAAGATCTG AGGTGCGTTT GGGGCTAAGT GC                          32

(2) INFORMATION FOR SEQ ID NO: 215:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 215:

CGCAGGATCC GGGGCGTCAG AGGCGGGCGA GGTG                      34

(2) INFORMATION FOR SEQ ID NO: 216:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 216:

GAGCGGATCC TGCAGGAGGA GACACAGAGC TG                          32

(2) INFORMATION FOR SEQ ID NO: 217:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 217:

GCGCGAATTC CATGTGCTGC CTCACCCCTG TG                          32

(2) INFORMATION FOR SEQ ID NO: 218:

(i) SEQUENCE CHARACTERISTICS:

(A) LENGTH: 34 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 218:

CGCAGGATCC GGGGCGTCAG AGGCGGGCGA GGTG                                           34

(2) INFORMATION FOR SEQ ID NO: 219:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 219:

GGGGAATTCA ATGCAACCCA CCGCGCCGCC CC                                             32

(2) INFORMATION FOR SEQ ID NO: 220:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 220:

GGGGATCCTA GGGCGCGCCC GCCGGCTCGC T                                              31

(2) INFORMATION FOR SEQ ID NO: 221:

(i) SEQUENCE CHARACTERISTICS:
        (A) LENGTH: 5785 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 221:

AAGCTTAAGA AAGAATGTAG GGAACGAAGA ATATAGAACC AAAGATTTAT TTACTGCATT    60

ATGGGTACCT GATTTATTTA TGGAACGCGT AGAAAAAGAT GAAGAATGGT CTCTAATGTG    120

TCCATGCGAA TGTCCAGGAT TATGCGATGT ATGGGGAAT GATTTTAACA AATTATATAT    180

AGAATACGAA ACAAGAAAAA AAATTAAAGC GATCGCTAAA GCAAGAAGTT TATGGAAATC    240

TATTATCGAG GCTCAAATAG AACAAGGAAC GCCGTATATA CTATATAAAG ATTCTTGTAA    300

```
TAAAAAATCC AATCAAAGCA ATTTGGGAAC AATTAGATCG AGTAATCTCT GTACAGAGAT    360

TATACAATTT AGTAACGAGG ATGAAGTTGC TGTATGTAAT CTAGGATCTA TTTCGTGGAG    420

TAAATTTGTT AATAATAACG TATTTATGTT CGACAAGTTG AGAATAATTA CGAAAATACT    480

AGTTAAAAAT CTAAATAAAA TAATAGATAT CAATTATTAT CCAGTGATAG AATCGTCTAG    540

ATCTAATAAG AAACATAGAC CCATAGGTAT CGGTGTTCAG GGTTTGGCTG ATGTGTTTAT    600

ATTATTGGGC TATGCATTCG ATAGCGAAGA AGCAAAAATA TTAAATATAC AAATTTCCGA    660

AACAATATAT TATGCCGCAC TAGAATCTAG TTGCGAACTA GCTAAAATTT ACGGACCTTA    720

TGAGACATAT AACGATTCTC CAGCGAGTAA AGGTATTCTA CAATATGATA TGTGGTTAAA    780

GAACCCAACA GATTTATGGG ATTGGAATGA ACTAAAAAAG AGAATTAATA CACATGGATT    840

GAGAAATAGC CTTCTAATAG CACCAATGCC TACTGCATCT ACATCTCAAA TATTAAGTAA    900

TAATGAGTCC ACCGAACCAT ATACTAGCAA TATATATACA AGAAGAGTAT TATCTGGAGA    960

TTTTCAGGTT GTAAATCCAC ACCTATTGAG AGAACTAATA AGTAGAAATA TGTGGAATAA   1020

TGACATAAAG AATACAATTG TGTTACATAA TGGTTCTATT CAACATTTAG ATTTACCAGA   1080

TAATATAAAA CCAATATATA AAACGGTTTG GGAGATATCT CCAAAATGTA TTTTAGAAAT   1140

GGCAGCCGAC AGAGGTGCGT TTATAGATCC AAGTCAATCA ATGACAATAT ATATAGATAA   1200

TCCTACATAC GCAAAACTGA CCAGTATGCA TTTTTACGGA TGGAGATTGG GGCTAAAAAC   1260

TGGGATGTAT TATATGAGAA CAAAATCGGC ATCAAATCCT ATAAAATTCA CAGTTGAGTG   1320

TAGTAATTGT TCTGCATAAT TTTTATAAAA ATGAAATACT ATCTCATGTA TCTTAATATA   1380

TTAAAAATGC GTAAAAGTGG CATTCCAAAA CAACCCGTTC CCAAAAAAGA TTATGTTCAA   1440

ACTGATAATA ATAAAAAACA ACAAATAACA ACGTGTTCAG AAGTCGTTGA GTATCTTAAA   1500

TCACTAAGTA AGAGCACCGA AAAATGTATA GAAAATGTAA TATTAACGCC TTCTCAATAT   1560

CCTTCTTGTT CATCGATAAC TATTAATTTA ACAGACTATC TATCATCTAA AATGACATCT   1620

ACATATATAG CATTAGAAGG TGAGTCTAAA ATATACAAGA ATAAAAAGAA TGAAAGTAGA   1680

TCGTTAGATC AATATTTTTT AAAAATACGA CTTACTGCAG CAAGTCCTAT AATGTATCAA   1740

TTATTAGATT GTATATATTC TAATATTAGA GATAATAAAC ATATACCCCC TTCCTTATCA   1800

AATATATCTA TATCGGACTT AGAAGAGAAA ACGCTTAACC AGGGGTGTTT GTTCATTAAT   1860

AAGATGGGTG GAGCTATTAT AGAATACAAG ATACCTGGTT CCAAATCTAT AACAAAATCT   1920

ATTTCCGAAG AACTAGAAAA TTTAACAAAG CGAGATAAAC AAATATCTAA AATTATAGTT   1980

ATTCCTATTG TATGTTACAG AAATGCAAAT AGTATAAAGG TTACATTTGC ACTAAAAAAG   2040

TTTATCATAG ATAAGGAGTT TAGTACAAAT GTAATAGACG TAGATGGTAA ACATGAAAAA   2100

ATGTCCATGA ATGAAACATG CGAAGAGGAT GTTGCTAGAG GATTGGGAAT TATAGATCTT   2160

GAAGATGAAT GCATAGAGGA AGATGATGTC GATACGTCAT TATTTAATGT ATAAATGGAT   2220

AAATTGTATG CGGCAATATT CGGCGTTTTT ATGACATCTA AGATGATGA TTTTAATAAC    2280

TTTATAGAAG TTGTAAAATC TGTATTAACA GATACATCAT CTAATCATAC AATATCGTCG   2340

TCCAATAATA ATACATGGAT ATATATATTT CTAGCGATAT TATTTGGTGT TATGGTATTA   2400

TTAGTTTTTA TTTTGTATTT AAAAGTTACT AAACCAACTT AAATGGAGGA AGCAGATAAC   2460

CAACTCGTTT TAAATAGTAT TAGTGCTAGA GCATTAAAGG CATTTTTTGT ATCTAAAATT   2520

AATGATATGG TCGATGAATT AGTTACCAAA AAATATCCAC CAAAGAAGAA ATCACAAATA   2580

AAACTCATAG ATACACGAAT TCCTATTGAT CTTATTAATC AACAATTCGT TAAAAGATTT   2640
```

```
AAACTAGAAA ATTATAAAAA TGGAATTTTA TCCGTTCTTA TCAATAGTTT AGTCGAAAAT    2700

AATTACTTTG AACAAGATGG TAAACTTAAT AGCAGTGATA TTGATGAATT AGTGCTCACA    2760

GACATAGAGA AAAAGATTTT ATCGTTGATT CCTAGATGTT CTCCTCTTTA TATAGATATC    2820

AGTGACGTTA AAGTTCTCGC ATCTAGGTTA AAAAAGTGCT AAATCATTTA CGTTAATGA    2880

TCATGAATAT ATTATACAAT CTGATAAAAT AGAGGAATTA ATAAATAGTT TATCTAGAAA    2940

CCATGATATT ATACTAGATG AAAAAAGTTC TATTAAAGAC AGCATATATA TACTATCTGA    3000

TGATCTTTTG AATATACTTC GTGAAAGATT ATTTAGATGT CCACAGGTTA AAGATAAATAC   3060

TATTTCTAGA ACACGTCTAT ATGATTATTT TACTAGAGTG TCAAAGAAAG AAGAAGCGAA    3120

AATATACGTT ATATTGAAAG ATTTAAAGAT TGCTGATATA CTCGGTATCG AAACAGTAAC    3180

GATAGGATCA TTTGTATATA CGAAATATAG CATGTTGATT AATTCAATTT CGTCTAATGT    3240

TGATAGATAT TCAAAAAGGT TCCATGACTC TTTTTATGAA GATATTGCGG AATTTATAAA    3300

GGATAATGAA AAAATTAATG TATCCAGAGT TGTTGAATGC CTTATCGTAC CTAATATTAA    3360

TATAGAGTTA TTAACTGAAT AAGTATATAT AAATGATTGT TTTTATAATG TTTGTTATGC    3420

CATTTAGTTT TGCTGTATGG TTATCATATA CATTTTTAAG GCCGTATATG ATAAATGAAA    3480

ATATATAAGC ACTTATTTTT GTTAGTATAA TAACACAATG CCGTCGTATA TGTATCCGAA    3540

GAACGCAAGA AAAGTAATTT CAAAGATTAT ATCATTACAA CTTGATATTA AAAAACTTCC    3600

TAAAAAATAT ATAAATACCA TGTTAGAATT TGGTCTACAT GGAAATCTAC CAGCTTGTAT    3660

GTATAAAGAT GCCGTATCAT ATGATATAAA TAATATAAGA TTTTTACCTT ATAATTGTGT    3720

TATGGTTAAA GATTAATAA ATGTTATAAA ATCATCATCT GTAATAGATA CTAGATTACA    3780

TCAATCTGTA TTAAAACATC GTAGAGCGTT AATAGATTAC GGCGATCAAG ACATTATCAC    3840

TTTAATGATC ATTAATAAGT TACTATCGAT AGATGATATA TCCTATATAT TAGATAAAAA    3900

AATAATTCAT GTAACAAAAA TATTAAAAAT AGACCCTACA GTAGCCAATT CAAACATGAA    3960

ACTGAATAAG ATAGAGCTTG TAGATGTAAT AACATCAATA CCTAAGTCTT CCTATACATA    4020

TTTATATAAT AAATATGATCA TTGATCTCGA TACATTATTA TATTTATCCG ATGCATTCCA    4080

CATACCCCCC ACACATATAT CATTACGTTC ACTTAGAGAT ATAAACAGGA TTATTGAATT    4140

GCTTAAAAAA TATCCGAATA ATAATATTAT TGATTATATA TCCGATAGCA TAAAATCAAA    4200

TAGTTCATTC ATTCACATAC TTCATATGAT AATATCAAAT ATGTTTCCTG CTATAATCCC    4260

TAGTGTAAAC GATTTATAT CTACCGTAGT TGATAAAGAT CGACTTATTA ATATGTATGG    4320

GATTAAGTGT GTTGCTATGT TTTCGTACGA TATAAACATG ATCGATTTAG AGTCATTAGA    4380

TGACTCAGAT TACATATTTA TAGAAAAAAA TATATCTATA TACGACGTTA AATGTAGAGA    4440

TTTTGCGAAT ATGATTAGAG ATAAGGTTAA AAGAGAAAAG AATAGAATAT TAACTACGAA    4500

ATGTGAAGAT ATTATAAGAT ATATAAAATT ATTCAGTAAA AATAGAATAA ACGATGAAAA    4560

TAATAAGGTG GAGGAGGTGT TGATACATAT TGATAATGTA TCTAAAAATA ATAAATTATC    4620

ACTGTCTGAT ATATCATCTT TAATGGATCA ATTTCGTTTA AATCCATGTA CCATAAGAAA    4680

TATATTATTA TCTTCAGCAA CTATAAAATC AAAACTATTA GCGTTACGGG CAGTAAAAAA    4740

CTGGAAATGT TATTCATTGA CAAATGTATC AATGTATAAA AAAATAAAGG GTGTTATCGT    4800

AATGGATATG GTTGATTATA TATCTACTAA CATTCTTAAA TACCATAAAC AATTATATGA    4860

TAAAATGAGT ACGTTTGAAT ATAAACGAGA TATTAAATCA TGTAAATGCT CGATATGTTC    4920

CGACTCTATA ACACATCATA TATATGAAAC AACATCATGT ATAAATTATA AATCTACCGA    4980

TAATGATCTT ATGATAGTAT TGTTCAATCT AACTAGATAT TTAATGCATG GGATGATACA    5040
```

```
TCCTAATCTT ATAAGCGTAA AAGGATGGGG TCCCCTTATT GGATTATTAA CGGGTGATAT        5100

AGGTATTAAT TTAAAACTAT ATTCCACCAT GAATATAAAT GGGCTACGGT ATGGAGATAT        5160

TACGTTATCT TCATACGATA TGAGTAATAA ATTAGTCTCT ATTATTAATA CACCCATATA        5220

TGAGTTAATA CCGTTTACTA CATGTTGTTC ACTCAATGAA TATTATTCAA AAATTGTGAT        5280

TTTAATAAAT GTTATTTTAG AATATATGAT ATCTATTATA TTATATAGAA TATTGATCGT        5340

AAAAAGATTT AATAACATTA AAGAATTTAT TTCAAAAGTC GTAAATACTG TACTAGAATC        5400

ATCAGGCATA TATTTTTGTC AGATGCGTGT ACATGAACAA ATTGAATTGG AAATAGATGA        5460

GCTCATTATT AATGGATCTA TGCCTGTACA GCTTATGCAT TTACTTCTAA AGGTAGCTAC        5520

CATAATATTA GAGGAAATCA AAGAAATATA ACGTATTTTT TCTTTTAAAT AAATAAAAAT        5580

ACTTTTTTTT TTAAACAAGG GGTGCTACCT TGTCTAATTG TATCTTGTAT TTTGGATCTG        5640

ATGCAAGATT ATTAAATAAT CGTATGAAAA AGTAGTAGAT ATAGTTTATA TCGTTACTGG        5700

ACATGATATT ATGTTTAGTT AATTCTTCTT TGGCATGAAT TCTACACGTC GGACAAGGTA        5760

ATGTATCTAT AATGGTATAA AGCTT                                             5785

(2) INFORMATION FOR SEQ ID NO: 222:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 222:

TTTTGATTTT ACGCCATTAT ACTGTTCTGT AGATGCAAAT AATGAAGATG TGTTCTTATT          60

TACTAGAGAG ATGCAGACCC TATATTATCA CAGTATTTGG TGAACGTGTA TACTAACAGC         120

TTCAATAATC ATAATCCCCC ATATTATATA ACTATTAAAT TATGATATAG ATATAAATAC         180

TATCCAAAAT ACATTATTTA AACTGGAACA AGATATTATT AACTCTACCA TAGATACTTA         240

CTATTACAAT AATCTTGTTA AAAAAGAACA TTTTATAAAA TTATTTCTAG CCTACATAGT         300

TAAGAGGTAT GAAAAAAATA TAGGAATATT ATTTCTTGAT TATCCCACTC TTGGTGAATA         360

TTTCGTGAAA TTTATAGATA CGTGTATGAT GGAAATATTT GAGATGAAAT CAGATAAGGT         420

GGTAAACGGA TATATATTCT ATTATATTTA CGAATAAGTA TATTCCTATC CCATATATAA         480

CGTGTAAAAA GCTAAAGAAA TACGAATCCT TTGTTGTATA TGGAACCGAA ATAAAATCAA         540

TAATAAAATC TTCAAAGATT AGATATGCGA GTGTTATAAA AGTAACGGAG TATATCACAT         600

CTATCTGTTC GGAAGAAACT AGTTTATGGA ACAGCATCCC AATTGAGATA AACATAAGA         660

TTATTAATAA TATAAACAAT CATGATATGT ATATATTATA TAAAAATAGA AAAAAAAAT         720

AA                                                                      722

(2) INFORMATION FOR SEQ ID NO: 223:

(i) SEQUENCE CHARACTERISTICS:
        (A) LENGTH: 234 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 223:

AAACAATGCG CTTTAATATC AAACATGCAG GTGGAATAGG ATTGTCGATA AGTAATATAC      60

GAGCTAAGGG TACTTATATA TCCGGTATAA ACGGCAAATC TATGGTATAG TACCTATGTT     120

AAGAATATAT AATAACACAG TTAGATATAT TAATCAGGGA GGTGATAAAA GACCAGGAGC     180

AATGTCGATT TATATAGAAC CATGGCACGC TGATATATTC GATTTTCTAA GCTT           234

(2) INFORMATION FOR SEQ ID NO: 224:

(i) SEQUENCE CHARACTERISTICS:
        (A) LENGTH: 1025 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 224:

GGTTGCTCCT AACTTAATAA GATAATCCAC CAAGATAGTT TTATCCGTGG TAGATGCATA      60

CACAACAGGA GAATATCCTA ATTTATCTCT ATAGTTTATG GTTGTGATAT CTATAGTATA     120

TGGGACCGCC GAAAAACATG TATAATCGTC GTGACAATAG TTTAACATCG TGTTTAATAT     180

CGACATCATT TCATCATTTT TATTATATTC ATGTTTTATA TGCGAACAAA GCAAATTCAA     240

TATATTTAAA TTAGTGTTAT TGATGTGTCT AATTGTAAAT ATATGAATAG GATTCTTCAG     300

ACTATTATTT AGTTTACATA CATCAAATCC TTTTCTTATT AAAAACTCAA CAACTTTATA     360

ATCTATATTC TCATTACCAA GGTATTTATG CAATATGGTG TCTCCACATC TATGTACACT     420

GTTAATGTCA CCACCATGAT AAATAAGAAA CTTTATTACT TTAATTGTAA CATTCGTATT     480

AAATGTAAAA TAACAATGAA ATGGTGTTTT ATCATATATA GATATCCCAT TTAAATTAGC     540

ACCTTTATTA AGCAGTAATA ATACAATTTC TTTCAACTCT TTTAATTTAA ATACGTGCAA     600

CGATGAACTT AAAAATGTAG CTAACATATC AGTGGCTATA TTATCATCCT GTTTTATATT     660

TGATATTATT CTTCTTATAT TATCCATTTC CTTCTTACAA ACTATTTAAA CGATAACCAA     720

AATGTATTCA TGGGCTACTA ATAATAGCCA CATTACTAGA AAAAAAATTT TTTTTCAATA     780

TTATGACATT ATTACTTAAG TATTATTGAT AAGTCCTTCA TTGTTAAATG TAATAATATA     840

TATCGTTGTA TTTCTATAGG AATCCTCATC CAGTAACTAT GTTTCTTGCA GTGCTTCATA     900

ATTACATAAA TCGCTTTATC AATGTTAGAA TAATACATAT ATGTATTTTT GATAAATATTT     960

TCTATATGTG ATCCATACAT TACTAAATTT TTTAATCTTA AAAAATTATC ATAATTGAGA    1020

AGCTT                                                                1025

(2) INFORMATION FOR SEQ ID NO: 225:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 225:

| | |
|---|---|
| AAGCTTGGAT GAGCAATAAG AGTATACAAA ATTTAGTGTT TCAATTCGCT CATGGATCAG | 60 |
| AAGTAGAATA TATAGGTCAA TACGATATGA GATTTTTAAA TAATATACCT ATTCATGATA | 120 |
| AGTTTGATGT GTTTTTAAAT AAGCACATAC TATCGTATGT ACTTAGAGAT AAAATAAAGA | 180 |
| AATCAGACCA CAGATATGTA ATGTTTGGAT TTTGGTTATT TATCTCATTG GAAATGTGTT | 240 |
| ATATTCGATA AGGAACATCA TATGTCTGTT TCTATGATTC AGGAGGAATT ACCAAACGAA | 300 |
| TTCCA | 305 |

(2) INFORMATION FOR SEQ ID NO: 226:

(i) SEQUENCE CHARACTERISTICS:
      (A) LENGTH: 27 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 226:

| | |
|---|---|
| GAATACAAGC TACCTTAAGA AAGAATG | 27 |

(2) INFORMATION FOR SEQ ID NO: 227:

(i) SEQUENCE CHARACTERISTICS:
      (A) LENGTH: 198 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 227:

| | |
|---|---|
| GAATCGTCTA GATCCCCAAG CTTGGCCTCG AGGGCCGCGG CCGCCTGCAG GTCGACTCTA | 60 |
| GATTTTTTTT TTTTTTTTTT TTGGCATATA AATAGATCTG TATCCTAAAA TTGAATTGTA | 120 |
| ATTATCGATA ATAAATGAAT TCACCCGCTG GTGGCGGTCT TTGGCGCGGG CCCCGTGGGC | 180 |
| ATCGGCCCGG GCACCACG | 198 |

(2) INFORMATION FOR SEQ ID NO: 228:

(i) SEQUENCE CHARACTERISTICS:
      (A) LENGTH: 88 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 228:

```
GAGCTCGAAT TCGAGCTCGC CCGGGGATCC TCTAGAATTT CATTTTGTTT TTTTCTATGC        60

TATAAATGAA TTCGGATCCC GTCGTTTT                                          88
```

(2) INFORMATION FOR SEQ ID NO: 229:

(i) SEQUENCE CHARACTERISTICS:
        (A) LENGTH: 129 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 229:

```
GAAATCCAGC TGAGCGCCGG TCGCTACCAT TACCAGTTGG TCTGGTGTCA AAAAGATCCA       60

TAATTAATTA ACCCGGGTCG ACCTGCAGGG CGGCCGCGGC CCTCGAGGCC AAGCTTGGGG      120

ATCTAATAA                                                             129
```

(2) INFORMATION FOR SEQ ID NO: 230:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 230:

```
TTTTAAAAAT ACGACTTACT GCAGGTCGAC TCTAGA                                 36
```

(2) INFORMATION FOR SEQ ID NO: 231:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 231:

```
GCCCGGGGAT CTTGAAGATG AATGCAT                                           27
```

(2) INFORMATION FOR SEQ ID NO: 232:

(i) SEQUENCE CHARACTERISTICS:
        (A) LENGTH: 117 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 232:

ATTTGGTCTG CTGCAGGTCG ACTCTAGAAA AAATTGAAAA ACTATTCTAA TTTATTGCAC 60

GGAGATCTTT TTTTTTTTTT TTTTTTTTGG CATATAAATG AATTCGCTCG CAGCGCT 117

(2) INFORMATION FOR SEQ ID NO: 233:

(i) SEQUENCE CHARACTERISTICS:
      (A) LENGTH: 90 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 233:

GCGTGCACCA CGAGGGACTC TAGAGGATCC ATAATTAATT AATTAATTTT TATCCCGGGT 60

CGACCTGCAG CCTACATGGA AATCTACCAG 90

(2) INFORMATION FOR SEQ ID NO: 234:

(i) SEQUENCE CHARACTERISTICS:
      (A) LENGTH: 186 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 234:

GCCGTATCAT ACAAGCTTGG CCTCGAGGGC CGCGGCCGCC TGCAGGTCGA CTCTAGATTT 60

TTTTTTTTTT TTTTTTTGGC ATATAAATAG ATCTGTATCC TAAAATTGAA TTGTAATTAT 120

CGATAATAAA TGAATTCACC CGCTGGTGGC GGTCTTTGGC GCGGGCCCCG TGGGCATCGG 180

CCCGGG 186

(2) INFORMATION FOR SEQ ID NO: 235:

(i) SEQUENCE CHARACTERISTICS:
      (A) LENGTH: 88 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 235:

GAGCTCGAAT TCGAGCTCGC CCGGGGATCC TCTAGAATTT CATTTTGTTT TTTTCTATGC 60

TATAAATGAA TTCGGATCCC GTCGTTTT 88

(2) INFORMATION FOR SEQ ID NO: 236:

(i) SEQUENCE CHARACTERISTICS:

(A) LENGTH: 129 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 236:

GAAATCCAGC TGAGCGCCGG TCGCTACCAT TACCAGTTGG TCTGGTGTCA AAAAGATCCA      60

TAATTAATTA ACCCGGGTCG ACCTGCAGGG CGGCCGCGGC CCTCGAGGCC AAGCTTGTAT     120

GATAATATC                                                            129

(2) INFORMATION FOR SEQ ID NO: 237:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 237:

TATAATGGTA TAAAGCTAGC TTGTATTCTA                                      30

(2) INFORMATION FOR SEQ ID NO: 238:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 238:

GAATACAAGC TAGCTTTATA CCATTAT                                         27

(2) INFORMATION FOR SEQ ID NO: 239:

(i) SEQUENCE CHARACTERISTICS:
        (A) LENGTH: 186 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 239:

ATATTATCAT ACAAGCTTGG CCTCGAGGGC CGCGGCCGCC TGCAGGTCGA CTCTAGATTT      60

TTTTTTTTTT TTTTTTTGGC ATATAAATAG ATCTGTATCC TAAAATTGAA TTGTAATTAT     120

CGATAATAAA TGAATTCACC CGCTGGTGGC GGTCTTTGGC GCGGGCCCCG TGGGCATCGG     180

CCCGGG                                                                         186

(2) INFORMATION FOR SEQ ID NO: 240:

(i) SEQUENCE CHARACTERISTICS:
        (A) LENGTH: 88 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 240:

CAGCTCGAAT TCGAGCTCGC CCGGGGATCC TCTAGAATTT CATTTTGTTT TTTTCTATGC            60

TATAAATGAA TTCGGATCCC GTCGTTTT                                                88

(2) INFORMATION FOR SEQ ID NO: 241:

(i) SEQUENCE CHARACTERISTICS:
        (A) LENGTH: 129 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 241:

GAAATCCAGC TGAGCGCCGG TCGCTACCAT TACCAGTTGG TCTGGTGTCA AAAAGATCCA            60

TAATTAATTA ACCCGGGTCG ACCTGCAGGG CGGCCGCGGC CCTCGAGGCC AAGCTTGTAT           120

GATACGGCA                                                                   129

(2) INFORMATION FOR SEQ ID NO: 242:

(i) SEQUENCE CHARACTERISTICS:
        (A) LENGTH: 123 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 242:

TGTAGGCTGC AGGTCGACTC TAGAAAAAAT TGAAAAACTA TTCTAATTTA TTGCACGGAG            60

ATCTTTTTTT TTTTTTTTTT TTTTGGCATA TAAATGAATT CCGGCATGGC CTCGCTCGCG           120

CGT                                                                         123

(2) INFORMATION FOR SEQ ID NO: 243:

(i) SEQUENCE CHARACTERISTICS:
        (A) LENGTH: 90 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 243:

CCATGCTCTA GAGGATCCCC GGGCGAGCTC GAATTCGGAT CCATAATTAA TTAATTAATT    60

TTTATCCCGG GTCGACCTGC AGCAGACCAA                                    90

(2) INFORMATION FOR SEQ ID NO: 244:

(i) SEQUENCE CHARACTERISTICS:
                (A) LENGTH: 36 base pairs
                (B) TYPE: nucleic acid
                (C) STRANDEDNESS: double
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 244:

CATTCATCTT CAAGATCCCC GGGCGAGCTC GAATTC                              36

(2) INFORMATION FOR SEQ ID NO: 245:

(i) SEQUENCE CHARACTERISTICS:
                (A) LENGTH: 27 base pairs
                (B) TYPE: nucleic acid
                (C) STRANDEDNESS: double
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 245:

GCCCGGGGAT CTTGAAGATG AATGCAT                                       27

(2) INFORMATION FOR SEQ ID NO: 246:

(i) SEQUENCE CHARACTERISTICS:
                (A) LENGTH: 117 base pairs
                (B) TYPE: nucleic acid
                (C) STRANDEDNESS: double
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 246:

ATTTGGTCTG CTGCAGGTCG ACTCTAGAAA AAATTGAAAA ACTATTCTAA TTTATTGCAC    60

GGAGATCTTT TTTTTTTTTT TTTTTTTGG CATATAAATG AATTCGCTCG CAGCGCT      117

(2) INFORMATION FOR SEQ ID NO: 247:

(i) SEQUENCE CHARACTERISTICS:
                (A) LENGTH: 90 base pairs
                (B) TYPE: nucleic acid
                (C) STRANDEDNESS: double
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 247:

GCGTGCACCA CGAGGGACTC TAGAGGATCC ATAATTAATT AATTAATTTT TATCCCGGGT    60

CGACCTGCAG CCTACATGGA AATCTACCAG    90

(2) INFORMATION FOR SEQ ID NO: 248:

(i) SEQUENCE CHARACTERISTICS:
       (A) LENGTH: 109 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 248:

GCCGTATCAT ACAAGCTTGG CCTCGAGGGC CGCGGCCGCC TGCAGGTCGA CTCTAGAATT    60

TCATTTTGTT TTTTTCTATG CTATAAATGA ATTCGGATCC CGTCGTTTT    109

(2) INFORMATION FOR SEQ ID NO: 249:

(i) SEQUENCE CHARACTERISTICS:
       (A) LENGTH: 177 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 249:

GAAATCCAGC TGAGCGCCGG TCGCTACCAT TACCAGTTGG TCTGGTGTCA AAAAGATCCA    60

TAATTAATTA ACCCGGTCGA CTCTAGAAAA AATTGAAAAA CTATTCTAAT TTATTGCACG    120

GAGATCTTTT TTTTTTTTTT TTTTTTTGGC ATATAAATGA ATTCCGGCAT GGCCTCG    177

(2) INFORMATION FOR SEQ ID NO: 250:

(i) SEQUENCE CHARACTERISTICS:
       (A) LENGTH: 135 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 250:

CCATGCTCTA GAGGATCCCC GGGCGAGCTC GAATTCGGAT CCATAATTAA TTAATTAATT    60

TTTATCCCGG GTCGACCGGG TCGACCTGCA GGGCGGCCGC GGCCCTCGAG GCCAAGCTTG    120

TATGATAATA TCAAA    135

(2) INFORMATION FOR SEQ ID NO: 251:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 251:

TATAATGGTA TAAAGCTAGC TTGTAATCTA                                        30

(2) INFORMATION FOR SEQ ID NO: 252:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 252:

GCCCGGGGAT CTTGAAGATG AATGCAT                                           27

(2) INFORMATION FOR SEQ ID NO: 253:

(i) SEQUENCE CHARACTERISTICS:
        (A) LENGTH: 120 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 253:

ATTTGGTCTG CTGCAGGTCG ACTCTAGATT TTTTTTTTTT TTTTTTTTGG CATATAAATA        60

GATCTGTATC CTAAAATTGA ATTGTAATTA TCGATAATAA ATGAATTCGC TCGCAGCGCT       120

(2) INFORMATION FOR SEQ ID NO: 254:

(i) SEQUENCE CHARACTERISTICS:
        (A) LENGTH: 88 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 254:

GAGCTCGAAT TCGAGCTCGC CCGGGGATCC TCTAGAATTT CATTTTGTTT TTTTCTATGC        60

```
TATAAATGAA TTCGGATCCC GTCGTTTT                                              88
```

(2) INFORMATION FOR SEQ ID NO: 255:

(i) SEQUENCE CHARACTERISTICS:
        (A) LENGTH: 129 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 255:

```
GAAATCCAGC TGAGCGCCGG TCGCTACCAT TACCAGTTGG TCTGGTGTCA AAAAGATCCA           60
TAATTAATTA ACCCGGGTCG ACCTGCAGGG CGGCCGCGGC CCTCGAGGCC AAGCTTGTAT          120
GATACGGCA                                                                 129
```

(2) INFORMATION FOR SEQ ID NO: 256:

(i) SEQUENCE CHARACTERISTICS:
        (A) LENGTH: 186 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 256:

```
GCCGTATCAT ACAAGCTTGG CCTCGAGGGC CGCGGCCGCC TGCAGGTCGA CTCTAGATTT           60
TTTTTTTTTT TTTTTTTGGC ATATAAATAG ATCTGTATCC TAAAATTGAA TTGTAATTAT          120
CGATAATAAA TGAATTCACC CGCTGGTGGC GGTCCTTGGC GCGGGCCCCG TGGGCATCGG          180
CCCGGG                                                                    186
```

(2) INFORMATION FOR SEQ ID NO: 257:

(i) SEQUENCE CHARACTERISTICS:
        (A) LENGTH: 88 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 257:

```
GAGCTCGAAT TCGAGCTCGC CCGGGGATCC TCTAGAATTT CATTTTGTTT TTTTCTATGC           60
TATAAATGAA TTCGGATCCC GTCGTTTT                                              88
```

(2) INFORMATION FOR SEQ ID NO: 258:

(i) SEQUENCE CHARACTERISTICS:
        (A) LENGTH: 129 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 258:

GAAATCCAGC TGAGCGCCGG TCGCTACCAT TACCAGTTGG TCTGGTGTCA AAAAGATCCA    60

TAATTAATTA ACCCGGGTCG ACCTGCAGGG CGGCCGCGGC CCTCGAGGCC AAGCTTGTAT   120

GATAATATC                                                          129

(2) INFORMATION FOR SEQ ID NO: 259:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 259:

TATAATGGTA TAAAGCTAGC TTGTATTCTA                                     30

(2) INFORMATION FOR SEQ ID NO: 260:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 260:

CACGAATTCT GACATTTTCA ACAGTCCACA GGCGC                               35

(2) INFORMATION FOR SEQ ID NO: 261:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 261:

GCTGTTGGAC ATCACGGGCC AGG                                            23

(2) INFORMATION FOR SEQ ID NO: 262:

(i) SEQUENCE CHARACTERISTICS:
        (A) LENGTH: 25 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 262:

ACCCGGAACA TATGGTCAGC TCCAT                                              25

(2) INFORMATION FOR SEQ ID NO: 263:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 263:

GGCGCGCCAG GCGAAGGCCG GGGATACGG                                          29

(2) INFORMATION FOR SEQ ID NO: 264:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 264:

GCGTGAATTC GGGGAATGGA CAGGGGCGAG AT                                      32

(2) INFORMATION FOR SEQ ID NO: 265:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 265:

GAGCCAGATC TGCTCTTTTT ACTTTCCC                                           28

(2) INFORMATION FOR SEQ ID NO: 266:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 266:

GCCCGGATCC TATGGCAGAA GGGTTTGCAG C                                       31

(2) INFORMATION FOR SEQ ID NO: 267:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 267:

CCGTGGATCC GGCACTCCAT CATTCCTCCT C                                       31

US 6,497,882 B1

RECOMBINANT SWINEPOX VIRUS

This application is a continuation-in-part of U.S. Ser. No. 08/375,992, filed Jan. 19, 1995, now U.S. Pat. No. 6,328,975 which is a continuation-in-part of international application PCT/US94/08277, filed Jul. 22, 1994, a continuation-in-part of U.S. Ser. No. 08/097,554, filed Jul. 22, 1993, now U.S. Pat. No. 5,869,312, and U.S. Ser. No. 07/820,154 filed Jan. 13, 1992, now U.S. Pat. No. 5,382,425 the contents of which are incorporated by reference into the present application.

Within this application several publications are referenced by arabic numerals within parentheses. Full citations for these publications may be found at the end of the specification immediately preceding the claims. The disclosures of these publications are hereby incorporated by reference into this application.

BACKGROUND OF THE INVENTION

Swinepox virus (SPV) belongs to the family Poxviridae. Viruses belonging to this group are large, double-stranded DNA viruses that characteristically develop in the cytoplasm of the host cell. SPV is the only member of the genus Suipoxvirus. Several features distinguish SPV from other poxviruses. SPV exhibits species specificity (18) compared to other poxviruses such as vaccinia which exhibit a broad host range. SPV infection of tissue culture cell lines also differs dramatically from other poxviruses (24). It has also been demonstrated that SPV does not exhibit antigenic cross-reactivity with vaccinia virus and shows no gross detectable homology at the DNA level with the ortho, lepori, avi or entomopox virus groups (24). Accordingly, what is known and described in the prior art regarding other poxviruses does not pertain a priori to swinepox virus.

SPV is only mildly pathogenic, being characterized by a self-limiting infection with lesions detected only in the skin and regional lymph nodes. Although the SPV infection is quite limited, pigs which have recovered from SPV are refractory to challenge with SPV, indicating development of active immunity (18).

The present invention concerns the use of SPV as a vector for the delivery of vaccine antigens and therapeutic agents to swine. The following properties of SPV support this rationale: SPV is only mildly pathogenic in swine, SPV is species specific, and SPV elicits a protective immune response. Accordingly, SPV is an excellent candidate for a viral vector delivery system, having little intrinsic risk which must be balanced against the benefit contributed by the vector's vaccine and therapeutic properties.

The prior art for this invention stems first from the ability to clone and analyze DNA while in bacterial plasmids. The techniques that are available are detailed for the most part in Maniatis et al., 1983 and Sambrook et al., 1989. These publications teach state of the art general recombinant DNA techniques.

Among the poxviruses, five (vaccinia, fowlpox, canarypox, pigeon, and raccoon pox) have been engineered, previous to this disclosure, to contain foreign DNA sequences. Vaccinia virus has been used extensively to vector foreign genes (25) and is the subject of U.S. Pat. Nos. 4,603,112 and 4,722,848. Similarly, fowlpox has been used to vector foreign genes and is the subject of several patent applications EPA 0 284 416, PCT WO 89/03429, and PCT WO 89/12684. Raccoon pox (10) and Canarypox (31) have been utilized to express antigens from the rabies virus. These examples of insertions of foreign genes into poxviruses do not include an example from the genus Suipoxvirus. Thus, they do not teach methods to genetically engineer swinepox viruses, that is, where to make insertions and how to get expression in swinepox virus.

The idea of using live viruses as delivery systems for antigens has a very long history going back to the first live virus vaccines. The antigens delivered were not foreign but were naturally expressed by the live virus in the vaccines. The use of viruses to deliver foreign antigens in the modern sense became obvious with the recombinant vaccinia virus studies. The vaccinia virus was the vector and various antigens from other disease causing viruses were the foreign antigens, and the vaccine was created by genetic engineering. While the concept became obvious with these disclosures, what was not obvious was the answer to a more practical question of what makes the best candidate virus vector. In answering this question, details of the pathogenicity of the virus, its site of replication, the kind of immune response it elicits, the potential it has to express foreign antigens, its suitability for genetic engineering, its probability of being licensed by regulatory agencies, etc, are all factors in the selection. The prior art does not teach these questions of utility.

The prior art relating to the use of poxviruses to deliver therapeutic agents relates to the use of a vaccinia virus to deliver interleukin-2 (12). In this case, although the interleukin-2 had an attenuating effect on the vaccinia vector, the host did not demonstrate any therapeutic benefit.

The therapeutic agent that is delivered by a viral vector of the present invention must be a biological molecule that is a by-product of swinepox virus replication. This limits the therapeutic agent in the first analysis to either DNA, RNA or protein. There are examples of therapeutic agents from each of these classes of compounds in the form of anti-sense DNA, anti-sense RNA (16), ribozymes (34), suppressor tRNAs (2), interferon-inducing double stranded RNA and numerous examples of protein therapeutics, from hormones, e.g., insulin, to lymphokines, e.g., interferons and interleukins, to natural opiates. The discovery of these therapeutic agents and the elucidation of their structure and function does not make obvious the ability to use them in a viral vector delivery system.

SUMMARY OF THE INVENTION

This invention provides a recombinant swinepox virus comprising a foreign DNA sequence inserted into the swinepox virus genomic DNA, wherein the foreign DNA sequence is inserted within a HindIII K fragment of the swinepox virus genomic DNA and is capable of being expressed in a swinepox virus infected host cell.

The invention further provides homology vectors, vaccines and methods of immunization.

BRIEF DESCRIPTION OF THE INVENTION

FIGS. 1A–1B:

Show a detailed diagram of SPV genomic DNA (Kasza strain) including the unique long and Terminal repeat (TR) regions. A restriction map for the enzyme HindIII is indicated (23). Fragments are lettered in order of decreasing size. Note that the terminal repeats are greater than 2.1 kb but less than 9.7 kb in size.

FIGS. 2A–2B:

Show the DNA sequence from homology vector 515-85.1. The sequence of two regions of the homology vector 515-85.1 are shown. The first region (FIG. 2A) (SEQ ID NO:1) covers a 599 base pair sequence which flanks the unique AccI site as indicated in FIGS. 3A–3C. The beginning (Met) and end (Val) of a 115 amino acid ORF is indicated by the translation of amino acids below the DNA sequence. The second region (FIG. 2B) (SEQ ID NO:3) covers the 899 base pairs upstream of the unique HindIII site as indicated in FIGS. 3A–3C. The beginning (Asp) and end (Ile) of a 220 amino acid ORF is indicated by the translation of amino acids below the DNA sequence.

FIGS. 3A–3C:

Show the homology which exists between the 515.85.1 ORF and the Vaccinia virus 01L ORF. FIG. 3A shows two maps: The first line of FIG. 3A is a restriction map of the SPV HindIII M fragment and the second is a restriction map of the DNA insertion in plasmid 515-85.1. The location of the 515-85.1 [VV 01L-like] ORF is also indicated on the map. The locations of the DNA sequences shown in FIGS. 3B and 3C are indicated below the map by heavy bars in FIG. 3A. FIG. 3B shows the homology between the VV 01L ORF (SEQ ID NO:5) and the 515-85.1 ORF (SEQ ID NO:6) at their respective N-termini. FIG. 3C shows the homology between the VV 01L ORF (SEQ ID NO:7) and the 515-85.1 ORF (SEQ ID NO:8) at their respective C-termini.

Figure 4A:
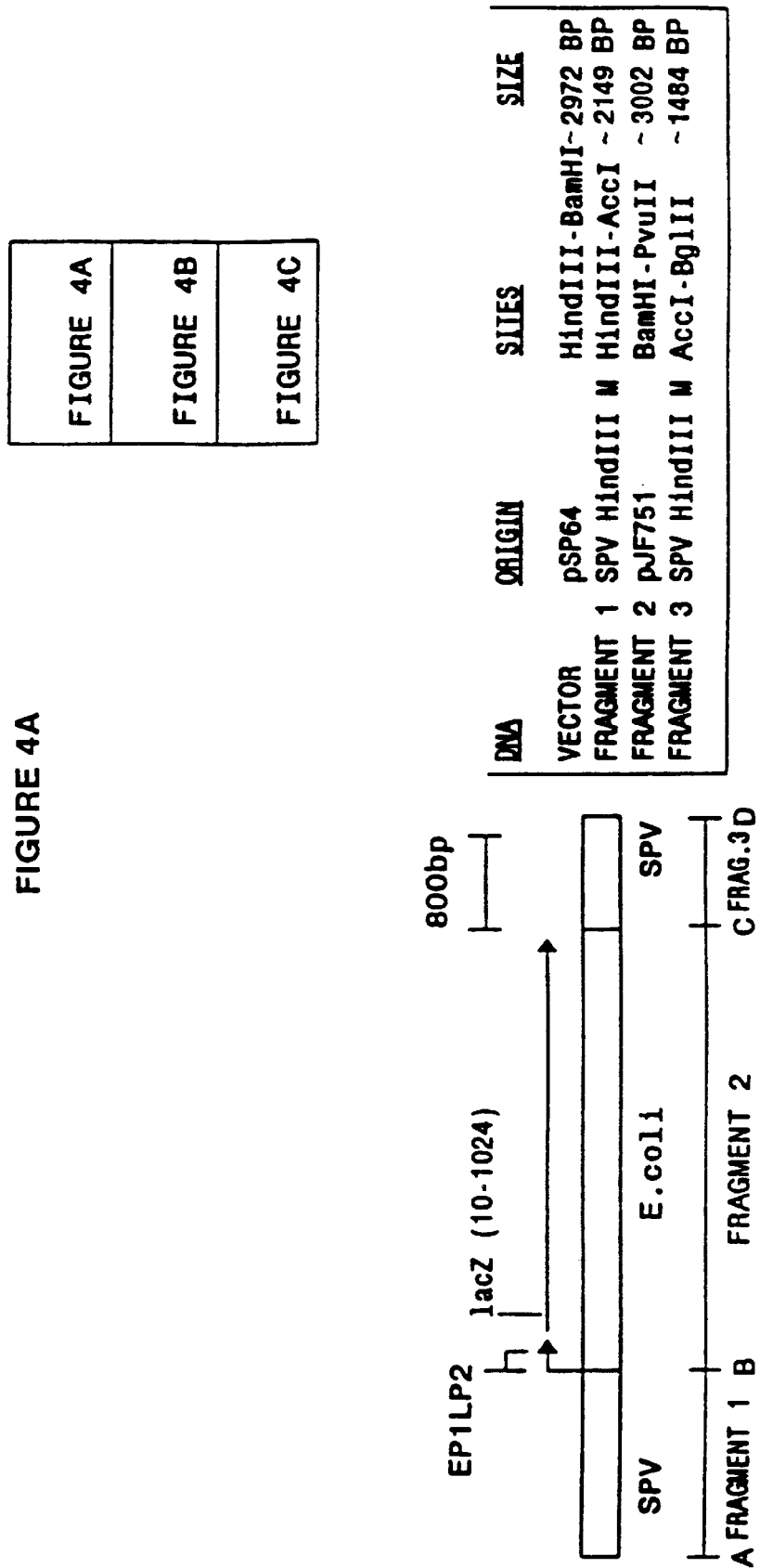
Figure 4B:
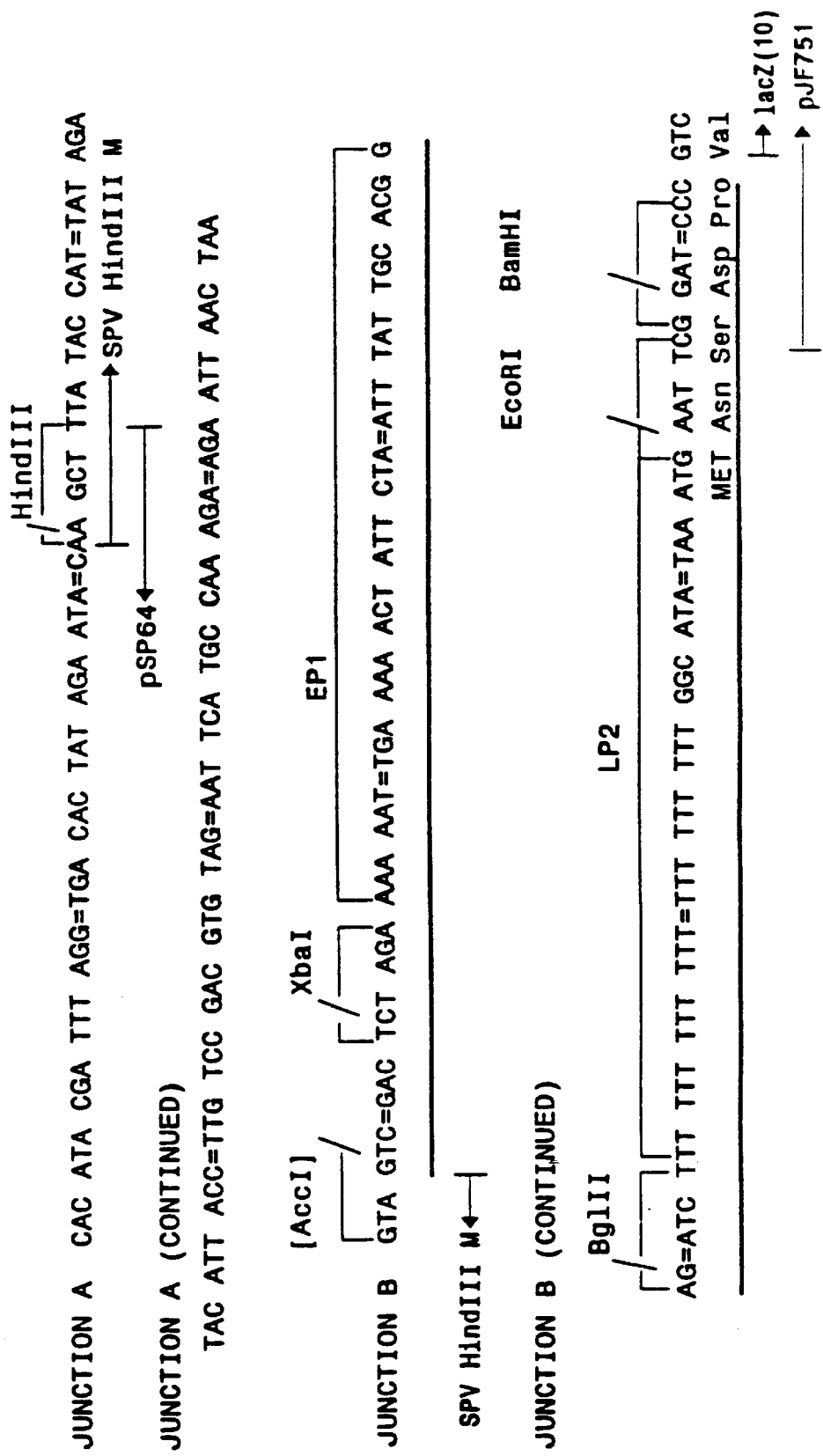
Figure 4C:
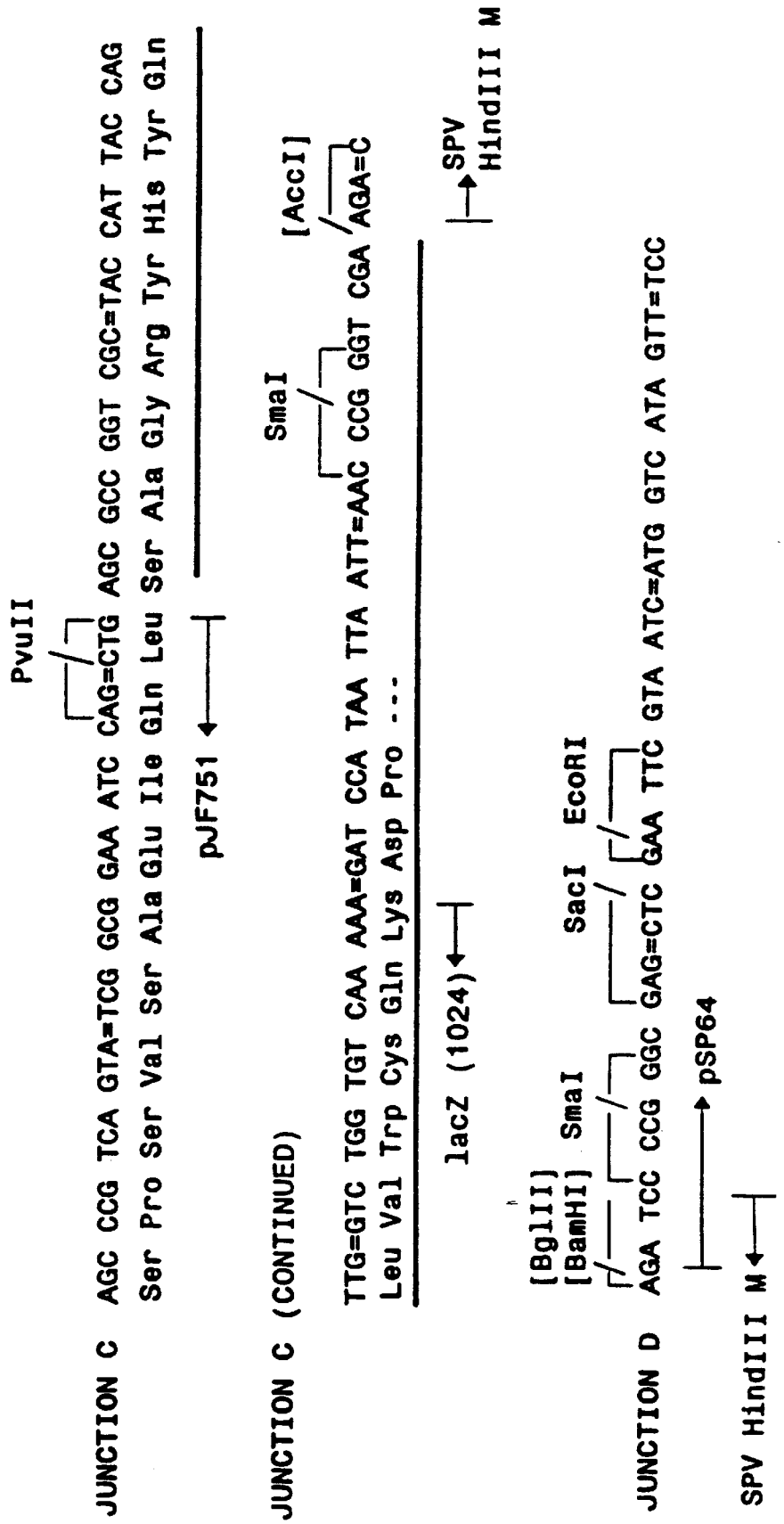

FIGS. 4A–4C:

Show a description of the DNA insertion in Homology Vector 520-17.5. FIG. 4A contains a diagram showing the orientation of DNA fragments assembled in plasmid 520-17.5 and table indicating the origin of each fragment. FIG. 4B shows the sequences located at each of the junctions A and B between fragments, and FIG. 4C shows the sequences located at Junctions C and D (SEQ ID NO's: 9, 10, 13, and 16). FIGS. 4B and 4C further describe the restriction sites used to generate each fragment as well as the synthetic linker sequences which were used to join the fragments are described for each junction. The synthetic linker sequences are underlined by a heavy bar. The location of several gene coding regions and regulatory elements are also given. The following two conventions are used: numbers in parenthesis ( ) refer to amino acids, and restriction sites in brackets [ ] indicate the remnants of sites which were destroyed during construction. The following abbreviations are used, swinepox virus (SPV), early promoter 1 (EP1), late promoter 2 (LP2), lactose operon Z gene (lacZ), and *Escherichia coli* (*E. coli*).

Figure 5B:
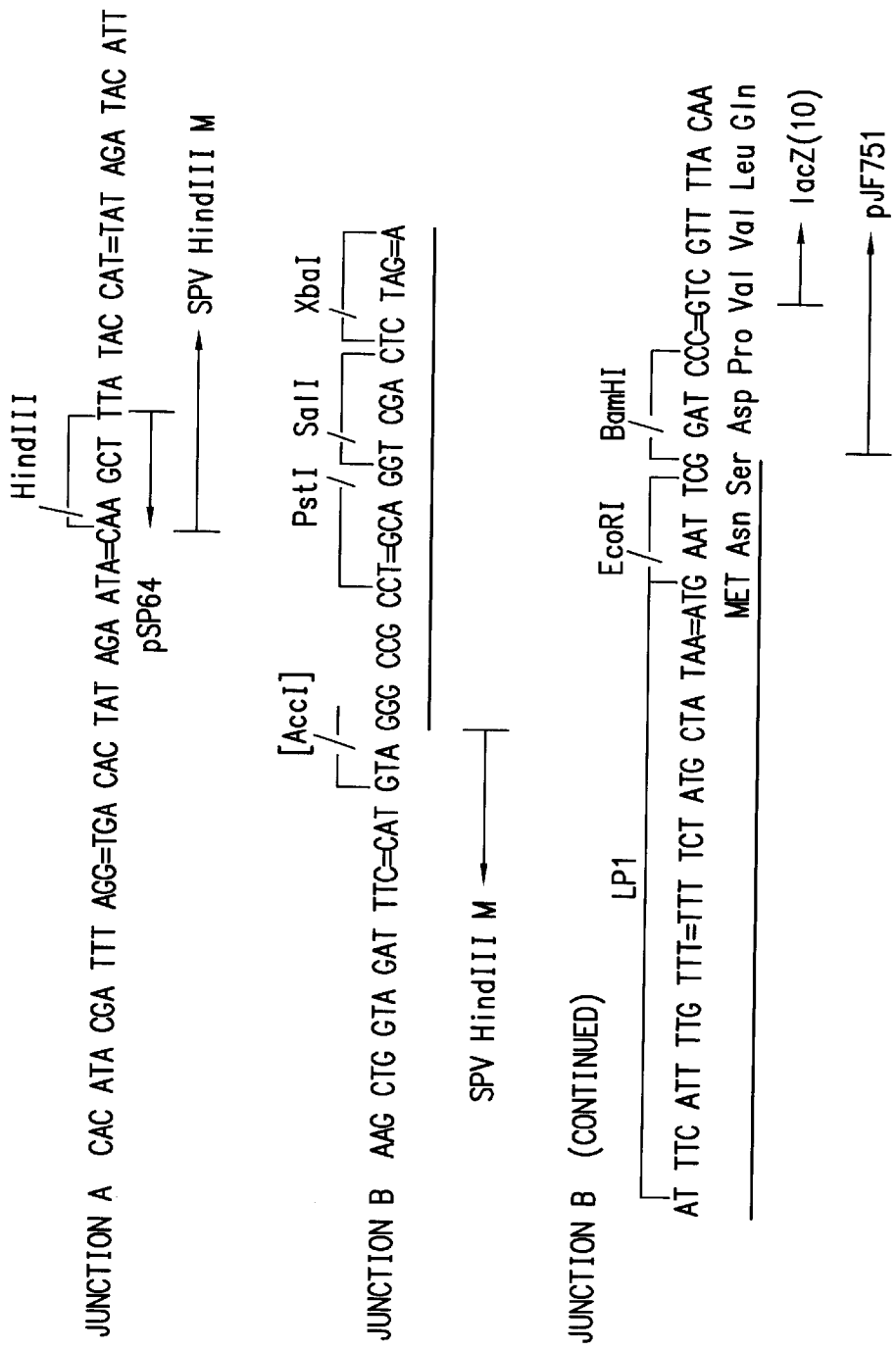
Figure 5C:
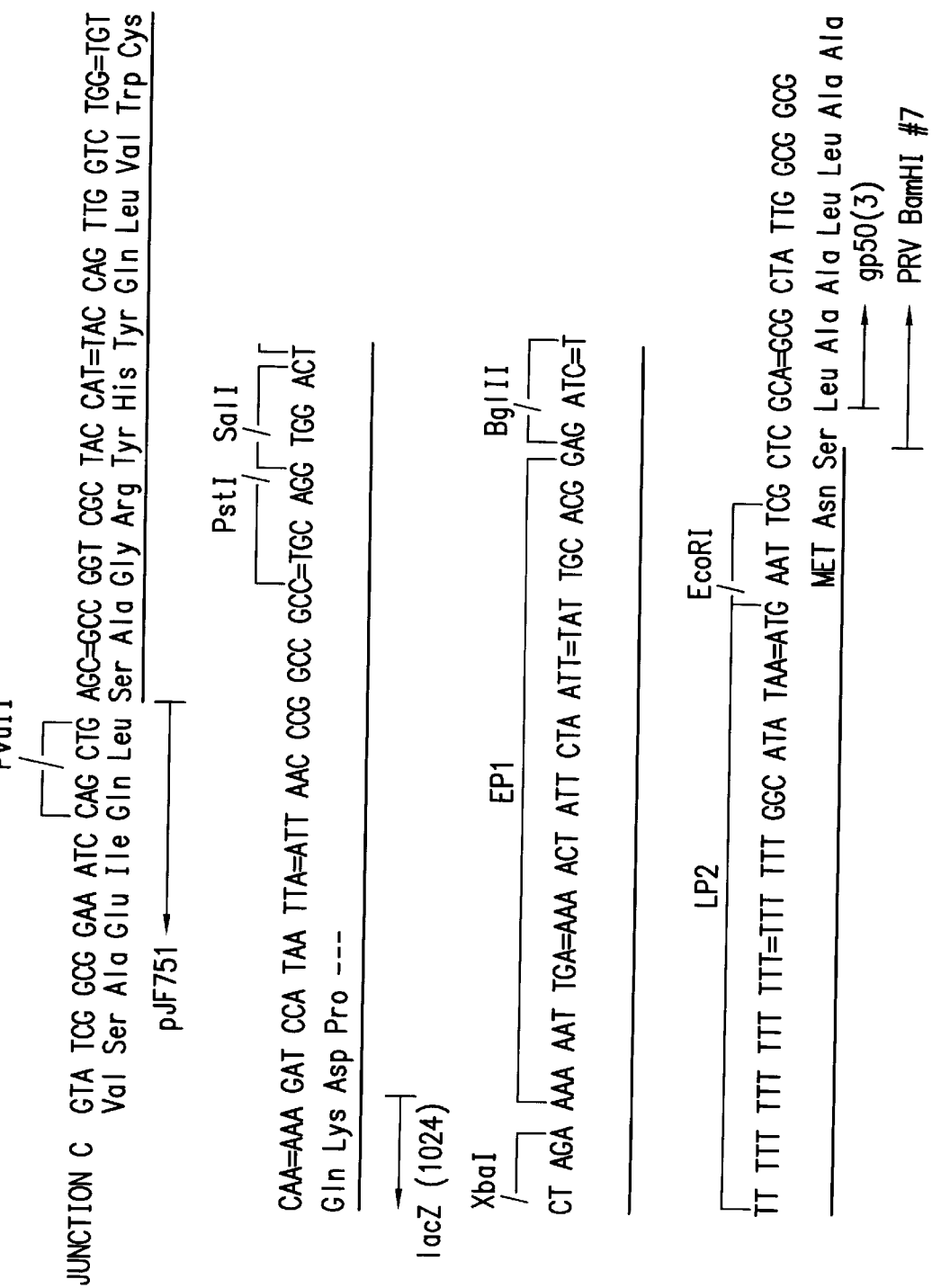

FIGS. 5A–5D:

Show a detailed description of the DNA insertion in Homology Vector 538-46.16. FIG. 5A contains a diagram showing the orientation of DNA fragments assembled in plasmid 538-46.16 and a table indicating the origin of each fragment. FIG. 5B shows the sequences located at Junctions A and B between fragments, FIG. 5C shows sequences located at Junction C and FIG. 5D shows sequences located at Junctions D and E (SEQ ID NO's: 17, 18, 21, 26, and 28). FIGS. 5B to 5D also describe the restriction sites used to generate each fragment as well as the synthetic linker sequences which were used to join the fragments are described for each junction. The synthetic linker sequences are underlined by a heavy bar. The location of several gene coding regions and regulatory elements is also given. The following two conventions are used: numbers in parenthesis ( ) refer to amino acids, and restriction sites in brackets [ ] indicate the remnants of sites which were destroyed during construction. The following abbreviations are used, swinepox virus (SPV), pseudorabies virus (PRV), g50 (gD), glycoprotein 63 (g63), early promoter 1 (EP1), late promoter 1 (LP1) (SEQ ID NO: 46), late promoter 2 (LP2), lactose operon Z gene (lacZ), and *Escherichia coli* (*E. coli*).

Figure 10A:
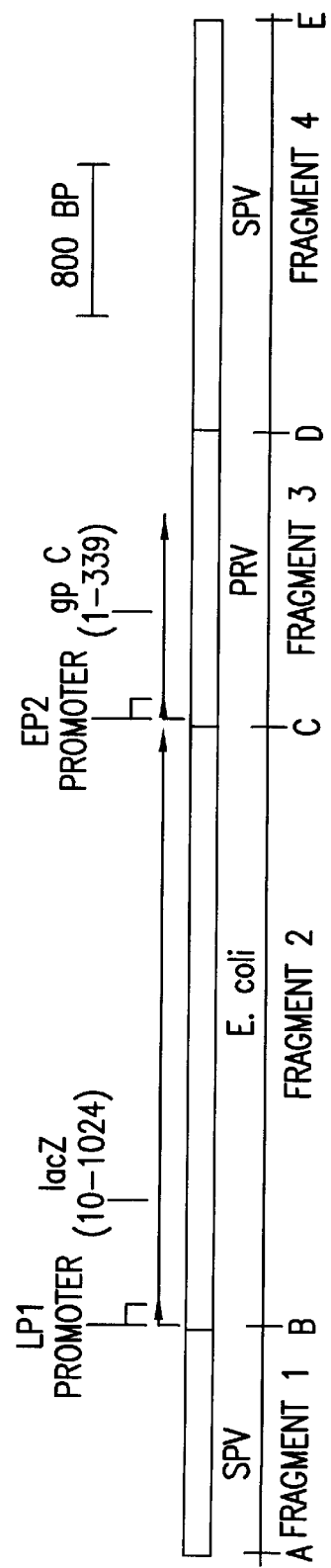
Figure 10C:
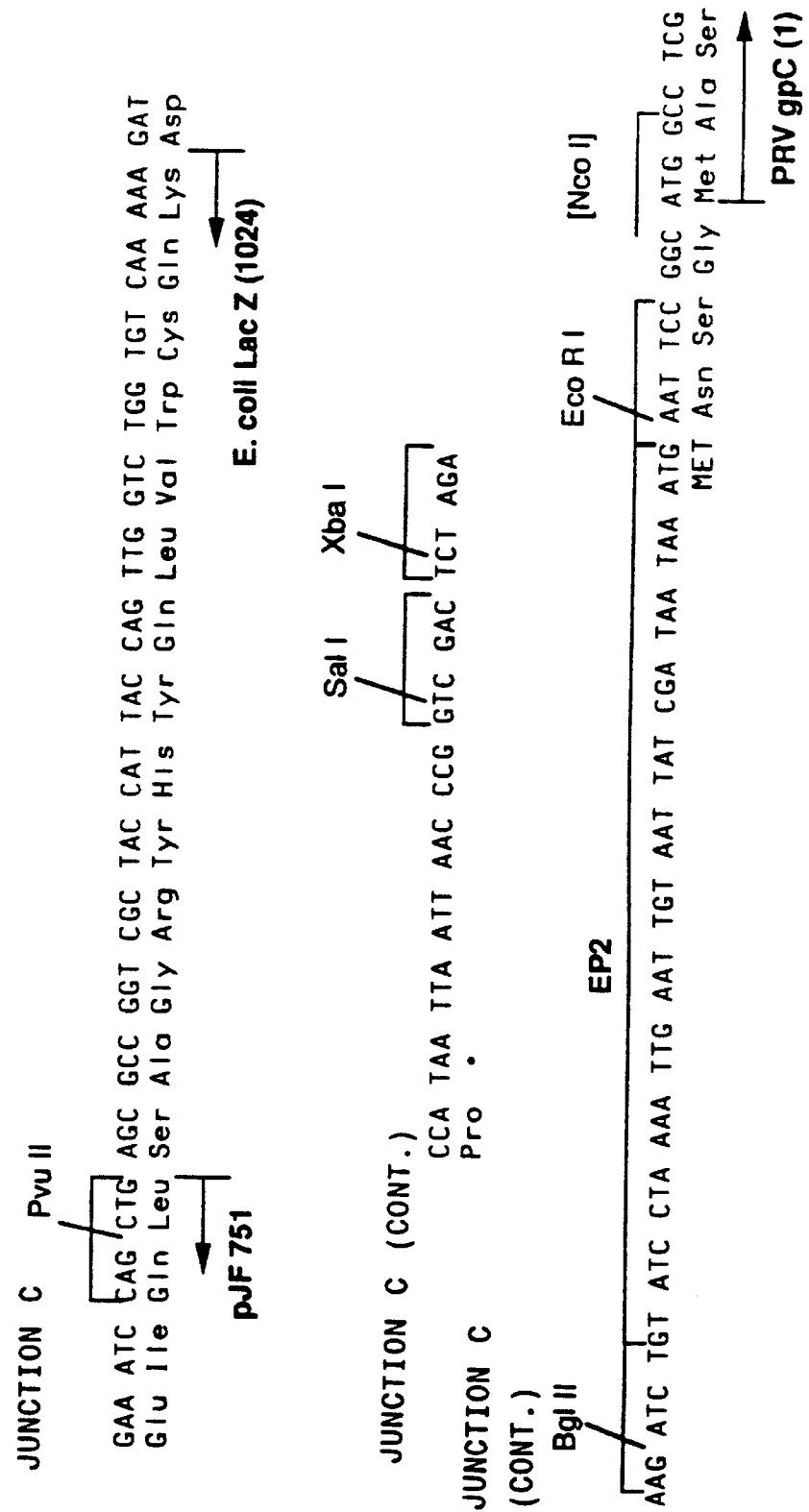

FIG. 6:

Western blot of lysates from recombinant SPV infected cells with anti-serum to PRV. Lanes (A) uninfected Vero cell lysate, (B) S-PRV-000 (pseudorabies virus S62/26) infected cell lysate, (C) pre-stained molecular weight markers, (D) uninfected EMSK cell lysate, (E) S-SPV-000 infected cell lysate, (F) S-SPV-003 infected cell lysate, (G) S-SPV-008 infected cell lysate. Cell lysates were prepared as described in the PREPARATION OF INFECTED CELL LYSATES. Approximately ⅕ of the total lysate sample was loaded in each lane.

FIG. 7:

DNA sequence of NDV Hemagglutinin-Neuraminidase gene (HN) (SEQ ID NO: 29). The sequence of 1907 base pairs of the NDV HN cDNA clone are shown. The translational start and stop of the HN gene is indicated by the amino acid translation below the DNA sequence.

FIGS. 8A–8D:

Show a detailed description of the DNA insertion in Homology Vector 538-46.26. FIG. 5A contains a diagram showing the orientation of DNA fragments assembled in plasmid 538-46.26 and table indicating the origin of each fragment. FIG. 8B shows the sequences located at Junctions A and B between fragments; FIG. 8C shows the sequences located at Junctions C and D, FIG. 8D shows the sequences located at Junction E (SEQ ID NO's: 31, 32, 34, 37, and 40). The restriction sites used to generate each fragment as well as the synthetic linker sequences which were used to join the fragments are described for each junction in FIGS. 8B and 8D. The synthetic linker sequences are underlined by a heavy bar. The location of several gene coding regions and regulatory elements is also given. The following two conventions are used: numbers in parenthesis ( ) refer to amino acids, and restriction sites in brackets [ ] indicate the remnants of sites which were destroyed during construction. The following abbreviations are used, swinepox virus (SPV), Newcastle Disease virus (NDV), hemagglutinin-neuraminidase (HN), early promoter 1 (EP1), late promoter 1 (LP1), late promoter 2 (LP2), lactose operon Z gene (lacZ), and *Escherichia coli* (*E. coli*).

FIGS. 9A–9C:

Show a detailed description of Swinepox Virus S-SPV-010 and the DNA insertion in Homology Vector 561-36.26. FIG. 9A contains a diagram showing the orientation of DNA fragments assembled in plasmid 561-36.26 and a table indicating the origin of each fragment. FIG. 9B shows the sequences located at Junctions A and B between fragments and FIG. 9C show the sequences located at junction C and D (SEQ ID NOS: 47, 48, 50, 52). The restriction sites used to generate each fragment as well as synthetic linker sequences which are used to join the fragments are described for each junction in FIGS. 9B and 9C. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), *Escherichia coli* (*E. coli*), thymidine kinase (TK), pox synthetic late promoter 1 (LP1), base pairs (BP).

FIGS. 10A–10B:

Show a detailed description of Swinepox Virus S-SPV-011 and the DNA insertion in Homology Vector 570-91.21. FIG. 10A contains a diagram showing the orientation of DNA fragments assembled in plasmid 570-91.21 and a table indicating the origin of each fragment. FIG. 10B show the sequences located at Junctions A and B between fragments; FIG. 10C shows the sequences located at Junction C, and FIG. 10D shows the sequences located at Junctions 10D and 10E (SEQ ID NOS: 53, 54, 56, 59, 60). The restriction sites used to generate each fragment as well as synthetic linker sequences which are used to join the fragments are described for each junction in FIGS. 10B to 10D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), Escherichia coli (E. coli), pox synthetic late promoter 1 (LP1), pox synthetic early promoter 2 (EP2) (SEQ ID NO: 45), gIII (gC), base pairs (BP).

Figure 11A:
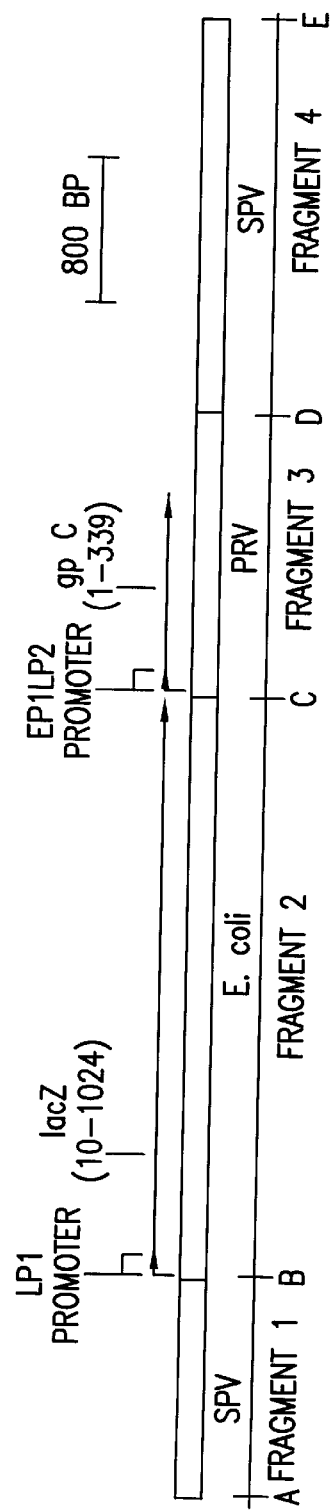

FIGS. 11A–11D:

Show a detailed description of Swinepox Virus S-SPV-012 and the DNA insertion in Homology Vector 570-91.41. FIG. 11A contains a diagram showing the orientation of DNA fragments assembled in plasmid 570-91.41 and a table indicating the origin of each fragment. FIG. 11B shows the sequences located at Junctions A and B between fragments, FIG. 11C shows the sequences located at Junction C, and FIG. 11D shows the sequences located at Junctions D and E (SEQ ID NOS: 61, 62, 64, 67, 68). The restriction sites used to generate each fragment as well as synthetic linker sequences which are used to join the fragments are described for each junction in FIGS. 11B to 11D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), Escherichia coli (E. coli), pox synthetic late promoter 1 (LP1), pox synthetic early promoter 1 late promoter 2(EP1LP2) (SEQ ID NO: 43), gIII (gC), base pairs (BP).

Figure 12A:
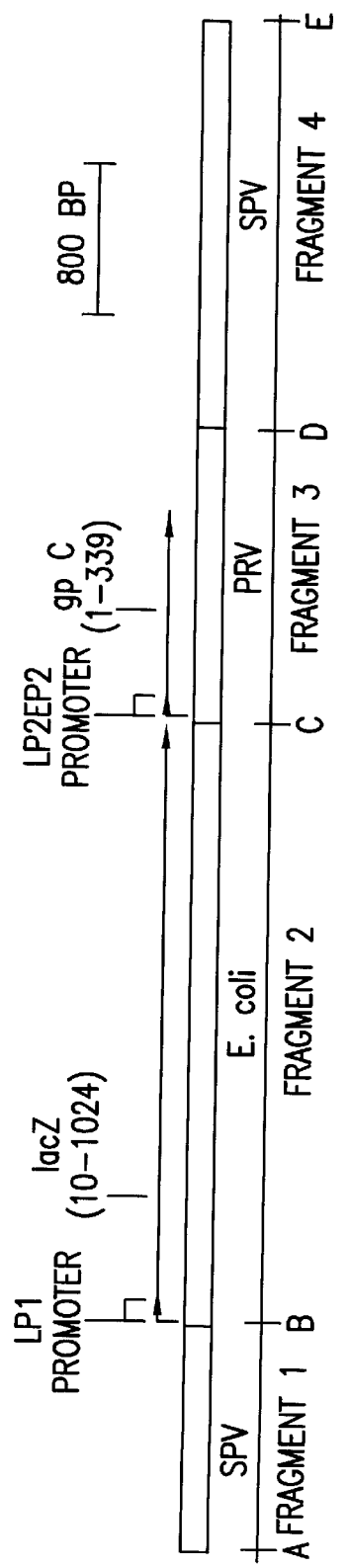
Figure 12B:
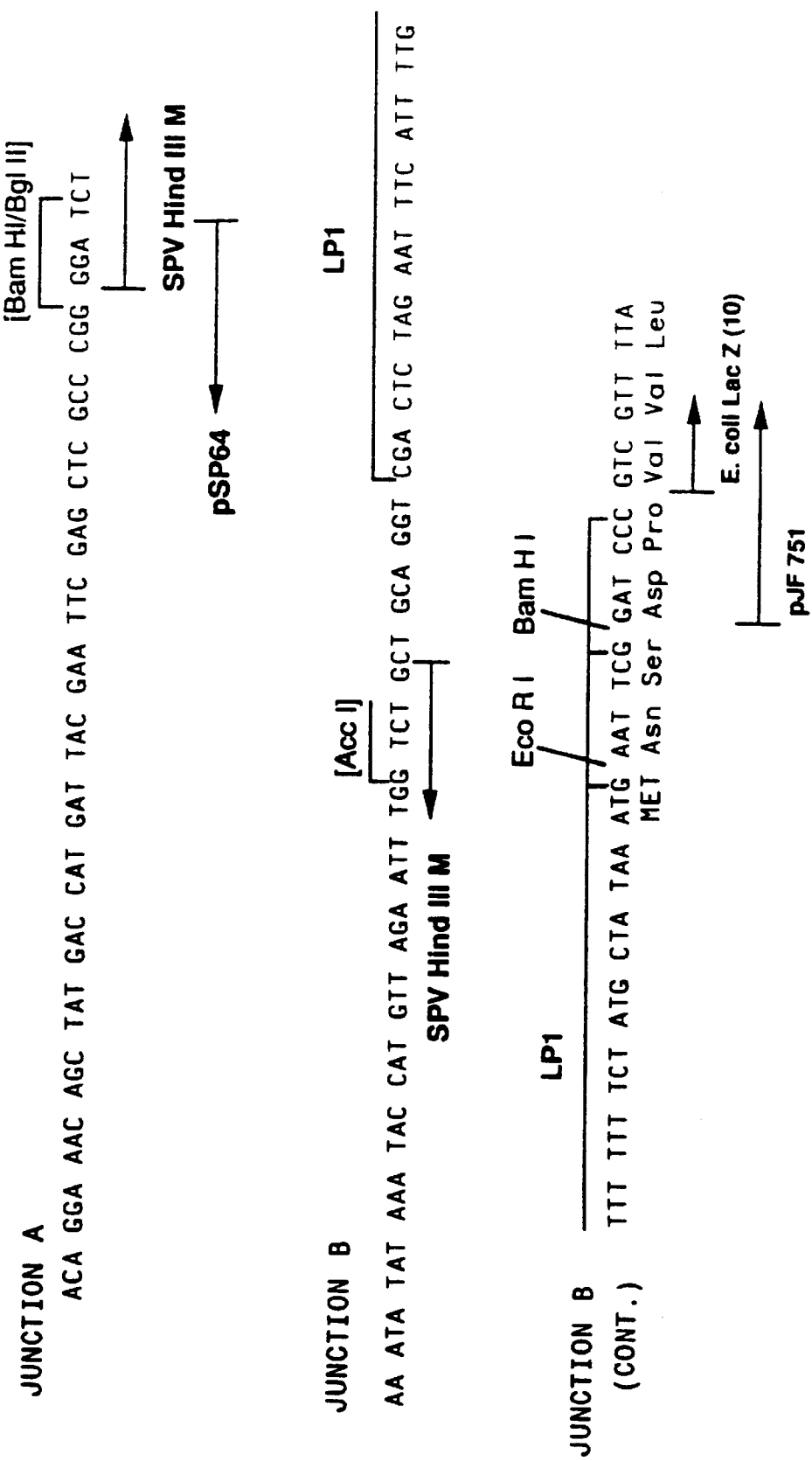

FIGS. 12A–12D:

Show a detailed description of Swinepox Virus S-SPV-013 and the DNA insertion in Homology Vector 570-91.64. FIG. 12A contains a diagram showing the orientation of DNA fragments assembled in plasmid 570-91.64 and a table indicating the origin of each fragment. FIG. 12B shows the sequences located at Junctions A and B between fragments, FIG. 12C shows the sequences located at Junction C, and FIG. 12D shows the sequences located at Junctions D and E (SEQ ID NOS: 69, 70, 72, 75, 76). The restriction sites used to generate each fragment as well as synthetic linker sequences which are used to join the fragments are described for each junction in FIGS. 12B to 12D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), Escherichia coli (E. coli), pox synthetic late promoter 1 (LP1), pox synthetic late promoter 2 early promoter 2(LP2EP2) (SEQ ID NO: 44), gIII (gC), base pairs (BP).

Figure 13A:
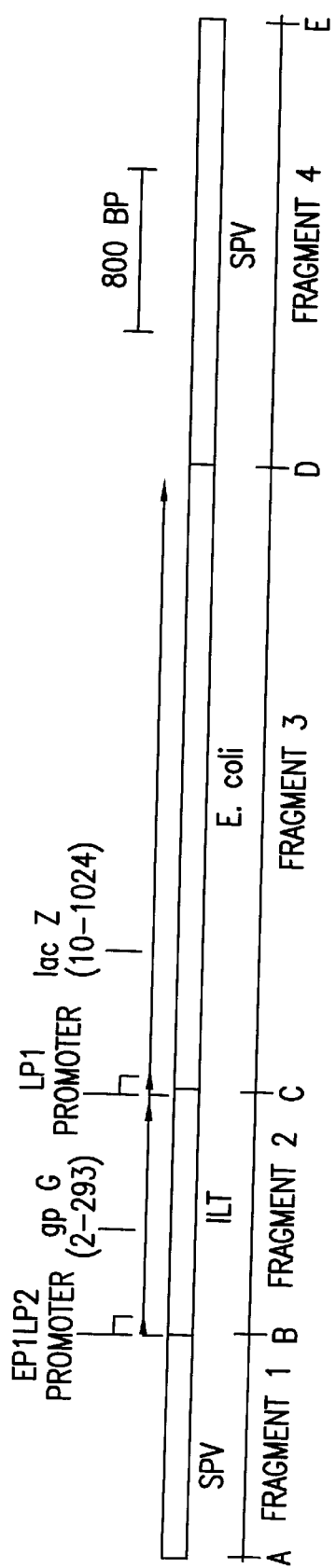
Figure 13B:
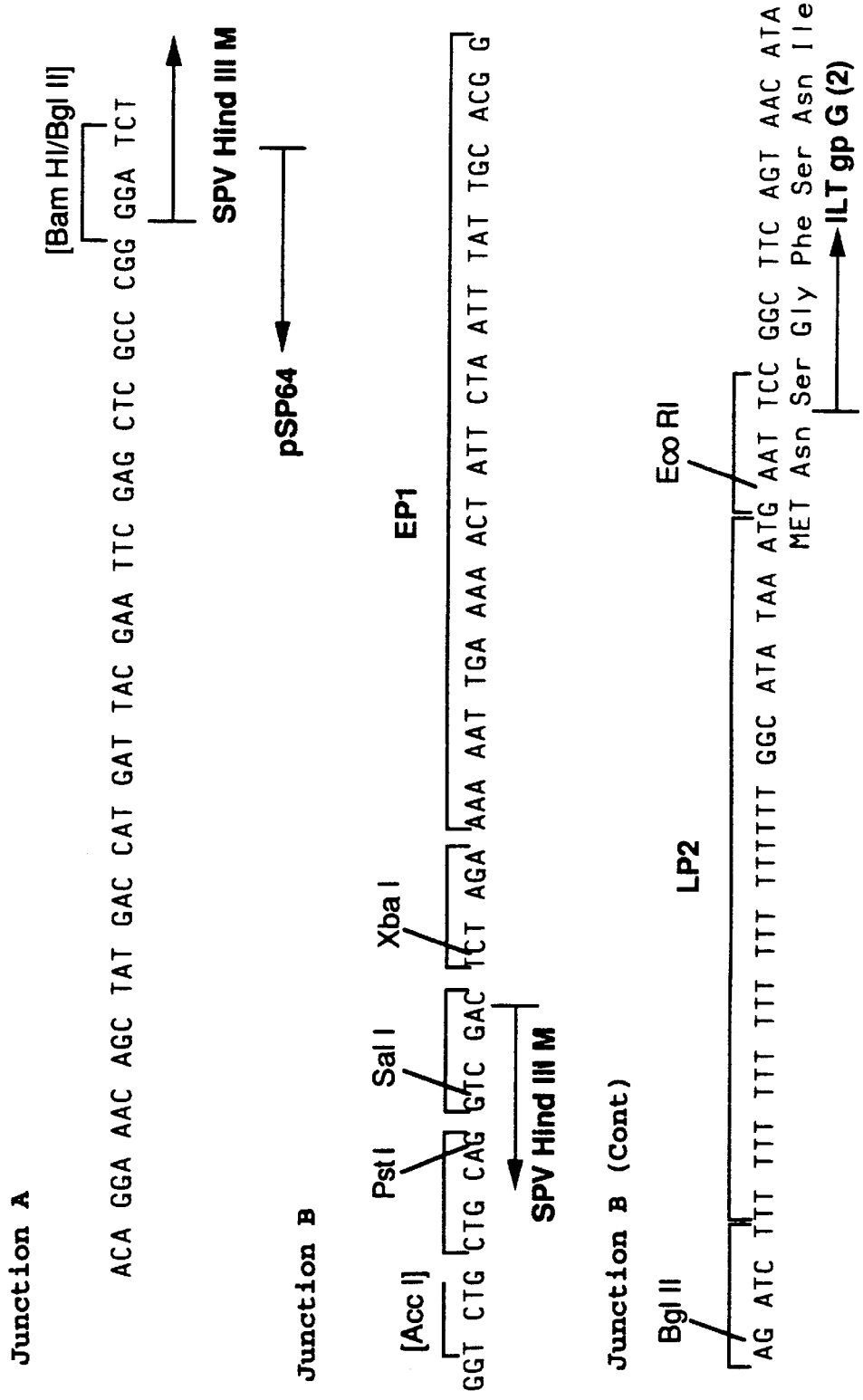
Figure 13C:
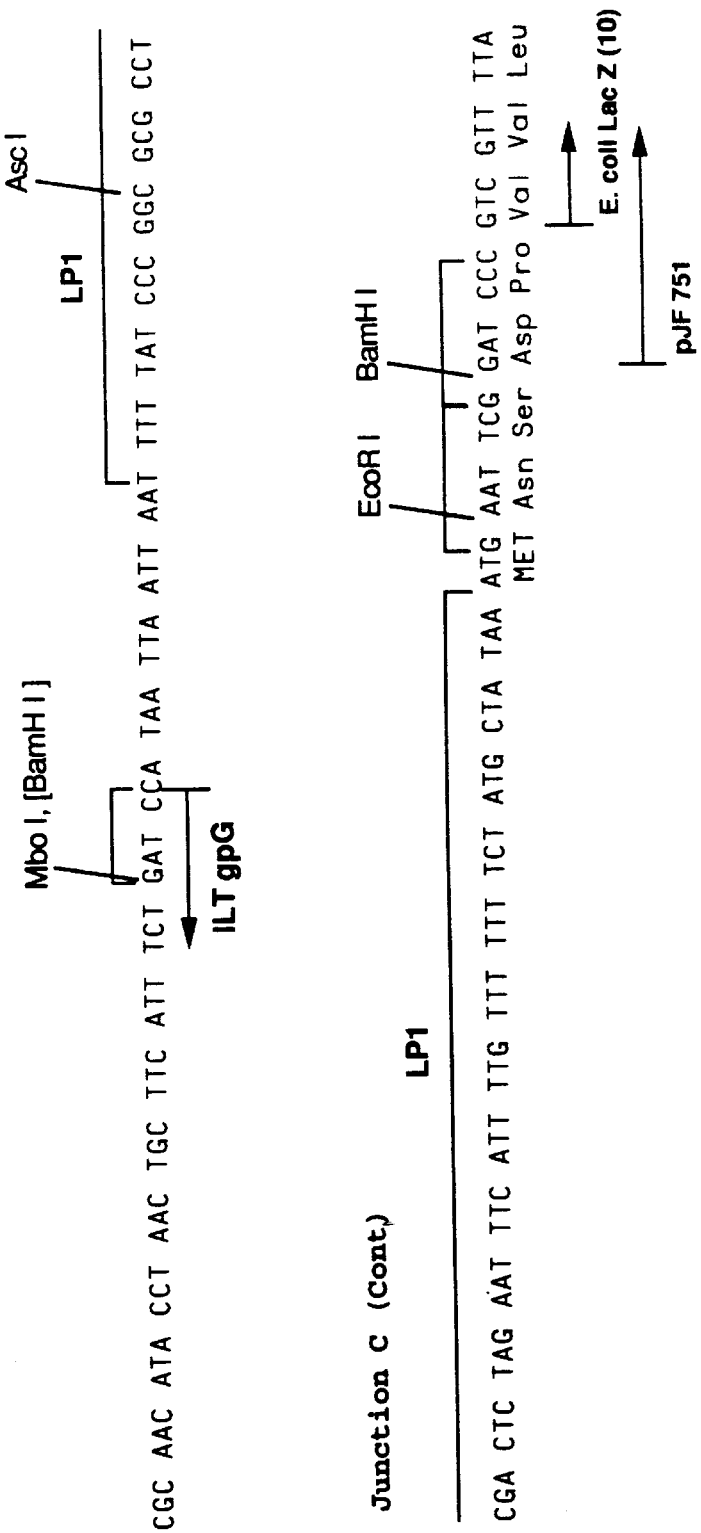
Figure 13D:
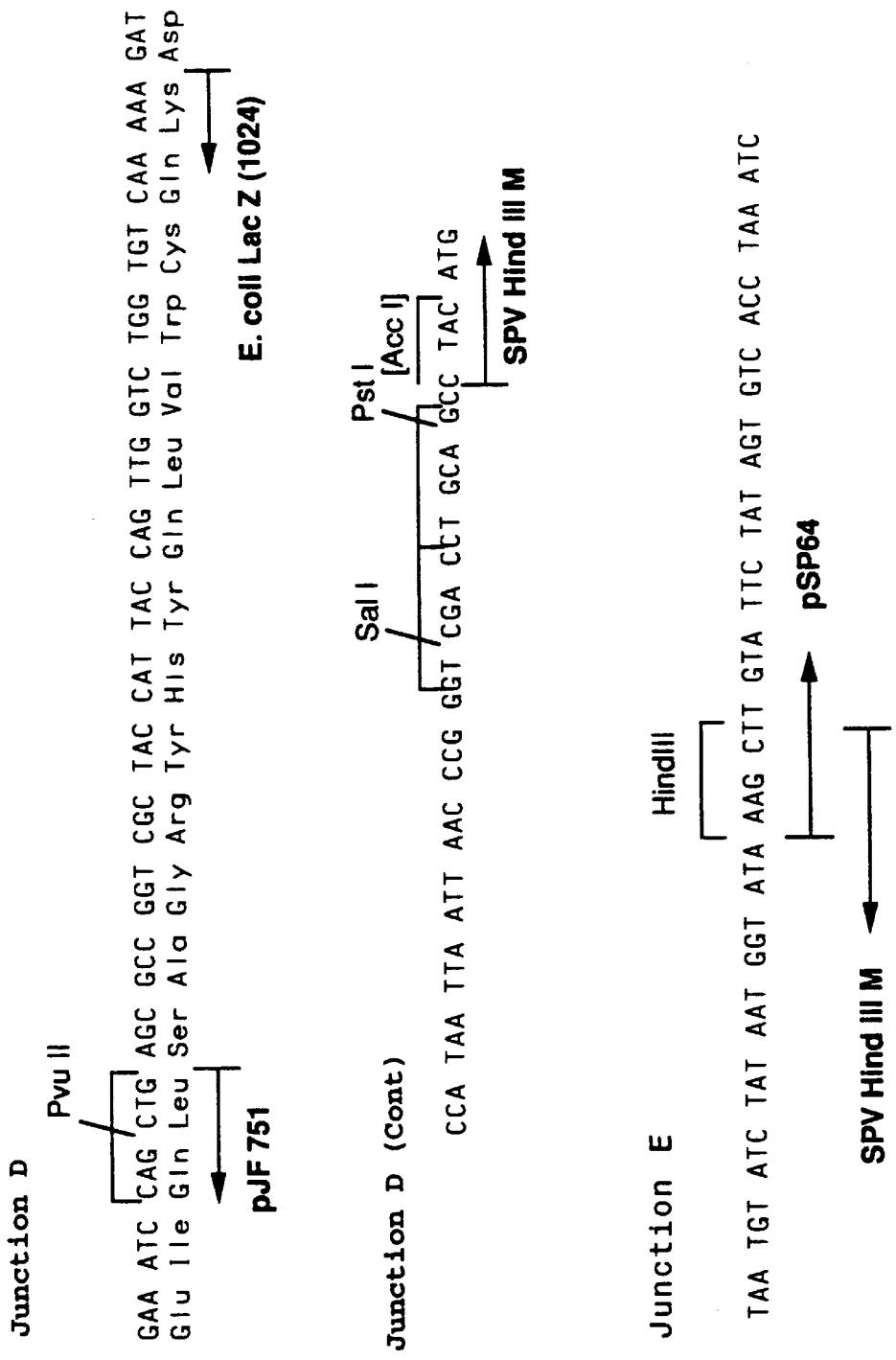

FIGS. 13A–13D:

Show a detailed description of Swinepox Virus S-SPV-014 and the DNA insertion in Homology Vector 599-65.25. FIG. 13A contains a diagram showing the orientation of DNA fragments assembled in plasmid 599-65.25 and a table indicating the origin of each fragment. FIG. 13B shows the sequences located at Junctions A and B between the fragments, FIG. 13C shows the sequences located at Junction C, and FIG. 13D shows the sequences located at Junctions D and E (SEQ ID NOS: 91, 92, 94, 96, 98). The restriction sites used to generate each fragment as well as synthetic linker sequences which are used to join the fragments are described for each junction in FIGS. 13B to 13D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), infectious laryngotracheitis virus (ILT), Escherichia coli (E. coli), pox synthetic late promoter 1 (LP1), pox synthetic early promoter 1 late promoter 2 (EP1LP2), glycoprotein G (gG), polymerase chain reaction (PCR), base pairs (BP).

Figure 14A:
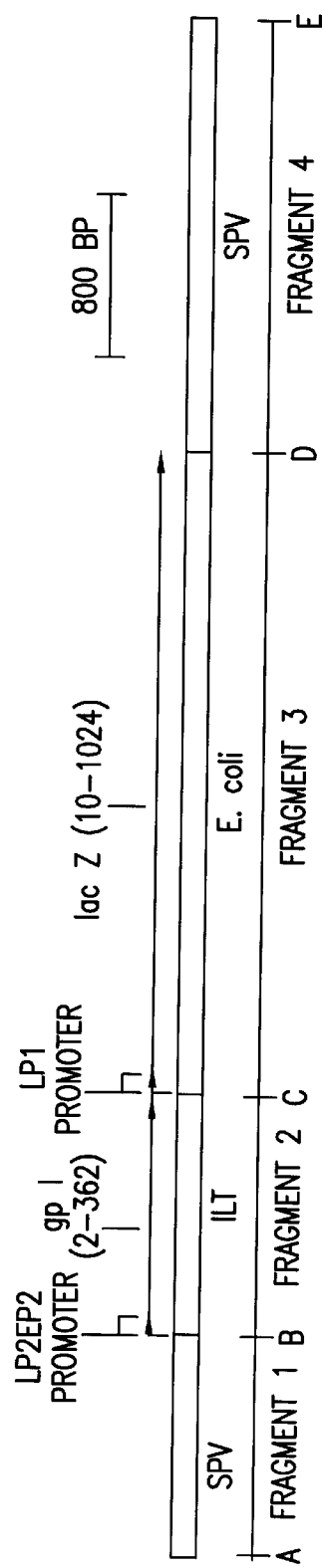
Figure 14B:
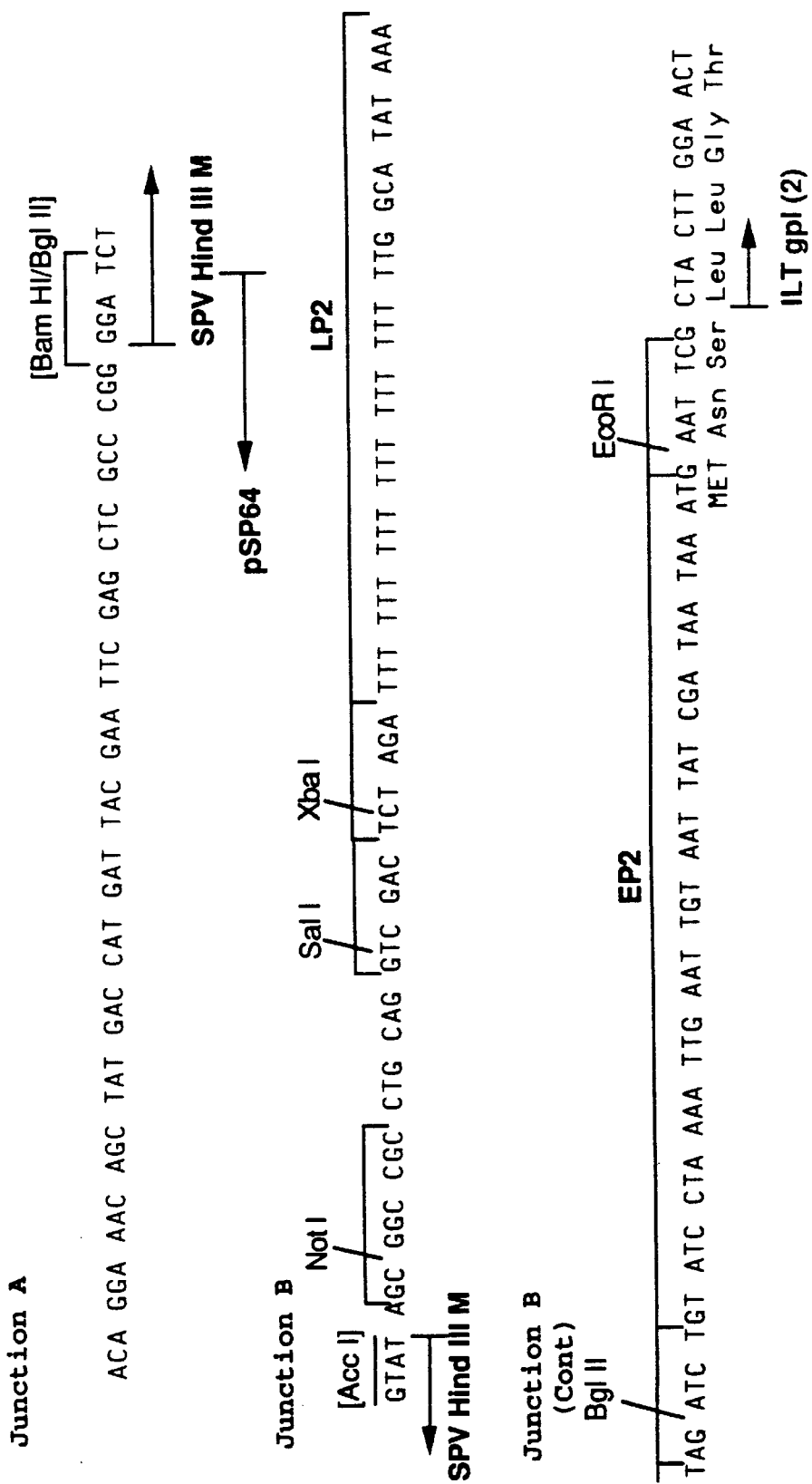
Figure 14C:
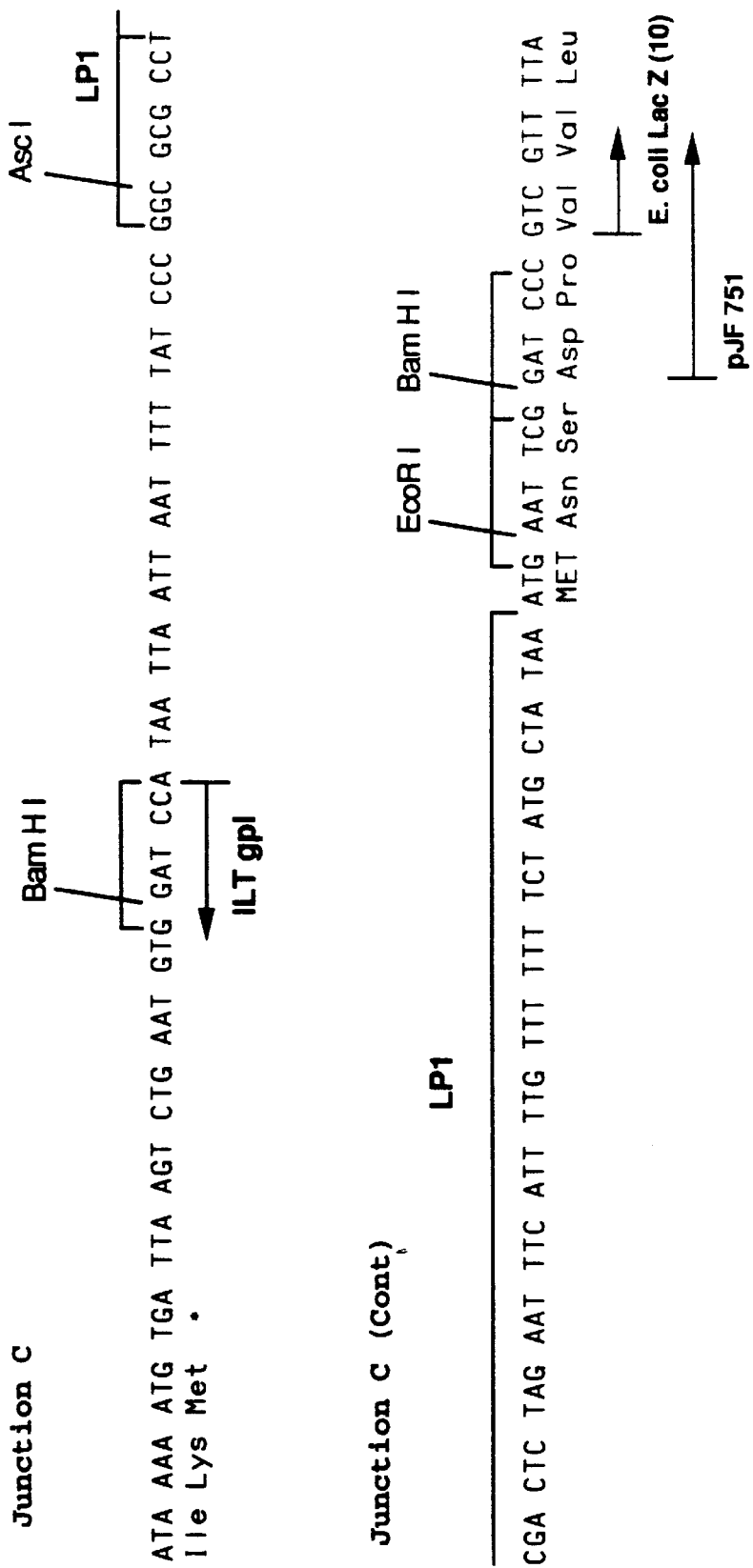
Figure 14D:
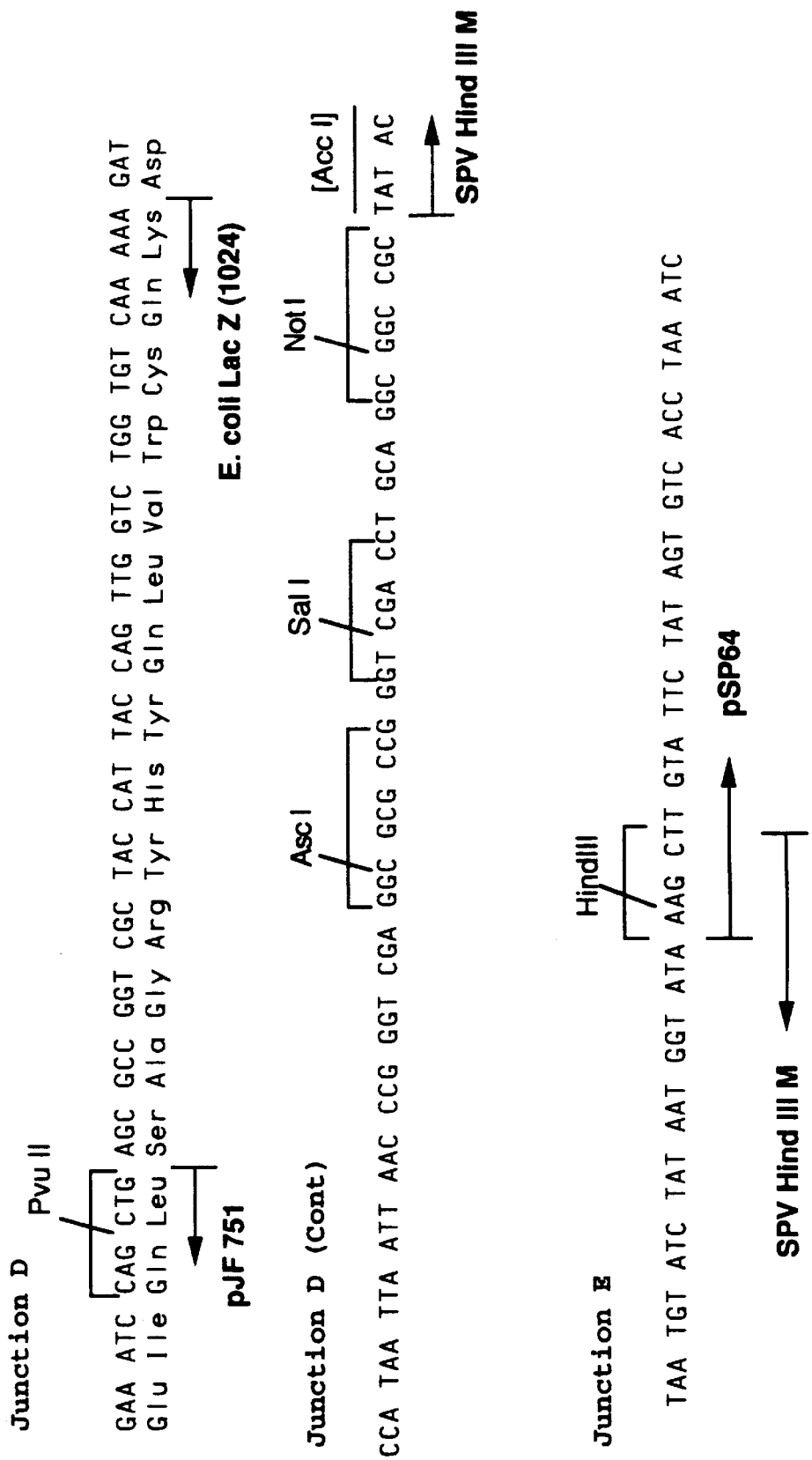

FIGS. 14A–14D:

Show a detailed description of Swinepox Virus S-SPV-016 and the DNA insertion in Homology Vector 624-20.1C. FIG. 14A contains a diagram showing the orientation of DNA fragments assembled in plasmid 624-20.1C and a table indicating the origin of each fragment. FIG. 14B shows the sequences located at Junctions A and B between fragments; FIG. 14C shows the sequences located at Junction C, and FIG. 14D shows the sequences located at Junctions D and E (SEQ ID NOS: 99, 100, 102, 104, 106). The restriction sites are used to generate each fragment as well as synthetic linker sequences which are used to join the fragments are described for each junction in FIGS. 14B to 14D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), infectious laryngotracheitis virus (ILT), Escherichia coli (E. coli), pox synthetic late promoter 1 (LP1), pox synthetic late promoter 2 early promoter 2 (LP2EP2), glycoprotein I (gI), polymerase chain reaction (PCR), base pairs (BP).

Figure 15A:
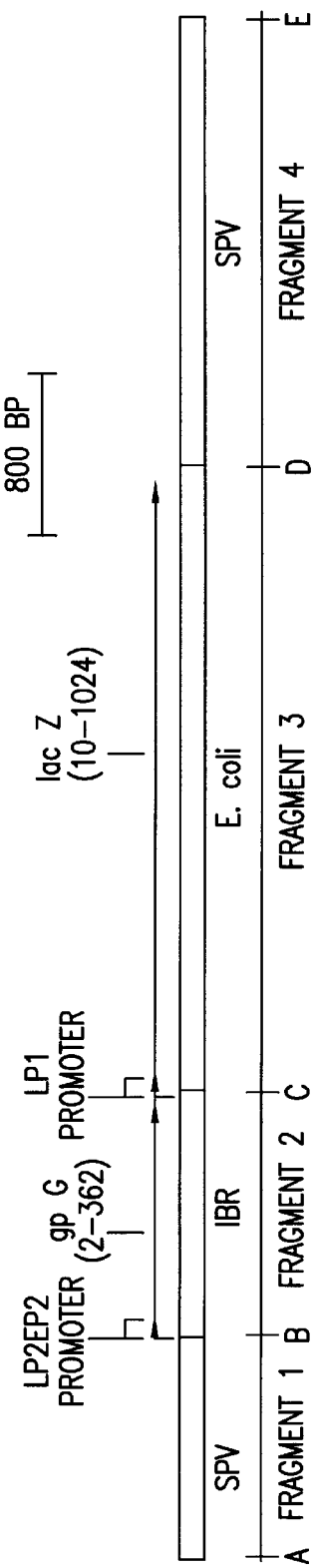
Figure 15B:
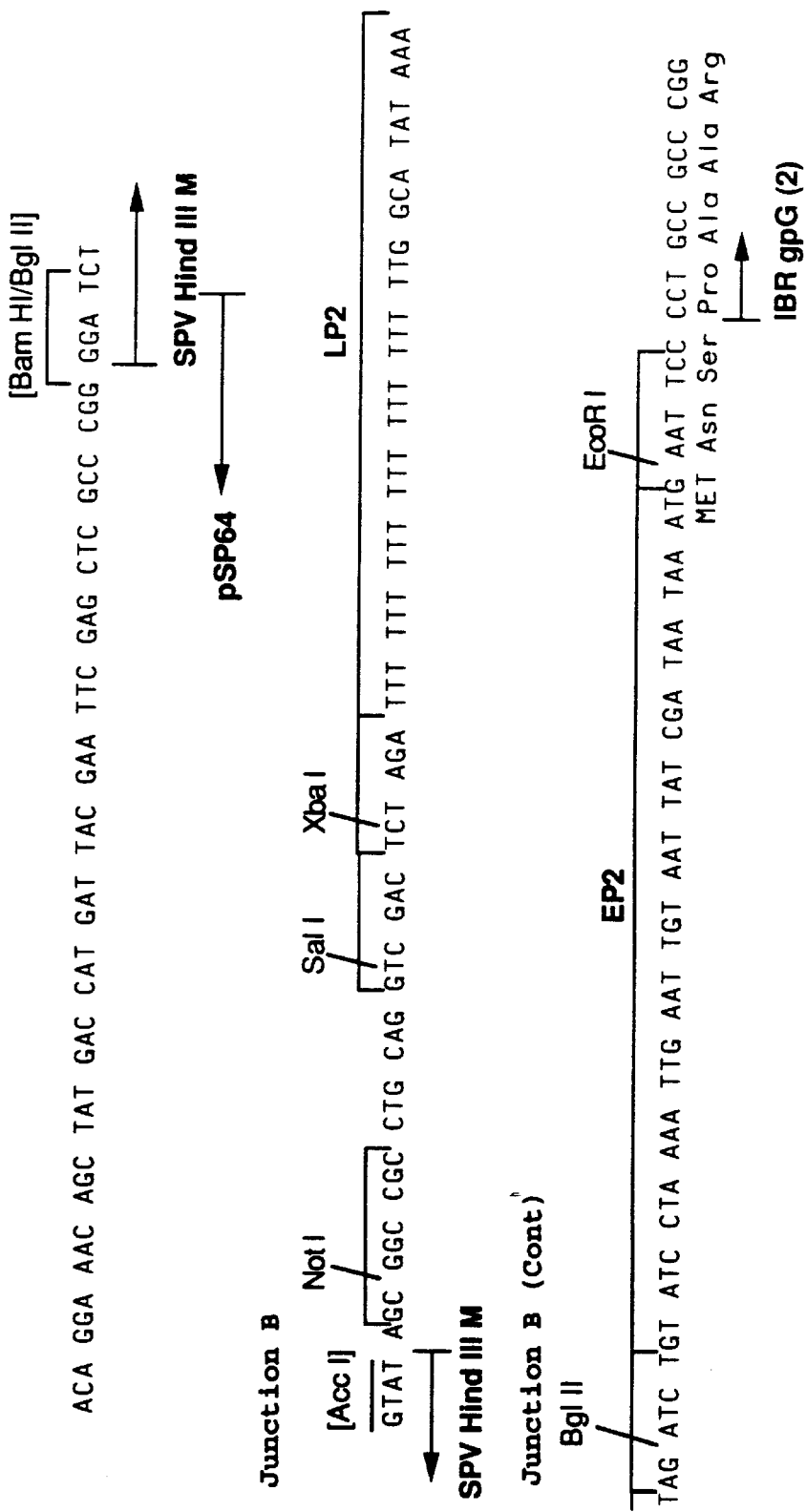
Figure 15C:
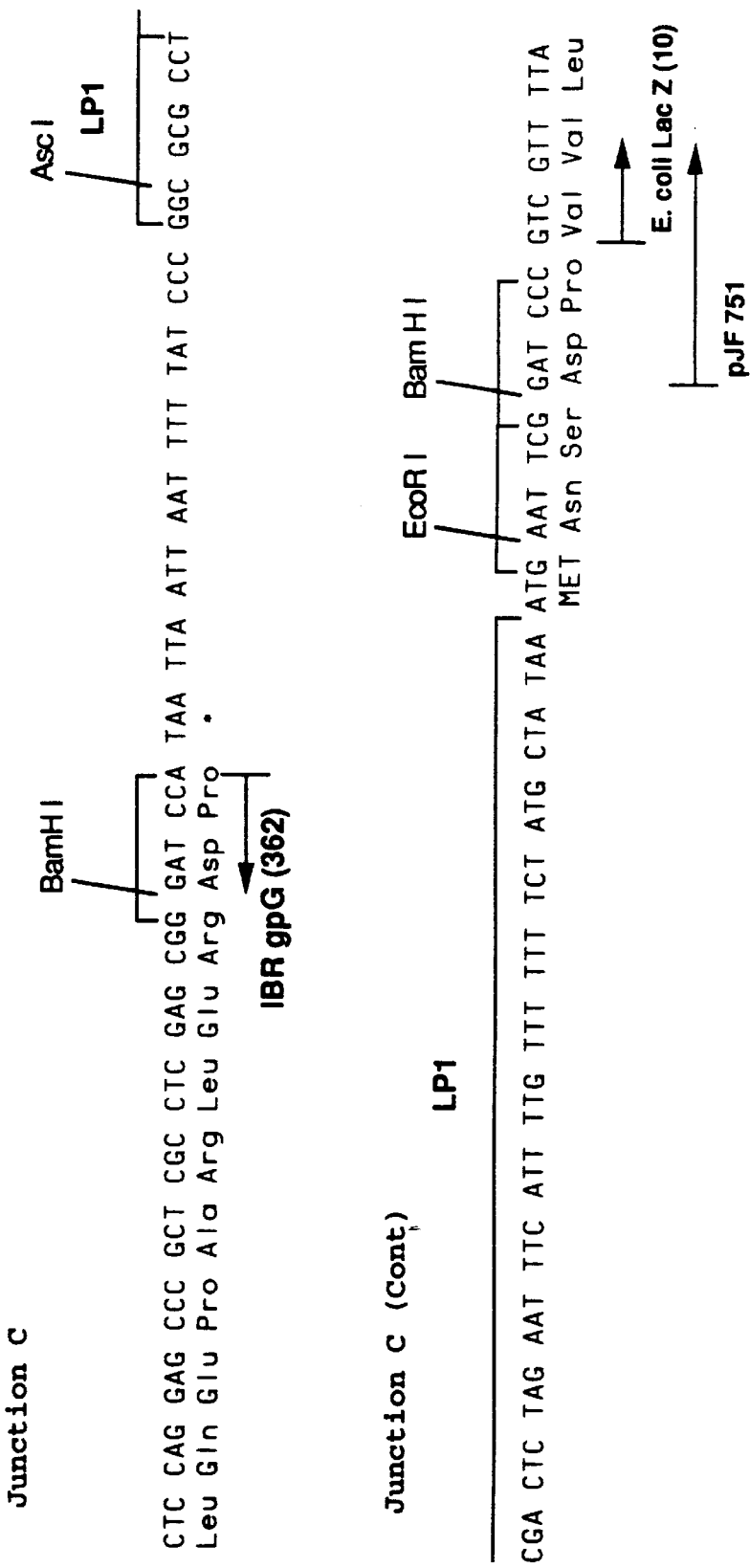
Figure 15D:
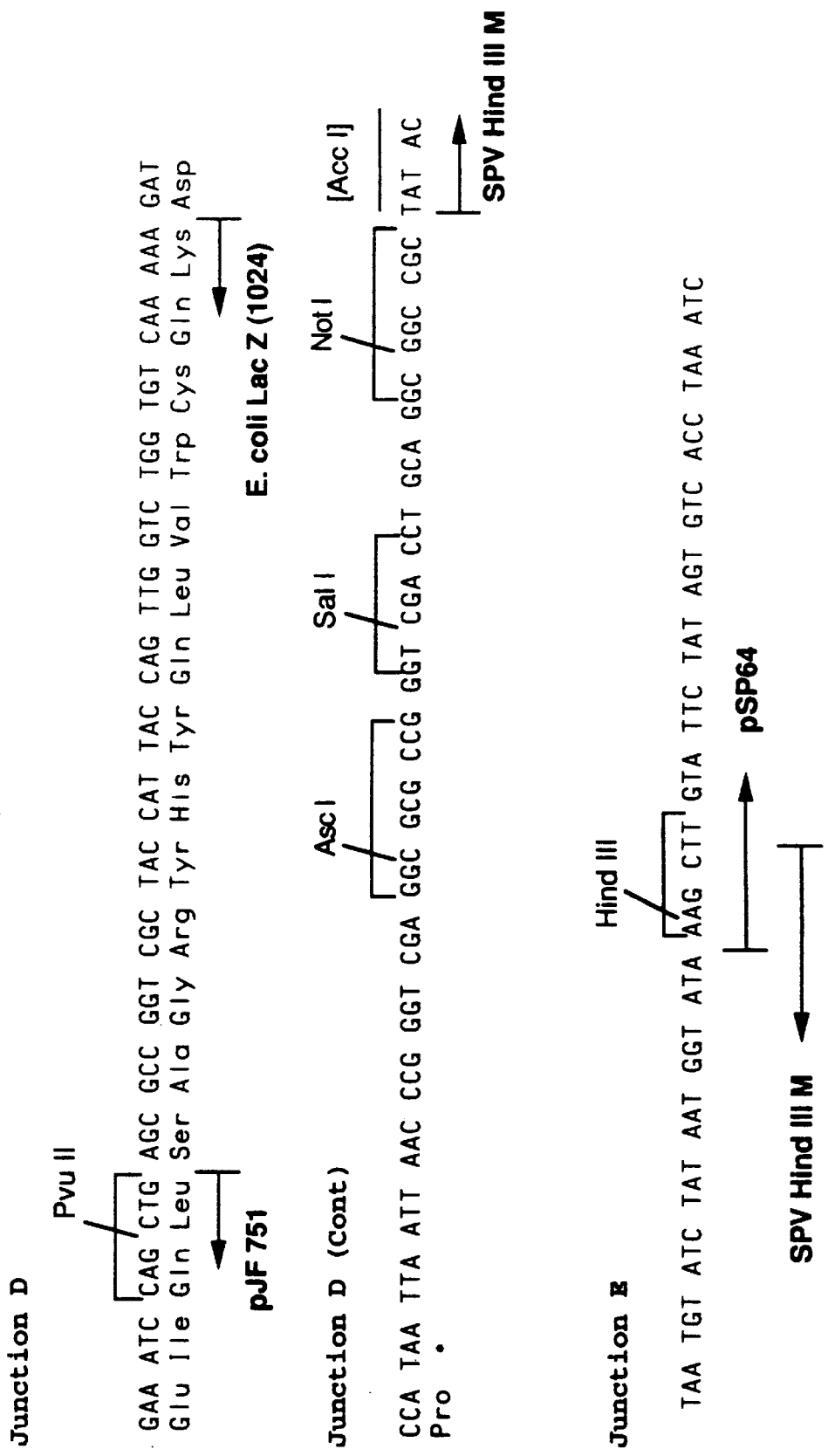

FIGS. 15A–15D:

Show a detailed description of Swinepox Virus S-SPV-017 and the DNA insertion in Homology Vector 614-83.18. FIG. 15A contains a diagram showing the orientation of DNA fragments assembled in plasmid 614-83.18 and a table showing the origin of each fragment. FIG. 15B shows the sequences located at Junctions A and B between fragments, FIG. 15C shows the sequences located at Junction C, and FIG. 15D shows the sequences located at Junctions D and E (SEQ ID NOS: 144, 145, 147, 150, 152). The restriction sites used to generate each fragment as well as synthetic linker sequences which are used to join the fragments are described for each junction in FIGS. 15B to 15D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), infectious bovine rhinotracheitis virus (IBR), Escherichia coli (E. coli), pox synthetic late promoter 1 (LP1), pox synthetic late promoter 2 early promoter 2 (LP2EP2), glycoprotein G (gG), polymerase chain reaction (PCR), base pairs (BP).

FIG. 16:

Western blot of lysates from recombinant SPV infected cells with polyclonal goat anti-PRV gIII (gC). Lanes (A)

S-PRV-002 (U.S. Pat. No. 4,877,737, issued Oct. 31, 1989) infected cell lysate, (B) molecular weight markers, (C) mock-infected EMSK cell lysate, (D) S-SPV-003 infected cell lysate, (E) S-SPV-008 infected cell lysate, (F) S-SPV-011 infected cell lysate, (G) S-SPV-012 infected cell lysate, (H) S-SPV-013 infected cell lysate. Cell lysates are prepared as described in the PREPARATION OF INFECTED CELL LYSATES. Approximately ⅕ of the total lysates sample is loaded in each lane.

FIG. 17:

Map showing the 5.6 kilobase pair HindIII M swinepox virus genomic DNA fragment. Open reading frames (ORF) are shown with the number of amino acids coding in each open reading frame. The swinepox virus ORFs show significant sequence identities to the vaccinia virus ORFs and are labeled with the vaccinia virus nomenclature (56 and 58). The I4L ORF (SEQ ID NO: 196) shows amino acid sequence homology to ribonucleotide reductase large subunit (57), and the O1L ORF (SEQ ID NO: 193) shows amino acid sequence homology to a leucine zipper motif characteristic of certain eukaryotic transcriptional regulatory proteins (13). The BglII site in the I4L ORF and the AccI site in the O1L ORF are insertion sites for foreign DNA into non-essential regions of the swinepox genome. The homology vector 738-94.4 contains a deletion of SPV DNA from nucleotides 1679 to 2452 (SEQ ID NO: 189). The black bar at the bottom indicates regions for which the DNA sequence is known and references the SEQ ID NOs: 189 and 195. Positions of restriction sites AccI, BglII, and HindIII are shown. I3L ORF (SEQ ID NO: 190), I2L ORF (SEQ ID NO: 191) and E1OR ORF (SEQ ID NO: 194) are shown. SEQ ID NO 221 contains the complete 5785 base pair sequence of the HindIII M fragment. Open reading frames within the SPV HindIII M fragment are the partial I4L ORF (445 AA; Nucl 2 to 1336); I3L ORF (275 AA; Nucl 1387 to 2211); I2L ORF (75 AA; Nucl 2215 to 2439); I1L ORF (313 AA; Nucl 2443 to 3381); O1L ORF (677 AA; Ncl 3520 to 5550); partial E1OR ORF (64 AA; Nucl 5787 to 5596).

Figure 18A:
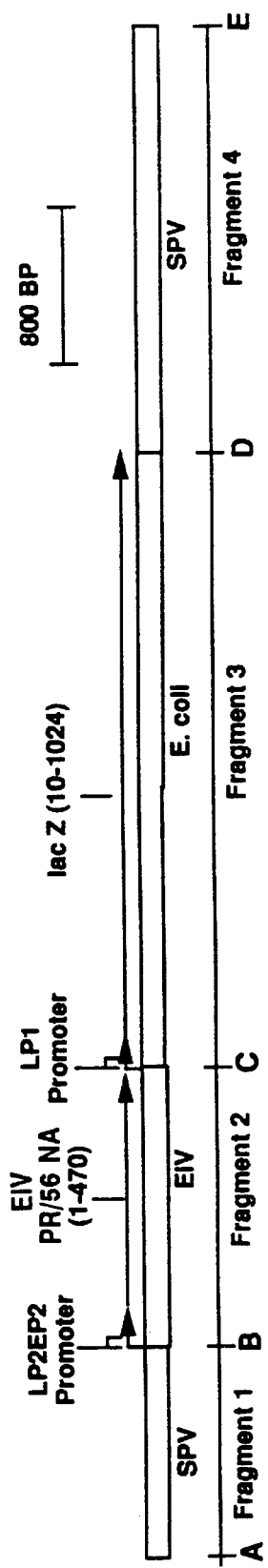
Figure 18C:
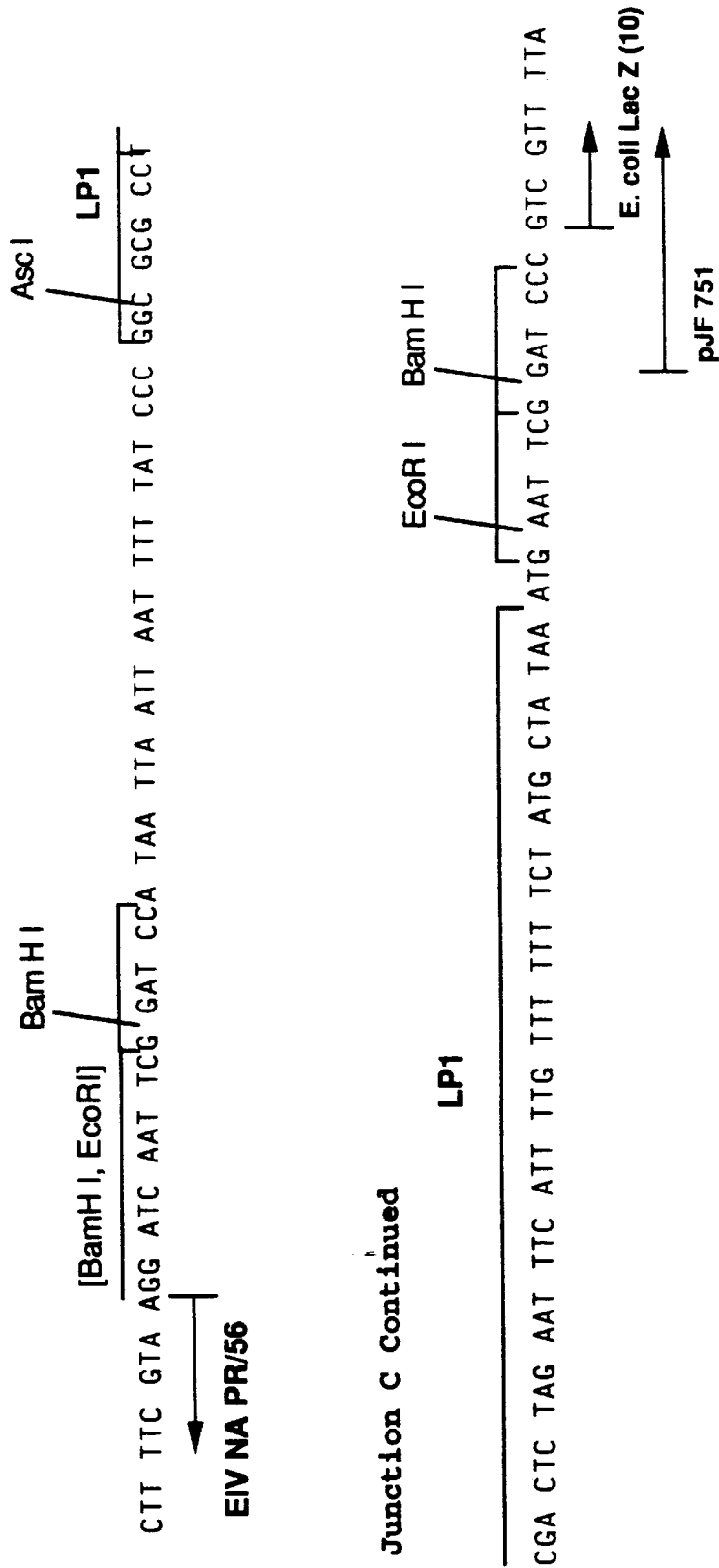

FIGS. 18A–18D:

Show a detailed description of Swinepox Virus S-SPV-034 and the DNA insertion in Homology Vector 723-59A9.22. FIG. 18A contains a diagram showing the orientation of DNA fragments assembled in plasmid 723-59A9.22 and a table indicating the origin of each fragment. FIG. 18B shows the sequences located at Junctions A and B between fragments, FIG. 18C shows the sequences located at Junction C, and FIG. 18D shows the sequences located at Junctions D and E (SEQ ID NOS: 153, 154, 155, 156, 157). The restriction sites used to generate each fragment as well as synthetic linker sequences which are used to join the fragments are described for each junction in FIGS. 18B to 18D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), equine influenza virus (EIV), Escherichia coli (E. coli), pox synthetic late promoter 1 (LP1), pox synthetic late promoter 2 early promoter 2 (LP2EP2), neuraminidase (NA), Prague (PR), polymerase chain reaction (PCR), base pairs (BP).

Figure 19A:
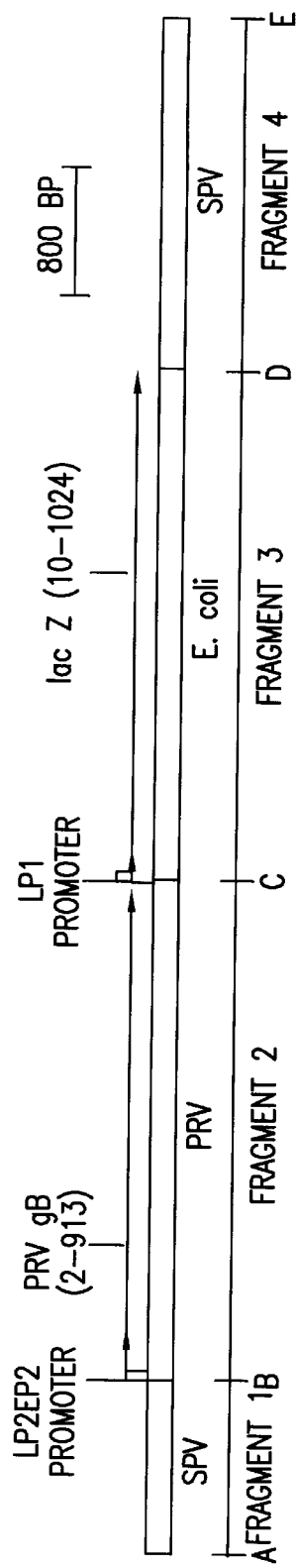
Figure 19B:
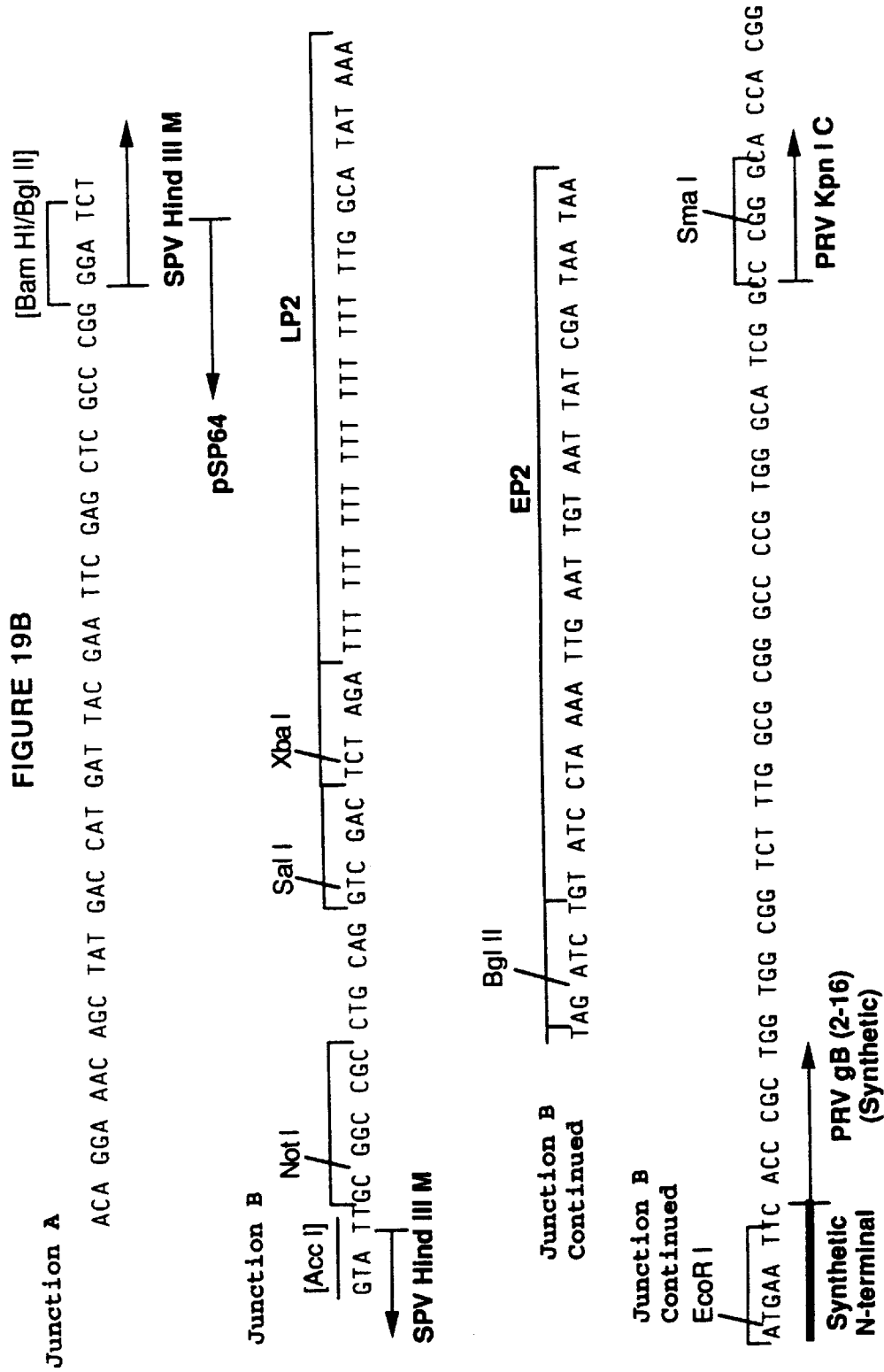
Figure 19D:
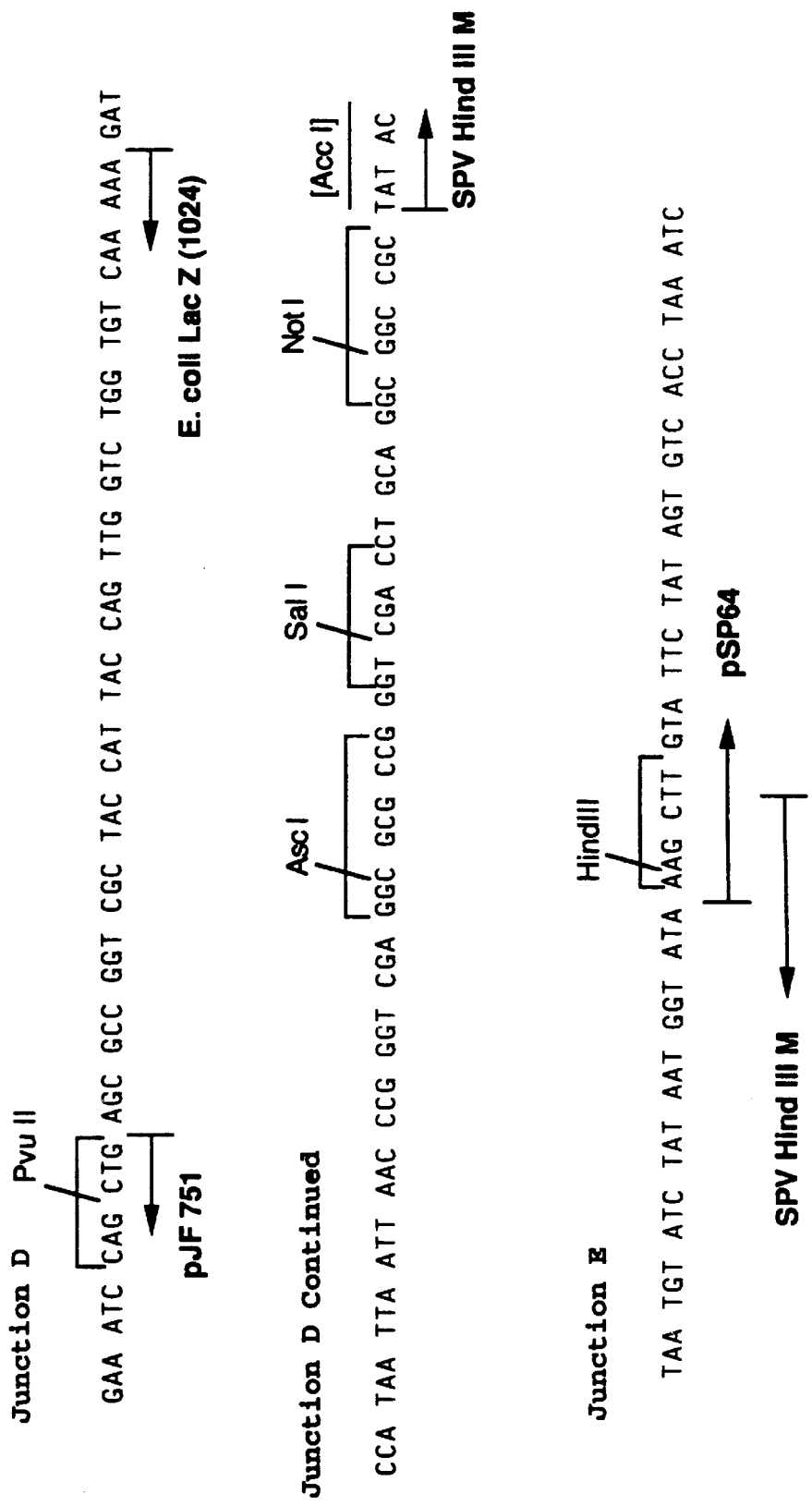

FIGS. 19A–19D:

Show a detailed description of Swinepox Virus S-SPV-015 and the DNA insertion in Homology Vector 727-54.60. FIG. 19A contains a diagram showing the orientation of DNA fragments assembled in plasmid 727-54.60 and a table indicating the origin of each fragment. FIG. 19B shows the sequences located at Junctions A and B between fragments, FIG. 19C shows the sequences located at Junction C, and FIG. 19D shows the sequences located at Junctions D and E (SEQ ID NOS: 158, 159, 160, 161, 162). The restriction sites used to generate each fragment as well as synthetic linker sequences which are used to join the fragments are described for each junction in FIGS. 19B to 19D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), Escherichia coli (E. coli), pox synthetic late promoter 1 (LP1), pox synthetic late promoter 2 early promoter 2 (LP2EP2), glycoprotein B (gB), base pairs (BP).

Figure 20A:
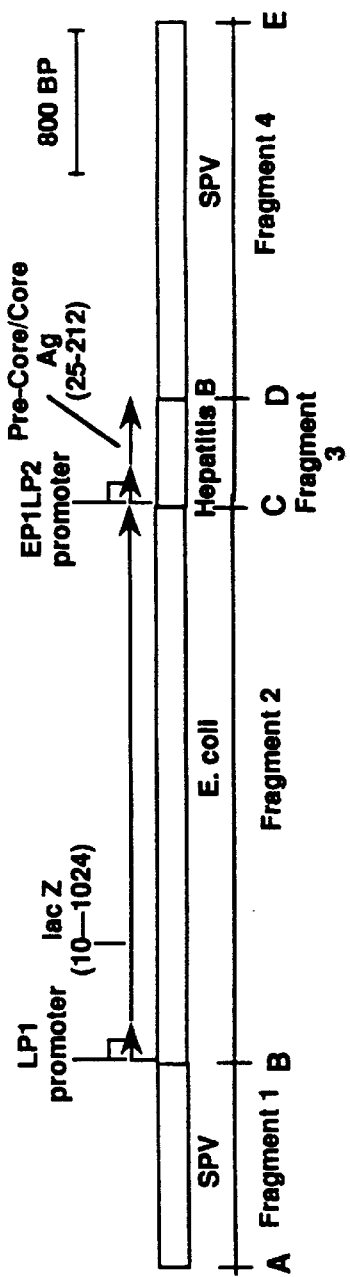
Figure 20B:
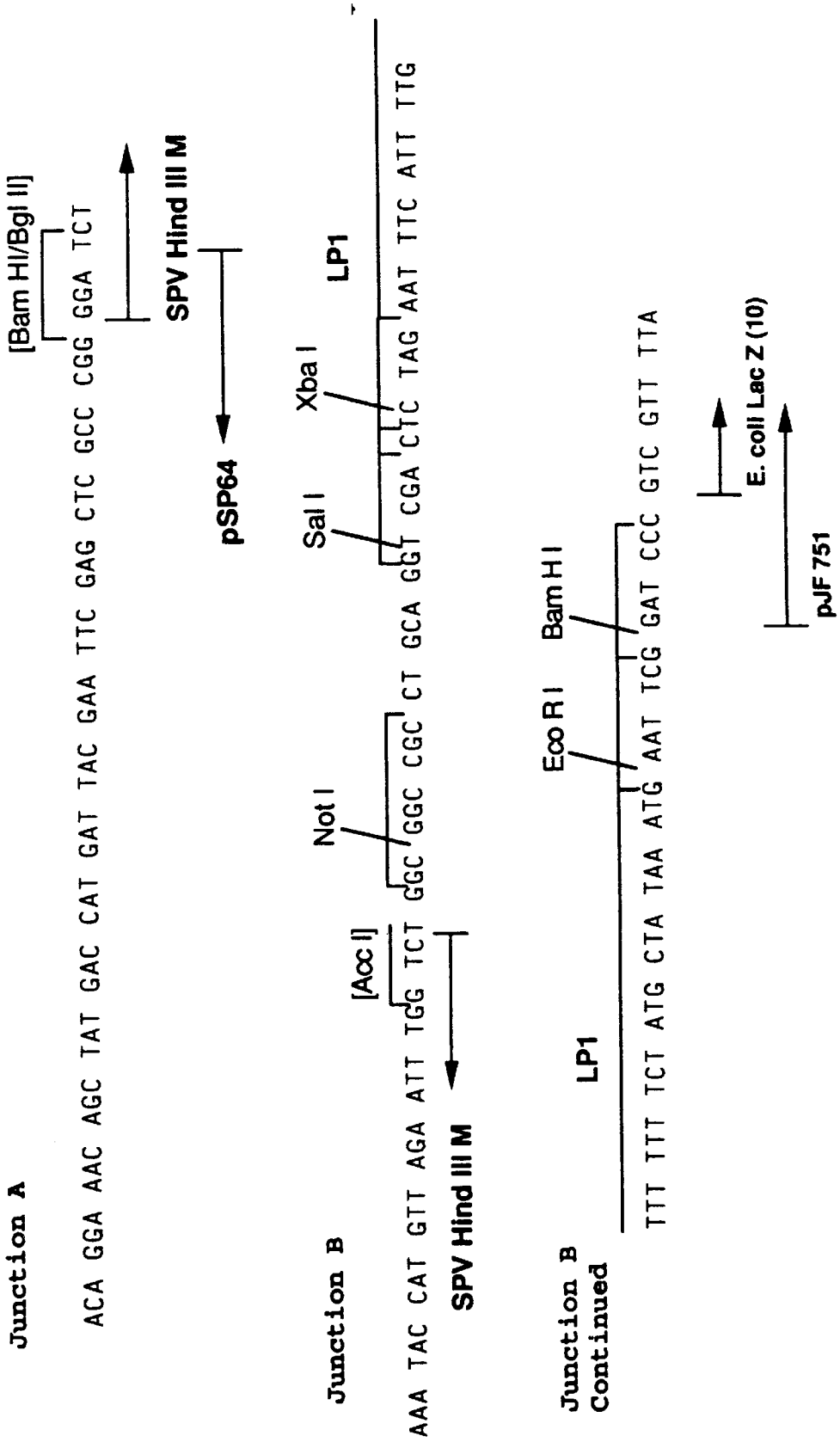
Figure 20C:
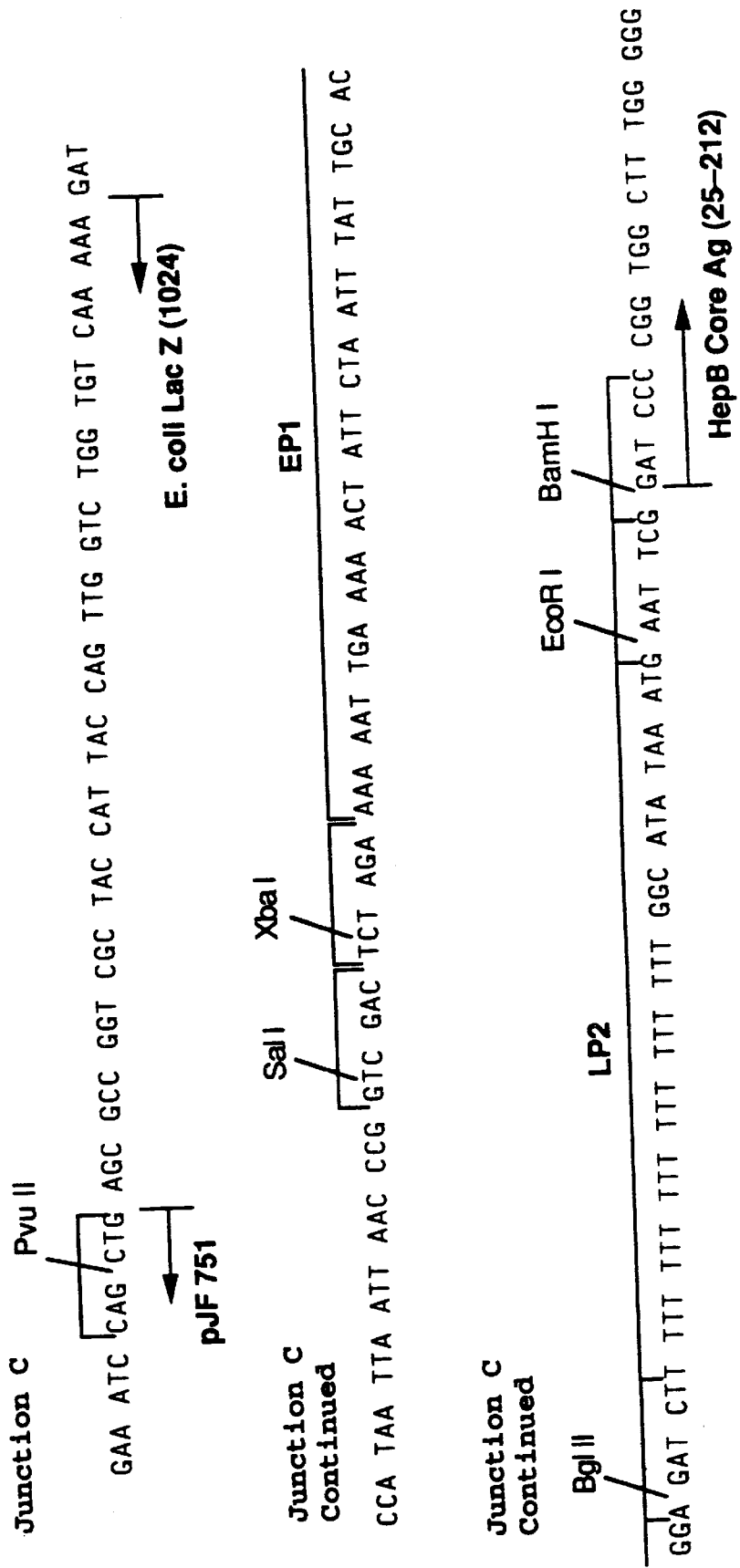
Figure 20D:
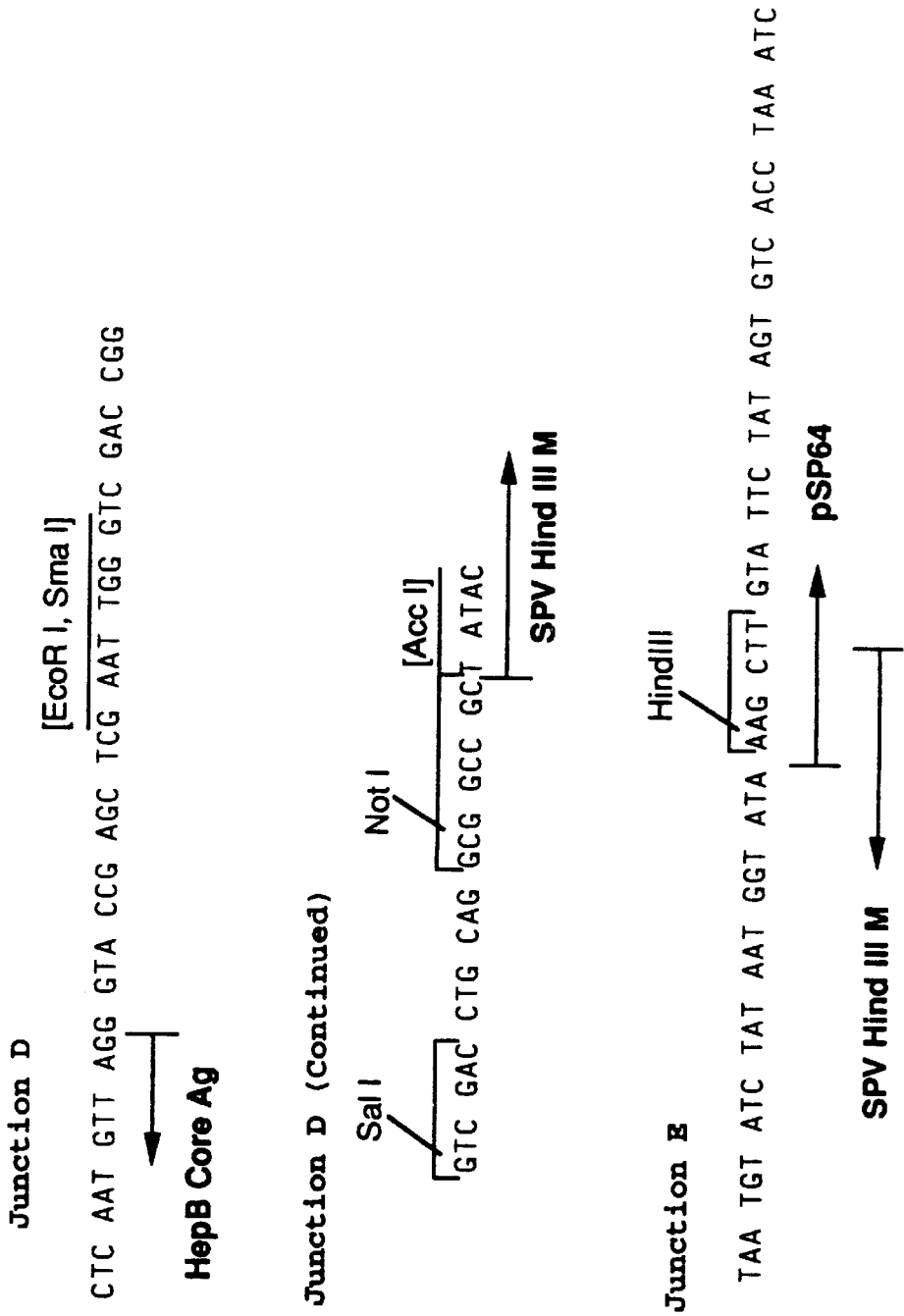

FIGS. 20A–20D:

Show a detailed description of Swinepox Virus S-SPV-031 and the DNA insertion in Homology Vector 727-67.18. FIG. 20A contains a diagram showing the orientation of DNA fragments assembled in plasmid 727-67.18 and a table indicating the origin of each fragment. FIG. 20B shows the sequences located at Junctions A and B between fragments, FIG. 20C shows the sequences located at Junction C, and FIG. 20D shows the sequences located at Junctions D and E (SEQ ID NOS: 163, 164, 165, 166, 167). The restriction sites used to generate each fragment as well as synthetic linker sequences which are used to join the fragments are described for each junction in FIGS. 20B to 20D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), Escherichia coli (E. coli), pox synthetic late promoter 1 (LP1), pox synthetic early promoter 1 late promoter 2 (EP1LP2), antigen (Ag), base pairs (BP).

Figure 21A:
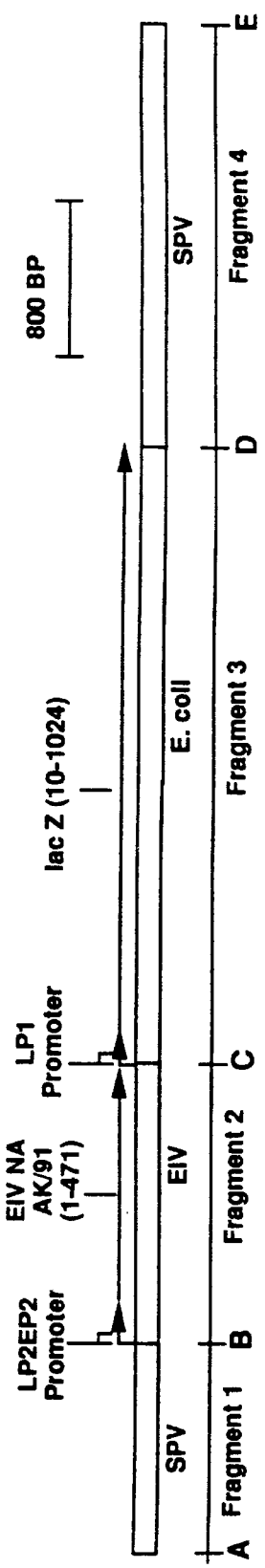
Figure 21B:
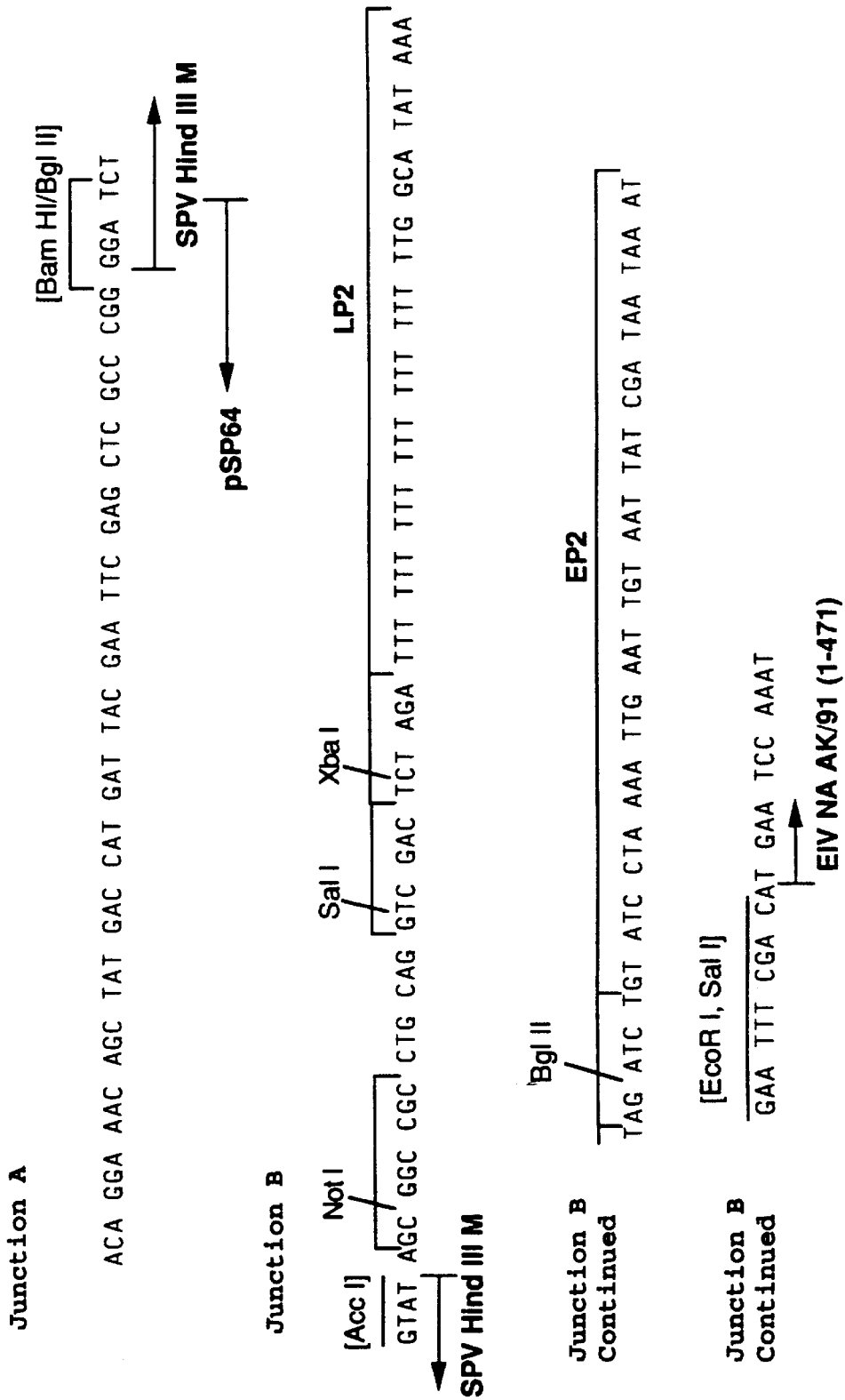
Figure 21C:
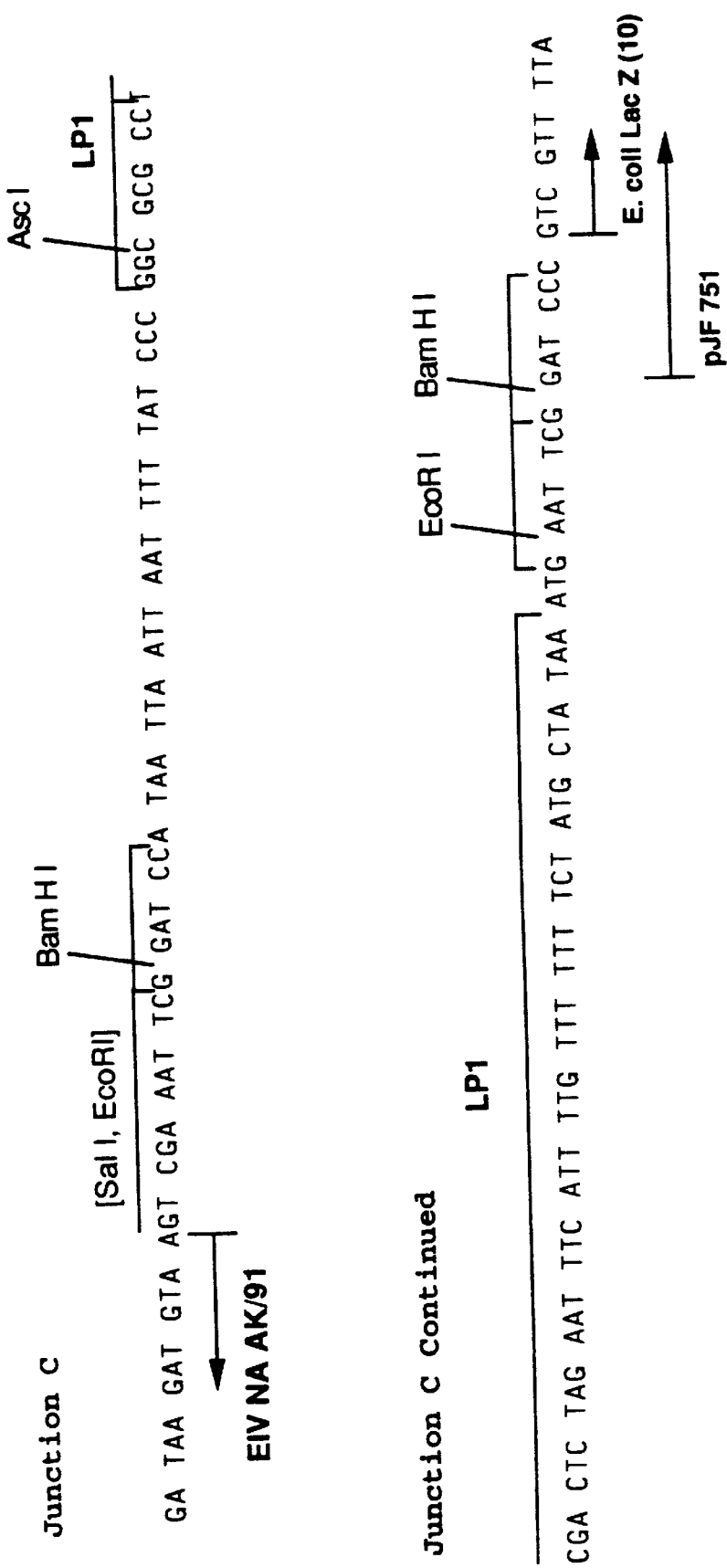
Figure 21D:
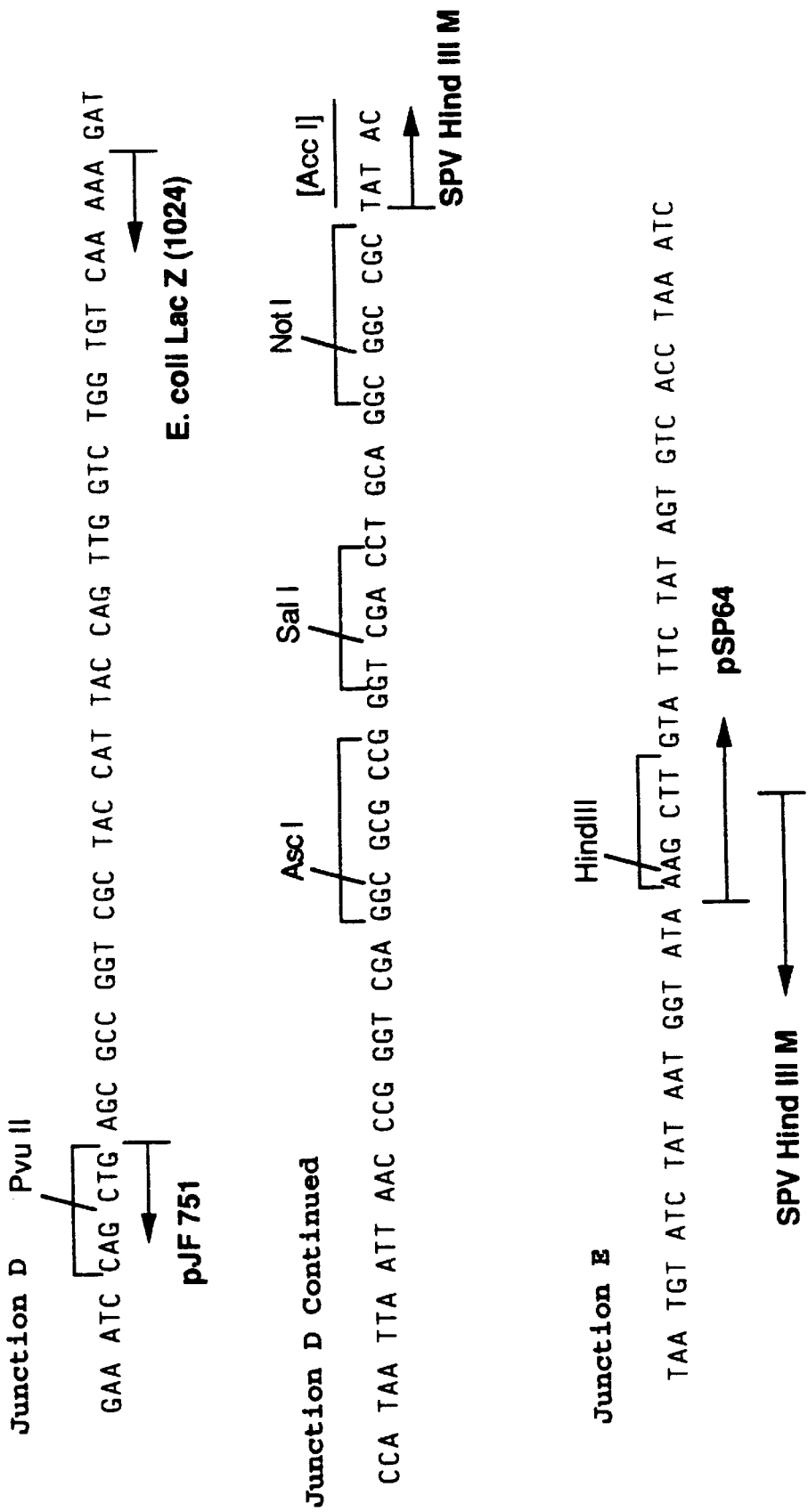

FIGS. 21A–21D:

Show a detailed description of Swinepox Virus S-SPV-033 and the DNA insertion in Homology Vector 732-18.4. FIG. 21A contains a diagram showing the orientation of DNA fragments assembled in plasmid 732-18.4 and a table indicating the origin of each fragment. FIG. 21B shows the sequences located at Junctions A and B between fragments, FIG. 21C shows the sequences located at Junction C, and FIG. 21D shows the sequences located at Junctions D and E (SEQ ID NOS: 168, 169, 170, 171, 172). The restriction sites used to generate each fragment as well as synthetic linker sequences which are used to join the fragments are described for each junction in FIGS. 21B to 21D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), Escherichia coli (E. coli), pox synthetic late promoter 1 (LP1), pox synthetic late promoter 2 early promoter 2 (LP2EP2), equine influenza virus (EIV), neuraminidase (NA), Alaska (AK), polymerase chain reaction (PCR), base pairs (BP)

FIGS. 22A–22C:

Show a detailed description of Swinepox Virus S-SPV-036 and the DNA insertion in Homology Vector 741-80.3.

Figure 22A:
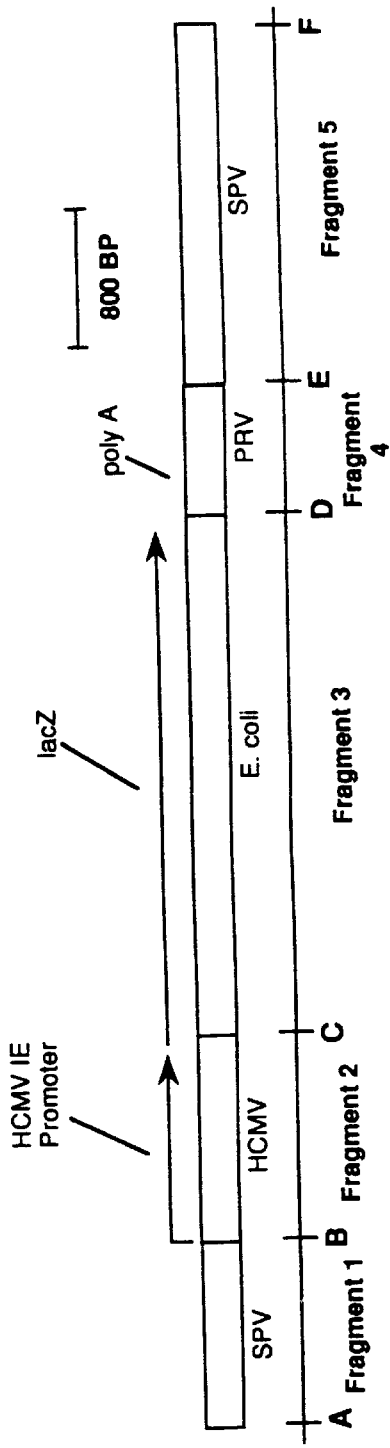
Figure 22B:
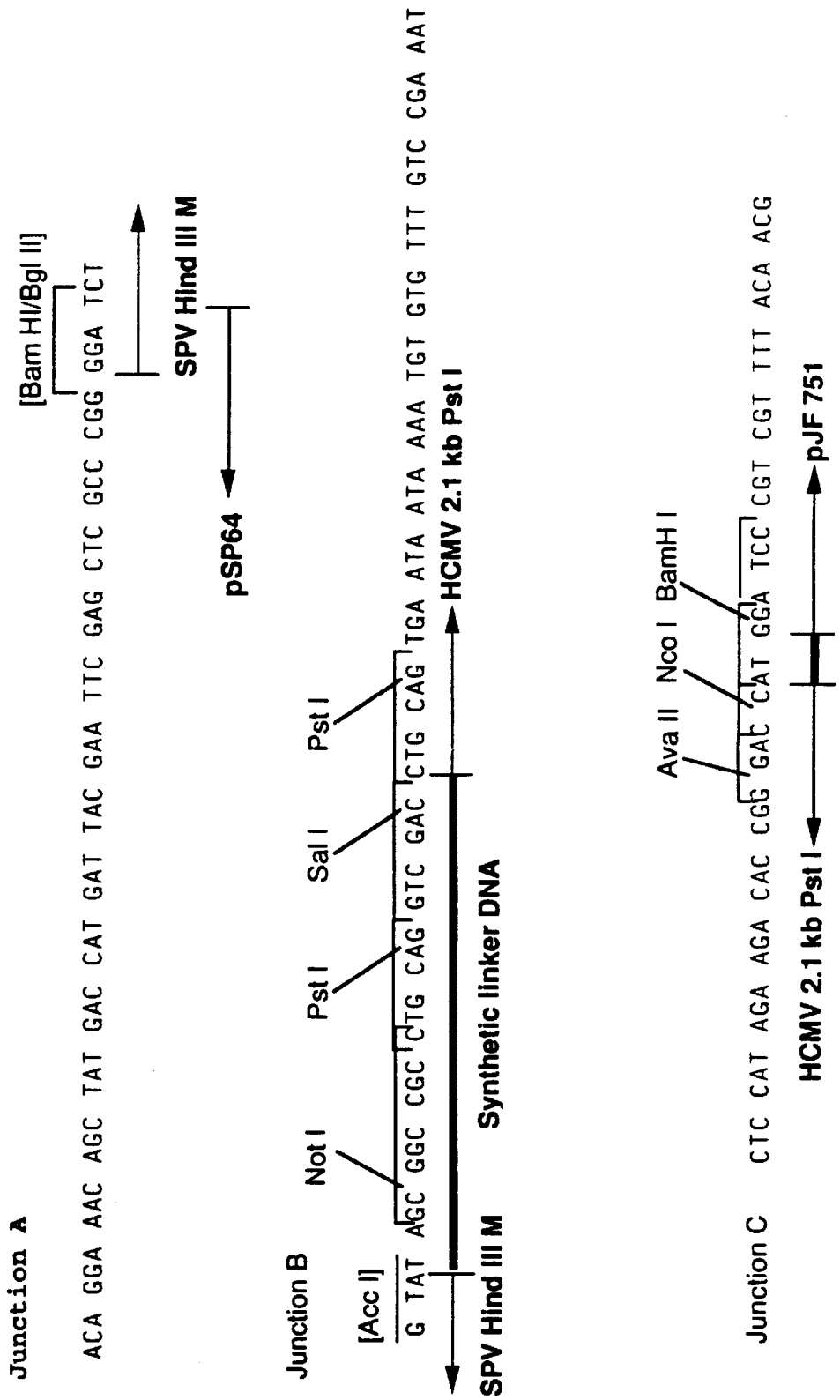
Figure 22C:
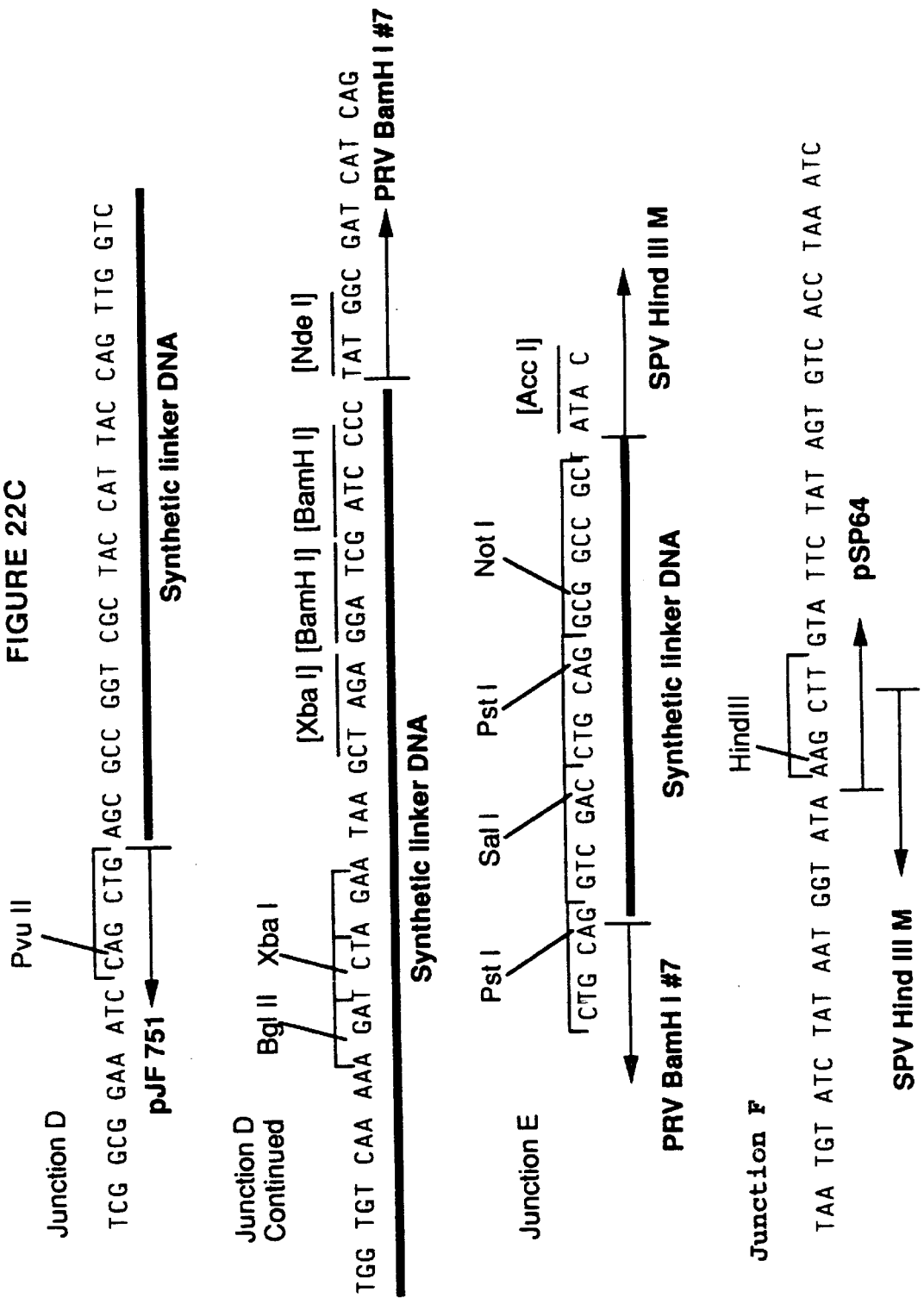

FIG. 22A contains a diagram showing the orientation of DNA fragments assembled in plasmid 741-80.3 and a table indicating the origin of each fragment. FIG. 22B shows the sequences located at Junctions A, B and C between fragments and FIG. 22C shows the sequences located at Junctions D, E and F (SEQ ID NOS: 173, 174, 175, 176, 177, 178). The restriction sites used to generate each fragment as well as synthetic linker sequences which are used to join the fragments are described for each junction in FIGS. 22B and 22C. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), *Escherichia coli* (*E. coli*), human cytomegalovirus immediate early (HCMV IE), pox synthetic late promoter 1 (LP1), pox synthetic late promoter 2 early promoter 2 (LP2EP2), polyadenylation site (poly A), base pairs (BP).

Figure 23A:
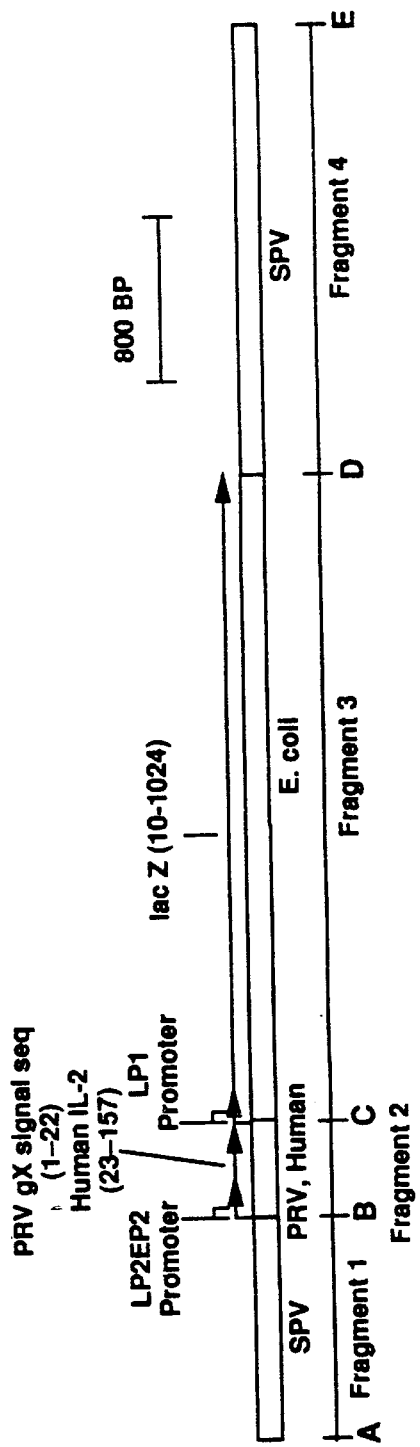
Figure 23B:
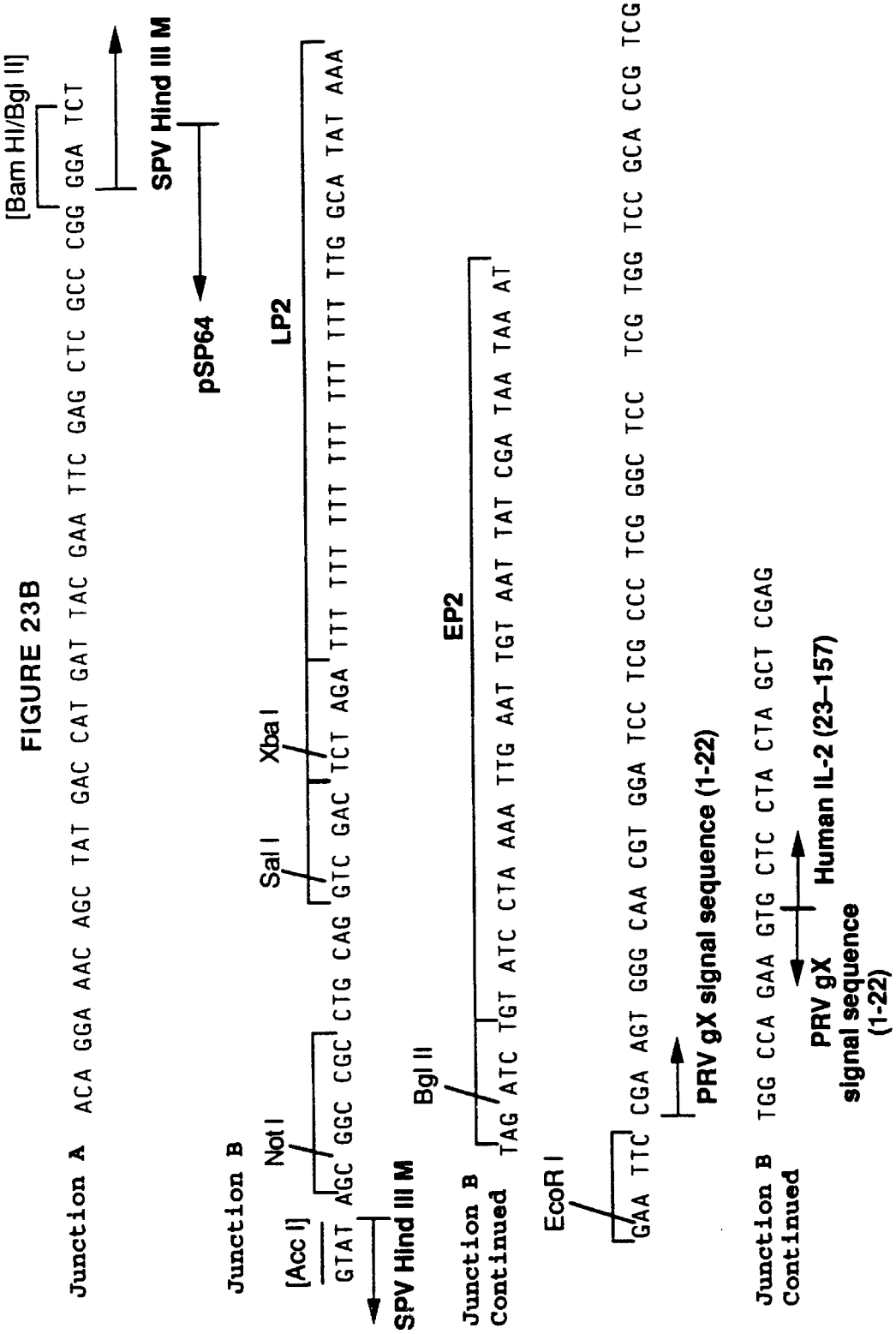

FIGS. 23A–23D:

Show a detailed description of Swinepox Virus S-SPV-035 and the DNA insertion in Homology Vector 741-81.14. FIG. 23A contains a diagram showing the orientation of DNA fragments assembled in plasmid 741-84.14 and a table indicating the origin of each fragment. FIG. 23B shows the sequences located at Junctions A and B between fragments, FIG. 23C shows the sequences located at Junction C, and FIG. 23D shows the sequences located at Junctions D and E (SEQ ID NOS: 179, 180, 181, 182, 183). The restriction sites used to generate each fragment as well as synthetic linker sequences which are used to join the fragments are described for each junction in FIGS. 23B to 23D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 1 (LP1), pox synthetic late promoter 2 early promoter 2 (LP2EP2), interleukin-2 (IL-2), glycoprotein X (gX) polymerase chain reaction (PCR), sequence (seq), base pairs (BP).

Figure 24A:
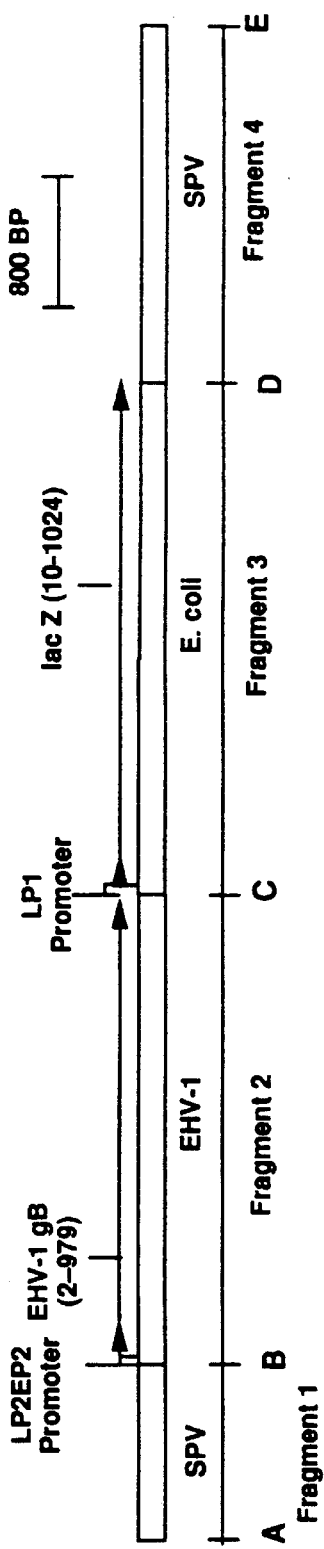
Figure 24B:
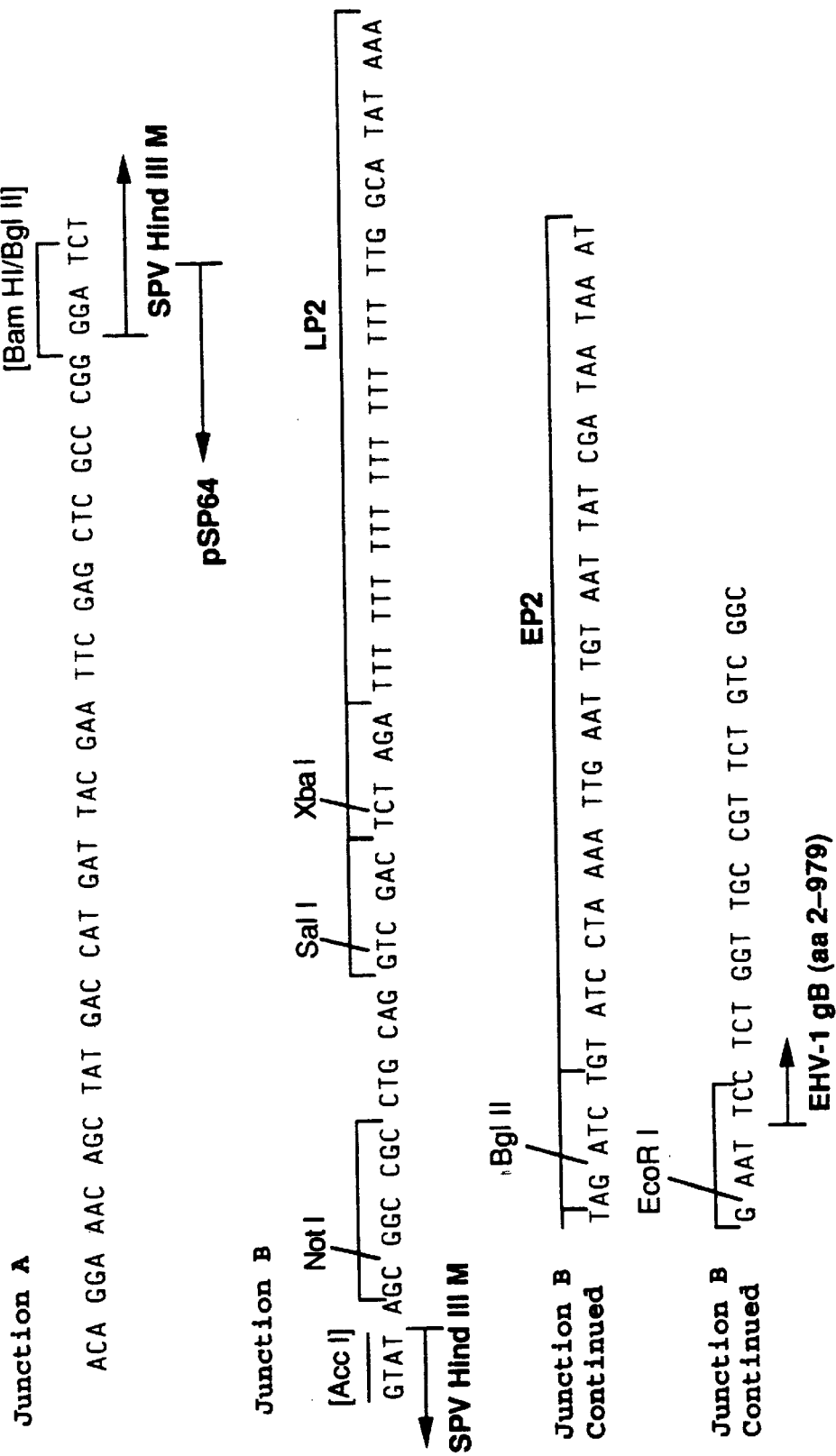
Figure 24C:
Figure 24D:
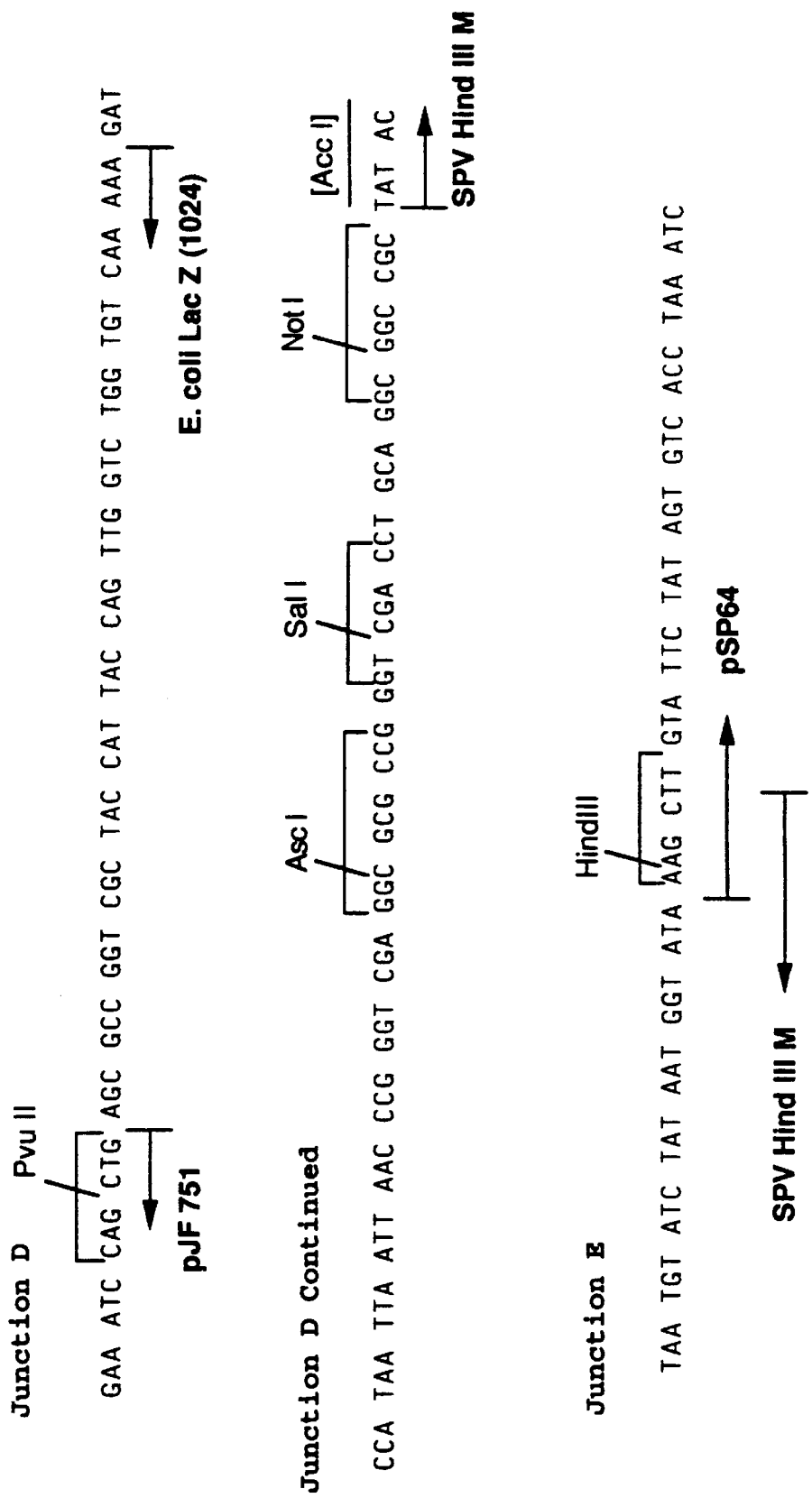

FIGS. 24A–24D:

Show a detailed description of Swinepox Virus S-SPV-038 and the DNA insertion in Homology Vector 744-34. FIG. 24A contains a diagram showing the orientation of DNA fragments assembled in plasmid 744-34 and a table indicating the origin of each fragment. FIG. 24B shows the sequences located at Junctions A and B between fragments, FIG. 24C shows the sequences located at Junction C, and FIG. 24D shows the sequences located at Junctions D and E (SEQ ID NOS: 108, 109, 110, 111, 112). The restriction sites used to generate each fragment as well as synthetic linker sequences which are used to join the fragments are described for each junction in FIGS. 24B to 24D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), equine herpesvirus type 1 (EHV-1), *Escherichia coli* (*E. coli*), pox synthetic late promoter 1 (LP1), pox synthetic late promoter 2 early promoter 2 (LP2EP2), glycoprotein B (gB), polymerase chain reaction (PCR), base pairs (BP).

Figure 25A:
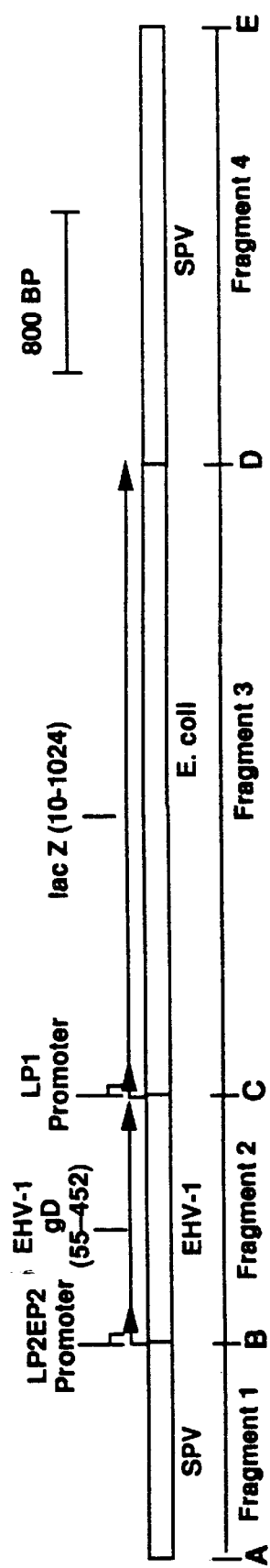
Figure 25B:
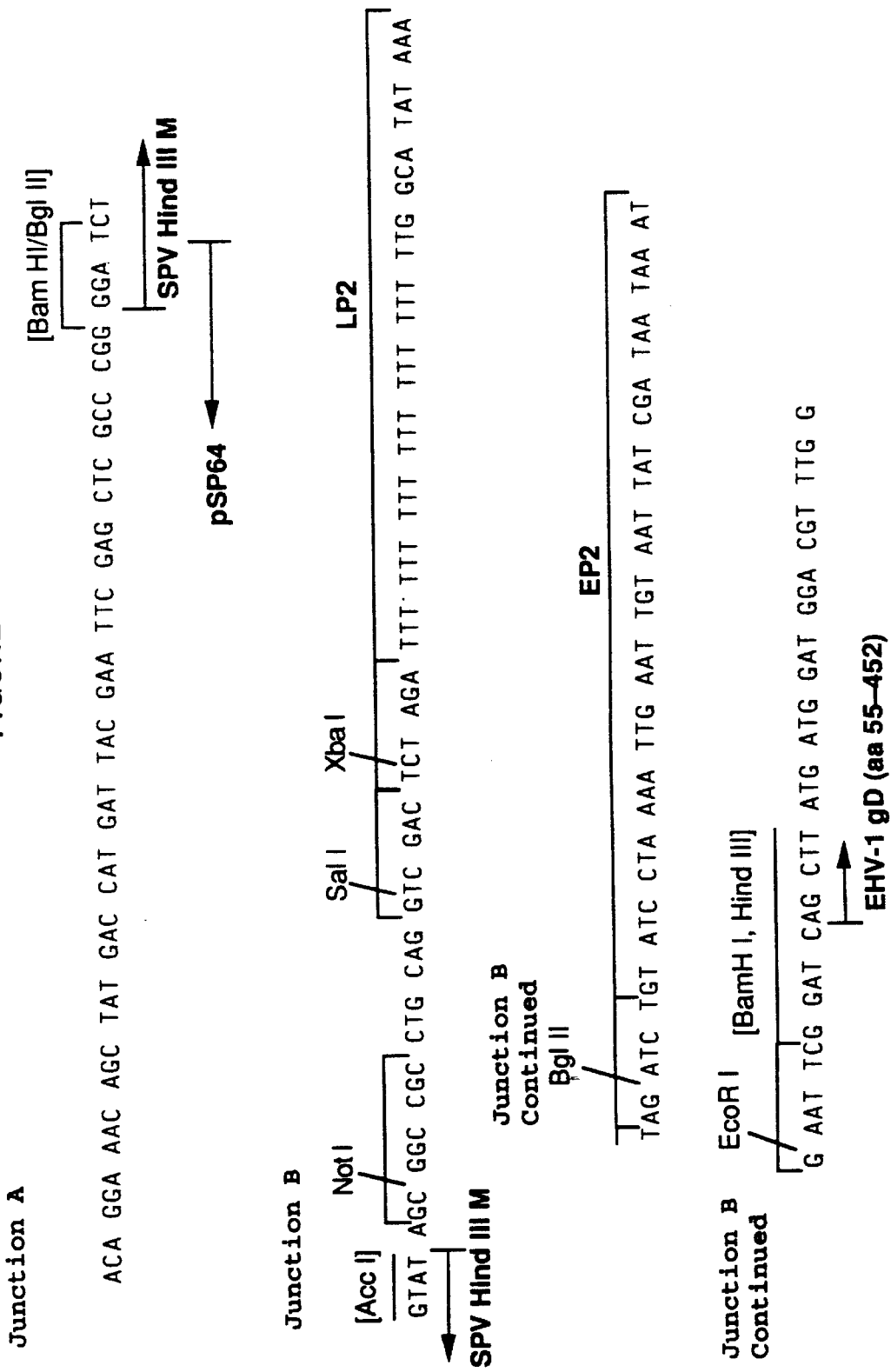
Figure 25C:
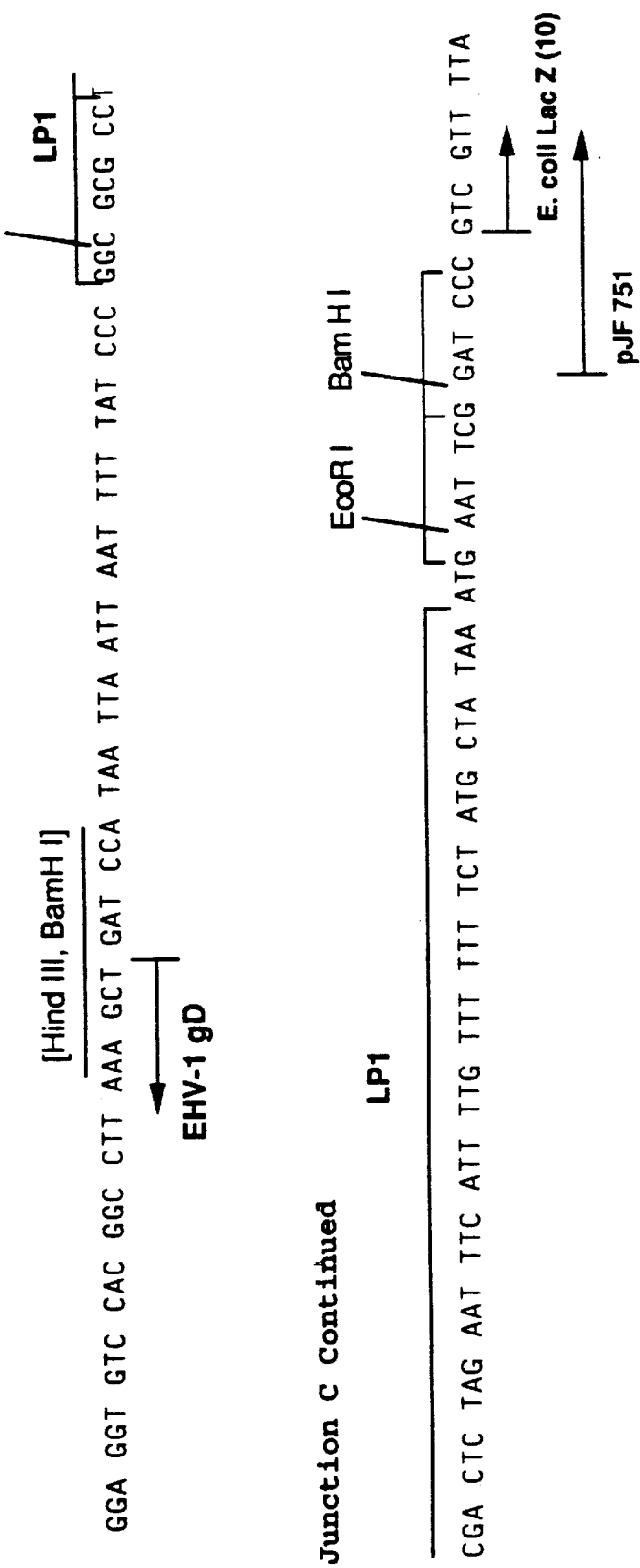
Figure 25D:
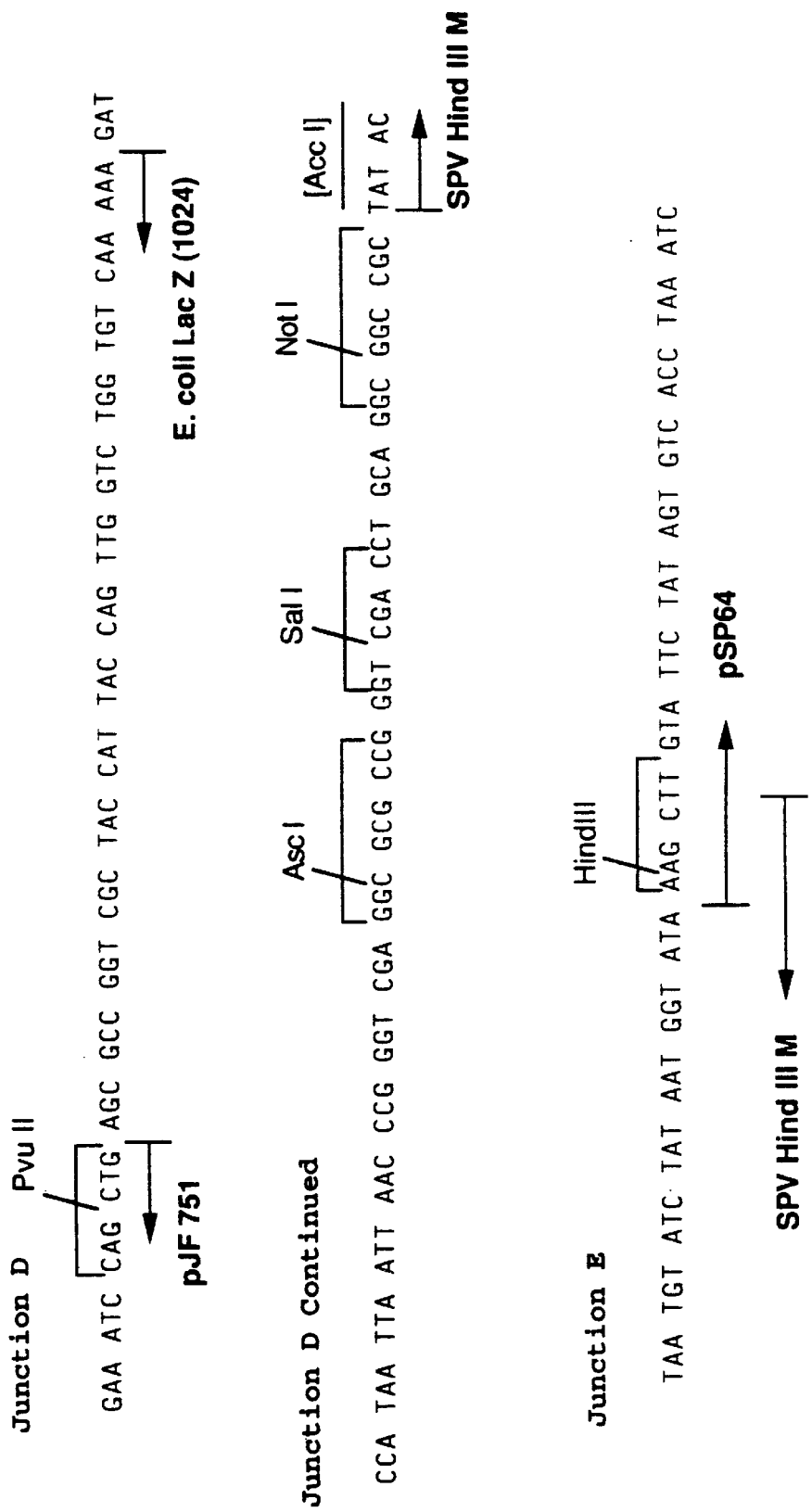
Figure 26A:
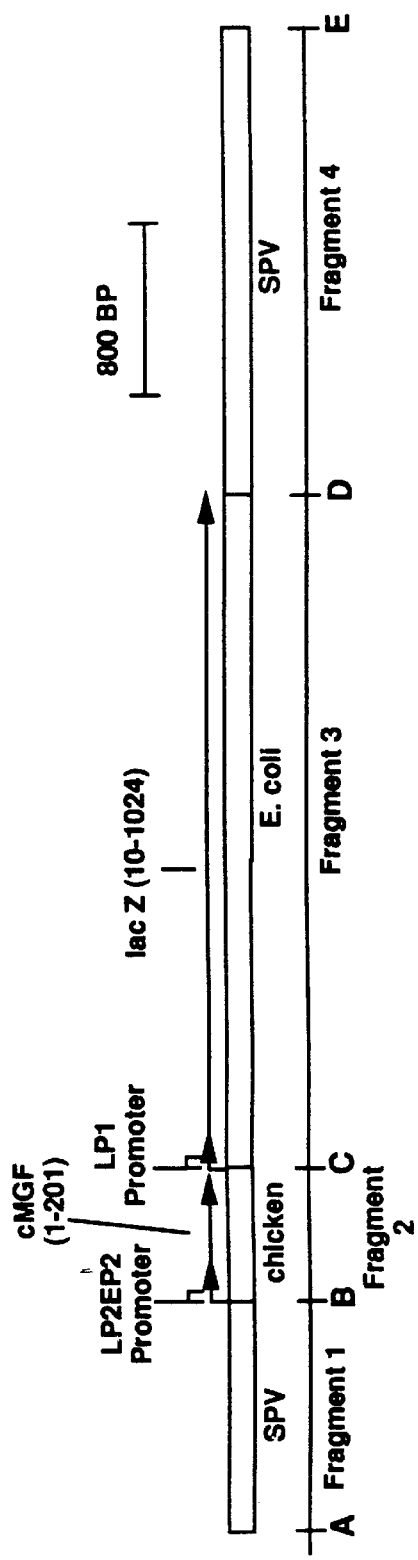
Figure 26B:
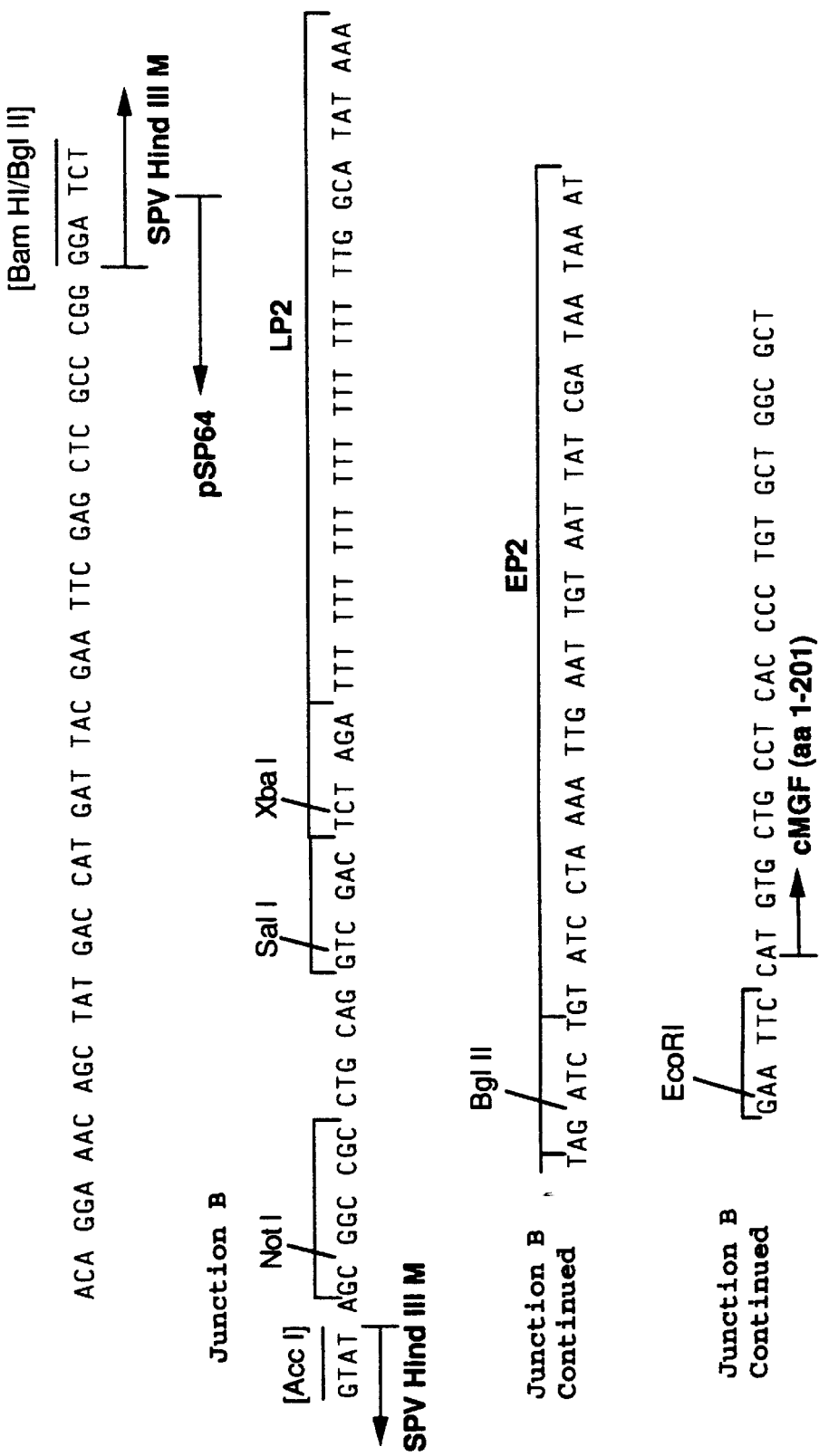
Figure 26C:
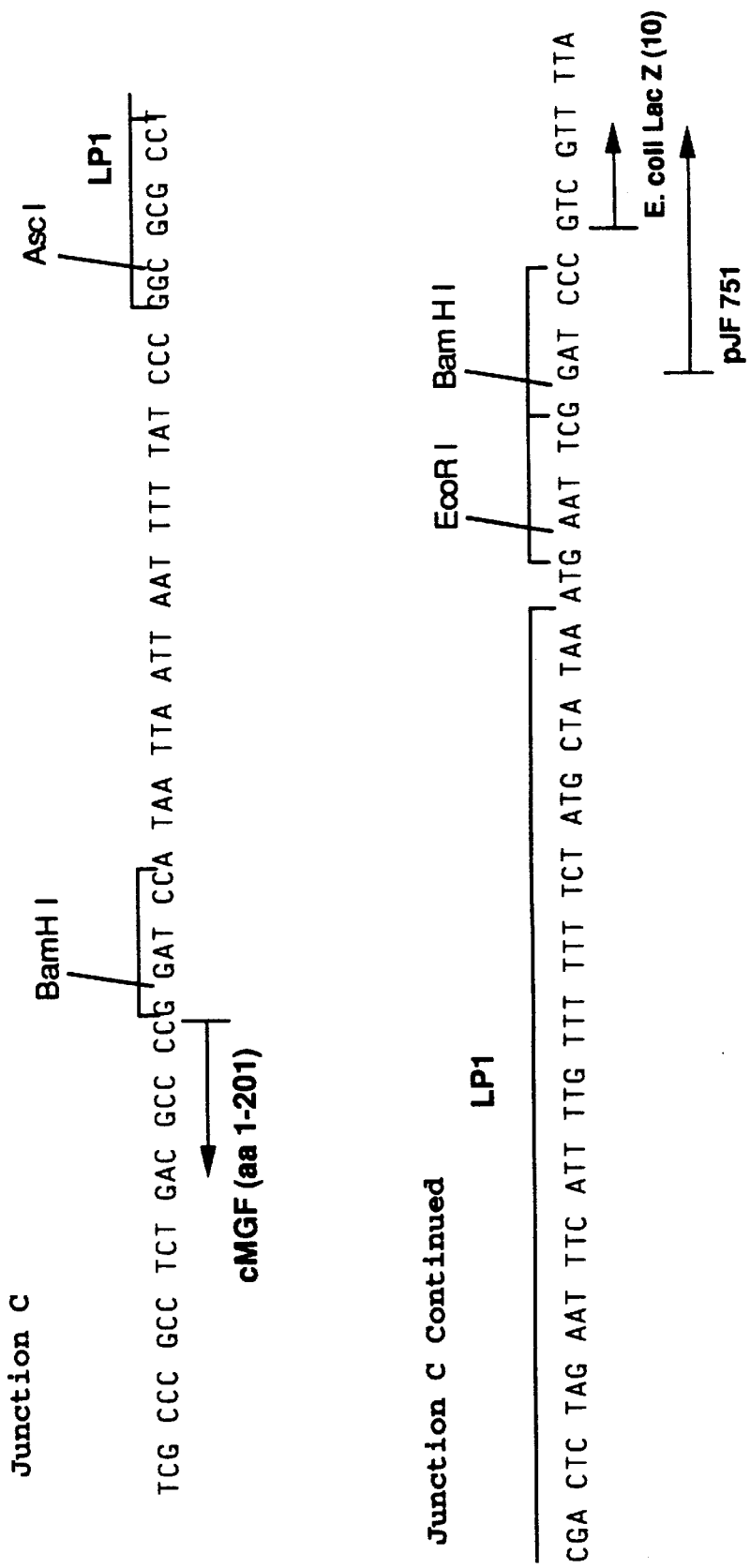
Figure 26D:
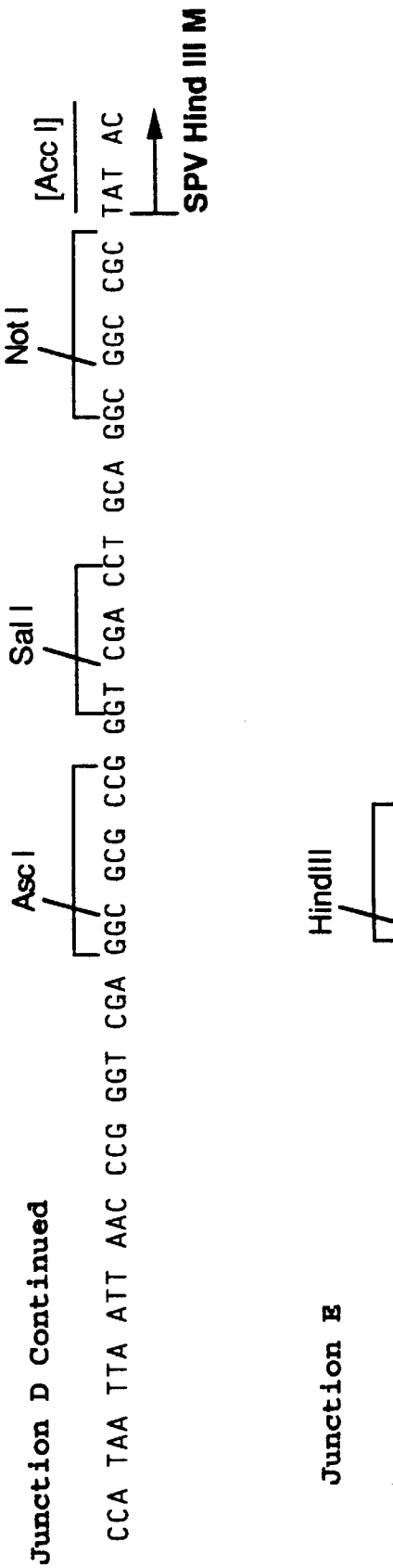
Figure 27A:
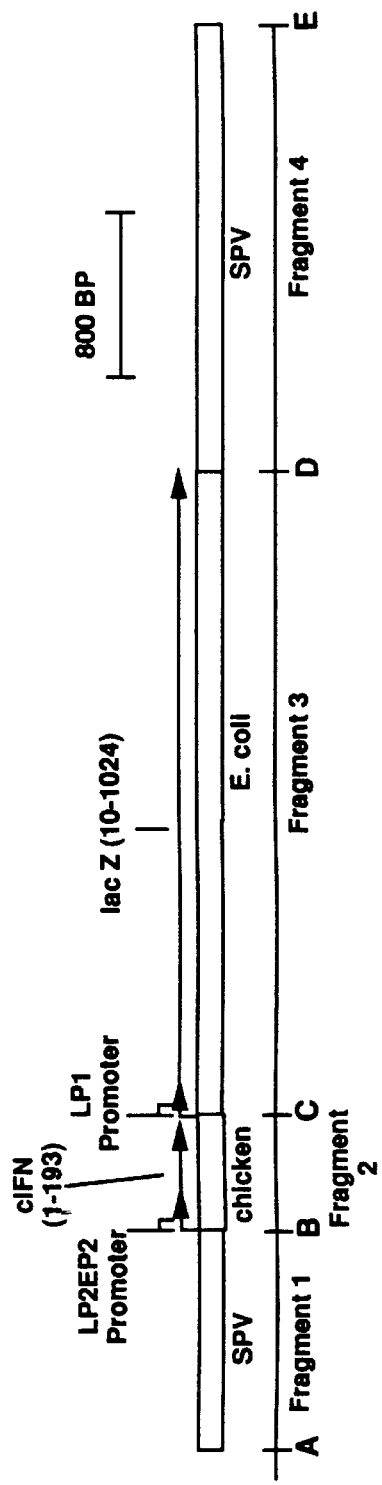
Figure 27B:
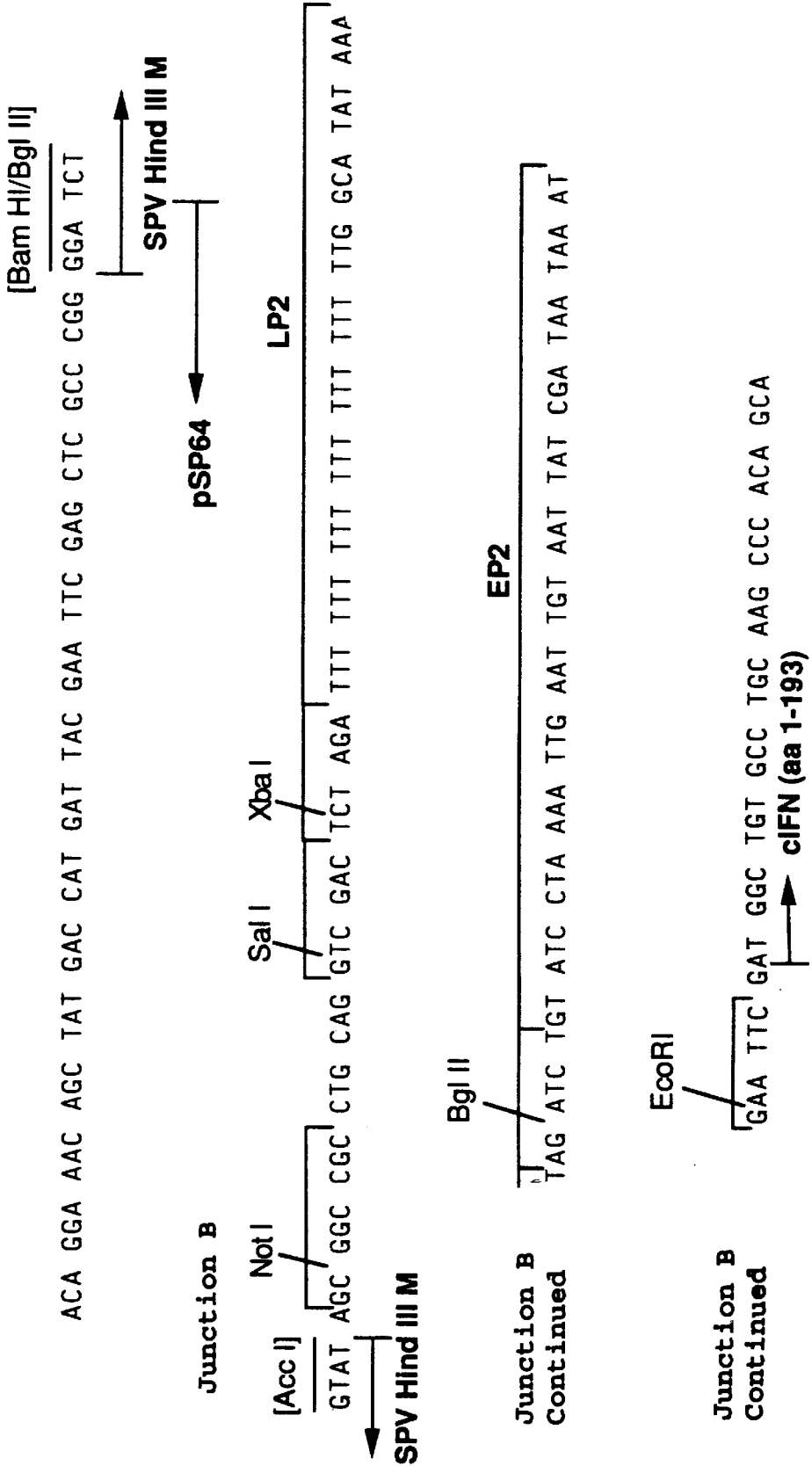
Figure 27C:
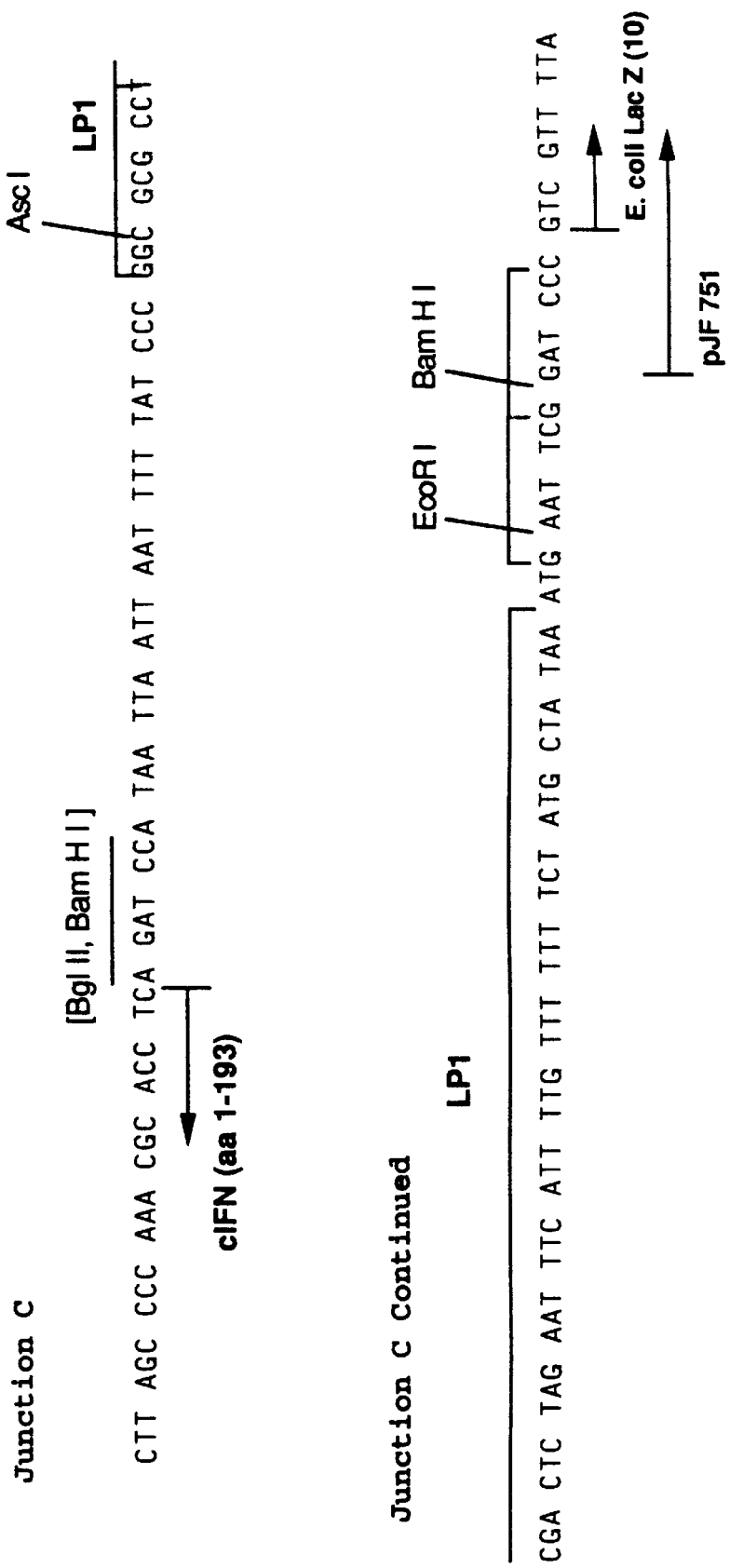
Figure 27D:
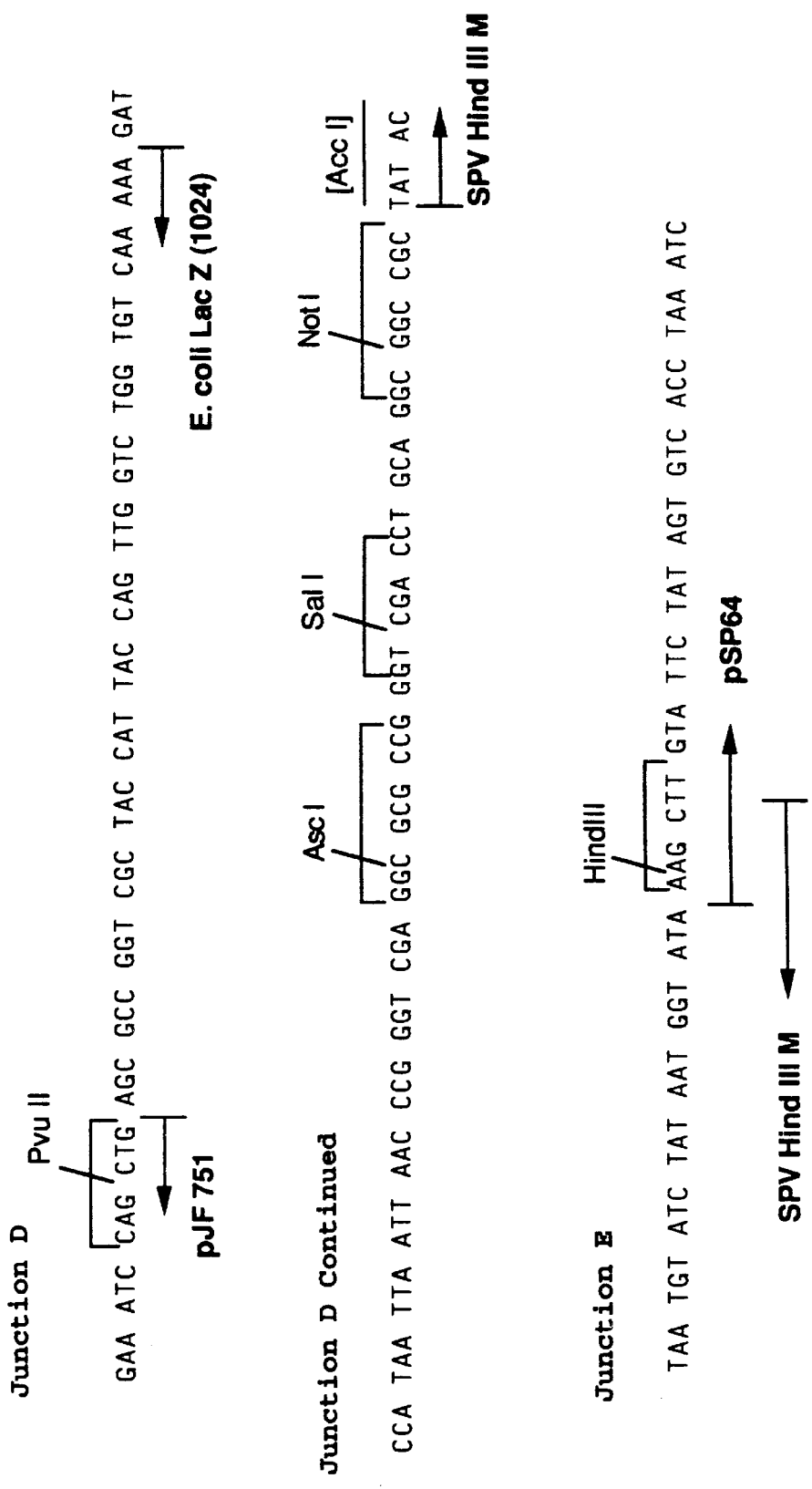

FIGS. 25A–25D:

Show a detailed description of Swinepox Virus S-SPV-039 and the DNA insertion in Homology Vector 744-38. FIG. 25A contains a diagram showing the orientation of DNA fragments assembled in plasmid 744-38 and a table indicating the origin of each fragment. FIG. 25B shows the sequences located at Junction A and B between fragments. FIG. 25C shows the sequences located at Junction C and FIG. 25D shows the sequences located at Junctions D and E (SEQ ID NOS: 268, 269, 270, 271, 272). The restriction sites used to generate each fragment as well as synthetic linker sequences which are used to join the fragments are described for each junction in FIGS. 25B to 25D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), equine herpesvirus type 1 (EHV-1), *Escherichia coli* (*E. coli*), pox synthetic late promoter 1 (LP1), pox synthetic late promoter 2 early promoter 2 (LP2EP2), glycoprotein D (gD), polymerase chain reaction (PCR), base pairs (BP).

FIGS. 26A–26D:

Detailed description of Swinepox Virus S-SPV-042 and the DNA insertion in Homology Vector 751-07.A1. Diagram showing the orientation of DNA fragments assembled in plasmid 751-07.A1. The origin of each fragment is indicated in the table. The sequence located at each of the junctions between fragments is also shown. The restriction sites used to generate each fragment as well as synthetic linker sequences which are used to join the fragments are described for each junction. FIGS. 26A–26D show the sequences located at Junction A (SEQ ID NOS: 197), (SEQ ID NO: 198), C (SEQ ID NO: 199), D (SEQ ID NO: 200) and E (SEQ ID NO: 201) between fragments and the sequences located at the junctions. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), chicken interferon (CIFN), *Escherichia coli* (*E. coli*), pox synthetic late promoter 1 (LP1), pox synthetic late promoter 2 early promoter 2 (LP2EP2), polymerase chain reaction (PCR), base pairs (BP).

FIGS. 27A–27D:

Detailed description of Swinepox Virus S-SPV-043 and the DNA insertion in Homology Vector 751-56.A1. Diagram showing the orientation of DNA fragments assembled in plasmid 751-56.A1. The origin of each fragment is indicated in the table. The sequences located at each of the junctions between fragments is also shown. FIGS. 27A–27D show the sequences located at Junction A (SEQ ID NOS: 202), (SEQ ID NO: 203), C (SEQ ID NO: 204), D (SEQ ID NO: 205) and E (SEQ ID NO: 206) between fragments and the sequences located at the junctions. The restriction sites used to generate each fragment as well as synthetic linker sequences which are used to join the several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), chicken myelomonocytic growth factor (cMGF), *Escherichia coli* (*E. coli*), pox synthetic late promoter 1

(LP1), pox synthetic late promoter 2 early promoter 2 (LPE2EP2), polymerase chain reaction (PCR), base pairs (BP).

FIGS. 28A–28D:

Detailed description of Swinepox Virus S-SPV-043 and the DNA insertion in Homology Vector 752-22.1. Diagram showing the orientation of DNA fragments assembled in plasmid 752-22.1. The origin of each fragment is indicated in the table. The sequences located at each of the junctions between fragments is also shown. FIGS. 28A–28D show the sequences located at Junction A (SEQ ID NOS: 207), (SEQ ID NO: 208), C (SEQ ID NO: 209), and D (SEQ ID NO: 210) between fragments and the sequences located at the junctions. The restriction sites used to generate each fragment as well as synthetic linker sequences which are used to join the fragments are described for each junction . The location of several gene coding regions and regulatory elements is also given. The following two coventions are used: numbers in parentheses, ( ), refer to amino acids, and restrictions sites in brackets, [ ], indicate the remnants of sites which are destroyed during construction. The following abbreviations are used: swine virus (SPV). *Escherichia coli* (*E. coli*), pox syntheic late promoter 2 early promoter 2 (LP2EP2), polymerase chain reaction (PCR), base pairs (BP).

Figure 29A:
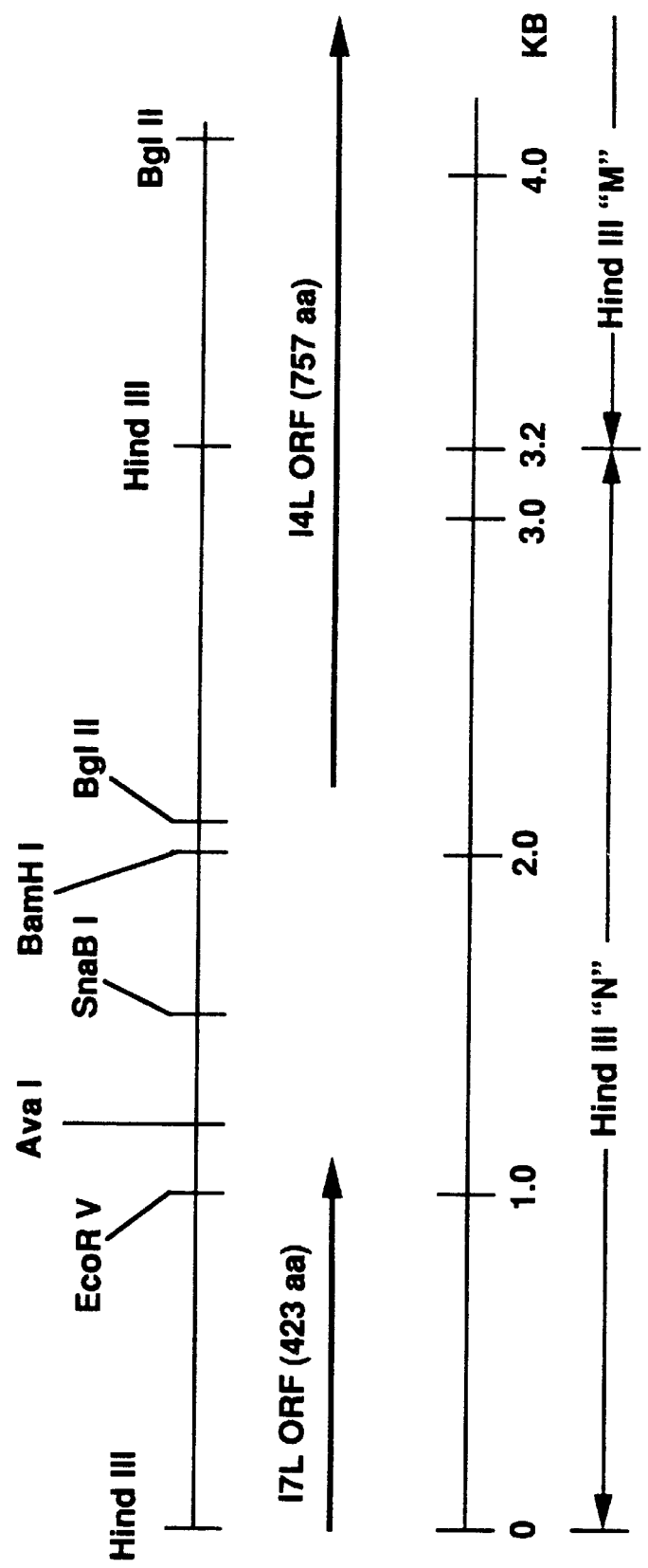

FIGS. 29A–29B:

FIG. 29A: Restriction Endonuclease Map and Open reading Frames in the SPV HindIII N fragment and part of SPV HindIII M fragment. Insertions of a foreign gene into a non-essential site of a swinepox virus Hind III N and Hind III M genomic DNA include the EcoR V site (S-SPV-060), SnaB I site (S-SPV-061), Bgl II site in Hind III N (S-SPV-062), and the Bgl II site in Hind III M (S-SPV-047). Insertions of a foreign gene into the I7L ORF and I4L ORF indicates that the sequence of the entire open reading frame is non-essential for replication of the swinepox virus and suitable for insertion of foreign genes. Additional sites for insertion of foreign genes include, but are not limited to the two Hind III sites, Ava I site, and the BamHI site.

Figure 29B:
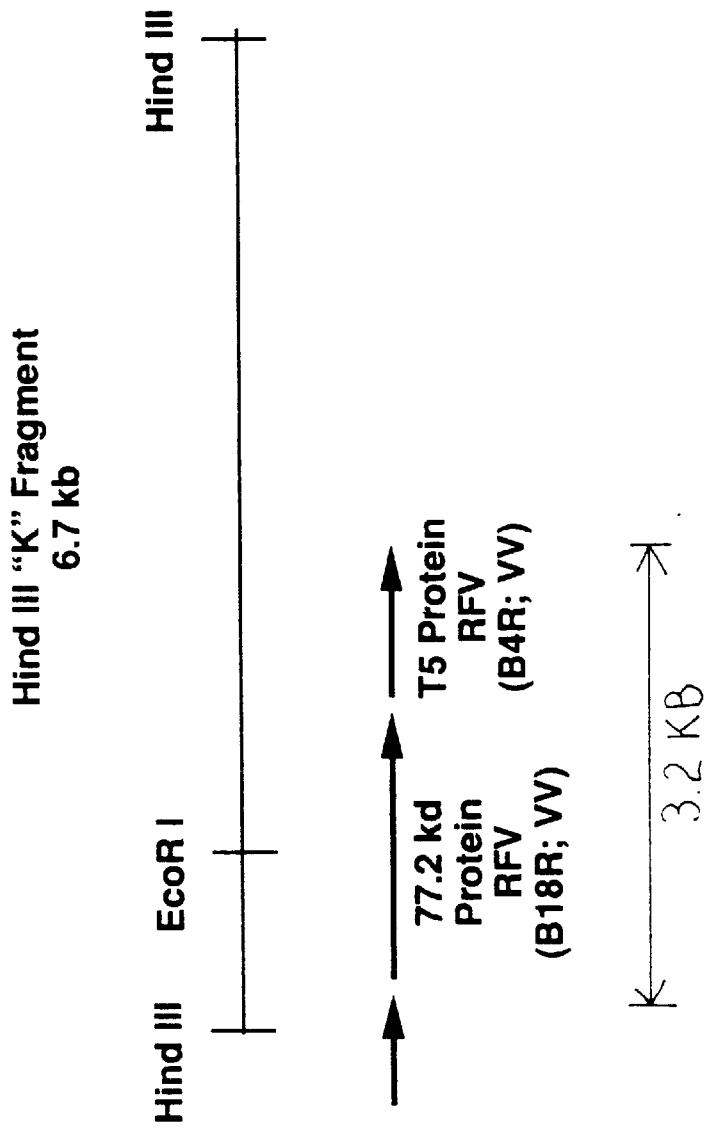

FIG. 29B: Restriction Endonuclease Map and Open Reading Frames in the SPV Hind III K fragment. Insertion of a foreign gene into a non-essential site of the swinepox virus Hind III K genomic DNA include, but is not limited to the EcoR I site (S-SPV-059). Three open reading frames are identified within a 3.2 kB region of the SPV HindIII K fragment. Insertions of a foreign gene into the B18R ORF indicates that the sequence of the entire open reading frame is non-essential for replication of the swinepox virus and suitable for insertion of foreign genes. Also identified is the B4R ORF which is a site for insertion of a foreign gene. SPV B18R ORF has homology to the vaccinia virus (VV) B18R ORF. SPV B18R ORF has more homology to the 77.2 kd protein of rabbit fibroma virus (RFV). SPV B4R ORF has homology to the vaccinia virus (w) B4R ORF. SPV B4R ORF has more homology to the T5 protein of rabbit fibroma virus (RFV). The identified open reading frames are within approximately 3200 base pairs of the SPV Hind III K fragment. The remaining approximately 3500 base pairs of the SPV Hind III K fragment has been sequenced previously (R.F. Massung, et al. Virology 197, 511–528 (1993)).

Figure 30A:
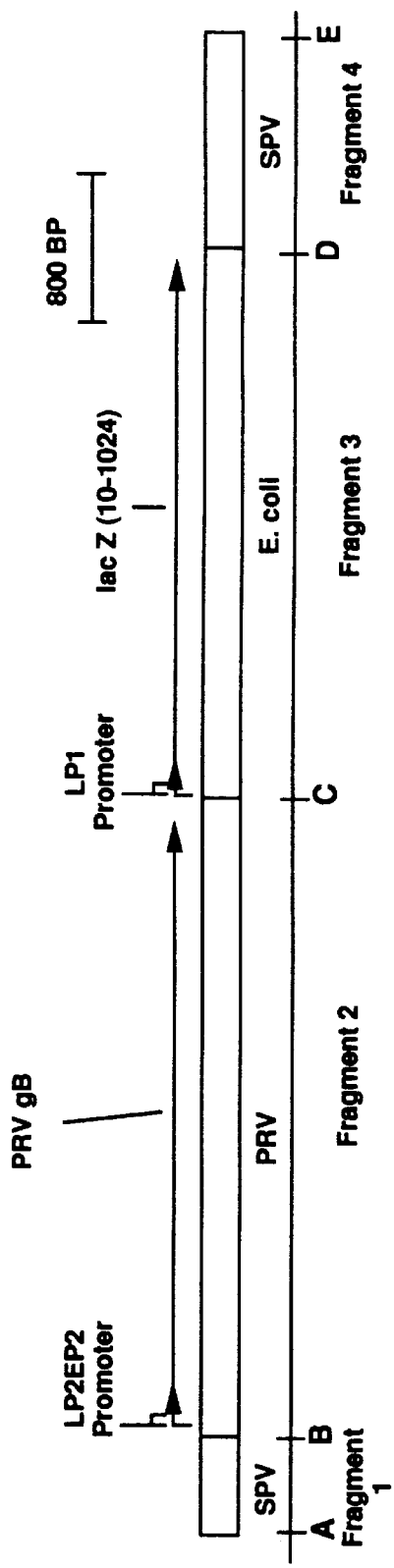
Figure 30B:
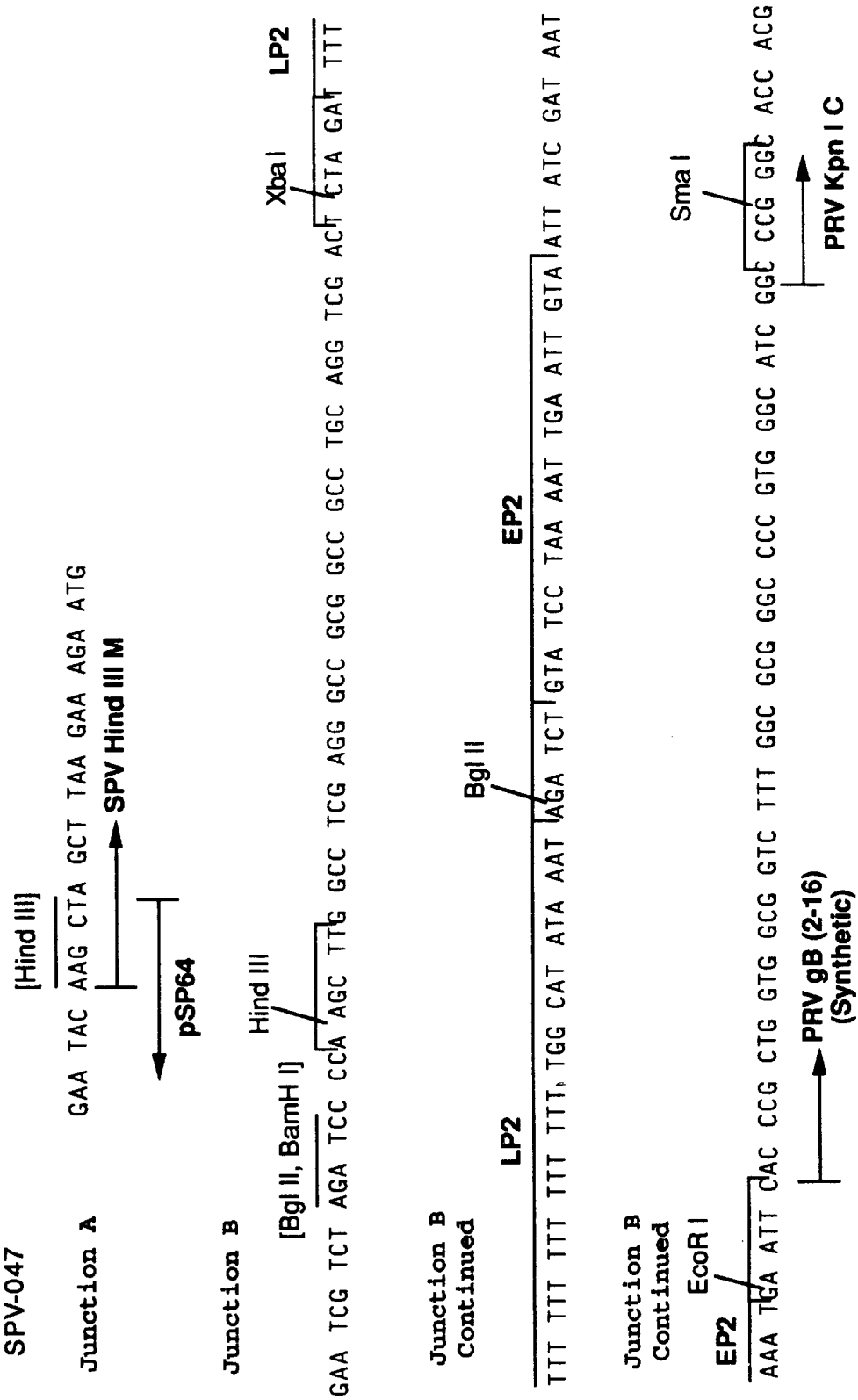
Figure 31A:
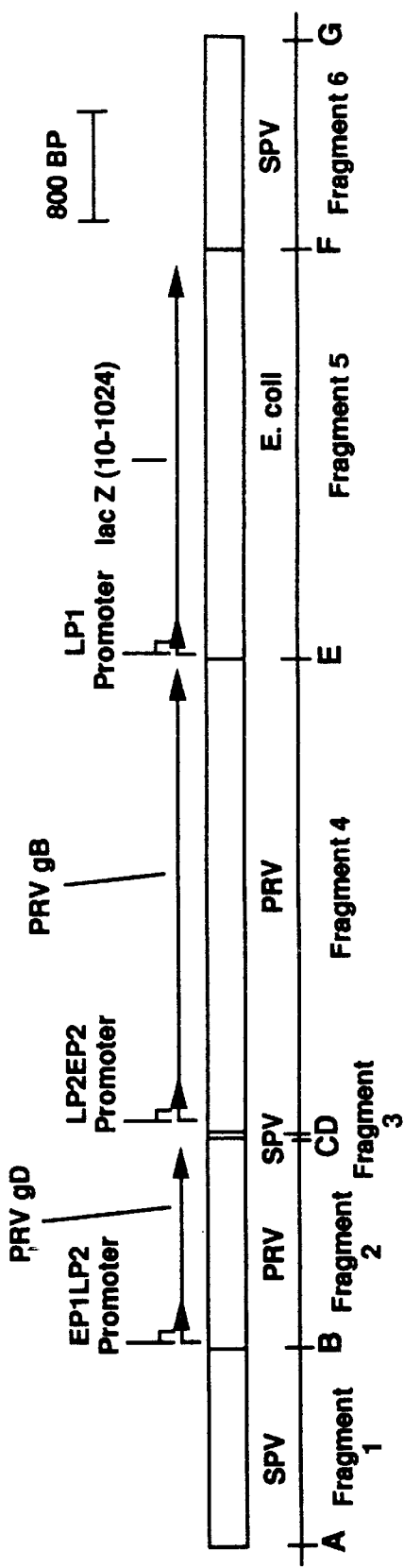
Figure 31B:
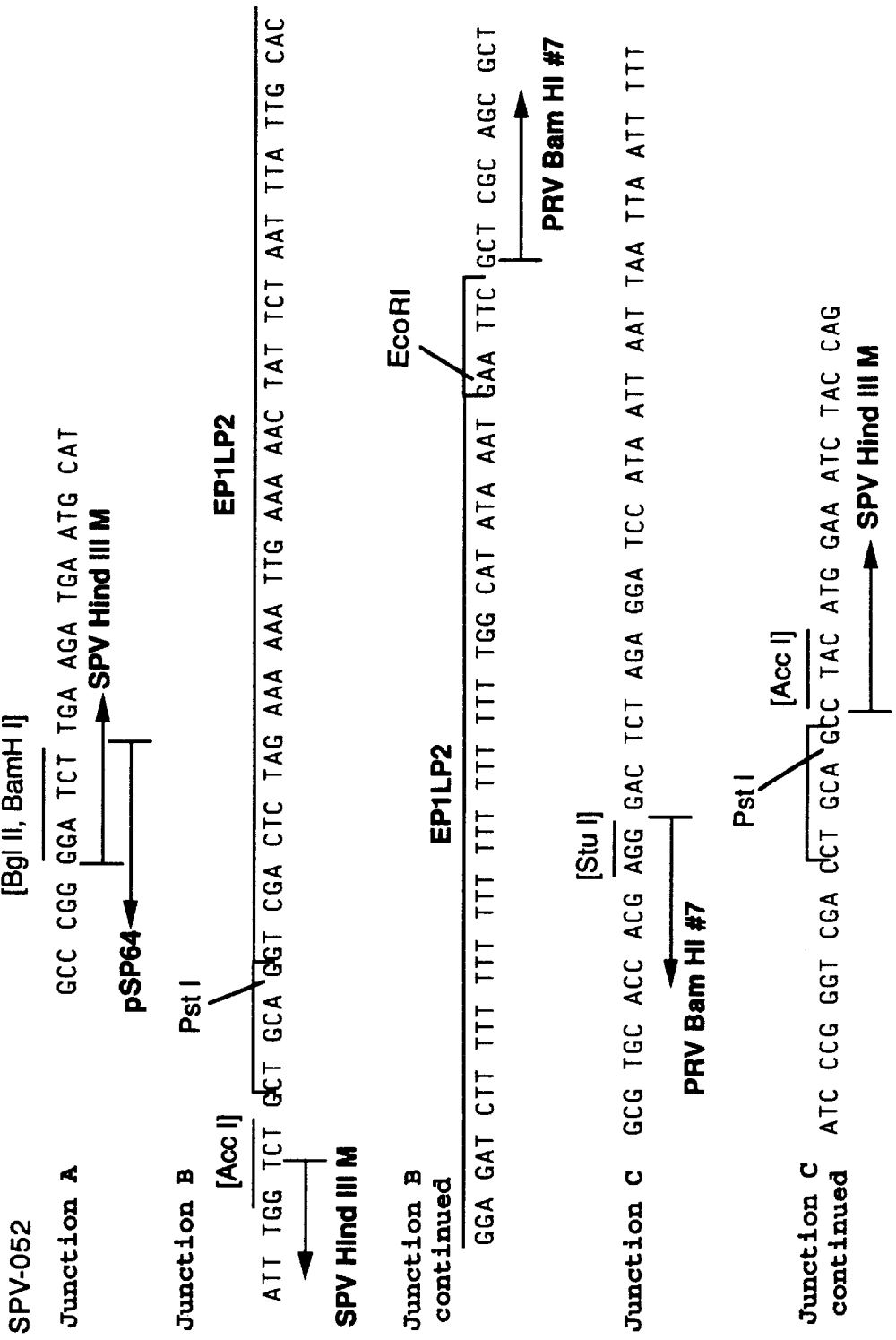
Figure 31C:
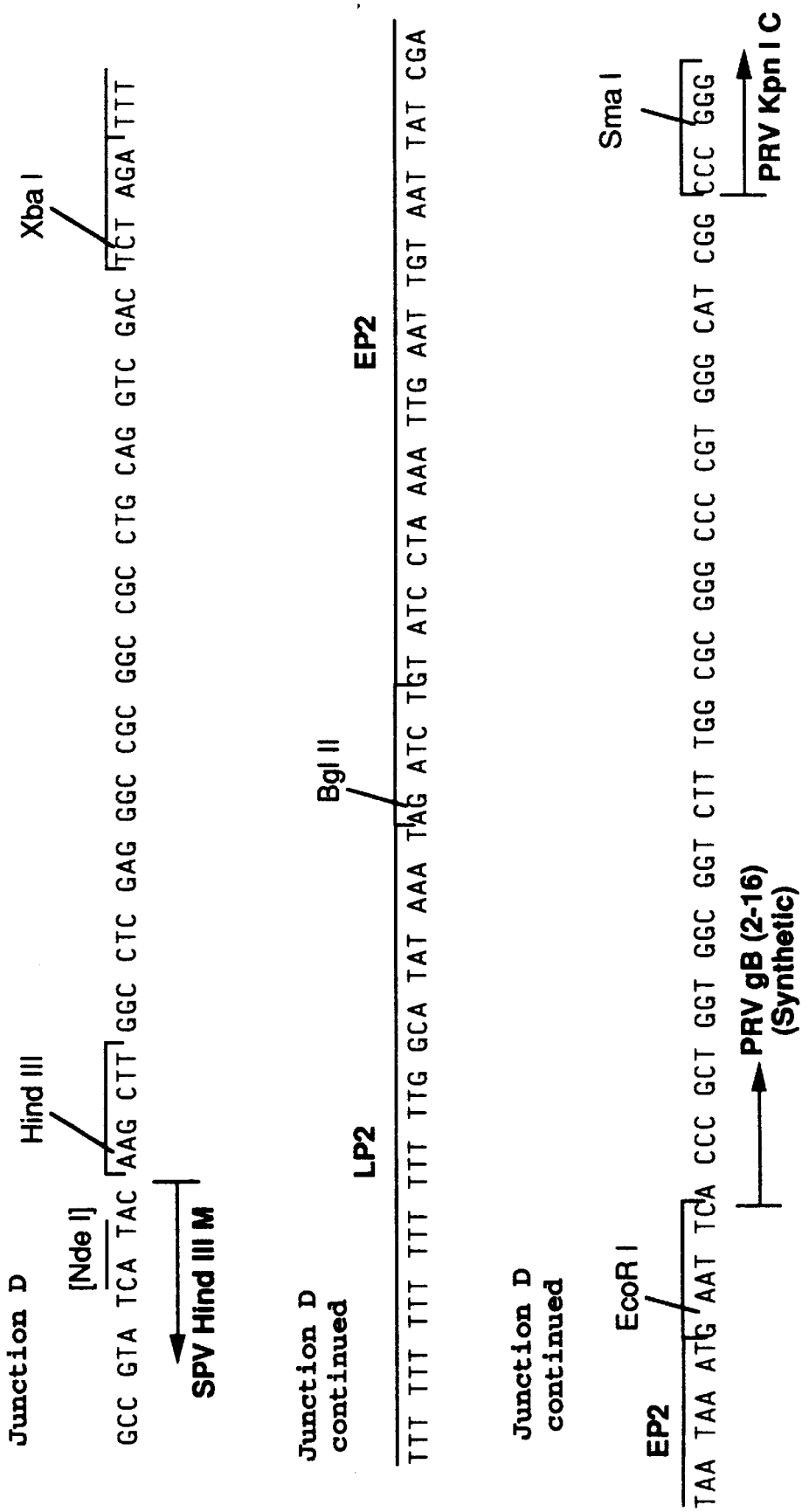
Figure 31D:
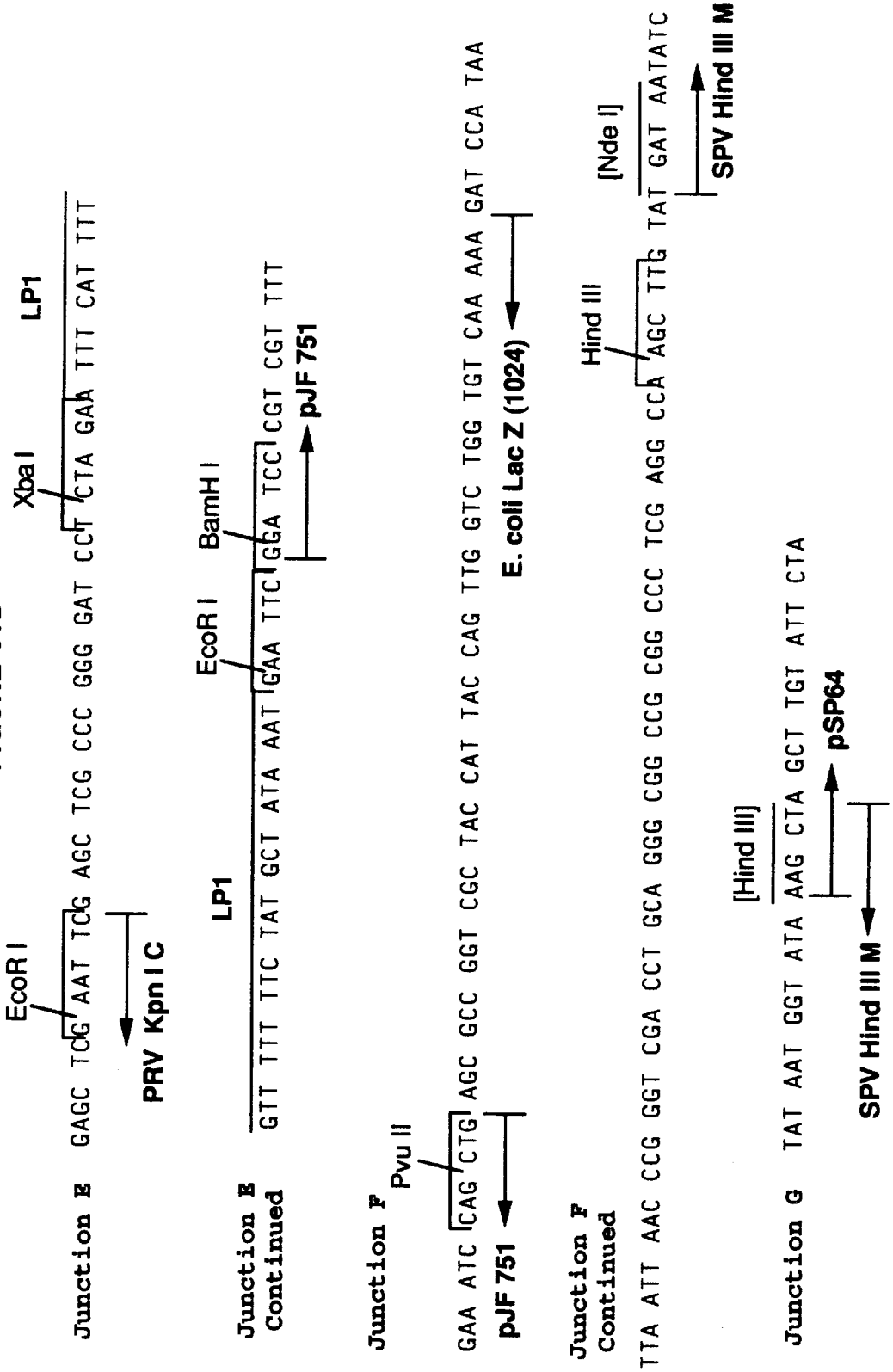
Figure 32A:
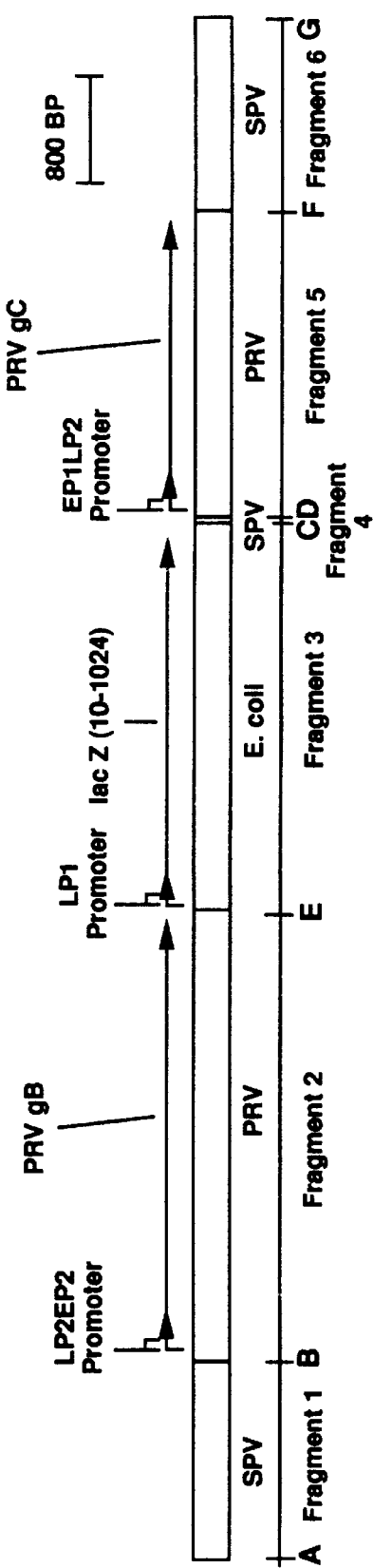
Figure 32B:
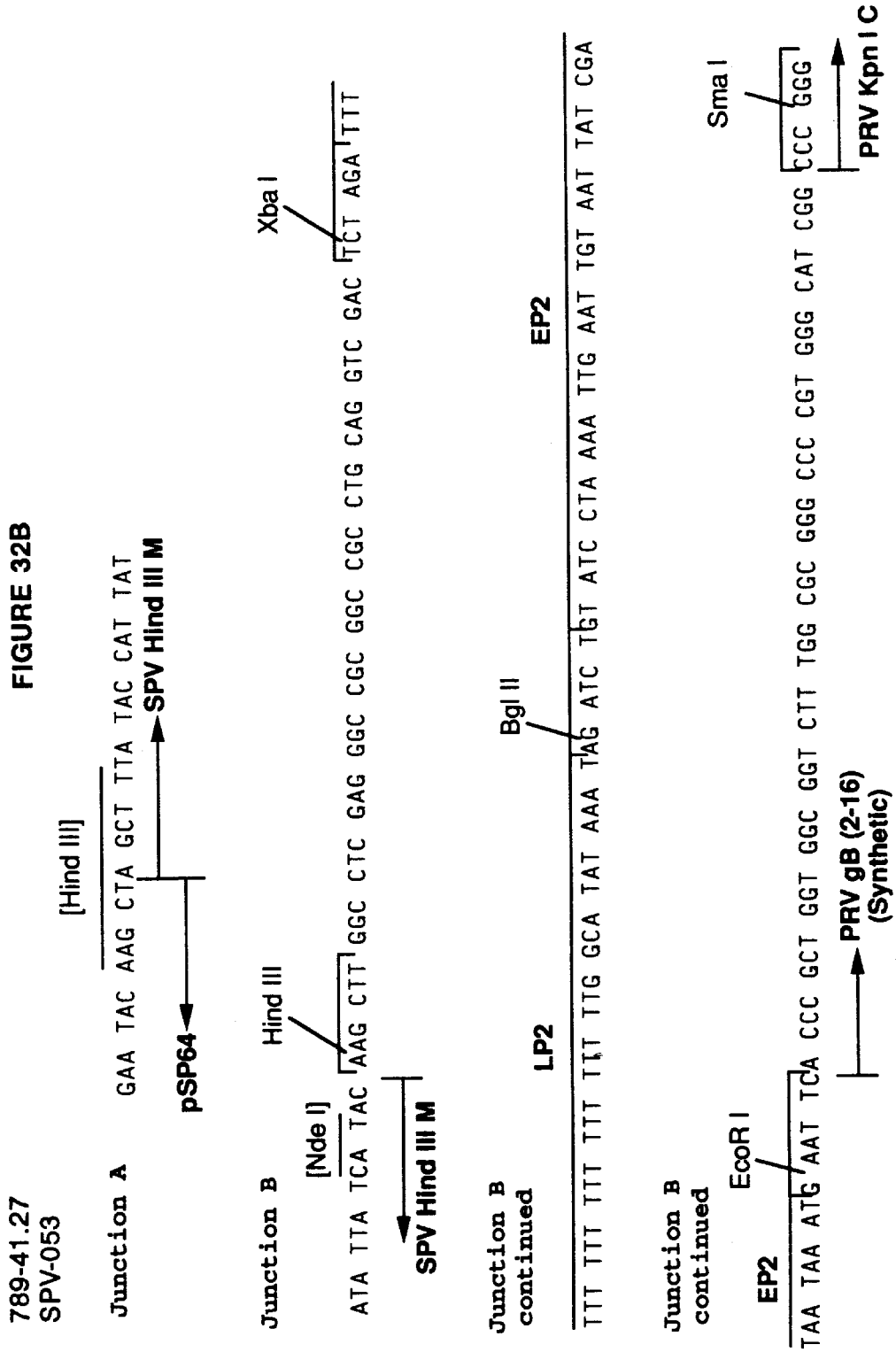
Figure 32C:
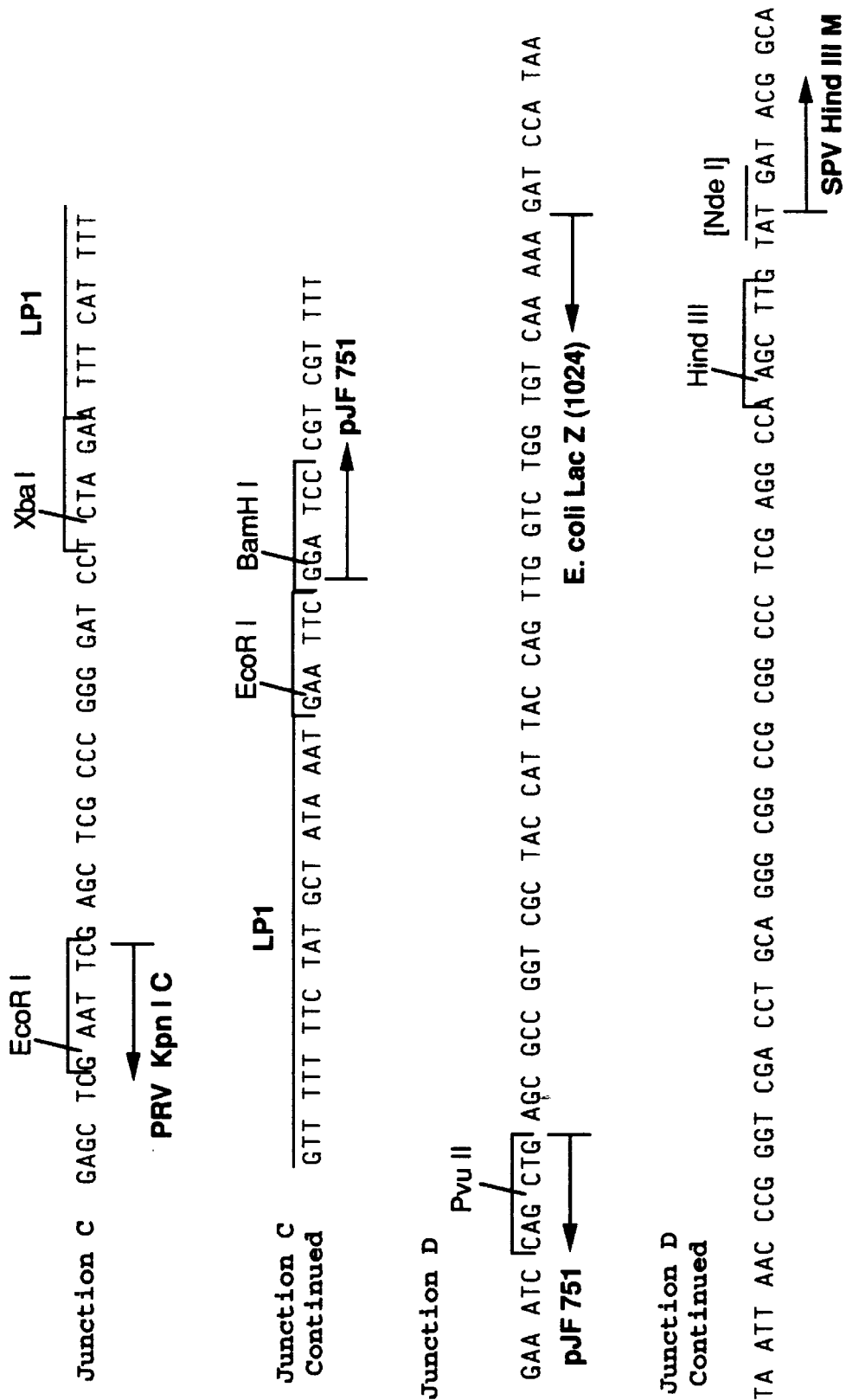
Figure 32D:
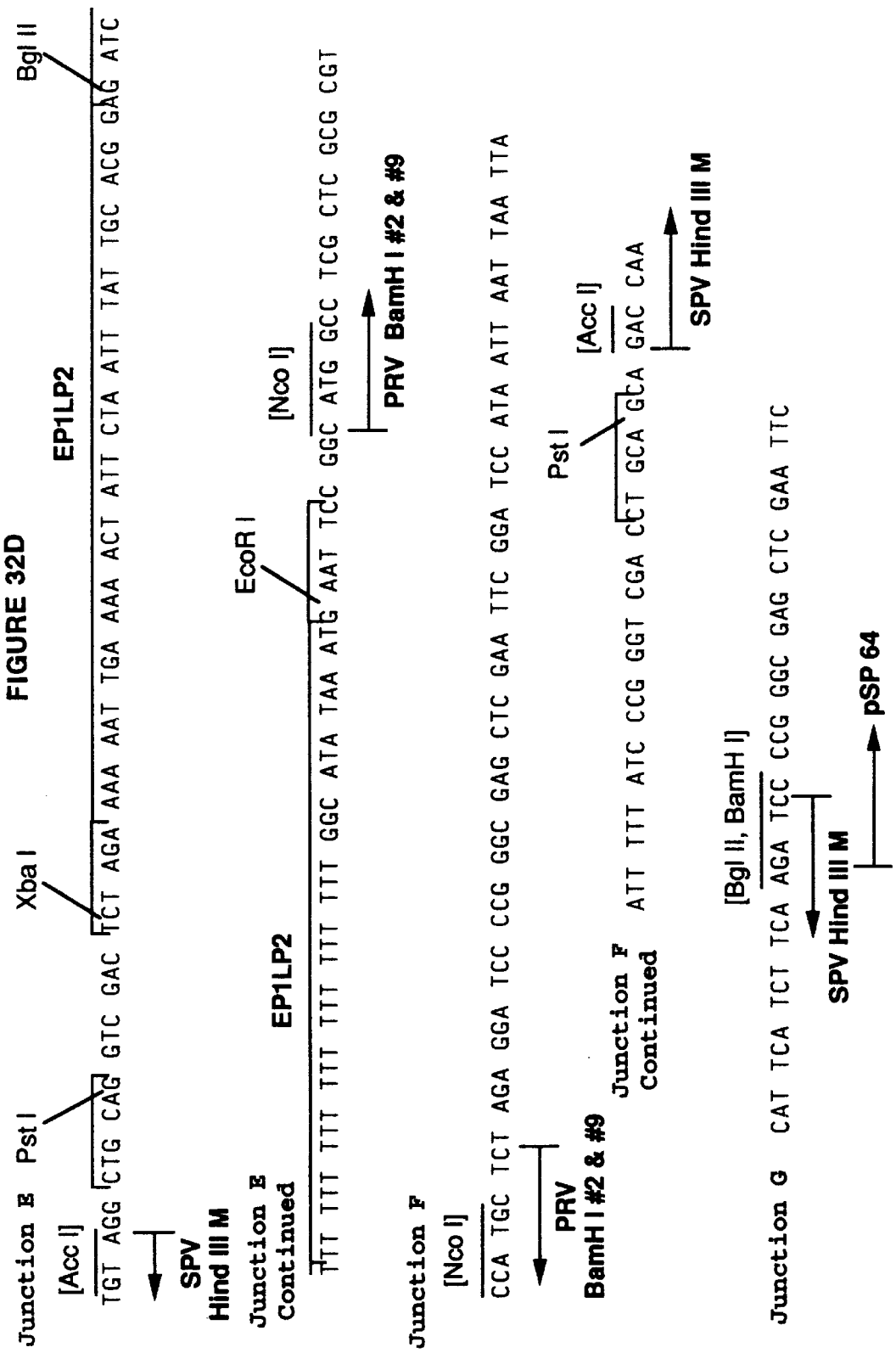
Figure 33A:
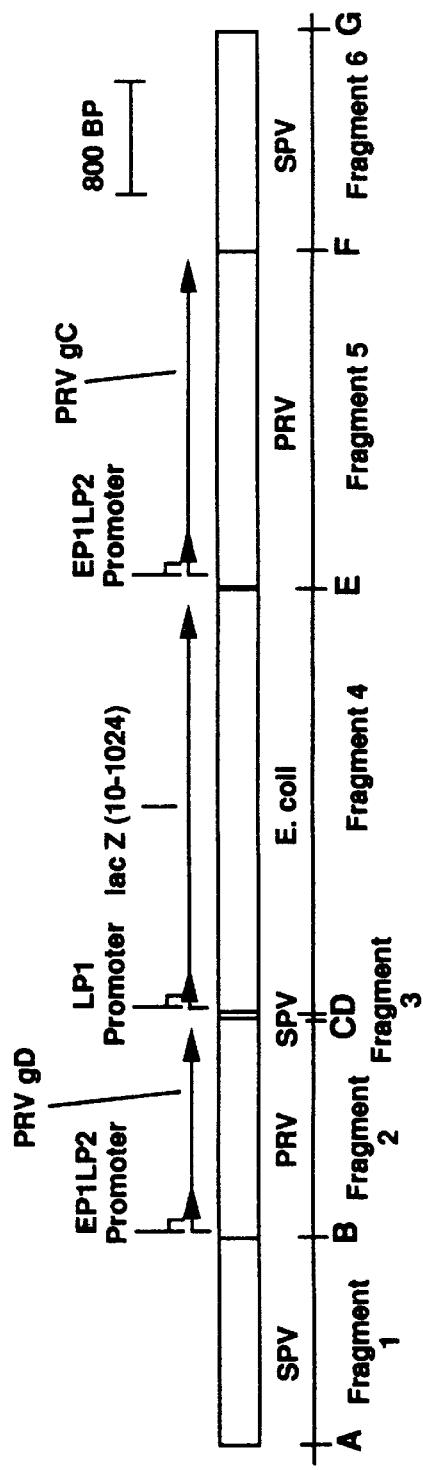
Figure 33B:
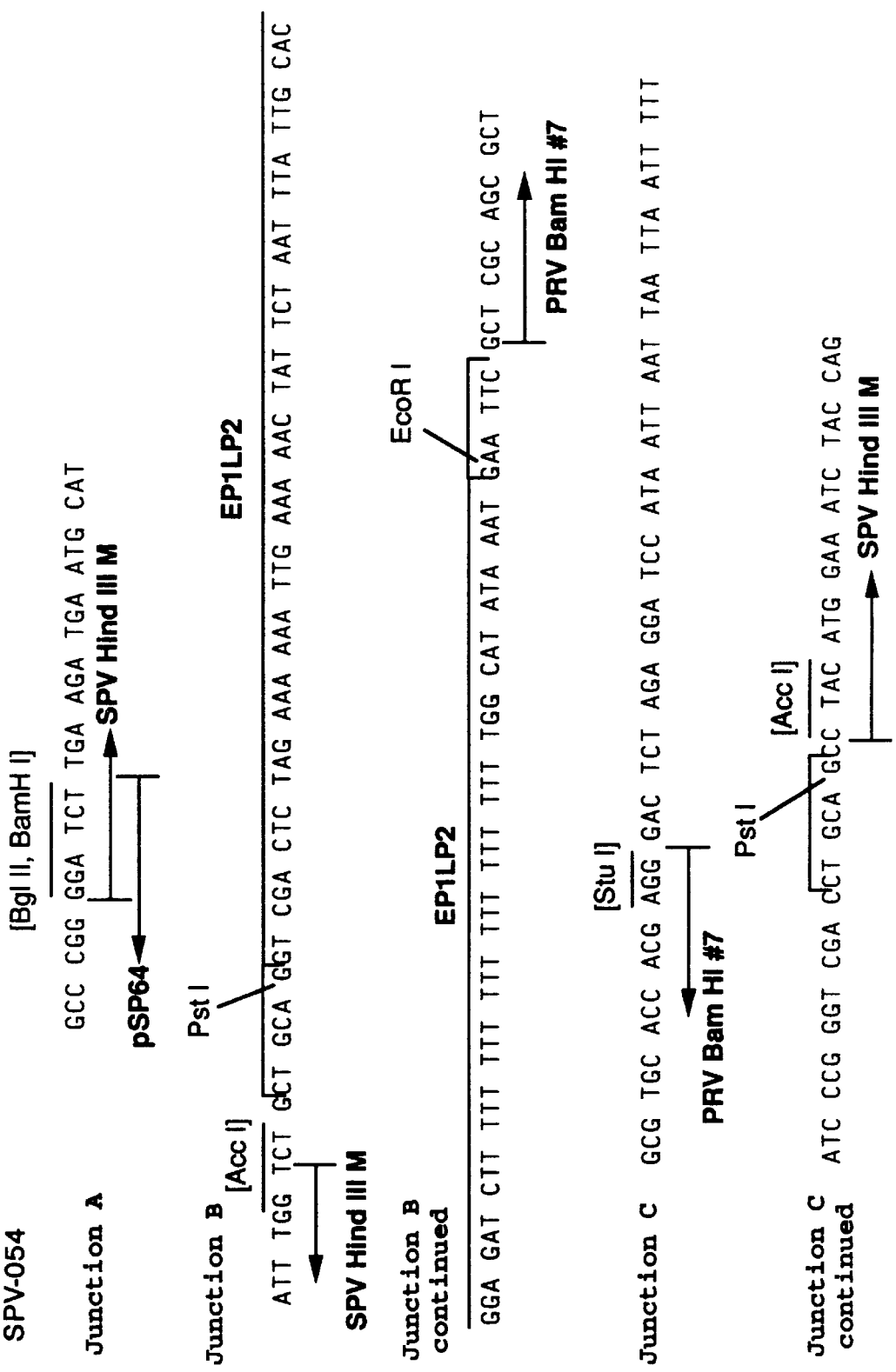
Figure 33C:
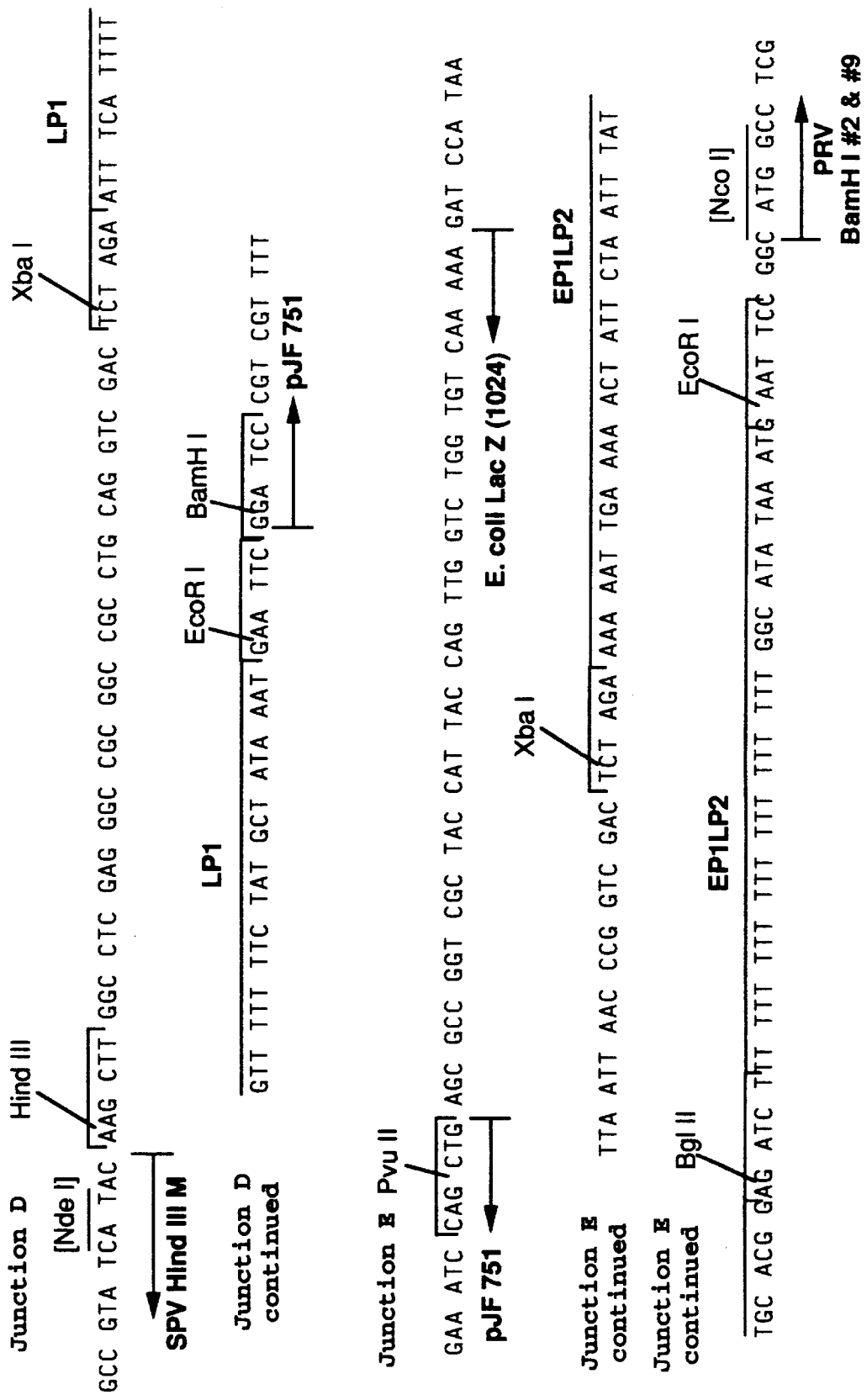
Figure 33D:
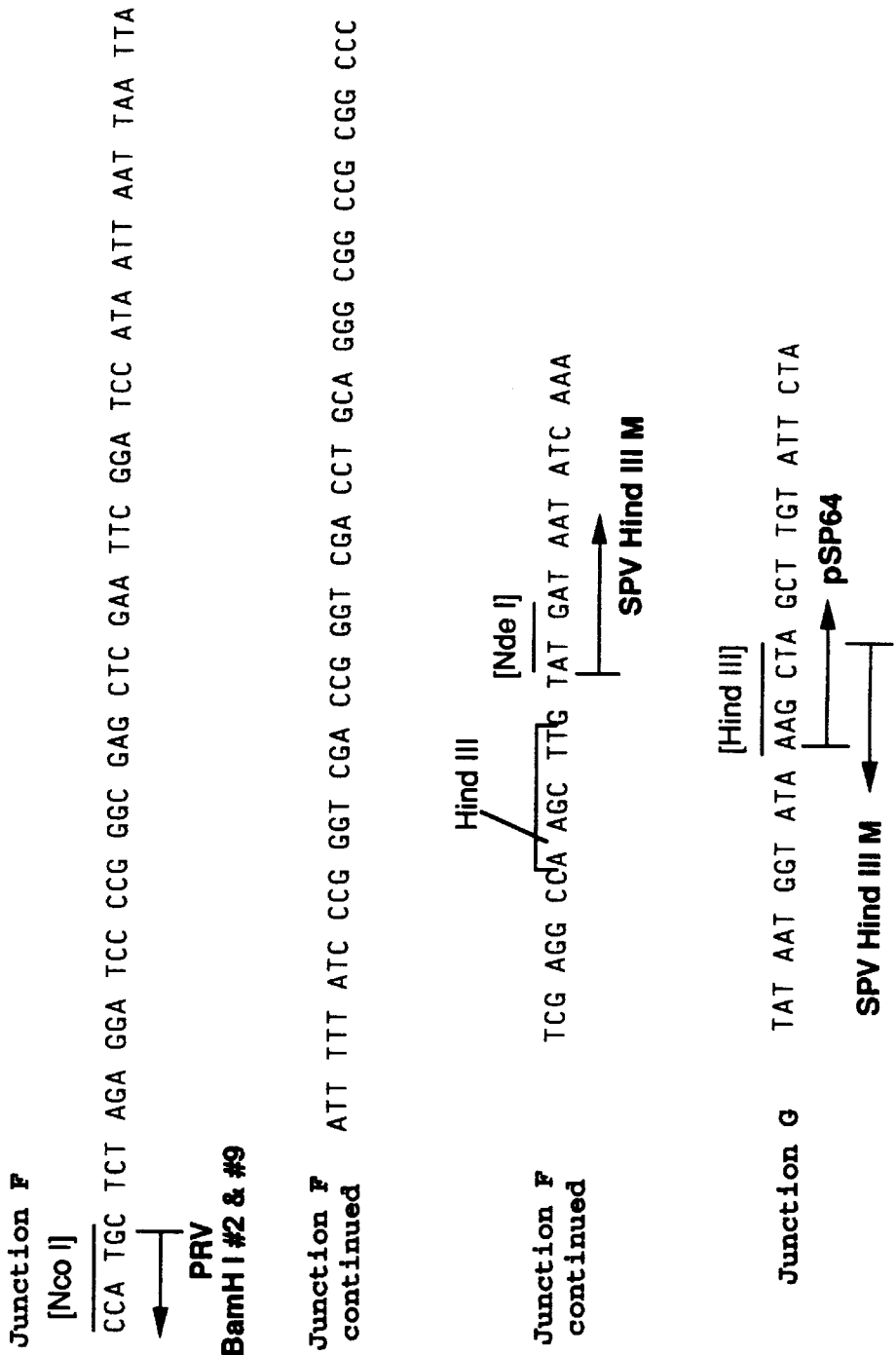
Figure 34A:
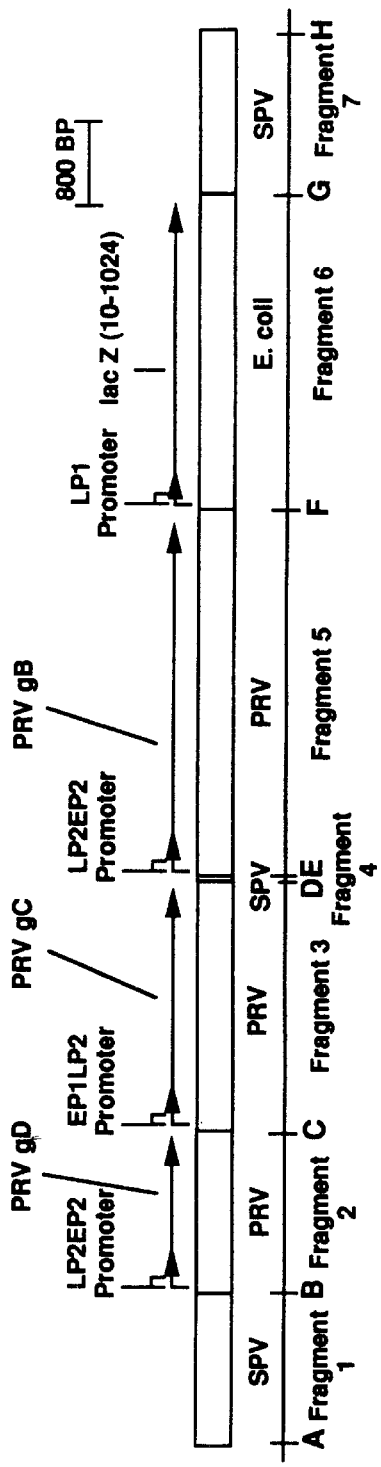
Figure 34B:
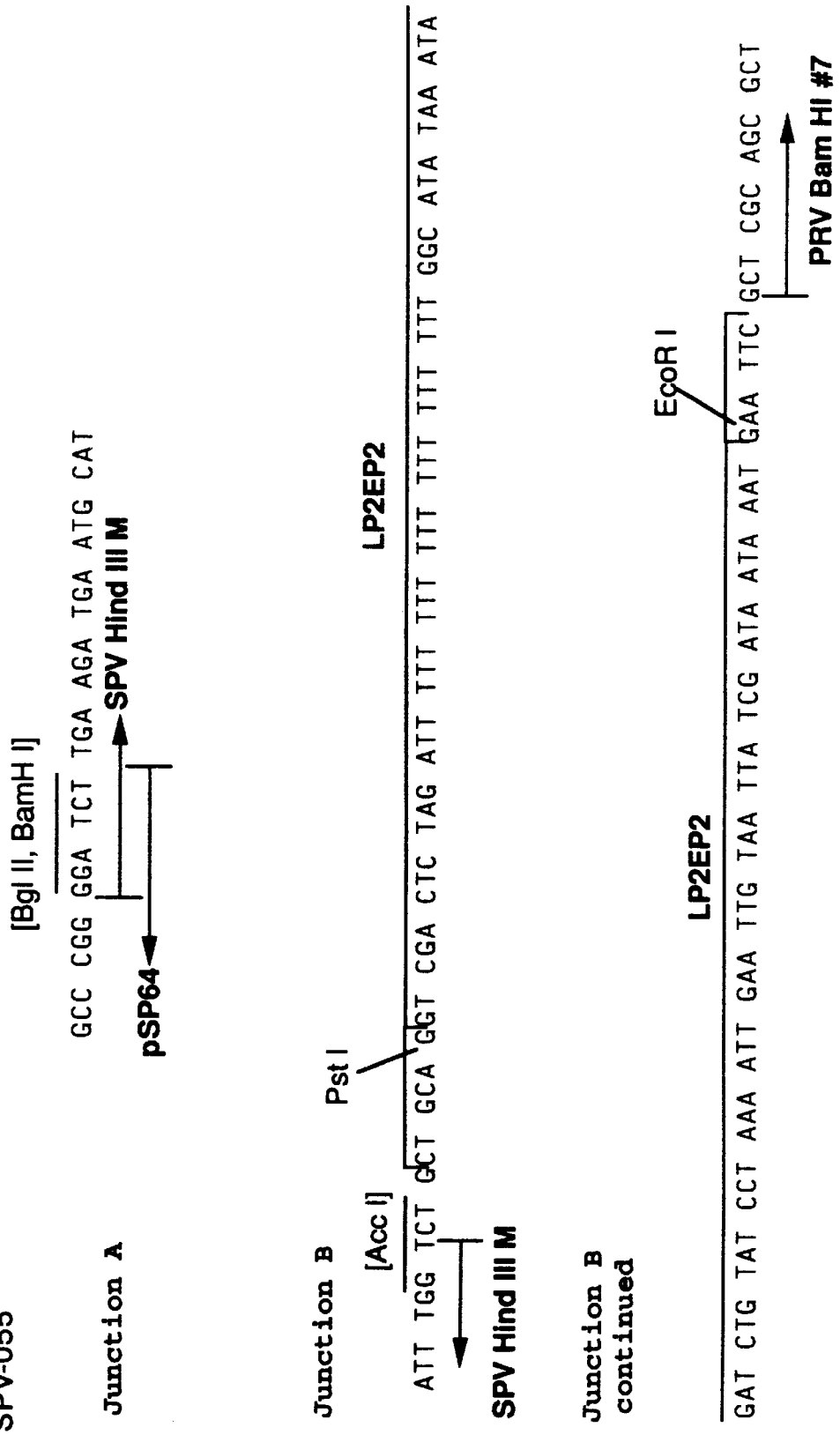
Figure 34C:
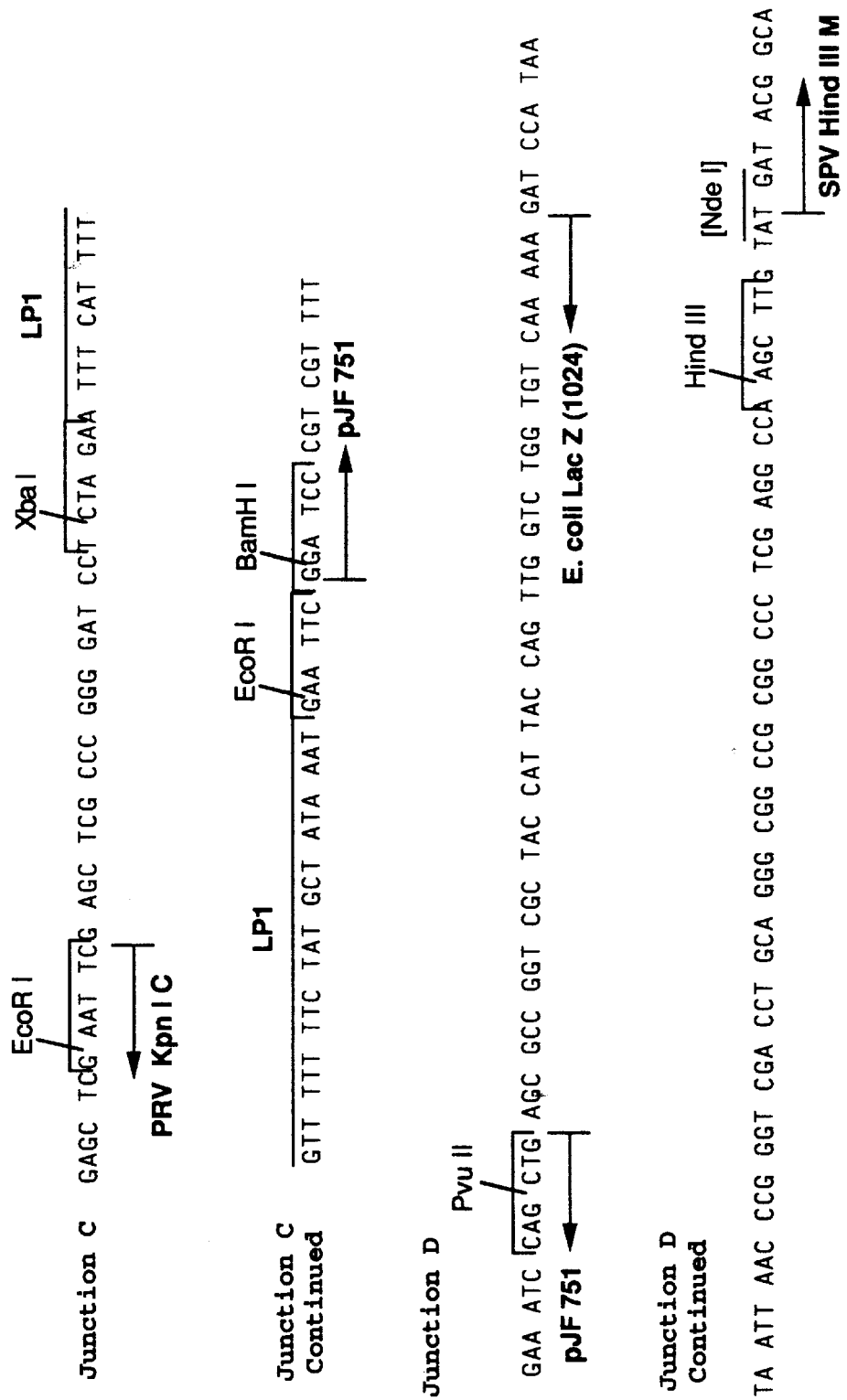
Figure 34D:
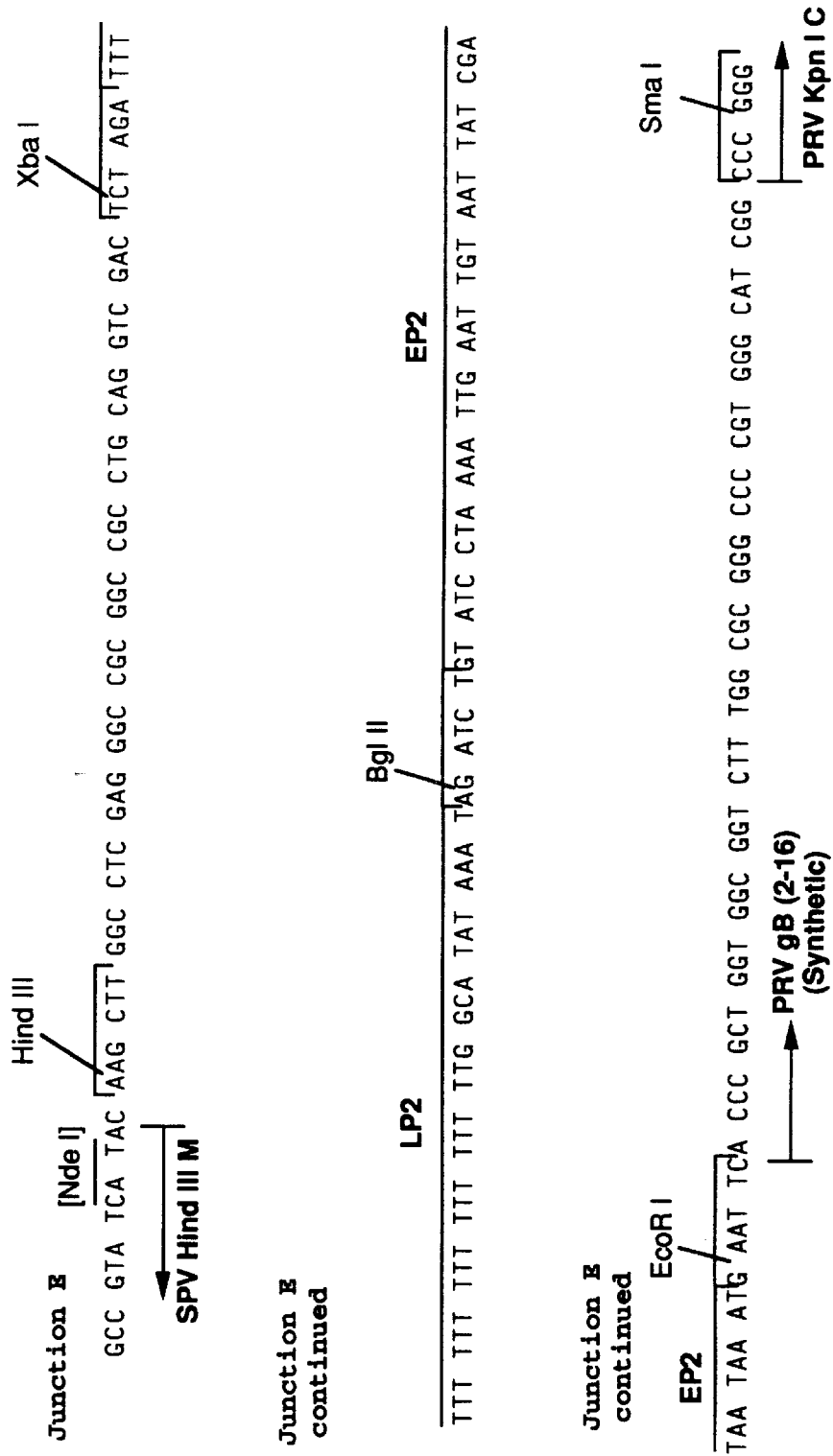

FIGS. 30A–30C:

Detailed description of Swinepox Virus S-SPV-047 and the DNA insertion in Homology Vector 779-94.31. Diagram showing the orientation of DNA fragments assembled in plasmid 779-94.31. The origin of each fragment is indicated in the table. The sequences located at each of the junctions between fragments is also shown. FIGS. 30A–30C show the sequences located at Junction A (SEQ ID NOS: 226) , (SEQ ID NO: 227) , C (SEQ ID NO: 228), D (SEQ ID NO: 229), and E (SEQ ID NO: 230) between fragments and the sequences located at the junctions. The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restrictions sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 2 early promoter 2 (LP2EP2), pox synthetic late promoter 1 (LP1), base pairs (BP).

FIGS. 31A–31D:

Detailed description of Swinepox Virus S-SPV-052 and the DNA insertion in Homology Vector 789-41.7. Diagram showing the orientation of DNA fragments assembled in plasmid 789-41.7. The origin of each fragment is indicated in the table. The sequences located at each of the junctions between fragments is also shown. FIGS. 31A–31D show the sequences located at Junction A (SEQ ID NOS: 231), (SEQ ID NO: 232), C (SEQ ID NO: 233), D (SEQ ID NO: 234), E (SEQ ID NO: 235), and F (SEQ ID NO: 236) and G (SEQ ID NO: 237) between fragments and the sequences located at the junctions. The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restrictions sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 2 early promoter 2 (LP2EP2), pox synthetic early promoter 1 late promoter 2 (EP1LP2), pox synthetic late promoter 1 (LP1), base pairs (BP).

FIGS. 32A–32D:

Detailed description of Swinepox Virus S-SPV-053 and the DNA insertion in Homology Vector 789-41.27. Diagram showing the orientation of DNA fragments assembled in plasmid 789-41.27. The origin of each fragment is indicated in the table. The sequences located at each of the junctions between fragments is also shown. FIGS. 32A–32D show the sequences located at Junction A (SEQ ID NOS: 238), (SEQ ID NO: 339), C (SEQ ID NO: 240), D (SEQ ID NO: 241), E (SEQ ID NO: 242), F (SEQ ID NO: 243), and G (SEQ ID NO: 244) between fragments and the sequences located at the junctions. The restriction sites used to generate each fragment as well as synthetic linker sequences which are used to join the fragments are described for each junction. The location of several gene coding regions and regulatory elements is also given. The following two conventions are used: numbers in parentheses, ( ) , refer to amino acids, and restrictions sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 2 early promoter 2 (LP2EP2), pox synthetic early promoter 1 late promoter 2 (EP1LP2), pox synthetic late promoter 1 (LP1), base pairs (BP).

FIGS. 33A–33D:

Detailed description of Swinepox Virus S-SPV-054 and the DNA insertion in Homology Vector 789-41.47. Diagram showing the orientation of DNA fragments assembled in plasmid 789-41.47. The origin of each fragment is indicated in the table. The sequences located at each of the junctions between fragments is also shown. FIGS. 33A–33D show the sequences located at Junction A (SEQ ID NOS: 245), (SEQ ID NO: 246), C (SEQ ID NO: 247), D (SEQ ID NO: 248), E (SEQ ID NO: 249), F (SEQ ID NO: 250), and G (SEQ ID NO: 251) between fragments and the sequences located at the junctions. The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restrictions sites in brackets, [ ], indicate the remnants of sites which are destroyed during construction. The following abbreviations are used: swinepox virus (SPV), pseudorabies virus (PRV), *Escherichia coli* (*E. coli*), pox synthetic early promoter 1 late promoter 2 (EP1LP2), pox synthetic late promoter 1 (LP1), base pairs (BP).

FIGS. 34A-34E:

Detailed description of Swinepox Virus S-SPV-055 and the DNA insertion in Homology Vector 789-41.73. Diagram showing the orientation of DNA fragments assembled in plasmid 789-41.73. The origin of each fragment is indicated in the table. The sequences located at each of the junctions between fragments is also shown. FIGS. 34A-34E show the sequences located at Junction A (SEQ ID NOS: 252), (SEQ ID NO: 253), C (SEQ ID NO: 254), D (SEQ ID NO: 255), E (SEQ ID NO: 256), F (SEQ ID NO: 257), G (SEQ ID NO: 258), and H (SEQ ID NO: 259) between fragments and the sequences located at the junctions. The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restrictions sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 2 early promoter 2 (LP2EP2), pox synthetic early promoter 1 late promoter 2 (EP1LP2), pox synthetic late promoter 1 (LP1), base pairs (BP).

DETAILED DESCRIPTION OF THE INVENTION

The present invention provides a recombinant swinepox virus comprising a foreign DNA sequence inserted into the swinepox virus genomic DNA, wherein the foreign DNA sequence is inserted within a HindIII K fragment of the swinepox virus genomic DNA and is capable of being expressed in a swinepox virus infected host cell.

In one embodiment the recombinant swinepox virus contains the foreign DNA sequence is inserted into an approximately 2 kB HindIII to BamHI subfragment of the HindIII N fragment of the swinepox virus genomic DNA. In another embodiment the foreign DNA sequence is inserted into an open reading frame within an approximately 2 kB HindIII to BamHI subfragment of the HindIII N fragment of the swinepox virus genomic DNA. In another embodiment the the open reading frame encodes a I7L gene.

In another embodiment the foreign DNA sequence is inserted within a EcoRV restriction endonuclease site within the approximately 2 kB HindIII to BamHI subfragment of the swinepox virus genomic DNA. In another embodiment the foreign DNA sequence is inserted within a SnaBi restriction endonuclease site within the approximately 2.0 kB HindIII to BamHI subfragment of the swinepox virus genomic DNA.

In another embodiment the foreign DNA sequence is inserted within an approximately 1.2 kB BamHI to HindIII subfragment of the HindIII N fragment of the swinepox virus genomic DNA. In another embodiment the foreign DNA sequence is inserted into an open reading frame within an approximately 1.2 kB BamHI to HindIII subfragment of the HindIII N fragment of the swinepox virus genomic DNA. In another embodiment the foriegn DNA sequence is inserted into an open reading frame which encodes a I4L gene. In another embodiment the foreign DNA sequence is inserted within a BglII restriction endonuclease site within the approximately 1.2 kB BamHI to HindIII subfragment of the swinepox virus genomic DNA.

The present invention provides a recombinant swinepox virus comprising a foreign DNA sequence inserted into the swinepox virus genomic DNA, wherein the foreign DNA sequence is inserted within a HindIII M fragment of the swinepox virus genomic DNA and is capable of being expressed in a swinepox virus infected host cell.

In one embodiment the recombinant swinepox virus contains the foreign DNA sequence inserted into an approximately 2 kB BglII to HindIII subfragment of the HindIII M fragment of the swinepox virus genomic DNA. In another embodiment the foreign DNA sequence is inserted into an open reading frame within an approximately 2 kB BglII to HindIII subfragment of the HindIII M fragment of the swinepox virus genomic DNA. In another embodiment the open reading frame encodes a O1L gene. In the preferred embodiment the foreign DNA sequence is inserted within a BglII restriction endonuclease site within the approximately 2 kB BglII to HindIII subfragment of the swinepox virus genomic DNA.

In another embodiment the recombinant swinepox virus contains the foreign DNA sequence inserted within an approximately 3.6 kB larger HindIII to BglII subfragment of the HindIII M fragment of the swinepox virus genomic DNA. In another embodiment the foreign DNA sequence is inserted into an open reading frame within an approximately 3.6 kB larger HindIII to BglII subfragment of the HindIII M fragment of the swinepox virus genomic DNA. In another embodiment the open reading frame encodes a I4L gene.

In one embodiment the foreign DNA sequence of the recombinant swinepox virus is inserted within a non-essential Open Reading Frame (ORF) of the HindIII M fragment. Example of ORF's include, but are not limited to: I4L, I2L, O1L, and E10L.

In another embodiment the foreign DNA sequence of the recombinant swinepox virus is inserted within an approximately 2 Kb HindIII to BglII subfragment of the HindIII M fragment of the swinepox virus genomic DNA. In a preferred embodiment the foreign DNA sequence is inserted within a BglII site located within the approximately 2 Kb HindIII to BglII subfragment of the swinepox virus genomic DNA.

In another embodiment the foreign DNA sequence is inserted within a larger HindIII to BglII subfragment of the HindIII M fragment of the swinepox virus genomic DNA. In a preferred embodiment the foreign DNA sequence is inserted within an AccI site located within the larger HindIII to BglII subfragment of the swinepox virus genomic DNA.

In another embodiment the recombinant swinepox virus further comprises a foreign DNA sequence inserted into an open reading frame encoding swinepox virus thymidine kinase. In one embodiment the foreign DNA sequence is inserted into a NdeI site located within the open reading frame encoding the swinepox virus thymidine kinase.

This invention provides a recombinant swinepox virus comprising a foreign DNA sequence inserted into the swinepox virus genomic DNA, wherein the foreign DNA sequence is inserted within a HindIII K fragment of the swinepox virus genomic DNA and is capable of being expressed in a swinepox virus infected host cell.

In one embodiment the foreign DNA sequence is inserted into an approximately 3.2 kB subfragment of the HindIII K fragment of the swinepox virus genomic DNA. In another embodiment the foreign DNA sequence is inserted into an open reading frame within an approximately 3.2 kB subfragment of the HindIII K fragment of the swinepox virus genomic DNA. In another embodiment the open reading frame encodes a B18R gene. In another embodiment the open reading frame encodes a B4R gene.

For purposes of this invention, "a recombinant swinepox virus capable of replication" is a live swinepox virus which has been generated by the recombinant methods well known to those of skill in the art, e.g., the methods set forth in HOMOLOGOUS RECOMBINATION PROCEDURE FOR GENERATING RECOMBINANT SPV in *Materials and Methods* and has not had genetic material essential for the replication of the recombinant swinepox virus deleted.

For purposes of this invention, "an insertion site which is not essential for replication of the swinepox virus" is a location in the swinepox viral genome where a sequence of DNA is not necessary for viral replication, for example, complex protein binding sequences, sequences which code for reverse transcriptase or an essential glycoprotein, DNA sequences necessary for packaging, etc.

For purposes of this invention, a "promoter" is a specific DNA sequence on the DNA molecule to which the foreign RNA polymerase attaches and at which transcription of the foreign RNA is initiated.

For purposes of this invention, an "open reading frame" is a segment of DNA which contains codons that can be transcribed into RNA which can be translated into an amino acid sequence and which does not contain a termination codon.

In addition, the present invention provides a recombinant swinepox virus (SPV) capable of replication in an animal into which the recombinant swinepox virus is introduced which comprises swinepox viral DNA and foreign DNA encoding RNA which does not naturally occur in the animal into which the recombinant swinepox virus is introduced, the foreign DNA being inserted into the swinepox viral DNA at an insertion site which is not essential for replication of the swinepox virus and being under the control of a promoter.

The invention further provides a foreign DNA sequence or foreign RNA which encodes a polypeptide. Preferably, the polypeptide is antigenic in the animal. Preferably, this antigenic polypeptide is a linear polymer of more than 10 amino acids linked by peptide bonds which stimulates the animal to produce antibodies.

The invention further provides a recombinant swinepox virus capable of replication which contains a foreign DNA encoding a polypeptide which is a detectable marker. Preferably the detectable marker is the polypeptide *E. coli* β-galactosidase or *E. coli* beta-glucuronidase. Preferably, the insertion site for the foreign DNA encoding *E. coli* β-galactosidase is the AccI restriction endonuclease site located within the HindIII M fragment of the swinepox viral DNA. Preferably, this recombinant swinepox virus is designated S-SPV-003 (ATCC Accession No. VR 2335). The S-SPV-003 swinepox virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2335.

For purposes of this invention, a "polypeptide which is a detectable marker" includes the bimer, trimer and tetramer form of the polypeptide. *E. coli* β-galactosidase is a tetramer composed of four polypeptides or monomer sub-units.

The invention further provides a recombinant swinepox virus capable of replication which contains foreign DNA encoding an antigenic polypeptide which is or is from pseudorabies virus (PRV) g50 (gD), pseudorabies virus (PRV) gII (gB), Pseudorabies virus (PRV) gIII (gC), pseudorabies virus (PRV) glycoprotein H, pseudorabies virus (PRV) glycoprotein E, Transmissible gastroenteritis (TGE) glycoprotein 195, Transmissible gastroenteritis (TGE) matrix protein, swine rotavirus glycoprotein 38, swine parvovirus capsid protein, *Serpulina hydodysenteriae* protective antigen, Bovine Viral Diarrhea (BVD) glycoprotein 55, Newcastle Disease Virus (NDV) hemagglutinin-neuraminidase, swine flu hemagglutinin or swine flu neuraminidase. Preferably, the antigenic polypeptide is Pseudorabies Virus (PRV) g50 (gD). Preferably, the antigenic protein is Newcastle Disease Virus (NDV) hemagglutinin-neuraminidase.

The invention further provides a recombinant swinepox virus capable of replication which contains foreign DNA encoding an antigenic polypeptide which is or is from *Serpulina hyodysenteriae*, Foot and Mouth Disease Virus, Hog Cholera Virus, Swine Influenza Virus, African Swine Fever Virus or *Mycoplasma hyopneumoniae*.

The invention further provides for a recombinant swinepox virus capable of replication which contains foreign DNA encoding pseudorabies virus (PRV) g50 (gD). This recombinant swinepox virus can be further engineered to contain foreign DNA encoding a detectable marker, such as *E. coli* β-galactosidase. A preferred site within the swinepox viral genome for insertion of the foreign DNA encoding PRV g50 (gD) and *E. coli* β-galactosidase is the AccI site within the HindIII M fragment of the swinepox viral DNA. Preferably, this recombinant swinepox virus is designated S-SPV-008 (ATCC Accession No. VR 2339). The S-SPV-008 swinepox virus has been deposited pursuant to the Budapest Treaty on the Purposes of Patent Procedure with the Patent Culture Depository of the American Type Culture Collection, 12301 Parklawn Drive, Rockville, Md. 20852 U.S.A. under ATCC Accession No. VR 2339.

The invention further provides for a recombinant swinepox virus capable of replication which contains foreign DNA encoding pseudorabies virus (PRV) gIII (gC). This recombinant swinepox virus can also be further engineered to contain foreign DNA encoding a detectable marker, such as *E. coli* β-galactosidase. A preferred site within the swinepox viral DNA for insertion of the foreign DNA encoding PRV C gene and *E. coli* β-galactosidase is the AccI site within the HindIII M fragment of the swinepox viral DNA. Preferably, this recombinant swinepox virus is designated S-SPV-011, S-SPV-012, or S-SPV-013. The swinepox virus designated S-SPV-013 has been deposited on Jul. 16, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2418.

The invention further provides for a recombinant swinepox virus capable of replication which contains foreign DNA encoding pseudorabies virus (PRV) gII (gB). This recombinant swinepox virus can also be further engineered to contain foreign DNA encoding a detectable marker, such as E. coli β-galactosidase. A preferred site within the swinepox viral DNA for insertion of the foreign DNA encoding PRV gII (gB) and E. coli β-galactosidase is the AccI site within the HindIII M fragment of the swinepox viral DNA. Preferably, this recombinant swinepox virus is designated S-SPV-015 (ATCC Accession No. VR 2466). The S-SPV-015 swinepox virus has been deposited on Jul. 22, 1994 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2466.

The invention further provides for a recombinant swinepox virus capable of replication which contains foreign DNA encoding pseudorabies virus (PRV) g50 (gD) and foreign DNA encoding pseudorabies virus (PRV) gIII (gC). This recombinant swinepox virus can also be further engineered to contain foreign DNA encoding a detectable marker, such as E. coli β-galactosidase. A preferred site within the swinepox viral DNA for insertion of the foreign DNA encoding PRV g50 (gD), PRV gIII (gC) and E. coli β-galactosidase is the AccI site within the HindIII M fragment of the swinepox viral DNA.

The invention further provides for a recombinant swinepox virus capable of replication which contains foreign DNA encoding pseudorabies virus (PRV) g50 (gD) and foreign DNA encoding pseudorabies virus (PRV) gII (gB). This recombinant swinepox virus can also be further engineered to contain foreign DNA encoding a detectable marker, such as E. coli β-galactosidase. A preferred site within the swinepox viral genome for insertion of foreign DNA encoding PRV g50 (gD), PRV gII (gB) and E. coli β-galactosidase is the AccI site within the HindIII M fragment of the swinepox viral DNA.

The invention further provides for a recombinant swinepox virus capable of replication which contains foreign DNA encoding pseudorabies virus (PRV) gIII (gC) and foreign DNA encoding pseudorabies virus (PRV) gII (gB). This recombinant swinepox virus can also be further engineered to contain foreign DNA encoding a detectable marker, such as E. coli β-galactosidase. A preferred site within the swinepox viral genome for insertion of foreign DNA encoding PRV gIII (gC), PRV gII (gB) and E. coli β-galactosidase is the AccI site within the HindIII M fragment of the swinepox viral DNA.

The invention further provides for a recombinant swinepox virus capable of replication which contains foreign DNA encoding pseudorabies virus (PRV) g50 (gD), foreign DNA encoding pseudorabies virus (PRV) gIII (gC), and foreign DNA encoding pseudorabies virus (PRV) gII (gB). This recombinant swinepox virus can also be further engineered to contain foreign DNA encoding a detectable marker, such as E. coli β-galactosidase.

A preferred site within the swinepox viral genome for insertion of foreign DNA encoding PRV g50 (gD), PRV gIII (gC), PRV gII (gB) and E. coli β-galactosidase is the AccI site within the HindIII M fragment of the swinepox viral DNA.

The invention further provides for a recombinant swinepox virus capable of replication which contains foreign DNA encoding RNA encoding the antigenic polypeptide Newcastle Disease Virus (NDV) hemagglutinin-neuraminidase further comprising foreign DNA encoding a polypeptide which is a detectable marker. Preferably, this recombinant swinepox virus is designated S-SPV-009 (ATCC Accession No. VR 2344). The S-SPV-009 swinepox virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2344.

The present invention further provides a recombinant swinepox virus which comprises a foreign DNA sequence inserted into a non-essential site of the swinepox genome, wherein the foreign DNA sequence encodes an antigenic polypeptide derived from infectious bovine rhinotracheitis virus and is capable of being expressed in a host infected by the recombinant swinepox virus. Examples of such antigenic polypeptide are infectious bovine rhinotracheitis virus glycoprotein E and glycoprotein G. Preferred embodiment of this invention are recombinant swinepox viruses designated S-SPV-017 and S-SPV-019.

The present invention further provides a recombinant swinepox virus which comprises a foreign DNA sequence inserted into a non-essential site of the swinepox genome, wherein the foreign DNA sequence encodes an antigenic polypeptide derived from infectious laryngotracheitis virus and is capable of being expressed in a host infected by the recombinant swinepox virus. Examples of such antigenic polypeptide are infectious laryngotracheitis virus glycoprotein G and glycoprotein I. Preferred embodiment of this invention are recombinant swinepox viruses designated S-SPV-014 and S-SPV-016.

In one embodiment of the recombinant swinepox virus the foreign DNA sequence encodes a cytokine. In another embodiment the cytokine is chicken myelomonocytic growth factor (cMGF) or chicken interferon (cIFN). Cytokines include, but are not limited to: transforming growth factor beta, epidermal growth factor family, fibroblast growth factors, hepatocyte growth factor, insulin-like growth factor, vascular endothelial growth factor, interleukin 1, IL-1 receptor antagonist, interleukin-2, interleukin-3, interleukin-4, interleukin-5, interleukin-6, IL-6 soluble receptor, interleukin-7, interleukin-8, interleukin-9, interleukin-10, interleukin-11, interleukin-12, interleukin-13, angiogenin, chemokines, colony stimulating factors, granulocyte-macrophage colony stimulating factors, erythropoietin, interferon, interferon gamma, c-kit ligand, leukemia inhibitory factor, oncostatin M, pleiotrophin, secretory leukocyte protease inhibitor, stem cell factor, tumor necrosis factors, and soluble TNF receptors. These cytokines are from humans, bovine, equine, feline, canine, porcine or avian. Preferred embodiments of such recombinant virus are designated S-SPV-042, and S-SPV-043.

The present invention further provides a recombinant swinepox virus which comprises a foreign DNA sequence inserted into a non-essential site of the swinepox genome, wherein the foreign DNA sequence encodes an antigenic polypeptide derived from a human pathogen and is capable of being expressed in a host infected by the recombinant swinepox virus.

Recombinant SPV expressing cytokines is used to enhance the immune response either alone or when combined with vaccines containing cytokines or antigen genes of disease causing microorganisms.

Antigenic polypeptide of a human pathogen which are derived from human herpesvirus include, but are not limited to: hepatitis B virus and hepatitis C virus hepatitis B virus surface and core antigens, hepatitis C virus, human immunodeficiency virus, herpes simplex virus-1, herpes simplex virus-2, human cytomegalovirus, Epstein-Barr virus, Varicella-Zoster virus, human herpesvirus-6, human herpesvirus-7, human influenza, measles virus, hantaan virus, pneumonia virus, rhinovirus, poliovirus, human respiratory syncytial virus, retrovirus, human T-cell leukemia virus, rabies virus, mumps virus, malaria (*Plasmodium falciparum*), *Bordetella pertussis,* Diptheria, *Rickettsia prowazekii, Borrelia berfdorferi,* Tetanus toxoid, malignant tumor antigens.

In one embodiment of the invention, a recombinant swinepox virus contains the foreign DNA sequence encoding hepatitis B virus core protein. Preferably, such virus recombinant virus is designated S-SPV-031.

The present invention further provides a recombinant swinepox virus which comprises a foreign DNA sequence inserted into a non-essential site of the swinepox genome, wherein the foreign DNA sequence encodes a cytokine capable of stimulating an immune in a host infected by the recombinant swinepox virus and is capable of being expressed in the host infected.

In one embodiment of the invention, a recombinant swinepox virus contains a foreign DNA sequence encoding human interleukin-2. Preferably, such recombinant virus is designated S-SPV-035.

The present invention further provides a recombinant swinepox virus which comprises a foreign DNA sequence inserted into a non-essential site of the swinepox genome, wherein the foreign DNA sequence encodes an antigenic polypeptide derived from an equine pathogen and is capable of being expressed in a host infected by the recombinant swinepox virus.

The antigenic polypeptide of an equine pathogen can derived from equine influenza virus, or equine herpesvirus. In one embodiment the antigenic polypeptide is equine influenza neuraminidase or hemagglutinin. Examples of such antigenic polypeptide are equine influenza virus type A/Alaska 91 neuraminidase, equine 5 influenza virus type A/Prague 56 neuraminidase, equine influenza virus type A/Miami 63 neuraminidase, equine influenza virus type A/Kentucky 81 neuraminidase, equine influenza virus type A/Kentucky 92 neuraminidase equine herpesvirus type 1 glycoprotein B, equine herpesvirus type 1 glycoprotein D, *Streptococcus equi,* equine infectious anemia virus, equine encephalitis virus, equine rhinovirus and equine rotavirus. Preferred embodiments of such recombinant virus are designated S-SPV-033, S-SPV-034, S-SPV-038, S-SPV-039 and S-SPV-041.

The present invention further provides an antigenic polypeptide which includes, but is not limited to: hog cholera virus gE1, hog cholera virus gE2, swine influenza virus hemagglutinin, neurominidase, matrix and nucleoprotein, pseudorabies virus gB, gC and gD, and PRRS virus ORF7.

The present invention further provides a recombinant swinepox virus which comprises a foreign DNA sequence inserted into a non-essential site of the swinepox genome, wherein the foreign DNA sequence encodes an antigenic polypeptide derived from bovine respiratory syncytial virus or bovine parainfluenza virus, and is capable of being expressed in a host infected by the recombinant swinepox virus.

For example, the antigenic polypeptide may be infectious bovine rhinotracheitis virus gE, bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase. In a preferred embodiment the recombinant swinepox virus is designated S-SPV-045.

Preferred embodiments of a recombinant virus containing a foreign DNA encoding a antigenic polypeptide from a bovine respiratory syncytial virus are designated S-SPV-020, S-SPV-029, and S-SPV-030. And a preferred embodiment of a recombinant virus containing a foreign DNA encoding an antigenic polypeptide from a bovine parainfluenza virus are designated S-SPV-028.

The present invention further provides a recombinant swinepox virus which comprises a foreign DNA sequence inserted into a non-essential site of the swinepox genome, wherein the foreign DNA sequence encodes bovine viral diarrhea virus (BVDV) glycoprotein 48 or glycoprotein 53, and wherein the foreign DNA sequence is capable of being expressed in a host infected by the recombinant swinepox virus. Preferred embodiments of such virus are designated S-SPV-032, S-SPV-040, S-SPV-049, and S-SPV-050.

The present invention further provides a recombinant swinepox virus which comprises a foreign DNA sequence inserted into a non-essential site of the swinepox genome, wherein the foreign DNA sequence encodes an antigenic polypeptide derived from infectious bursal disease virus and wherein the foreign DNA sequence is capable of being expressed in a host infected by the recombinant swinepox virus. Examples of such antigenic polypeptide are infectious bursal disease virus polyprotein and VP2. Preferred embodiments of such virus are designated S-SPV-026 and S-SPV-027.

The present invention further provides a recombinant swinepox virus in which the foreign DNA sequence encodes an antigenic polypeptide which includes, but is not limited to: MDV gA, MDV gB, MDV gD, NDV HN, NDV F, ILT gB, ILT gI, ILT gD, IBDV VP2, IBDV VP3, IBDV VP4, IBDV polyprotein, IBV spike, IBV matrix, avian encephalomyelitis virus, avian reovirus, avian paramyxovirus, avian influenza virus, avian adenovirus, fowl pox virus, avian coronavirus, avian rotavirus, chick anemia virus, Salmonella spp. *E. coli,* Pasteurella spp., Bordetella spp., Eimeria spp., Histomonas spp., Trichomonas spp., Poultry nematodes, cestodes, trematodes, poultry mites/lice, and poultry protozoa.

The invention further provides that the inserted foreign DNA sequence is under the control of a promoter. In one embodiment the is a swinepox viral promoter. In another embodiment the foreign DNA sequence is under control of an endogenous upstream poxvirus promoter. In another embodiment the foreign DNA sequence is under control of a heterologous upstream promoter.

For purposes of this invention, promoters include but is not limited to: synthetic pox viral promoter, pox synthetic late promoter 1, pox synthetic late promoter 2 early promoter 2, pox O1L promoter, pox I4L promoter, pox I3L promoter, pox I2L promoter, pox IlL promoter, pox ELOR promoter, PRV gX, HSV-1 alpha 4, HCMV immediate early, MDV gA, MDV gB, MDV gD, ILT gB, BHV-1.1 VP8 and ILT gD. Alternate promoters are generated by methods well known to those of skill in the art, for example, as set forth in the STRATEGY FOR THE CONSTRUCTION OF SYNTHETIC POX VIRAL PROMOTERS in *Materials and Methods.*

The invention provides for a homology vector for producing a recombinant swinepox virus by inserting foreign DNA into the genomic DNA of a swinepox virus.

The homology vector comprises a double-stranded DNA molecule consisting essentially of a double-stranded foreign DNA sequence or (RNA) which does not naturally occur in an animal into which the recombinant swinepox virus is introduced, with at one end of the foreign DNA, double-stranded swinepox viral DNA homologous to genomic DNA located at one side of a site on the genomic DNA which is not essential for replication of the swinepox virus, and at the other end of the foreign DNA, double-stranded swinepox viral DNA homologous to genomic DNA located at the other side of the same site on the genomic DNA. Preferably, the RNA encodes a polypeptide.

In another embodiment of the present invention, the double-stranded swinepox viral DNA of the homology vectors described above is homologous to genomic DNA present within the HindIII M fragment. In another embodiment the double-stranded swinepox viral DNA of the homology vectors described above is homologous to genomic DNA present within an approximately 2 Kb HindIII to BglII sub-fragment. In a preferred embodiment the double-stranded swinepox viral DNA is homologous to genomic DNA present within the BglII site located in this HindIII to BglII subfragment.

In another embodiment the double-stranded swinepox viral DNA is homologous to genomic DNA present within the open reading frame contained in the larger HindIII to BglII subfragment. Preferably, the double-stranded swinepox viral DNA is homologous to genomic DNA present within the AccI restriction endonuclease site located in the larger HindIII to BglII subfragment.

In a preferred embodiment the homology vectors are designated 752-29.33, 751-07.A1, 751-56.A1, 751-22.1, 746-94.1, 767-67.3, 738-94.4, and 771-55.11.

In one embodiment, the polypeptide is a detectable marker. Preferably, the polypeptide which is a detectable marker is E. coli β-galactosidase.

In one embodiment, the polypeptide is antigenic in the animal. Preferably, the antigenic polypeptide is or is from pseudorabies virus (PRV) g50 (gD), pseudorabies virus (PRV) gII (gB), Pseudorabies virus (PRV) gIII (gC), Pseudorabies virus (PRV) glycoprotein H, Transmissible gastroenteritis (TGE) glycoprotein 195, Transmissible gastroenteritis (TGE) matrix protein, swine rotavirus glycoprotein 38, swine parvovirus capsid protein, Serpulina hydodysenteriae protective antigen, Bovine Viral Diarrhea (BVD) glycoprotein 53 and g48, Newcastle Disease Virus (NDV) hemagglutinin-neuraminidase, swine flu hemagglutinin or swine flu neuraminidase. Preferably, the antigenic polypeptide is or is from Serpulina hyodysenteriae, Foot and Mouth Disease Virus, Hog Cholera Virus gE1 and gE2, Swine Influenza Virus, African Swine Fever Virus or Mycoplasma hyopneumoniae, swine influenza virus hemagglutinin, neuraminidase and matrix and nucleoprotein, PRRS virus ORF7, and hepatitis B virus core protein.

In an embodiment of the present invention, the double stranded foreign DNA sequence in the homology vector encodes an antigenic polypeptide derived from a human pathogen.

For example, the antigenic polypeptide of a human pathogen is derived from human herpesvirus, herpes simplex virus-1, herpes simplex virus-2, human cytomegalovirus, Epstein-Barr virus, Varicell-Zoster virus, human herpesvirus-6, human herpesvirus-7, human influenza, human immunodeficiency virus, rabies virus, measles virus, hepatitis B virus and hepatitis C virus. Furthermore, the antigenic polypeptide of a human pathogen may be associated with malaria or malignant tumor from the group conisting of Plasmodium falciparum, Bordetella pertusis, and malignant tumor.

In an embodiment of the present invention, the double stranded foreign DNA sequence in the homology vector encodes a cytokine capable of stimulating human immune response. In one embodiment the cytokine is a chicken myelomonocytic growth factor (cMGF) or chicken interferon (cIFN). For example, the cytokine can be, but not limited to, interleukin-2, interleukin-6, interleukin-12, interferons, granulocyte-macrophage colony stimulating factors, and interleukin receptors.

In an embodiment of the present invention, the double stranded foreign DNA sequence in the homology vector encodes an antigenic polypeptide derived from an equine pathogen.

The antigenic polypeptide of an equine pathogen can derived from equine influenza virus or equine herpesvirus. Examples of such antigenic polypeptide are equine influenza virus type A/Alaska 91 neuraminidase, equine influenza virus type A/Prague 56 neuraminidase, equine influenza virus type A/Miami 63 neuraminidase, equine influenza virus type A/Kentucky 81 neuraminidaseequine herpesvirus type 1 glycoprotein B, and equine herpesvirus type 1 glycoprotein D.

In an embodiment of the present invention, the double stranded foreign DNA sequence of the homology vector encodes an antigenic polypeptide derived from bovine respiratory syncytial virus or bovine parainfluenza virus.

For example, the antigenic polypeptide is derived from infectious bovine rhinotracheitis gE, bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase.

In an embodiment of the present invention, the double stranded foreign DNA sequence of the homology vector encodes an antigenic polypeptide derived from infectious bursal disease virus. Examples of such antigenic polypeptide are infectious bursal disease virus polyprotein and infectious bursal disease virus VP2, VP3, or VP4.

For purposes of this invention, a "homology vector" is a plasmid constructed to insert foreign DNA in a specific site on the genome of a swinepox virus.

In one embodiment of the invention, the double-stranded swinepox viral DNA of the homology vectors described above is homologous to genomic DNA present within the open reading frame encoding swinepox thymidine kinase.

Preferably, the double-stranded swinepox viral DNA is homologous to genomic DNA present within the NdeI restriction endonuclease site located in the open reading frame encoding swinepox thymidine kinase.

The invention further provides a homology vectors 30 described above, the foreign DNA sequence of which is under control of a promoter located upstream of the foreign DNA sequence. The promoter can be an endogenous swinepox viral promoter or an exogenous promoter.

Promoters include, but are not limited to: synthetic pox viral promoter, pox synthetic late promoter 1, pox synthetic late promoter 2 early promoter 2, pox O1L promoter, pox I4L promoter, pox I3L promoter, pox I2L promoter, pox I1L promoter, pox ELOR promoter, PRV gX, HSV-1 alpha 4, HCMV immediate early, BHV-1.1 VP8, infectious laryngotracheitis virus glycoprotein B, infectious laryngotracheitis virus gD, marek's disease virus glycoprotein A, marek's disease virus glycoprotein B, and marek's disease virus glycoprotein D.

This invention provides a recombinant swinpox virus designated S-SPV-044, S-SPV-046, S-SPV-047, S-SPV-048, S-SPV-052, S-SPV-051, S-SPV-053, S-SPV-054, S-SPV-055, S-SPV-056, S-SPV-057, S-SPV-058, S-SPV-059, S-SPV-060, S-SPV-061, and S-SPV-062.

The invention further provides a vaccine which comprises an effective immunizing amount of a recombinant swinepox virus of the present invention and a suitable carrier.

Suitable carriers for the swinepox virus are well known in the art and include proteins, sugars, etc. One example of such a suitable carrier is a physiologically balanced culture medium containing one or more stabilizing agents such as stabilized, hydrolyzed proteins, lactose, etc.

For purposes of this invention, an "effective immunizing amount" of the recombinant swinepox virus of the present invention is within the range of $10^3$ to $10^9$ PFU/dose.

The present invention also provides a method of immunizing an animal, wherein the animal is a human, swine, bovine, equine, caprine or ovine. For purposes of this invention, this includes immunizing the animal against the virus or viruses which cause the disease or diseases pseudorabies, transmissible gastroenteritis, swine rotavirus, swine parvovirus, *Serpulina hyodysenteriae*, bovine viral diarrhea, Newcastle disease, swine influenza, PRRS, bovine respiratory synctial virus, bovine parainfluenza virus type 3, foot and mouth disease, hog cholera, African swine fever or *Mycoplasma hyopneumoniae*. For purposes of this invention, the method of immunizing also includes immunizing the animal against human pathogens, bovine pathogens, equine pathogens, avian pathogens described in the preceding part of this section.

The method comprises administering to the animal an effective immunizing dose of the vaccine of the present invention. The vaccine may be administered by any of the methods well known to those skilled in the art, for example, by intramuscular, subcutaneous, intraperitoneal or intravenous injection. Alternatively, the vaccine may be administered intranasally or orally.

The present invention also provides a method for testing a swine to determine whether the swine has been vaccinated with the vaccine of the present invention, particularly the embodiment which contains the recombinant swinepox virus S-SPV-008 (ATCC Accession No. VR 2339), or is infected with a naturally-occurring, wild-type pseudorabies virus. This method comprises obtaining from the swine to be tested a sample of a suitable body fluid, detecting in the sample the presence of antibodies to pseudorabies virus, the absence of such antibodies indicating that the swine has been neither vaccinated nor infected, and for the swine in which antibodies to pseudorabies virus are present, detecting in the sample the absence of antibodies to pseudorabies virus antigens which are normally present in the body fluid of a swine infected by the naturally-occurring pseudorabies virus but which are not present in a vaccinated swine indicating that the swine was vaccinated and is not infected.

The present invention provides a recombinant SPV which when inserted with a foreign DNA sequence or gene may be employed as a diagnostic assay. In one embodiment FIV env and gag genes and *D. immitis* p39 and 22kd are employed in a diagnostic assay to detect feline immunodeficiency caused by FIV and to detect heartworm caused by *D. immits*, respectively.

The present invention also provides a host cell infected with a recombinant swinepox virus capable of replication. In one embodiment, the host cell is a mammalian cell. Preferably, the mammalian cell is a Vero cell. Preferably, the mammalian cell is an ESK-4 cell, PK-15 cell or EMSK cell.

For purposes of this invention a "host cell" is a cell used to propagate a vector and its insert. Infecting the cells was accomplished by methods well known to those of skill in the art, for example, as set forth in INFECTION—TRANSFECTION PROCEDURE in *Material and Methods*.

Methods for constructing, selecting and purifying recombinant swinepox viruses described above are detailed below in *Materials and Methods*.

Experimental Details
Materials and Methods

PREPARATION OF SWINEPOX VIRUS STOCK SAMPLES. Swinepox virus (SPV) samples were prepared by infecting embryonic swine kidney (EMSK) cells, ESK-4 cells, PK-15 cells or Vero cells at a multiplicity of infection of 0.01 PFU/cell in a 1:1 mixture of Iscove's Modified Dulbecco's Medium (IMDM) and RPMI 1640 medium containing 2 mM glutamine, 100 units/ml penicillin, 100 units/ml streptomycin (these components were obtained from Sigma or equivalent supplier, and hereafter are referred to as EMSK negative medium). Prior to infection, the cell monolayers were washed once with EMSK negative medium to remove traces of fetal bovine serum. The SPV contained in the initial inoculum (0.5 ml for 10 cm plate; 10 ml for T175 cm flask) was then allowed to absorb onto the cell monolayer for two hours, being redistributed every half hour. After this period, the original inoculum was brought up to the recommended volume with the addition of complete EMSK medium (EMSK negative medium plus 5% fetal bovine serum). The plates were incubated at 37° C. in 5% $CO_2$ until cytopathic effect was complete. The medium and cells were harvested and frozen in a 50 ml conical screw cap tube at −70° C. Upon thawing at 37° C., the virus stock was aliquoted into 1.0 ml vials and refrozen at −70° C. The titers were usually about $10^6$ PFU/ml.

PREPARATION OF SPV DNA. For swinepox virus DNA isolation, a confluent monolayer of EMSK cells in a T175 $cm^2$ flask was infected at a multiplicity of 0.1 and incubated 4–6 days until the cells were showing 100% cytopathic effect. The infected cells were then harvested by scraping the cells into the medium and centrifuging at 3000 rpm for 5 minutes in a clinical centrifuge. The medium was decanted, and the cell pellet was gently resuspended in 1.0 ml Phosphate Buffer Saline (PBS: 1.5 g $Na_2HPO_{41}$ 0.2 g $KH_2PO_4$, 0.8g NaCL and 0.2g KCl per liter $H_2O$) (per T175) and subjected to two successive freeze-thaws (−70° C. to 37° C). Upon the last thaw, the cells (on ice) were sonicated two times for 30 seconds each with 45 seconds cooling time in between. Cellular debris was then removed by centrifuging (Sorvall RC-5B superspeed centrifuge) at 3000 rpm for 5 minutes in a HB4 rotor at 4° C. SPV virions, present in the supernatant, were then pelleted by centrifugation at 15,000 rpm for 20 minutes at 40° C. in a SS34 rotor (Sorvall) and resuspended in 10 mM Tris (pH 7.5). This fraction was then layered onto a 36% sucrose gradient (w/v in 10 mM tris pH 7.5) and centrifuged (Beckman L8-70M Ultracentrifuge) at 18,000 rpm for 60 minutes in a SW41 rotor (Beckman) at 4° C. The virion pellet was resuspended in 1.0 ml of 10 mM tris pH 7.5 and sonicated on ice for 30 seconds. This fraction was layered onto a 20% to 50% continuous sucrose gradient and centrifuged 16,000 rpm for 60 minutes in a SW41 rotor at 40° C. The SPV virion band located about three quarters down the gradient was harvested, diluted with 20% sucrose and pelleted by centrifugation at 18,000 rpm for 60 minutes in a SW41 rotor at 40° C. The resultant pellet was then washed once with 10 mM Tris pH 7.5 to remove traces of sucrose and finally resuspended in 10 mM Tris pH 7.5. SPV DNA was then extracted from the purified virions by lysis (4 hours at 60° C.) induced by the addition of EDTA, SDS, and proteinase K to final concentrations of 20 mM, 0.5% and 0.5 mg/ml, respectively. After digestion, three phenol:chloroform (1:1) extractions were conducted and the sample precipitated by the addition of two volumes of absolute ethanol and incubation at −20° C. for 30 minutes. The sample was then centrifuged in an Eppendorf minifuge for 5 minutes at full speed. The supernatant was decanted, and the pellet air dried and rehydrated in 0.01 M Tris pH 7.5, 1 mM EDTA at 4° C.

PREPARATION OF INFECTED CELL LYSATES. For cell lysate preparation, serum free medium was used. A confluent monolayer of cells (EMSK, ESK-4, PK-15 or Vero for SPV or VERO for PRV) in a 25 cm$^2$ flask or a 60 mm petri dish was infected with 100 µl of virus sample. After cytopathic effect was complete, the medium and cells were harvested and the cells were pelleted at 3000 rpm for 5 minutes in a clinical centrifuge. The cell pellet was resuspended in 250 µl of disruption buffer (2% sodium dodecyl sulfate, 2% β-mercapto-ethanol). The samples were sonicated for 30 seconds on ice and stored at −20° C.

WESTERN BLOTTING PROCEDURE. Samples of lysates and protein standards were run on a polyacrylamide gel according to the procedure of Laemnli (1970). After gel electrophoresis the proteins were transferred and processed according to Sambrook et al. (1982). The primary antibody was a swine anti-PRV serum (Shope strain; lot370, PDV8201, NVSL, Ames, IA) diluted 1:100 with 5% non-fat dry milk in Tris-sodium chloride, and sodium Azide (TSA: 6.61g Tris-HCl, 0.97g Tris-base, 9.0 g NaCl and 2.0 g Sodium Azide per liter H$_2$O). The secondary antibody was a goat anti-swine alkaline phosphatase conjugate diluted 1:1000 with TSA.

MOLECULAR BIOLOGICAL TECHNIQUES. Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al. (1982) and Sambrook et al. (1989). Except as noted, these were used with minor variation.

DNA SEQUENCING. Sequencing was performed using the USB Sequenase Kit and $^{35}$S-DATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with Superclone™ and Supersee™ programs from Coral Software.

CLONING WITH THE POLYMERASE CHAIN REACTION. The polymerase chain reaction (PCR) was used to introduce restriction sites convenient for the manipulation of various DNAs. The procedures used are described by Innis, et al. (1990). In general, amplified fragments were less than 500 base pairs in size and critical regions of amplified fragments were confirmed by DNA sequencing. The primers used in each case are detailed in the descriptions of the construction of homology vectors below.

HOMOLOGOUS RECOMBINATION PROCEDURE FOR GENERATING RECOMBINANT SPV. This method relies upon the homologous recombination between the swinepox virus DNA and the plasmid homology vector DNA which occurs in the tissue culture cells containing both swinepox virus DNA and transfected plasmid homology vector. For homologous recombination to occur, the monolayers of EMSK cells are infected with S-SPV-001 (Kasza SPV strain, 17) at a multiplicity of infection of 0.01 PFU/cell to introduce replicating SPV (i.e. DNA synthesis) into the cells. The plasmid homology vector DNA is then transfected into these cells according to the INFECTION—TRANSFECTION PROCEDURE. The construction of homology vectors used in this procedure is described below INFECTION—TRANSFECTION PROCEDURE. 6 cm plates of EMSK cells (about 80% confluent) were infected with S-SPV-001 at a multiplicity of infection of 0.01 PFU/cell in EMSK negative medium and incubated at 37° C. in a humidified 5% $CO_2$ environment for 5 hours. The transfection procedure used is essentially that recommended for Lipofectin™ Reagent (BRL). Briefly, for each 6 cm plate, 15 $\mu$g of plasmid DNA was diluted up to 100 $\mu$l with $H_2O$. Separately, 50 micrograms of Lipofectin Reagent was diluted to 100 $\mu$l with $H_2O$. The 100 $\mu$l of diluted Lipofectin Reagent was then added dropwise to the diluted plasmid DNA contained in a polystyrene 5 ml snap cap tube and mixed gently. The mixture was then incubated for 15–20 minutes at room temperature. During this time, the virus inoculum was removed from the 6 cm plates and the cell monolayers washed once with EMSK negative medium. Three ml of EMSK negative medium was then added to the plasmid DNA/lipofectin mixture and the contents pipetted onto the cell monolayer. The cells were incubated overnight (about 16 hours) at 37° C. in a humidified 5% $CO_2$ environment. The next day the 3 ml of EMSK negative medium was removed and replaced with 5 ml EMSK complete medium. The cells were incubated at 37° C. in 5% $CO_2$ for 3–7 days until cytopathic effect from the virus was 80–100%. Virus was harvested as described above for the preparation of virus stocks. This stock was referred to as a transfection stock and was subsequently screened for recombinant virus by the BLUOGAL SCREEN FOR RECOMBINANT SWINEPOX VIRUS OR CPRG SCREEN FOR RECOMBINANT SWINEPOX VIRUS.

SCREEN FOR RECOMBINANT SPV EXPRESSING β-galactosidase (BLUOGAL AND CPRG ASSAYS). When the *E. coli* β-galactosidase (lacZ) marker gene was incorporated into a recombinant virus the plaques containing the recombinants ere visualized by one of two simple methods. In the first method, the chemical Bluogal™ (Bethesda Research Labs) was incorporated (200 $\mu$g/ml) into the agarose overlay during the plaque assay, and plaques expressing active β-galactosidase turned blue. The blue plaques were then picked onto fresh cells (EMSK) and purified by further blue plaque isolation. In the second method, CPRG (Boehringer Mannheim) was incorporated (400 $\mu$g/ml) into the agarose overlay during the plaque assay, and plaques expressing active β-galactosidase turned red. The red plaques were then picked onto fresh cells (EMSK) and purified by further red plaque isolation. In both cases viruses were typically purified with three rounds of plaque purification.

SCREEN FOR FOREIGN GENE EXPRESSION IN RECOMBINANT SPV USING BLACK PLAQUE ASSAYS. To analyze expression of foreign antigens expressed by recombinant swinepox viruses, monolayers of EMSK cells were infected with recombinant SPV, overlayed with nutrient agarose media and incubated for 6–7 days at 37° C. for plaque development to occur. The agarose overlay was then removed from the dish, the cells fixed with 100% methanol for 10 minutes at room temperature and the cells air dried. Fixation of the cells results in cytoplasmic antigen as well as surface antigen detection whereas specific surface antigen expression can be detected using non-fixed cells. The primary antibody was then diluted to the appropriate dilution with PBS and incubated on the cell monolayer for 2 hours at room temperature. To detect PRV g50 (gD) expression from S-SPV-008, swine anti-PRV serum (Shope strain; lot370, PDV8201, NVSL, Ames, Iowa) was used (diluted 1:100). To detect NDV HN expression from S-SPV-009, a rabbit antiserum specific for the HN protein (rabbit anti-NDV#2) was used (diluted 1:1000). Unbound antibody was then removed by washing the cells three times with PBS at room temperature. The secondary antibody, either a goat anti-swine (PRV g50 (gD); S-SPV-008) or goat anti-rabbit (NDV HN; S-SPV-009), horseradish peroxidase conjugate was diluted 1:250 with PBS and incubated with the cells for 2 hours at room temperature. Unbound secondary antibody was then removed by washing the cells three times with PBS at room temperature. The cells were then incubated 15–30 minutes at room temperature with freshly prepared substrate solution (100 μg/ml 4-chloro-1-naphthol, 0.003% $H_{2O2}$ in PBS). Plaques expressing the correct antigen stain black.

PROCEDURE FOR PURIFICATION OF VIRAL GLYCOPROTEINS FOR USE AS DIAGNOSTICS. Viral glycoproteins are purified using antibody affinity columns. To produce monoclonal antibodies, 8 to 10 week old BALB/c female mice are vaccinated intraperitoneally seven times at two to four week intervals with $10^7$ PFU of S-SPV-009, -014, -016, -017, -018, or -019. Three weeks after the last vaccination, mice are injected intraperitoneally with 40 mg of the corresponding viral glycoprotein. Spleens are removed from the mice three days after the last antigen dose.

Splenocytes are fused with mouse NS1/Ag4 plasmacytoma cells by the procedure modified from Oi and Herzenberg, (41). Splenocytes and plasmacytoma cells are pelleted together by centrifugation at 300×g for 10 minutes. One ml of a 50% solution of polyethylene glycol (m.w. 1300–1600) is added to the cell pellet with stirring over one minute. Dulbecco's modified Eagles's medium (5 ml) is added to the cells over three minutes. Cells are pelleted by centrifugation at 300×g for 10 minutes and resuspended in medium with 10% fetal bovine serum and containing 100 mM hypoxanthine, 0.4 mM aminopterin and 16 mM thymidine (HAT). Cells (100 ml) are added to the wells of eight to ten 96-well tissue culture plates containing 100 ml of normal spleen feeder layer cells and incubated at 37° C. Cells are fed with fresh HAT medium every three to four days.

Hybridoma culture supernatants are tested by the ELISA ASSAY in 96-well microtiter plates coated with 100 ng of viral glycoprotein. Supernatants from reactive hybridomas are further analyzed by black-plaque assay and by Western Blot. Selected hybridomas are cloned twice by limiting dilution. Ascetic fluid is produced by intraperitoneal injection of $5\times10^6$ hybridoma cells into pristane-treated BALB/c mice.

Cell lysates from S-SPV-009, -014, -016, -017, -018, or -019 are obtained as described in PREPARATION OF INFECTED CELL LYSATES. The glycoprotein-containing cell lysates (100 mls) are passed through a 2-ml agarose affinity resin to which 20 mg of glycoprotein monoclonal antibody has been immobilized according to manufacturer's instructions (AFC Medium, New Brunswick Scientific, Edison, N.J.). The column is washed with 100 ml of 0.1% Nonidet P-40 in phosphate-buffered saline (PBS) to remove nonspecifically bound material. Bound glycoprotein is eluted with 100 mM carbonate buffer, pH 10.6 (40). Pre- and posteluted fractions are monitored for purity by reactivity to the SPV monoclonal antibodies in an ELISA system.

ELISA ASSAY. A standard enzyme-linked immunosorbent assay (ELISA) protocol is used to determine the immune status of cattle following vaccination and challenge.

A glycoprotein antigen solution (100 ml at ng/ml in PBS) is allowed to absorb to the wells of microtiter dishes for 18 hours at 4° C. The coated wells are rinsed one time with PBS. Wells are blocked by adding 250 ml of PBS containing 1% BSA (Sigma) and incubating 1 hour at 37° C. The blocked wells are rinsed one time with PBS containing 0.02% Tween 20. 50 ml of test serum (previously diluted 1:2 in PBS containing 1% BSA) are added to the wells and incubated 1 hour at 37° C. The antiserum is removed and the wells are washed 3 times with PBS containing 0.02% Tween 20. 50 ml of a solution containing anti-bovine IgG coupled to horseradish peroxidase (diluted 1:500 in PBS containing 1% BSA, Kirkegaard and Perry Laboratories, Inc.) is added to visualize the wells containing antibody against the specific antigen. The solution is incubated 1 hour at 37° C., then removed and the wells are washed 3 times with PBS containing 0.02% Tween 20. 100 ml of substrate solution (ATBS, Kirkegaard and Perry Laboratories, Inc.) are added to each well and color is allowed to develop for 15 minutes. The reaction is terminated by addition of 0.1M oxalic acid. The color is read at absorbance 410 nm on an automatic plate reader.

STRATEGY FOR THE CONSTRUCTION OF SYNTHETIC POX VIRAL PROMOTERS. For recombinant swinepox vectors synthetic pox promoters offer several advantages including the ability to control the strength and timing of foreign gene expression. Three promoter cassettes LP1, EP1 and LP2 based on promoters that have been defined in the vaccinia virus (1, 7 and 8) were designed. Each cassette was designed to contain the DNA sequences defined in vaccinia flanked by restriction sites which could be used to combine the cassettes in any order or combination. Initiator methionines were also designed into each cassette such that inframe fusions could be made at either EcoRI or BamHI sites. A set of translational stop codons in all three reading frames and an early transcriptional termination signal (9) were also engineered downstream of the inframe fusion site. DNA encoding each cassette was synthesized according to standard techniques and cloned into the appropriate homology vectors (see FIGS. 4, 5 and 8).

VACCINATION STUDIES IN SWINE USING RECOMBINANT SWINEPOX VIRUS CONTAINING PSEUDORABIES VIRUS GLYCOPROTEIN GENES: Young weaned pigs from pseudorabies-free herd are used to test the efficacy of the recombinant swinepox virus containing one or more of the pseudorabies virus glycoprotein genes (SPV/PRV). The piglets are inoculated intramuscularly, intradermally or orally about $10^3$ to $10^7$ plaque forming units (PFU) of the recombinant SPV/PRV viruses.

Immunity is determined by measuring PRV serum antibody levels and by challenging the vaccinated pigs with virulent strain of pseudorabies virus. Three to four weeks post-vaccination, both vaccinated and non-vaccinated groups of pigs are challenged with virulent strain of pseudorabies virus (VDL4892). Post challenge, the pigs are observed daily for 14 days for clinical signs of pseudorabies.

Serum samples are obtained at the time of vaccination, challenge, and at weekly intervals for two to three weeks post-vaccination and assayed for serum neutralizing antibody.

CLONING OF EQUINE INFLUENZA VIRUS HEMAGGLUTININ AND NEURAMINIDASE GENES. The equine influenza virus hemagglutinin (HA) and Neuraminidase (NA) genes was cloned essentially as described by Katz et al. (42) for the HA gene of human influenza virus. Viral RNA was prepared from virus grown in MDBK cells (for Influenza A/equine/Alaska/91 and Influenza A/equine/Miami/63) and MDCK cells (for Influenza A/equine/Prague/56 and Influenza A/equine/Kentucky/81) was first converted to cDNA utilizing an oligo nucleotide primer specific for the target gene. The cDNA was used as a template for PCR cloning (51) of the targeted gene region. The PCR primers were designed to incorporate restriction sites which permit the cloning of the amplified coding regions into vectors containing the appropriate signals for expression in EHV. One pair of oligo nucleotide primers was required for each coding region. The HA gene coding regions from the serotype 2 (H3) viruses (Influenza A/equine/Miami/63, Influenza A/equine/Kentucky/81, and Influenza A/equine/Alaska/91) was cloned utilizing the following primers 5'-GGAGGCCTTCATGACAGACAACCA TTATTTTGATACTACTGA-3' (SEQ ID NO: 120) for cDNA priming and combined with 5'-GAAGGCCTTCT CAAATGCAAATGTTGCATCTGATGTTGCC-3' (SEQ ID NO: 121) for PCR. The HA gene coding region from the serotype 1 (H7) virus (Influenza A/equine/Prague/56) was be cloned utilizing the following primers 5'-GGGATCCATGAACACTCAAATTCTAATATTAG-3' (SEQ ID NO: 122) for cDNA priming and combined with 5'-GGGATCCTTATATACAAATAGTGCACCGCA-3' (SEQ ID NO: 123) for PCR. The NA gene coding regions from the serotype 2 (N8) viruses (Influenza A/equine/Miami/63, Influenza A/equine/Kentucky/81, and Influenza A/equine/Alaska/91) was cloned utilizing the following primers 5'-GGGTCGACATGAATCCAAATCAAAAGATAA-3' (SEQ ID NO: 124) for cDNA priming and combined with 5'-GGGTCGACTTACATCTTATCGATGTCAAA-3' (SEQ ID NO: 125) for PCR. The NA gene coding region from the serotype 1 (N7) virus (Influenza/A/equine/Prague/56) was cloned utilizing the following primers 5'-GGGATCCATGAATCCTAATCAAAAACTCTTT-3' (SEQ ID NO: 118) for cDNA priming and combined with 5'-GGGATCCTTACGAAAAGTATTTAATTTGTGC-3' (SEQ ID NO: 119) for PCR. Note that this general strategy was used to clone the coding regions of HA and NA genes from other strains of equine influenza A virus. The EIV HA or NA genes were cloned as a blunt ended SalI or BamHI fragment into a blunt ended EcoRI site behind the LP2EP2 promoter of the SPV homology vector.

CLONING OF PARAINFLUENZA-3 VIRUS FUSION AND HEMAGGLUTININ GENES. The parainfluenza-3 virus fusion (F) and hemagglutinin (HN) genes were cloned by a PCR CLONING procedure essentially as described by Katz et al. (42) for the HA gene of human influenza. Viral RNA prepared from bovine PI-3 virus grown in Madin-Darby bovine kidney (MDBK) cells was first converted to cDNA utilizing an oligonucleotide primer specific for the target gene. The cDNA was then used as a template for polymerase chain reaction (PCR) cloning (15) of the targeted region. The PCR primers were designed to incorporate restriction sites which permit the cloning of the amplified coding regions into vectors containing the appropriate signals for expression in SPV. One pair of oligonucleotides were required for each coding region. The F gene coding region from the PI-3 strain SF-4 (VR-281) was cloned using the following primers: 5'-TTATGGATCCTGCTGCTGTG TTGAACAACTTTGT-3' (SEQ ID NO: 130) for cDNA priming and combined with 5'-CCGCGGATCCCATGACC ATCACAACCATAATCATAGCC-3' (SEQ ID NO: 131) for PCR. The HN gene coding region from PI-3 strain SF-4 (VR-281) was cloned utilizing the following primers: 5'-CG TCGGATCCCTTAGCTGCAGTTTTTTGGAACTTCTG TTTTGA-3' (SEQ ID NO: 132) for CDNA priming and combined with 5'-CATAGGATCCCATGGAATATTGGAA ACACACAAACAGCAC-3' (SEQ ID NO: 133) for PCR. Note that this general strategy is used to clone the coding region of F and HN genes from other strains of PI-3. The DNA fragment for PI-3 HN or F was digested with BamHI to yield an 1730 bp or 1620 bp fragment, respectively. The PI-3 HN fragment is cloned into the BamHI site next to the LP2EP2 promoter of the SPV homology vector. The PI-3 F fragment was cloned into the BamHI site next to the LP2EP2 promoter of the SPV homology vector to yield homology vector 713-55.10.

CLONING OF BOVINE VIRAL DIARRHEA VIRUS g48 and g53 GENES. The bovine viral diarrhea g48 and g53 genes were cloned by a PCR CLONING procedure essentially as described by Katz et al. (42) for the HA gene of human influenza. Viral RNA prepared from BVD virus Singer strain grown in Madin-Darby bovine kidney (MDBK) cells was first converted to cDNA utilizing an oligonucleotide primer specific for the target gene. The cDNA was then used as a template for polymerase chain reaction (PCR) cloning (15) of the targeted region. The PCR primers were designed to incorporate restriction sites which permit the cloning of the amplified coding regions into vectors containing the appropriate signals for expression in SPV. One pair of oligonucleotides were required for each coding region. The g48 gene coding region from the BVDV Singer strain (49) was cloned using the following primers: 5'-ACGTCGGATCCCTTACCAAACCACGTCTTACTCT TGTTTTCC-3' (SEQ ID NO: 134) for cDNA priming and combined with 5'-ACATAGGATCCCATGGGAGAAAAC ATAACACAGTGGAACC-3' (SEQ ID NO: 135) for PCR. The g53 gene coding region from the BVDV Singer strain (49) was cloned using the following primers: 5'-CGTGGATCCTCAATTACAAGAGGTATCGTCTAC-3' (SEQ ID NO: 136) for cDNA priming and combined with 5'-CATAGATCTTGTGGTGCTGTCCGACTTCGCA-3' (SEQ ID NO: 137) for PCR. Note that this general strategy is used to clone the coding region of g48 and g53 genes from other strains of BVDV. The DNA fragment for BVDV g 48 was digested with BamHI to yield an 678 bp fragment. The DNA fragment for BVDV g53 was digested with BglII and BamHI to yield an 1187 bp fragment. The BVDV g48 or g53 DNA fragments were cloned into the BamHI site next to the LP2EP2 promoter of the SPV homology vector to yield homology vectors, 727-78.1 and 738-96, respectively.

CLONING OF BOVINE RESPIRATORY SYNCYTIAL VIRUS FUSION, NUCLEOCAPSID AND GLYCOPROTEIN GENES. The bovine respiratory syncytial virus fusion (F), nucleocapsid (N), and glycoprotein (G) genes were cloned by a PCR CLONING procedure essentially as described by Katz et al. (42) for the HA gene of human influenza. Viral RNA prepared from BRSV virus grown in bovine nasal turbinate (BT) cells was first converted to cDNA utilizing an oligonucleotide primer specific for the target gene. The cDNA was then used as a template for polymerase chain reaction (PCR) cloning (15) of the targeted region. The PCR primers were designed to incorporate restriction sites which permit the cloning of the amplified coding regions into vectors containing the appropriate signals for expression in SPV. One pair of oligonucleotides were required for each coding region. The F gene coding region from the BRSV strain 375 (VR-1339) was cloned using the following primers: 5 '-TGCAGGATCC TCATTTACTAAAGGAAAGATTGTTGAT-3' (SEQ ID NO: 138) for cDNA priming and combined with 5'-CT CTGGATCCTACAGCCATGAGGATGATCATCAGC-3' (SEQ ID NO: 139) for PCR. The N gene coding region from BRSV strain 375 (VR-1339) was cloned utilizing the following primers: 5'-CGTCGGATCCCTCACAGTTCCAC ATCATTGTCTTTGGGAT-3' (SEQ ID NO: 140) for cDNA priming and combined with 5'-CTTAGGATCCCATGGC TCTTAGCAAGGTCAAACTAAATGAC-3' (SEQ ID NO: 141) for PCR. The G gene coding region from BRSV strain 375 (VR-1339) was cloned utilizing the following primers: 5'-CGTTGGATCCCTAGATCTGTGTAGTTGATTGATT TGTGTGA-3' (SEQ ID NO: 142) for cDNA priming and combined with 5'-CTCTGGATCCTCATACCCATCAT CTTAAATTCAAGACATTA-3' (SEQ ID NO:

143) for PCR. Note that this general strategy is used to clone the coding region of F, N and G genes from other strains of BRSV. The DNA fragments for BRSV F, N, or G were digested with BamHI to yield 1722 bp, 1173 bp, or 771 bp fragments, respectively. The BRSV F, N, and G DNA fragments were cloned into the BamHI site next to the LP2EP2 promoter of the SPV homology vector to yield homology vectors, 727-20.10, 713-55.37 and 727-20.5, respectively.

RNA ISOLATED FROM CONCANAVALIN A STIMULATED CHICKEN SPLEEN CELLS. Chicken spleens were dissected from 3 week old SPAFAS hatched chicks, washed, and disrupted through a syringe/needle to release cells. After allowing stroma and debri to settle out, the cells were pelleted and washed twice with PBS. The cell pellet was treated with a hypotonic lysis buffer to lyse red blood cells, and splenocytes were recovered and washed twice with PBS. Splenocytes were resuspended at $5\times10^6$ cells/ml in RPMI containing 5%. FBS and 5 $\mu$g/ml Concanavalin A and incubated at 39° for 48 hours. Total RNA was isolated from the cells using guanidine isothionate lysis reagents and protocols from the Promega RNA isolation kit (Promega Corporation, Madison Wis.). 4 $\mu$g of total RNA was used in each 1st strand reaction containing the appropriate antisense primers and AMV reverse transcriptase (Promega Corporation, Madison Wis.). cDNA synthesis was performed in the same tube following the reverse transcriptase reaction, using the appropriate sense primers and Vent® DNA polymerase (Life Technologies, Inc. Bethesda, Md.).

SCREEN FOR RECOMBINANT HERPESVIRUS EXPRESSING ENZYMATIC MARKER GENES. When the *E.coli* β-glucuronidase (uida) marker gene was incorporated into a recombinant virus the plaques containing recombinants were visualized by a simple assay. The enzymatic substrate was incorporated (300 $\mu$g/ml) into the agarose overlay during the plaque assay. For the uida marker gene the substrate X-Glucuro Chx (5-bromo-4-chloro-3-indolyl-β-D-glucuronic acid Cyclohexylammonium salt, Biosynth AG) was used. Plaques that expressed active marker enzyme turned blue. The blue plaques were then picked onto fresh ESK-4 cells and purified by further blue plaque isolation. In recombinant virus strategies in which the enzymatic marker gene is removed the assay involves plaque purifying white plaques from a background of parental blue plaques. In both cases viruses were typically purified with three rounds of plaque purification.

HOMOLOGY VECTOR 515-85.1. The plasmid 515-85.1 was constructed for the purpose of inserting foreign DNA into SPV. It contains a unique AccI restriction enzyme site into which foreign DNA may be inserted. When a plasmid, containing a foreign DNA insert at the AccI site, is used according to the HOMOLOGOUS RECOMBINATION PROCEDURE FOR GENERATING RECOMBINANT SPV a virus containing the foreign DNA will result. A restriction map of the DNA insert in homology vector 515-85.1 is given in FIGS. 4A–4C. It may be constructed utilizing standard recombinant DNA techniques (22 and 29), by joining two restriction fragments from the following sources. The first fragment is an approximately 2972 base pair HindIII to BamHI restriction fragment of pSP64 (Promega). The second fragment is an approximately 3628 base pair HindIII to BglII restriction sub-fragment of the SPV HindIII restriction fragment M (23).

HOMOLOGY VECTOR 520-17.5. The plasmid 520-17.5 was constructed for the purpose of inserting foreign DNA into SPV. It incorporates an *E. coli* β-galactosidase (lacZ) marker gene flanked by SPV DNA. Upstream of the marker gene is an approximately 2149 base pair fragment of SPV DNA. Downstream of the marker gene is an approximately 1484 base pair fragment of SPV DNA. When this plasmid is used according to the HOMOLOGOUS RECOMBINATION PROCEDURE FOR GENERATING RECOMBINANT SPV a virus containing DNA coding for the marker gene will result. Note that the β-galactosidase (lacZ) marker gene is under the control of a synthetic early/late pox promoter. A detailed description of the plasmid is given in FIGS. 4A–4C. It may be constructed utilizing standard recombinant DNA techniques (22 and 30), by joining restriction fragments from the following sources with the synthetic DNA sequences indicated in FIGS. 4A–4C. The plasmid vector was derived from an approximately 2972 base pair HindIII to BamHI restriction fragment of pSP64 (Promega). Fragment 1 is an approximately 2149 base pair HindIII to AccI restriction sub-fragment of the SPV HindIII restriction fragment M (23). Fragment 2 is an approximately 3006 base pair BamHI to PvuII restriction fragment of plasmid pJF751 (11). Fragment 3 is an approximately 1484 base pair AccI to BglII restriction sub-fragment of the SPV HindIII fragment M (23).

HOMOLOGY VECTOR 538-46.16. The plasmid 538-46.16 was constructed for the purpose of inserting foreign DNA into SPV. It incorporates an *E. coli* β-galactosidase (lacZ) marker gene and the PRV g50 (gD) gene flanked by SPV DNA. Upstream of the foreign genes is an approximately 2149 base pair fragment of SPV DNA. Downstream of the foreign genes is an approximately 1484 base pair fragment of SPV DNA. When this plasmid is used according to the HOMOLOGOUS RECOMBINATION PROCEDURE FOR GENERATING RECOMBINANT SPV a virus containing DNA coding for the foreign genes will result. Note that the β-galactosidase (lacZ) marker gene is under the control of a synthetic late pox promoter (LP1) and the g50 (gD) gene is under the control of a synthetic early/late pox promoter (EP1LP2). A detailed description of the plasmid is given in FIGS. 5A–5D. It may be constructed utilizing standard recombinant DNA techniques (22 and 30), by joining restriction fragments from the following sources with the synthetic DNA sequences indicated in FIGS.

5A–5D. The plasmid vector was derived from an approximately 2972 base pair HindIII to BamHI restriction fragment of pSP64 (Promega). Fragment 1 is an approximately 2149 base pair HindIII to AccI restriction sub-fragment of the SPV HindIII restriction fragment M (23). Fragment 2 is an approximately 3006 base pair BamHI to PvuII restriction fragment of plasmid pJF751 (11). Fragment 3 is an approximately 1571 base pair EcoRI to StuI restriction sub-fragment of the PRV BamHI fragment 7 (21). Note that the EcoRI site was introduced in to this fragment by PCR cloning. In this procedure the primers described below were used along with a template consisting of a PRV BamHI #7 fragment subcloned into pSP64. The first primer 87.03 (5'-CGCGAATTCGCTCGCAGCGCTATTGGC-3') (SEQ ID NO:41) sits down on the PRV g50 (gD) sequence (26) at approximately amino acid 3 priming toward the 3' end of the gene. The second primer 87.06 (5'-GTAGGAGTGGCTGCTGAAG-3') (SEQ ID NO:42) sits down on the opposite strand at approximately amino acid 174 priming toward the 5' end of the gene. The PCR product may be digested with EcoRI and SalI to produce an approximately 509 base pair fragment. The approximately 1049 base pair SalI to StuI sub-fragment of PRV BamHI #7 may then be ligated to the approximately 509 base pair EcoRI to SalI fragment to generate the approximately 1558 base pair EcoRI to StuI fragment 3. Fragment 4 is an approximately 1484 base pair AccI to BglII restriction sub-fragment of the SPV HindIII fragment M (23). HOMOLOGY VECTOR 570-91.21. The plasmid 570-91.21 was constructed for the purpose of inserting foreign DNA into SPV. It incorporates an *E. coli* β-galactosidase (lacZ) marker gene and the PRV gIII (gC) gene flanked by SPV DNA. Upstream of the foreign DNA genes is an approximately 1484 base pair fragment of SPV DNA. Downstream of the foreign genes is an approximately 2149 base pair fragment of SPV DNA. When this plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the gIII (gC) gene is under the control of a synthetic early pox promoter (EP2). A detailed description of the plasmid is given in FIGS. 10A–10D. It may be constructed utilizing standard recombinant DNA techniques (22 and 30), by joining restriction fragments from the following sources with the synthetic DNA sequences indicated in FIGS. 10A–10D. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3002 base pair BamHI to PvuII restriction fragment of plasmid pJF751 (11). Fragment. 3 is an approximately 2378 base pair NcoI to NcoI fragment of plasmid 251-41.A, a subfragment of PRV BamHI #2 and #9. EcoRI linkers have replaced the NcoI and NcoI sites at the ends of this fragment. Fragment 4 is an approximately 2149 base pair AccI to HindIII restriction sub-fragment of the SPV HindIII fragment M (23). The AccI sites in fragments 1 and 4 have been converted to PstI sites using synthetic DNA linkers.

HOMOLOGY VECTOR 570-91.41. The plasmid 570-91.41 was constructed for the purpose of inserting foreign DNA into SPV. It incorporates an *E. coli* β-galactosidase (lacZ) marker gene and the PRV gIII (gC) gene flanked by SPV DNA. Upstream of the foreign DNA genes is an approximately 2149 base pair fragment of SPV DNA. Downstream of the foreign genes is an approximately 1484 base pair fragment of SPV DNA. When this plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the gIII (gC) gene is under the control of a synthetic early late pox promoter (EP1LP2). A detailed description of the plasmid is given in FIGS. 11A–11D. It may be constructed utilizing standard recombinant DNA techniques (22 and 30), by joining restriction fragments from the following sources with the synthetic DNA sequences indicated in FIGS. 11A–11D. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3002 base pair BamHI to PvuII restriction fragment of plasmid pJF751 (11). Fragment 3 is an approximately 2378 base pair NcoI to NcoI fragment of plasmid 251-41.A, a subfragment of PRV BamHI #2 and #9. EcoRI linkers have replaced the NcoI and NcoI sites at the ends of this fragment. Fragment 4 is an approximately 2149 base pair AccI to HindIII restriction sub-fragment of the SPV HindIII fragment M (23). The AccI sites in fragments 1 and 4 have been converted to PstI sites using synthetic DNA linkers.

HOMOLOGY VECTOR 570-91.64. The plasmid 570-91.64 was constructed for the purpose of inserting foreign DNA into SPV. It incorporates an *E. coli* β-galactosidase (lacZ) marker gene and the PRV gIII (gC) gene flanked by SPV DNA. Upstream of the foreign DNA genes is an approximately 1484 base pair fragment of SPV DNA. Downstream of the foreign genes is an approximately 2149 base pair fragment of SPV DNA. When this plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the gIII (gC) gene is under the control of a synthetic late early pox promoter (LP2EP2). A detailed description of the plasmid is given in FIGS. 12A–12D. It may be constructed utilizing standard recombinant DNA techniques (22 and 30), by joining restriction fragments from the following sources with the synthetic DNA sequences indicated in FIGS. 12A–12D. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3002 base pair BamHI to PvuII restriction fragment of plasmid pJF751 (11). Fragment 3 is an approximately 2378 base pair NcoI to NcoI fragment of plasmid 251-4l.A, a subfragment of PRV BamHI #2 and #9. EcoRI linkers have replaced the NcoI and NcoI sites at the ends of this fragment. Fragment 4 is an approximately 2149 base pair AccI to HindIII restriction sub-fragment of the SPV HindIII fragment M (23). The AccI sites in fragments 1 and 4 have been converted to PstI sites using synthetic DNA linkers.

HOMOLOGY VECTOR 538-46.26. The plasmid 538-46.26 was constructed for the purpose of inserting foreign DNA into SPV. It incorporates an *E. coli* β-galactosidase (lacZ) marker gene and the Newcastle Disease Virus (NDV) hemagglutinin-Neuraminidase (HN) gene flanked by SPV DNA. Upstream of the foreign genes is an approximately 2149 base pair fragment of SPV DNA. Downstream of the foreign genes is an approximately 1484 base pair fragment of SPV DNA. When this plasmid is used according to the HOMOLOGOUS RECOMBINATION PROCEDURE FOR GENERATING RECOMBINANT SPV a virus containing DNA coding for the foreign genes will result. Note that the β-galactosidase (lacZ) marker gene is under the control of a synthetic late pox promoter (LP1) and the HN gene is under the control of a synthetic early/late pox promoter (EP1LP2). A detailed description of the plasmid is given in FIGS. 8A–8D. It may be constructed utilizing standard recombinant DNA techniques (22 and 30), by joining restriction fragments from the following sources with the synthetic DNA sequences indicated in FIGS. 8A–8D. The plasmid vector was derived from an approximately 2972 base pair HindIII to BamHI restriction fragment of pSP64 (Promega). Fragment 1 is an approximately 2149 base pair HindIII to AccI restriction sub-fragment of the SPV HindIII restriction fragment M (23). Fragment 2 is an approximately 1810 base pair AvaII to NaeI restriction fragment of a NDV HN cDNA clone. The sequence of the HN cDNA clone is given in FIG. 7. The cDNA clone was generated from the B1 strain of NDV using standard cDNA cloning techniques (14). Fragment 3 is an approximately 3006 base pair BamHI to PvuII restriction fragment of plasmid pJF751 (11). Fragment 4 is an approximately 1484 base pair AccI to BglII restriction sub-fragment of the SPV HindIII fragment M (23).

HOMOLOGY VECTOR 599-65.25. The plasmid 599-65.25 was constructed for the purpose of inserting foreign DNA into SPV. It incorporates an *E. coli* β-galactosidase (lacZ) marker gene and the ILT gG gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the ILT gG gene is under the control of a synthetic early/late pox promoter (EP1LP2). A detailed description of the plasmid is given in FIGS. 13A–13D.

It may be constructed utilizing standard recombinant DNA techniques (22, 30), by joining restriction fragments from the following sources with the synthetic DNA sequences indicated in FIGS. 13A–13D. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1073 base pair EcoRI to MboI fragment. Note that the EcoRI site was introduced by PCR cloning. In this procedure, the primers described below were used with a template consisting of a 2.6 kb Sst I to Asp718I subfragment of a 5.1 kb Asp718I fragment of ILT virus genome. The first primer 91.13 (5'-CCGAATTCCGGCTTCAGTAACATAGGATCG -3') (SEQ ID NO: 81) sits down on the ILT gG sequence at amino acid 2. It adds an additional asparagine residue between amino acids 1 and 2 and also introduces an EcoRI restriction site. The second primer 91.14 (5'-GTACCCATACTGGTCGTGGC-3') (SEQ ID NO: 82) sits down on the opposite strand at approximately amino acid 196 priming toward the 5' end of the gene. The PCR product is digested with EcoRI and BamHI to produce an approximately 454 base pair fragment. The approximately 485 base pair MboI sub-fragment of ILT Asp718I (5.1 kb) fragment is ligated to the approximately 454 base pair EcoRI to BamHI fragment to generate fragment 2 from EcoRI to MboI which is approximately 939 base pairs (293 amino acids) in length. Fragment 3 is an approximately 3002 base pair BamHI to PvuII restriction fragment of plasmid pJF751 (11). Fragment 4 is an approximately 2149 base pair AccI to HindIII subfragment of the SPV HindIII fragment M. The AccI sites of fragments 1 and 4 have been converted to PstI sites using synthetic DNA linkers.

HOMOLOGY VECTOR 624-20.1C. The plasmid 624-20.1C was constructed for the purpose of inserting foreign DNA into SPV. It incorporates an *E. coli* β-galactosidase (lacZ) marker gene and the ILT gI gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the ILT gI gene is under the control of a synthetic late/early pox promoter (LP2EP2). A detailed description of the plasmid is given in FIGS. 14A–14D. It may be constructed utilizing standard recombinant DNA techniques (22, 30), by joining restriction fragments from the following sources with the synthetic DNA sequences indicated in FIGS. 14A–14D.

The plasmid vector was derived from an approximately 2972 base pair HindIII to BamHI restriction fragment of pSP64 (Promega). Fragment 1 is an approximately 1484 base pair Bgl II to AccI restriction sub-fragment of the SPV HindIII restriction fragment M (23). Fragment 2 is an approximately 1090 base pair fragment with EcoRI and BamHI restriction sites at the ends synthesized by PCR cloning and containing the entire amino acid coding sequence of the ILT gI gene. The ILT gI gene was synthesized in two separate PCR reactions. In this procedure, the primers described below were used with a template consisting the 8.0 kb ILT Asp 718I fragment. The first primer 103.6 (5'-CCGGAATTCGCTACTT GGAACTCTGG-3') (SEQ ID NO: 83) sits down on the ILT gI sequence at amino acid number 2 and introduces an EcoRI site at the 5' end of the ILT gI gene. The second primer 103.3 (5'-25 CATTGTCCCGAGACGGACAG-3') (SEQ ID NO: 84) sits down on the ILT gI sequence at approximately amino acid 269 on the opposite strand to primer 103.6 and primes toward the 5' end of the gene. The PCR product was digested with EcoRI and BglI (BglI is located approximately at amino acid 209 which is 179 base pairs 5' to primer 2) to yield a fragment 625 base pairs in length corresponding to the 5' end of the ILT gI gene. The third primer 103.4 (5'-CGCGATCCAACTATCGGTG-3') (SEQ ID NO: 85) sits down on the ILT gI gene at approximately amino acid 153 priming toward the 3' end of the gene. The fourth primer 103.5 (5'GCGGATCCACATTCAG ACTTAATCAC-3') (SEQ ID NO: 86) sits down at the 3' end of the ILT gI gene 14 base pairs beyond the UGA stop codon, introducing a BamHI restriction site and priming toward the 5' end of the gene. The PCR product is digested with Bgl I (at amino acid 209) and BamHI to yield a fragment 476 base pairs in length corresponding to the 3' end of the ILT gI gene. Fragment 2 consists of the products of the two PCR reactions ligated together to yield an ILT gI gene which is a EcoRI to BamHI fragment approximately 1101 base pairs (361 amino acids)

in length. Fragment 3 is an approximately 3002 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 614-83.18. The plasmid 614-83.18 was constructed for the purpose of inserting foreign DNA into SPV. It incorporates an E. coli β-galactosidase (lacZ) marker gene and the IBR gG gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the IBR gG gene is under the control of a synthetic late/early pox promoter (LP2EP2). A detailed description of the plasmid is given in FIGS. 15–15D. It may be constructed utilizing standard recombinant DNA techniques (22, 30), by joining restriction fragments from the following sources with the synthetic DNA sequences indicated in FIGS. 15–15D. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1085 base pair fragment synthesized by PCR cloning with EcoRI and BamHI restriction sites at the ends and containing the amino acid coding sequence from amino acids 2 to 362 of the IBR gG gene. In the PCR cloning procedure, the primers described below were used with a template consisting of the IBR-000 virus (Cooper strain). The first primer 106.9 (5'-ATGAATTCCCCTGCCGCCCGGACCGGCACC-3') (SEQ ID NO: 87) sits down on the IBR gG sequence at amino acid number 1 and introduces an EcoRI site at the 5' end of the IBR gG gene and two additional amino acids between amino acids 1 and 2. The second primer 106.8 (5'-CATGGATCCCGCTCGAGGCGAGCGGGCTCC-3') (SEQ ID NO: 88) sits down on the IBR gG sequence at approximately amino acid 362 on the opposite strand to primer 1 and primes synthesis toward the 5' end of the IBR gG gene. Fragment 2 was generated by digesting the PCR product with EcoRI and BamHI to yield a fragment 1085 base pairs in length corresponding to the amino terminal 362 amino acids (approximately 80%) of the IBR gG gene. Fragment 3 is an approximately 3002 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR FOR CONSTRUCTING S-SPV-019 (LacZ/IBR gE HOMOLOGY VECTOR): This lacZ/IBR gE homology vector is used to insert foreign DNA into SPV. It incorporates an E. coli β-galactosidase (lacZ) marker gene and the IBR gE gene flanked by SPV DNA. When this plasmid is used according to the HOMOLOGOUS RECOMBINATION PROCEDURE FOR GENERATING RECOMBINANT SPV a virus containing DNA coding for the foreign genes will result. Note that the β-galactosidase (lacZ) marker gene is under the control of a synthetic late pox promoter and the gE gene is under the control of a synthetic late/early pox promoter. The homology vector may be constructed utilizing standard recombinant DNA techniques (22 and 30), by joining restriction fragments from the following sources with the appropriate synthetic DNA sequences. The plasmid vector is derived from an approximately 2972 base pair HindIII to BamHI restriction fragment of pSP64 (Promega). The upstream SPV homology is an approximately 1146 base pair BglIII to AccI restriction sub-fragment of the SPV HindIII fragment M (23). The IBR gE gene is an approximately 1888 base pair fragment synthesized by PCR cloning with EcoRI and BamHI ends. In the PCR cloning procedure, the primers described below were used with a template consisting of the IBR-000 VIRUS (Cooper strain). The first primer 4/93.17DR (5'-CTGGTTCGGCCCAGAATTCTATGGGTCTCGCGCGGCTCGTGG-3' (SEQ ID NO: 89) sits down on the IBR gE gene at amino acid number 1 and introduces an EcoRI site at the 5' end of the IBR gE gene and adds two additional amino acids at the amino terminus of the protein. The second primer 4/93.18DR (5'-CTCGCTCGCCCAG GATCCCTAGCGGAGGATGGACTTGAGTCG-3') (SEQ ID NO: 90) sits down on the IBR gE sequence at approximately amino acid 648 on the opposite strand to primer 1 and primes synthesis toward the 5' end of the IBR gE gene. The lacZ promoter and marker gene is identical to the one used in plasmid 520-17.5. The downstream SPV homology is an approximately 2156 base pair AccI to HindIII restriction sub-fragment of the SPV HindIII restriction fragment M (23). The AccI site in the SPV homology vector is converted to a unique XbaI site.

HOMOLOGY VECTOR FOR CONSTRUCTING S-SPV-018 (LacZ/PRV gE HOMOLOGY VECTOR): This homology vector is constructed for the purpose of inserting foreign DNA into SPV. It incorporates an E. coli β-galactosidase (lacZ) marker gene and the PRV gE gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing the DNA coding for the foreign genes results. Note that the β-galactosidase (lacZ) marker gene is under the control of a synthetic late pox promoter (LP1), and the PRV gE gene is under the control of a synthetic early/late pox promoter (EP1LP2). The homology vector is constructed utilizing standard recombinant DNA techniques (22,30), by joining restriction fragments from the following sources with synthetic DNA sequences. The plasmid vector is derived from an approximately 2972 base pair HindIII to BamHI restriction fragment pSP64 (Promega). Fragment 1 is an approximately 1484 base pair BglII to AccI restriction sub-fragment of the SPV HindIII restriction fragment M (23). Fragment 2 is the lacZ promoter and marker gene which is identical to the one used in plasmid 520-17.5. Fragment 3 is an approximately 2484 base pair DraI to MluI sub-fragment of PRV derived from the PRV BamHI #7 DNA fragment. The DraI site is converted to an EcoRI site through the use of a synthetic DNA linker. The DraI site sits 45 base pairs upstream of the natural gE start codon and extends the open reading frame at the amino terminus of the protein for 15 amino acids. The synthetic pox promoter/EcoRI DNA linker contributes another 4 amino acids. Therefore, the engineered gE gene contains 19 additional amino acids fused to the amino terminus of gE. The nineteen amino acids are Met-Asn-Ser-Gly-Asn-Leu-Gly-Thr-Pro-Ala-Ser-Leu-Ala-His-Thr-Gly-Val-Glu-Thr. Fragment 4 is an approximately 2149 base pair AccI to HindIII sub-fragment of the SPV HindIII fragment M (23). The AccI sites of fragments 1 and 4 are converted to PstI sites using synthetic DNA linkers.

HOMOLOGY VECTOR 520-90.15. The plasmid 520-90.15 was constructed for the purpose of inserting foreign DNA into SPV. It contains a unique NdeI restriction enzyme site into which foreign DNA may be inserted. When a plasmid, containing a foreign DNA insert at the NdeI site, is used according to the HOMOLOGOUS RECOMBINATION PROCEDURE FOR GENERATING RECOMBINANT SPV a virus containing the foreign DNA will result. Plasmid 520-90.15 was constructed utilizing standard recombinant DNA techniques (22 and 30), by joining two restriction fragments from the following sources. The first fragment is an approximately 2972 base pair HindIII to BamHI restriction fragment of pSP64 (Promega). The second fragment is an approximately 1700 base pair HindIII to BamHI restriction subfragment of the SPV HindIII restriction fragment G (23).

HOMOLOGY VECTOR 708-78.9. The plasmid 708-78.9 was constructed for the purpose of inserting foreign DNA into SPV. It incorporates an *E. coli* β-galactosidase (lacZ) marker gene and the infectious bovine rhinotracheitis virus (IBRV) gE gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the IBRV gE gene is under the control of a synthetic late/early pox promoter (LP2EP2). It may be constructed utilizing standard recombinant DNA techniques (22, 30), by joining restriction fragments from the following sources. The plasmid vector was derived from an approximately 2972 base pair HindIII to BamHI restriction fragment of pSP64 (Promega). Fragment 1 is an approximately 1484 base pair Bgl II to AccI restriction sub-fragment of the SPV HindIII restriction fragment M (23). Fragment 2 is an approximately 475 base pair fragment with EcoRI and BamHI restriction sites at the ends. The EcoRI and BamHI sites are synthesized by PCR cloning. The PCR product contains the entire amino acid coding sequence of the IBRV gE gene. In the PCR cloning procedure, the primers described below were used with a template consisting of the IBR-000 virus (Cooper strain) (44). The first primer 2/94.5DR (5'-CTGGTTCGGC CCAGAATTCGATGCAACCCACCGCGCCGCCCCG-3') (SEQ ID NO: 116) sits down on the IBR gE gene at amino acid number 1 and introduces an EcoRI site at the 5' end of the IBRV gE gene and adds two additional amino acids at the amino terminus of the protein. The second primer 4/93.18DR (5'-CTCGCTCGCCCAGGATCCCTAGCGG AGGATGGACTTGAGTCG-3') (SEQ ID NO: 117) sits down on the IBRV gE sequence (44) at approximately amino acid 648 on the opposite strand to the first primer and primes synthesis toward the 5' end of the IBRV gE gene. The PCR product was digested with EcoRI and BamHI to yield a fragment approximately 1950 base pairs in length corresponding to the IBRV gE gene. Fragment 3 is an approximately 3002 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 723-59A9.22. The plasmid 723-59A9.22 was used to insert foreign DNA into SPV. It incorporates an *E. coli* β-galactosidase (lacZ) marker gene and the equine influenza virus NA PR/56 gene flanked by SPV DNA. When this plasmid was used according to the HOMOLOGOUS RECOMBINATION PROCEDURE FOR GENERATING RECOMBINANT SPV a virus containing DNA coding for the foreign genes results. Note that the β-galactosidase (lacZ) marker gene is under the control of a synthetic late pox promoter (LP1) and the EIV PR/56 NA gene is under the control of a synthetic late/early pox promoter (LP2EP2). A detailed description of the plasmid is given in FIGS. 18–18D. The homology vector was constructed utilizing standard recombinant DNA techniques (22 and 30), by joining restriction fragments from the following sources with the appropriate synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII fragment M (23). Fragment 2 is the NA gene coding region from the equine Influenza A/Prague/56 (serotype 1 (N7) virus) cloned as an approximately 1450 base pair BamHI fragment utilizing the following primers 5'-G GGATCCATGAATCCTAATCAAAAACTCTTT-3' (SEQ ID NO: 118) for cDNA priming and combined with 5'-G GGATCCTTACGAAAAGTATTTAATTTGTGC-3' (SEQ ID NO: 119) for PCR. (see CLONING OF EQUINE INFLUENZA VIRUS HEMAGGLUTININ AND NEURAMINIDASE GENES). Fragment 3 is an approximately 3010 base pair BamHI to PvuII restriction fragment of plasmid pJF751 (11). Fragment 4 is an approximately 2149 base pair AccI to HindIII restriction sub-fragment of the SPV HindIII restriction fragment M (23). The AccI site in the SPV homology vector was converted to a unique NotI site.

HOMOLOGY VECTOR 727-54.60. The plasmid 727-54.60 was constructed for the purpose of inserting foreign DNA into SPV. It incorporates an *E. coli* β-galactosidase (lacZ) marker gene and the pseudorabies virus (PRV) gII (gB) gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the PRV gB gene is under the control of a synthetic late/early pox promoter (LP2EP2). A detailed description of the plasmid is given in FIGS. 19–19D. It may be constructed utilizing standard recombinant DNA techniques (22, 30), by joining restriction fragments from the following sources with the synthetic DNA sequences indicated in FIGS. 19–19D. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3500 base pair fragment which contains the coding sequence for the PRV gB gene within the KpnI C fragment of genomic PRV DNA (21). Fragment 2 contains an approximately 53 base pair synthetic fragment containing the amino terminus of the PRV gB gene, an approximately 78 base pair SmaI to Nhe I fragment from the PRV KpnI C genomic fragment, and an approximately 3370 base pair NheI to EcoRI fragment from the PRV KpnI C genomic fragment (21). Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 727-67.18. The plasmid 727-67.18 was constructed for the purpose of inserting foreign DNA into SPV. It incorporates an E. coli β-galactosidase (lacZ) marker gene and the hepatitis B virus core antigen gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the hepatitis B core antigen gene is under the control of a synthetic early/late pox promoter (EP1LP2). A detailed description of the plasmid is given in FIGS. 20–20D. It may be constructed utilizing standard recombinant DNA techniques (22, 30), by joining restriction fragments from the following sources with the synthetic DNA sequences indicated in FIGS. 20–20D. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3002 base pair BamHI to PvuII restriction fragment of plasmid pJF751 (11). Fragment 3 is an approximately 589 base pair fragment with BamHI and EcoRI restriction sites at the ends. This fragment contains the hepatitis B core antigen coding sequences (amino acids 25–212) (Ref. 45, 50). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 732-18.4. The plasmid 732-18.4 was used to insert foreign DNA into SPV. It incorporates an E. coli β-galactosidase (lacZ) marker gene and the equine influenza virus AK/91 NA gene flanked by SPV DNA. When this plasmid was used according to the HOMOLOGOUS RECOMBINATION PROCEDURE FOR GENERATING RECOMBINANT SPV a virus containing DNA coding for the foreign genes results. Note that the β-galactosidase (lacZ) marker gene is under the control of a synthetic late pox promoter (LP1) and the EIV AK/91 NA gene is under the control of a synthetic late/early pox promoter (LP2EP2). A detail description of the plasmid is given in FIGS. 21–21D. The homology vector was constructed utilizing standard recombinant DNA techniques (22 and 30), by joining restriction fragments from the following sources with the appropriate synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII fragment M (23). Fragment 2 is the NA gene coding region from the equine Influenza A/Alaska/91 (serotype 2 (N8) virus) cloned as an approximately 1450 base pair SalI fragment utilizing the following primers 5'-GG GTCGACATGAATCCAAATCAAAAGATA-3' (SEQ ID NO: 124) for cDNA priming and combined with 5'-GG GTCGACTTACATCTTATCGATGTCAA-3' (SEQ ID NO: 125) for PCR (see CLONING OF EQUINE INFLUENZA VIRUS HEMAGGLUTININ AND NEURAMINIDASE GENES). Fragment 3 is an approximately 3010 base pair BamHI to PvuII restriction fragment of plasmid pJF751 (11). Fragment 4 is an approximately 2149 base pair AccI to HindIII restriction sub-fragment of the SPV HindIII restriction fragment M (23). The AccI site in the SPV homology vector was converted to a unique NotI site HOMOLOGY VECTOR 741-80.3 The plasmid 741-80.3 was constructed for the purpose of inserting foreign DNA into SPV. It incorporates an E. coli β-galactosidase (lacZ) marker gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a human cytomegalovirus immediate early (HCMV IE) promoter. A detailed description of the plasmid is given in FIGS. 22–22C. It may be constructed utilizing standard recombinant DNA techniques (22, 30), by joining restriction fragments from the following sources with the synthetic DNA sequences indicated in FIGS. 22–22C. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is a 1154 base pair PstI to AvaII fragment derived from a HCMV 2.1 kb PstI fragment containing the HCMV IE promoter (46). Fragment 3 is a 3010 base pair BamHI to PvuII fragment derived from plasmid pJF751 (49) containing the E. coli lacZ gene. Fragment 4 is an approximately 750 base pair NdeI to SalI fragment derived from PRV BamHI #7 which contains the carboxy-terminal 19 amino acids and the polyadenylation signal of the PRV gx gene. Fragment 5 is an approximately 2149 base pair AccI to HindIII subfragment of the SPV HindIII fragment M. The AccI sites in fragments 1 and 5 were converted to unique NotI sites using NotI linkers.

HOMOLOGY VECTOR 741-84.14. The plasmid 741-84.14 was constructed for the purpose of inserting foreign DNA into SPV. It incorporates an E. coli β-galactosidase (lacZ) marker gene and the human interleukin-2 (IL-2) gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the human IL-2 gene is under the control of a synthetic late/early pox promoter (LP2EP2). The coding sequence for the human IL-2 protein is fused at the amino terminus to the PRV gX signal sequence for membrane transport. A detailed description of the plasmid is given in FIGS. 23–23D. It may be constructed utilizing standard recombinant DNA techniques (22, 30), by joining restriction fragments from the following sources with the synthetic DNA sequences indicated in FIGS. 23–23D. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 475 base pair fragment with EcoRI and BglII restriction sites at the ends. The EcoRI site is synthesized by PCR cloning and the BglII site is at the 3' end of the human IL-2 cDNA (43, 47). The PCR product contains the entire amino acid coding sequence of the PRV gX signal sequence-human IL-2 gene. In this procedure, the primers described below were used with a template consisting of the cDNA for PRV gX signal sequence-human IL-2 (43). The first primer 5/94.23 (5'-CTCGAATTCGAAGTGGGCAACGTGGATCCTCGC-3') (SEQ ID NO: 126) sits down on the PRV gX signal sequence at amino acid number 1 and introduces an EcoRI site at the 5' end of the gene. The second primer 5/94.24 (5'-CAGTTAGCCTCCCCCATCTCCCC-3') (SEQ ID NO: 127) sits down on the human IL-2 gene sequence within the 3' untranslated region on the opposite strand to primer 5/94.23 and primes toward the 5' end of the gene. The PCR product was digested with EcoRI and BglII (BglII is located approximately 3 nucleotides beyond the stop codon for the human IL-2 gene) to yield a fragment 475 base pairs in length corresponding to the PRV gX signal sequence-human IL-2 gene. Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 744-34. The plasmid 744-34 was constructed for the purpose of inserting foreign DNA into SPV. It incorporates an E. coli β-galactosidase (lacZ) marker gene and the equine herpesvirus type 1 gB gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the EHV-1 gB gene is under the control of a synthetic late/early pox promoter (LP2EP2). A detailed description of the plasmid is given in FIGS. 24–24D. It may be constructed utilizing standard recombinant DNA techniques (22, 30), by joining restriction fragments from the following sources with the synthetic DNA sequences indicated in FIGS. 24–24D The plasmid vector was derived from an approximately 2972 base pair HindIII to BamHI restriction fragment of pSP64 (Promega). Fragment 1 is an approximately 1484 base pair Bgl II to AccI restriction sub-fragment of the SPV HindIII restriction fragment M (23). Fragment 2 is an approximately 2941 base pair fragment with EcoRI and PmeI restriction sites at the ends. Fragment 2 is an approximately 2941 base pair EcoRI to PmeI fragment. Fragment 2 was synthesized as an approximately 429 base pair PCR fragment at the 5' end of the gene having a synthetic EcoRI site and a natural BamHI site within the BamHI "a" fragment of EHV-1 genomic DNA and an approximately 2512 base pair restriction fragment at the 3' end of the gene from BamHI to PmeI within the BamHI "i" fragment of EHV-1 genomic DNA (48). In the procedure to produce the 5' end PCR fragment, the primers described below were used with a template consisting of the EHV-1 BamHI "a" and "i" fragments. The first primer 5/94.3 (5'-CGGAATTCCTCTGGTTGCCGT-3') (SEQ ID NO: 128) sits down on the EHV-1 gB sequence at amino acid number 2 and introduces an EcoRI site at the 5' end of the EHV-1 gB gene and an ATG start codon. The second primer 5/94.4 (5'-GACGGTGGATCCGGTAGGCGGT-3') (SEQ ID NO: 129) sits down on the EHV-1 gB sequence at approximately amino acid 144 on the opposite strand to primer 5/94.3 and primes toward the 5' end of the gene. The PCR product was digested with EcoRI and BamHI to yield a fragment 429 base pairs in length corresponding to the 5' end of the EHV-1 gB gene. Fragment 2 consists of the products of the PCR reaction (EcoRI to BamHI) and the restriction fragment (BamHI to PmeI) ligated together to yield an EHV-1 gB gene which is an EcoRI to PmeI fragment approximately 2941 base pairs (979 amino acids) in length. Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 744-38. The plasmid 744-38 was constructed for the purpose of inserting foreign DNA into SPV. It incorporates an E. coli β-galactosidase (lacZ) marker gene and the equine herpesvirus type 1 gD gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the EHV-1 gD gene is under the control of a synthetic late/early pox promoter (LP2EP2). A detailed description of the plasmid is given in FIGS. 25–25D. It may be constructed utilizing standard recombinant DNA techniques (22, 30), by joining restriction fragments from the following sources with the synthetic DNA sequences indicated in FIGS. 25–25D. The plasmid vector was derived from an approximately 2972 base pair HindIII to BamHI restriction fragment of pSP64 (Promega). Fragment 1 is an approximately 1484 base pair Bgl II to AccI restriction sub-fragment of the SPV HindIII restriction fragment M (23). Fragment 2 is an approximately 1240 base pair HindIII fragment within the BamHI "d" fragment of EHV-1 (48). Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 689-50.4. The plasmid 689-50.4 was constructed for the purpose of inserting foreign DNA into SPV. It incorporates an E. coli β-galactosidase (lacZ) marker gene and the infectious bursal disease virus (IBDV) polyprotein gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the IBDV polyprotein gene is under the control of a synthetic late/early pox promoter (LP2EP2). It may be constructed utilizing standard recombinant DNA techniques (22, 30), by joining restriction fragments from the following sources. The plasmid vector was derived from an approximately 2972 base pair Hind III to BamHI restriction fragment of pSP64 (Promega). Fragment 1 is an approximately 1484 base pair BglII to AccI restriction subfragment of the SPV HindIII restriction fragment M (23). Fragment 2 is an approximately 3400 base pair fragment with SmaI and HpaI restriction sites at the ends from plasmid 2-84/2-40 (51). This fragment contains the IBDV polyprotein coding sequences. Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 689-50.7. The plasmid 689-50.7 was constructed for the purpose of inserting foreign DNA into SPV. It incorporates an E. coli β-galactosidase (lacZ) marker gene and the infectious bursal disease virus (IBDV) VP2 gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the IBDV VP2 gene is under the control of a synthetic late/early pox promoter (LP2EP2). It may be constructed utilizing standard recombinant DNA techniques (22, 30), by joining restriction fragments from the following sources. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1081 base pair fragment with BclI and BamHI restriction sites at the ends. This fragment codes for the IBDV VP2 protein and is derived from a full length IBDV cDNA clone (51). Fragment 3 is an approximately 3010 base pair BamHI to PvuII restriction fragment of plasmid pJF751 (11). Fragment 4 is an approximately 2149 base pair AccI to HindIII sub-fragment of the SPV HindIII fragment M. The AccI sites in fragments 1 and 4 were converted to unique NotI sites using NotI linkers.

HOMOLOGY VECTOR 751-07.A1. The plasmid 751-07.A1 was used to insert foreign DNA into SPV. It incorporates an E. coli β-galactosidase (lacZ) marker gene and the chicken interferon (cIFN) gene flanked by SPV DNA. When this plasmid was used according to the HOMOLOGOUS RECOMBINATION PROCEDURE FOR GENERATING RECOMBINANT SPV a virus containing DNA coding for the foreign genes results. Note that the β-galactosidase (lacZ) marker gene is under the control of a synthetic late pox promoter (LP1) and the cIFN gene is under the control of a synthetic late/early pox promoter (LP2EP2). The homology vector was constructed utilizing standard recombinant DNA techniques (22 and 30), by joining restriction fragments from the following sources with the appropriate synthetic DNA sequences. The plasmid vector was derived from an approximately 2972 base pair HindIII to BamHI restriction fragment of pSP64 (Promega). Fragment 1 is an approximately 1146 base pair BglII to AccI restriction sub-fragment of the SPV HindIII fragment M (23). Fragment 2 is an approximately 577 base pair EcoRI to BglII fragment coding for the CIFN gene (54) derived by reverse transcription and polymerase chain reaction (PCR) (Sambrook, et al., 1989) of RNA ISOLATED FROM CONCANAVALIN A STIMULATED CHICKEN SPLEEN CELLS. The antisense primer (6/94.13) used for reverse transcription and PCR was 5'-CGAC GGATCCGAGGTGCGTTTGGGGCTAAGTGC-3' (SEQ ID NO: 211). The sense primer (6/94.12) used for PCR was 5' - CCACGGATCCAGCACAACGCGAGTCCCACCATG GCT-3' (SEQ ID NO: 212). The BamHI fragment resulting from reverse transcription and PCR was gel purified and used as a template for a second PCR reaction to introduce a unique EcoRI site at the 5' end and a unique BglII site at the 3' end. The second PCR reaction used primer 6/94.22 (5'-CCACGAATTCGATGGCTGTGCCTGCAAGCCCACA G-3'; SEQ ID NO: 213) at the 5' end and primer 6/94.34 (5'-CGAAGATCTGAGGTGCGTTTGGGGCTAAGTGC-3'; SEQ ID NO: 214) at the 3' end to yield an approximately 577 base pair fragment. The DNA fragment contains the coding sequence from amino acid 1 to amino acid 193 of the chicken interferon protein (54) which includes a 31 amino acid signal sequence at the amino terminus and 162 amino acids of the mature protein encoding chicken interferon. Fragment 3 is an approximately 3002 base pair BamHI to PvuII restriction fragment of plasmid pJF751 (11). Fragment 4 is an approximately 2156 base pair AccI to HindIII restriction sub-fragment of the SPV HindIII restriction fragment M (23). The AccI site in the SPV homology vector was converted to a unique NotI site.

HOMOLOGY VECTOR 751-56.A1. The plasmid 751-56.A1 was used to insert foreign DNA into SPV. It incorporates an E. coli β-galactosidase (lacZ) marker gene and the chicken myelomonocytic growth factor (cMGF) gene flanked by SPV DNA. When this plasmid was used according to the HOMOLOGOUS RECOMBINATION PROCEDURE FOR GENERATING RECOMBINANT SPV a virus containing DNA coding for the foreign genes results. Note that the β-galactosidase (lacZ) marker gene is under the control of a synthetic late pox promoter (LP1) and the cMGF gene is under the control of a synthetic late/early pox promoter (LP2EP2). The homology vector was constructed utilizing standard recombinant DNA techniques (22 and 30), by joining restriction fragments from the following sources with the appropriate synthetic DNA sequences. The plasmid vector was derived from an approximately 2972 base pair HindIII to BamHI restriction fragment of pSP64 (Promega). Fragment 1 is an approximately 1146 base pair BglII to AccI restriction sub-fragment of the SPV HindIII fragment M (23). Fragment 2 is an approximately 640 base pair EcoRI to BamHI fragment coding for the cMGF gene(55) derived by reverse transcription and polymerase chain reaction (PCR) (Sambrook, et al., 1989) of RNA ISOLATED FROM CONCANAVALIN A STIMULATED CHICKEN SPLEEN CELLS. The antisense primer (6/94.20) used for reverse transcription and PCR was 5'-CGCA GGATCCGGGGCGTCAGAGGCGGGCGAGGTG-3' (SEQ ID NO: 215). The sense primer (5/94.5) used for PCR was 5'-GAGC GGATCCTGCAGGAGGAGACACAGAGCTG-3' (SEQ ID NO: 216). The BamHI fragment derived from PCR was subcloned into a plasmid and used as a template for a second PCR reaction using primer 6/94.16 (5' -GCGC GAATTCCATGTGCTGCCTCACCCCTGTG-3'; SEQ ID NO: 217) at the 5' end and primer 6/94.20 (5'-CGCA GGATCCGGGGCGTCAGAGGCGGGCGAGGTG-3'; SEQ ID NO: 218) at the 3' end to yield an approximately 640 base pair fragment. The DNA fragment contains the coding sequence from amino acid 1 to amino acid 201 of the cMGF protein (55) which includes a 23 amino acid signal sequence at the amino terminus and 178 amino acids of the mature protein encoding cMGF. Fragment 3 is an approximately 3002 base pair BamHI to PvuII restriction fragment of plasmid pJF751 (11). Fragment 4 is an approximately 2156 base pair AccI to HindIII restriction sub-fragment of the SPV HindIII restriction fragment M (23). The AccI site in the SPV homology vector was converted to a unique NotI site.

Figure 28A:
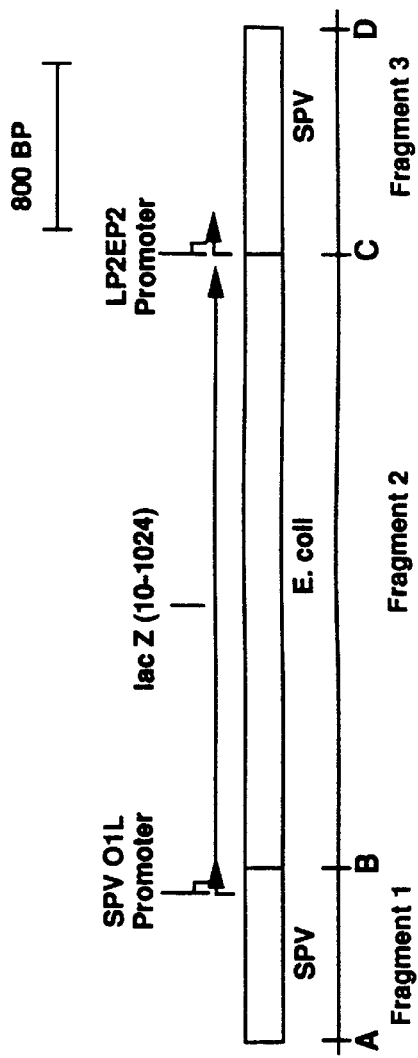
Figure 28B:
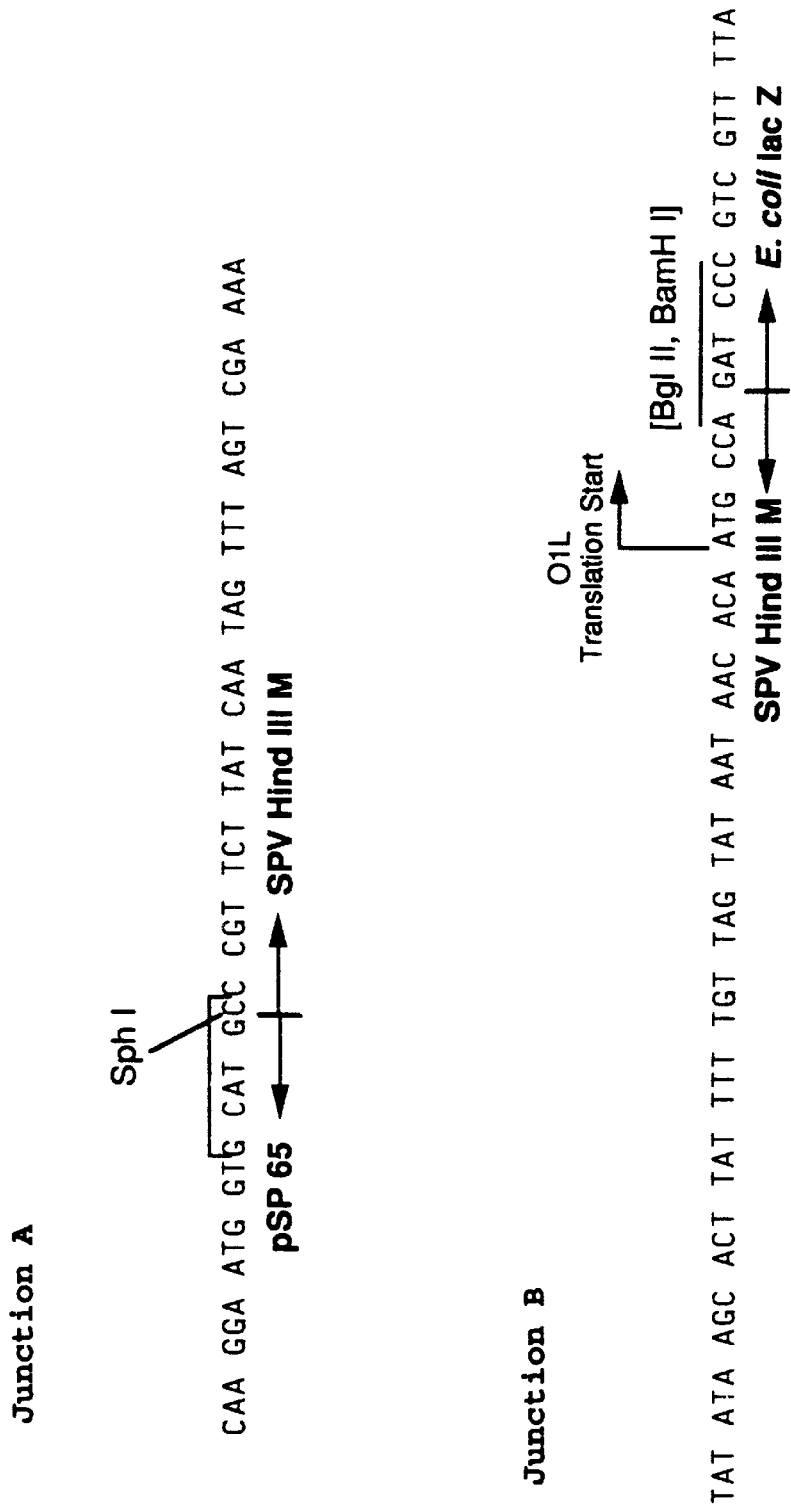
Figure 28C:
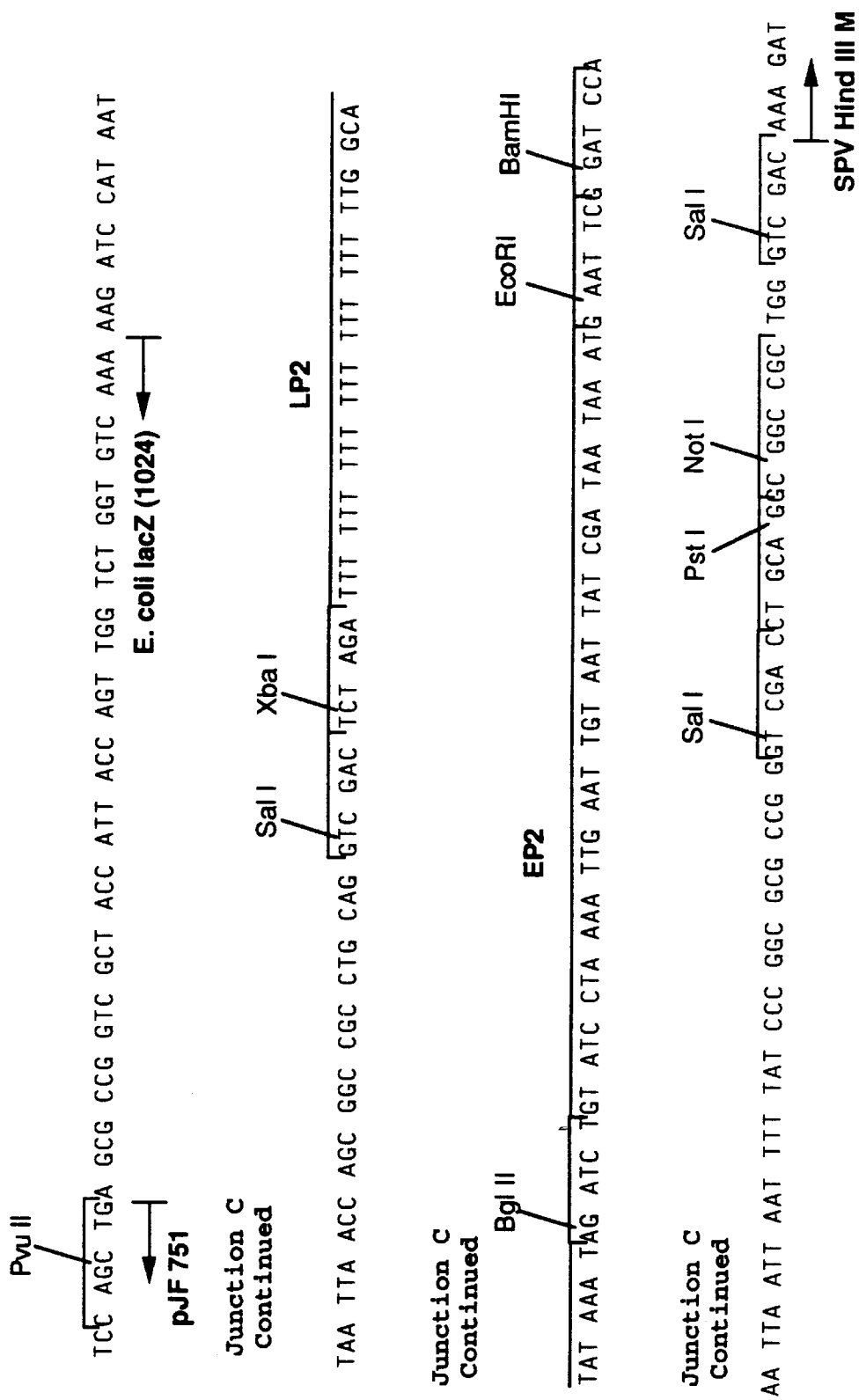
Figure 28D:
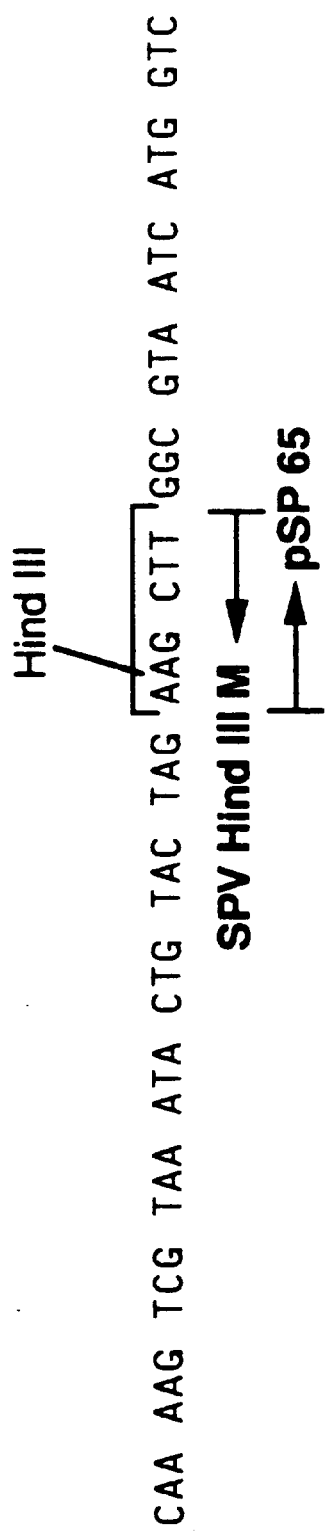

HOMOLOGY VECTOR 752-22.1. The plasmid 752-22.1 was constructed for the purpose of inserting foreign DNA into SPV. It incorporates an *E. coli* β-galactosidase (lacZ) marker gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a swinepox virus OlL gene promoter. The homology vector also contains the synthetic late/early promoter (LP2EP2) into which a second foreign gene is inserted into a unique BamHI or EcoRI site. A detailed description of the plasmid is given in FIGS. 28–28D. It was constructed utilizing standard recombinant DNA techniques (22, 30), by joining restriction fragments from the following sources with the synthetic DNA sequences indicated in FIGS. 28–28D. The plasmid vector was derived from an approximately 2519 base pair HindIII to SphI restriction fragment of pSP65 (Promega). Fragment 1 is an approximately 855 base pair sub-fragment of the SPV HindIII restriction fragment M (23) synthesized by polymerase chain reaction using DNA primers 5'-GAAGCATGCCCGTTCTTATCAATAGTTTAGTCGAAAAT-3' (SEQ ID NO: 185) and 5'-CATAAGATCTGGCATTGTGTTATTATACTAACAAAAATAAG-3' (SEQ ID NO: 186) to produce an 855 base pair fragment with SphI and BglII ends. Fragment 2 is a 3002 base pair BamHI to PvuII fragment derived from plasmid pJF751 (49) containing the *E. coli* lacZ gene. Fragment 3 is an approximately 1113 base pair subfragment of the SPV HindIII fragment M synthesized by polymerase chain reaction using DNA primers 5'-CCGTAGTCGACAAAGATCGACTTATTAATATGTATGGGATT-3' (SEQ ID NO: 187) and 5'-GCCTGAAGCTTCTAGTACAGTATTTACGACTTTTGAAAT-3' (SEQ ID NO: 188) to produce an 1113 base pair fragment with SalI and HindIII ends.

HOMOLOGY VECTOR 752-29.33. The plasmid 759.33 was constructed for the purpose of inserting foreign DNA into SPV. It incorporates an *E. coli* β-galactosidase (lac Z) marker gene and an equine herpesvirus type 1 gB gene flanked by SPV DNA. Upstream of the foreign gene is an approximately 855 base pair fragment of SPV DNA. Downstream of the foreign genes is an approximately 113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a swinepox virus 01L gene promoter and the EHV-1 gB gene is under the control of the late/early promoter (LP2EP2). The LP2EP2 promoter-EHV-1 gB gene cassette was inserted into a NotI site of homology vector 738-94.4. Homology vector 752-29.33 was constructed utilizing standard recombinant DNA techniques (22, 30), by joining restriction fragments from the following sources with the synthetic DNA sequences. The plasmid vector was derived from an approximately 2519 base pair HindIII to SphI restriction fragment of pSP65 (Promega). Fragment 1 is an approximately 855 base pair sub-fragment of the SPV HindIII restriction fragment M (23) synthesized by polymerase chain reaction using DNA primers 5'-GAAGCATGCCCGTTCTTATCAATAGTTTAGTCGAAAAT-3' (SEQ ID NO: 185) and 5'-CATAAGATCTGGCATTGTGTTATTATACTAACAAAAATAAG-3' (SEQ ID NO: 186) to produce an 855 base pair fragment with SphI and BglII ends. Fragment 2 is a 3002 base pair BamHI to PvuII fragment derived from plasmid pJF751 (49) containing the *E. coli* lacz gene. Fragment 3 is the product of a PCR reaction (EcoRI to BamHI) and a restriction fragment (BamHI to PmeI) ligated together to yield an EHV-1 gB gene which is an EcoRI to PmeI fragment approximately 2941 base pairs (979 amino acids) in length. The PCR fragment is an approximately 429 base pair fragment having a synthetic EcoRI site at the 5' end of the gene and a natural BamHI site at the 3' end within the BamHI "a" fragment of EHV-1 genomic DNA. The restriction fragment is an approximately 2512 base pair fragment from BamHI to PmeI within the BamHI "I" fragment of EHV-1 genomic DNA. In the procedure to produce the 5' end PCR fragment, the primers described below were used with a template consisting of the EHV-1 BamHI "a" and "i" fragments.

The first primer 5/94.3 (5'-CGGAATTCCTCTGGTTCGCCGT-3') (SEQ ID NO: 128) sits down on the EHV-1 gB sequence at amino acid number 2 and introduces an EcoRI site at the 5' end of the EHV-1 gB gene and an ATG start codon. The second primer 5/94.4 (5'-GACGGTGGATCCGGTAGGCGGT-3') (SEQ ID NO: 129) sits down on the EHV-1 gB sequence at approximately amino acid 144 on the opposite strand to primer 5/94.3 and primes toward the 5' end of the gene. The PCR product was digested with EcoRI and BamHI to yield a fragment 429 base pairs in length corresponding to the 5' end of the EHV-1 gB gene. Fragment 3 consists of the products of the PCR reaction (EcoRI to BamHI) and the restriction fragment (BamHI to PmeI) ligated together to yield an EHV-1 gB gene which is an EcoRI to PmeI fragment approximately 2941 base pairs (979 amino acids) in length. Fragment 4 is an approximately 1113 base pair subfragment of the SPV HindIII fragment M synthesized by polymerase chain reaction using DNA primers 5'-CCGTAGTCGACAAAGATCGACTTATTAATATGTATGGGATT-3' (SEQ ID NO: 187) and 5'-GCCTGAAGCTTCTAGTACAGTATTTACGACTTTTGAAAT-3' (SEQ ID NO: 188) to produce an 1113 base pair fragment with SalI and HindIII ends.

HOMOLOGY VECTOR 746-94.1. The plasmid 746-94.1 was constructed for the purpose of inserting foreign DNA into SPV. It incorporates an *E. coli* β-galactosidase (lacz) marker gene and an infectious bovine rhinotracheitis virus glycoprotein E (gE) gene flanked by SPV DNA.

Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a swinepox virus O1L gene promoter and the IBRV gE gene is under the control of the late/early promoter (LP2EP2). It was constructed utilizing standard recombinant DNA techniques (22, 30), by joining restriction fragments from the following sources with the synthetic DNA sequences. A 1250 base pair EcoRI to BamHI fragment coding for amino acids 1 to 417 of the IBRV gE gene (missing 158 amino acids of the carboxy terminal transmembrane region) was inserted into unique EcoRI and BamHI sites of homology vector 752-22.1 (FIGS. 28–28D). The 1250 base pair EcoRI to BamHI fragment was synthesized by polymerase chain reaction (15) using IBRV (Cooper) genomic DNA as a template and primer 10/94.23 (5'-GGG GAATTCAATGCAACCCACCGCGCCGCCCC-3'; SEQ ID NO: 219) at the 5' end of the IBRV gE gene (amino acid 1) and primer 10/94.22 (5-GGG GGATCCTAGGGCGCGCCCGCCGGCTCGCT-3'; SEQ ID NO: 220) at amino acid 417 of the IBRV gE gene.

HOMOLOGY VECTOR 767-67.3. The plasmid 767-67.3 was constructed for the purpose of inserting foreign DNA into SPV. It incorporates an *E. coli* β-galactosidase (lacZ) marker gene and an bovine viral diarrhea virus glycoprotein 53 (BVDV gp53) gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a swinepox virus O1L gene promoter and the BVDV gp53 gene is under the control of the late/early promoter (LP2EP2). It was constructed utilizing standard recombinant DNA techniques (22, 30), by joining restriction fragments from the following sources with the synthetic DNA sequences. A 1187 base pair BamHI fragment coding for the BVDV gp53 was inserted into the unique BamHI sites of homology vector 752-22.1 (FIGS. 28–28D). The 1187 base pair BamHI fragment was synthesized by polymerase chain reaction (15) as described in CLONING OF BOVINE VIRAL DIARRHEA VIRUS gp48 AND gp53 GENES.

HOMOLOGY VECTOR 771-55.11. The plasmid 771-55.11 was constructed for the purpose of inserting foreign DNA into SPV. It incorporates an *E. coli* β-galactosidase (lacZ) marker gene and an bovine viral diarrhea virus glycoprotein 48 (BVDV gp48) gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a swinepox virus OiL gene promoter and the BVDV gp48 gene is under the control of the late/early promoter (LP2EP2). It was constructed utilizing standard recombinant DNA techniques (22, 30), by joining restriction fragments from the following sources with the synthetic DNA sequences. A 678 base pair BamHI fragment coding for the BVDV gp48 was inserted into the unique BamHI sites of homology vector 752-22.1 (FIGS. 28–28D). The 678 base pair BamHI fragment was synthesized by polymerase chain reaction (15) as described in CLONING OF BOVINE VIRAL DIARRHEA VIRUS gp48 AND gp53 GENES.

PLASMID 551-47.23. The plasmid 551-47.23 was constructed for the purpose of inserting foreign DNA into SPV. It incorporates the *E. coli* β-glucuronidase (β-glu) marker gene under the control of a late/early pox promoter (LP2EP2). It is useful to insert the marker gene into sites in the SPV genome to produce a recombinant swinepox virus. It was constructed utilizing standard recombinant DNA techniques (22, 30), by joining restriction fragments from the following sources. The plasmid vector was derived from an approximately 3005 base pair HindIII restriction fragment of pSP65 (Promega). Fragment 1 is an approximately 1823 base pair EcoRI to SmaI fragment of the plasmid pRAJ260 (Clonetech). Note that the EcoRI and SmaI sites were introduced by PCR cloning. Plasmid 551-47.23 was used to make recombinant swinepox viruses S-SPV-059, S-SPV-060, S-SPV-061, and S-SPV-062.

HOMOLOGY VECTOR 779-94.31. The plasmid 779-94.31 was constructed for the purpose of inserting foreign DNA into SPV. It incorporates an *E. coli* β-galactosidase (lacZ) marker gene and the pseudorabies virus (PRV) gB (gII) gene flanked by SPV DNA. Upstream of the foreign genes is an approximately 538 base pair fragment of SPV DNA. Downstream of the foreign genes is an approximately 1180 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1) and the PRV gB gene is under the control of a synthetic late/early pox promoter (LP2EP2). A detailed description of the plasmid is given in FIGS. 30–30E. It was constructed utilizing standard recombinant DNA techniques (22, and 30), by joining restriction fragments from the following sources with the synthetic DNA sequences. The plasmid vector was derived from an approximately 2986 base pair HindIII to PstI restriction fragment of pSP64 (Promega). Fragment 1 is an approximately 542 base pair HindIII to BglII restriction sub-fragment of the SPV HindIII restriction fragment M (23). Fragment 2 is an approximately 3500 base pair fragment which contains the coding sequence for the PRV gB gene within the KpnI C fragment of genomic PRV DNA (21). Fragment 2 contains an approximately 53 base pair synthetic fragment containing the amino terminus of the PRV gB gene, an approximately 78 base pair SmaI to Nhe I fragment from the PRV KpnI C genomic fragment, and an approximately 3370 base pair NheI to EcoRI fragment from the PRV KpnI C genomic fragment (21). Fragment 3 is an approximately 3010 base pair BamHI to PvuII restriction fragment of plasmid pJF751 (11). Fragment 4 is an approximately 1180 base pair BglII to PstI subfragment of the SPV HindIII fragment M. The BglII sites in fragments 1 and 4 were converted to unique HindIII sites using HindIII linkers.

HOMOLOGY VECTOR 789-41.7. The plasmid 789-41.7 was constructed for the purpose of inserting foreign DNA into SPV. It incorporates an *E. coli* β-galactosidase (lacZ) marker gene, the pseudorabies virus (PRV) gB (gII) gene and the PRV gD (g50) gene flanked by SPV DNA. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the PRV gB gene is under the control of a synthetic late/early pox promoter (LP2EP2), and the PRV gD gene is under the control of a synthetic early/late pox promoter (EP1LP2). A detailed description of the plasmid is given in FIGS. 31–31D. It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1552 base pair subfragment of the PRV BamHI #7 fragment which contains the coding sequence of the PRV gD gene from amino acid 3 to amino acid 279. The EcoRI site and the ATG translation start codon are derived from a polymerase chain reaction using a 5' primer with an EcoRI site. The StuI site at the 3' end is normally within the PRV gI gene 3' to the PRV gD gene. The entire open reading frame beginning at the EcoRI site codes for 405 amino acids. Fragment 3 is an approximately 48 base pair AccI to NdeI subfragment of the SPV HindIII M fragment. Fragment 4 is an approximately 3500 base pair fragment which contains the coding sequence for the PRV gB gene within the KpnI C fragment of genomic PRV DNA(21). Fragment 4 contains an approximately 53 base pair synthetic fragment containing the amino terminus of the PRV gB gene, an approximately 78 base pair SmaI to NheI fragment from the PRV KpnI C genomic fragment, and an approximately 3370 base pair NheI to EcoRI fragment from the PRV KpnI C genomic fragment (21). Fragment 5 is an approximately 3010 base pair BamHI to PvuII restriction fragment of plasmid pJF751 (11). Fragment 6 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 6 were converted to unique HindIII sites using HindIII linkers. An approximately 545 base pair NdeI to NdeI subfragment (Nucleotides 1560 to 2104; SEQ ID NO.) of the SPV HindIII M fragment has been deleted which would span SPV fragments 3 and 6.

HOMOLOGY VECTOR 789-41.27. The plasmid 789-41.27 was constructed for the purpose of inserting foreign DNA into SPV. It incorporates an *E. coli* β-galactosidase (lacZ) marker gene, the pseudorabies virus (PRV) gB (gII) gene and the PRV gC (gIII) gene flanked by SPV DNA. Upstream of the foreign genes is an approximately 1560 base pair fragment of SPV DNA. Downstream of the foreign genes is an approximately 1484 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the PRV gB gene is under the control of a synthetic late/early pox promoter (LP2EP2), and the PRV gC gene is under the control of a synthetic early/late pox promoter (EP1LP2). A detailed description of the plasmid is given in FIGS. 32–32D. It was constructed utilizing standard recombinant DNA techniques (22, 30), by joining restriction fragments from the following sources with the synthetic DNA sequences indicated. The plasmid vector was derived from an approximately 2972 base pair HindIII to BamHI restriction fragment of pSP64 (Promega). Fragment 1 is an approximately 1560 base pair HindIII to NdeI subfragment of the SPV HindIII fragment M. Fragment 2 is an approximately 3500 base pair fragment which contains the coding sequence for the PRV gB gene within the KpnI C fragment of genomic PRV DNA(21). Fragment 2 contains an approximately 53 base pair synthetic fragment containing the amino terminus of the PRV gB gene, an approximately 78 base pair SmaI to Nhe I fragment from the PRV KpnI C genomic fragment, and an approximately 3370 base pair NheI to EcoRI fragment from the PRV KpnI C genomic fragment (21). Fragment 3 is an approximately 3010 base pair BamHI to PvuII restriction fragment of plasmid pJF751 (11). Fragment 4 is an approximately 48 base pair AccI to NdeI subfragment of the SPV HindIII M fragment. Fragment 5 is an approximately 2378 base pair NcoI to NcoI fragment of plasmid 251-41.A, a subfragment of PRV BamHI #2 and #9. EcoRI linkers have replaced the NcoI sites at the ends of the fragment. Fragment 6 is an approximately 1484 base pair AccI to BglII restriction sub-fragment of the SPV HindIII restriction fragment M (23). The NdeI sites in fragments 1 and 4 were converted to unique HindIII sites using HindIII linkers. The AccI site in fragments 4 and 6 were converted to unique PstI sites using PstI linkers. An approximately 545 base pair NdeI to NdeI (Nucleotides 1560 to 2104; SEQ ID NO. ) subfragment of the SPV HindIII M fragment has been deleted which would span SPV fragments 4 and 6.

HOMOLOGY VECTOR 789-41.47. The plasmid 789-41.47 was constructed for the purpose of inserting foreign DNA into SPV. It incorporates an *E. coli* β-galactosidase (lacZ) marker gene, the pseudorabies virus (PRV) gC (gIII) gene and the PRV gD (g50) gene flanked by SPV DNA. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the PRV gC gene is under the control of a synthetic early/late pox promoter (EP1LP2), and the PRV gD gene is under the control of a synthetic early/late pox promoter (EP1LP2). A detailed description of the plasmid is given in FIGS. 33–33D. It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1552 base pair subfragment of the PRV BamHI #7 fragment which contains the coding sequence of the PRV gD gene from amino acid 3 to amino acid 279. The EcoRI site and the ATG translation start codon are derived from a polymerase chain reaction using a 5' primer with an EcoRI site. The StuI site at the 3' end is normally within the PRV gI gene 3' to the PRV gD gene. The entire open reading frame beginning at the EcoRI site codes for 405 amino acids. Fragment 3 is an approximately 48 base pair AccI to NdeI subfragment of the SPV HindIII M fragment. Fragment 4 is an approximately 3010 base pair BamHI to PvuII restriction fragment of plasmid pJF751 (11). Fragment 5 is an approximately 2378 base pair NcoI to NcoI fragment of plasmid 251-41.A, a subfragment of PRV BamHI #2 and #9. EcoRI linkers have replaced the NcoI sites at the ends of the fragment. Fragment 6 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 6 were converted to unique HindIII sites using HindIII linkers. An approximately 545 base pair NdeI to NdeI subfragment (Nucleotides 1560 to 2104 of the SPV HindIII M fragment has been deleted which would span SPV fragments 3 and 6.

HOMOLOGY VECTOR 789-41.73. The plasmid 789-41.73 was constructed for the purpose of inserting foreign DNA into SPV. It incorporates an E. coli β-galactosidase (lacZ) marker gene, the pseudorabies virus (PRV) gB (gII) gene, the PRV gC (gIII) gene and the PRV gD (g50) gene flanked by SPV DNA. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the βgalactosidase (lacZ) marker gene is under the control of a synthetic late pox promoter (LP1), the PRV gB gene is under the control of a synthetic late/early pox promoter (LP2EP2), the PRV gC gene is under the control of a synthetic early/late promoter (EP1LP2), and the PRV gD gene is under the control of a synthetic late/early pox promoter (LP2EP2). A detailed description of the plasmid is given in FIGS. 34–34E. It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1552 base pair subfragment of the PRV BamHI #7 fragment which contains the coding sequence of the PRV gD gene from amino acid 3 to amino acid 279. The EcoRI site and the ATG translation start codon are derived from a polymerase chain reaction using a 5' primer with an EcoRI site. The StuI site at the 3' end is normally within the PRV gI gene 3' to the PRV gD gene. The entire open reading frame beginning at the EcoRI site codes for 405 amino acids. Fragment 3 is an approximately 2378 base pair NcoI to NcoI fragment of plasmid 251-41.A, a subfragment of PRV BamHI #2 and #9. EcoRI linkers have replaced the NcoI sites at the ends of the fragment. Fragment 4 is an approximately 48 base pair AccI to NdeI subfragment of the SPV HindIII M fragment. Fragment 5 is an approximately 3500 base pair fragment which contains the coding sequence for the PRV gB gene within the KpnI C fragment of genomic PRV DNA (21). Fragment 5 contains an approximately 53 base pair synthetic fragment containing the amino terminus of the PRV gB gene, an approximately 78 base pair SmaI to Nhe I fragment from the PRV KpnI C genomic fragment, and an approximately 3370 base pair NheI to EcoRI fragment from the PRV KpnI C genomic fragment (21). Fragment 6 is an approximately 3010 base pair BamHI to PvuII restriction fragment of plasmid pJF751 (11). Fragment 7 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 6 were converted to unique HindIII sites using HindIII linkers. An approximately 545 base pair NdeI to NdeI subfragment (Nucleotides 1560 to 2104 of the SPV HindIII M fragment has been deleted which would span SPV fragments 3 and 6.

HOMOLOGY VECTOR 791-63.19. The plasmid 791-63.19 was constructed for the purpose of inserting foreign DNA into SPV. It incorporates an *E. coli* β-galactosidase (lacZ) marker gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1). It was constructed utilizing standard recombinant DNA techniques (22, 30), by joining restriction fragments from the following sources with the synthetic DNA sequence. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 2149 base pair AccI to HindIII subfragment of the SPV HindIII fragment M. The AccI sites in fragments 1 and 3 were converted to unique NotI sites using NotI linkers.

HOMOLOGY VECTOR 791-63.41. The plasmid 791-63.41 was constructed for the purpose of inserting foreign DNA into SPV. It incorporates an *E. coli* β-galactosidase (lacZ) marker gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 2149 base pair AccI to HindIII subfragment of the SPV HindIII fragment M. The AccI sites in fragments 1 and 3 were converted to unique NotI sites using NotI linkers.

HOMOLOGY VECTOR 796-18.9. The plasmid 796-18.9 was constructed for the purpose of inserting foreign DNA into SPV. It incorporates an *E. coli* β-galactosidase (lacZ) marker gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic early pox promoter (EP1). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 2149 base pair AccI to HindIII subfragment of the SPV HindIII fragment M. The AccI sites in fragments 1 and 3 were converted to unique NotI sites using NotI linkers.

HOMOLOGY VECTOR 783-39.2. The plasmid 783-39.2 was constructed for the purpose of inserting foreign DNA into SPV. It incorporates an *E. coli* β-galactosidase (lacZ) marker gene and an bovine viral diarrhea virus glycoprotein 53 (BVDV gp53) gene flanked by SPV DNA. Upstream of the foreign gene is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a late promoter (LP1) and the BVDV gp53 gene is under the control of the late/early promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1187 base pair BamHI fragment coding for the BVDV gp53. The 1187 base pair BamHI fragment was synthesized by polymerase chain reaction (15) as described in CLONING OF BOVINE VIRAL DIARRHEA VIRUS gp48 AND gp53 GENES. Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 749-75.78. The plasmid 749-75.78 was constructed for the purpose of inserting foreign DNA into SPV. It incorporates an *E. coli* β-galactosidase (lacZ) marker gene and the infectious bursal disease virus (IBDV) polymerase gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1) and the IBDV polymerase gene is under the control of a synthetic late/early promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 2700 EcoRI to AscI restriction fragment synthesized by cDNA cloning and polymerase chain reaction (PCR) from an IBDV RNA template. cDNA and PCR primers (5'-CAC GAATTCTGACATTTTCAACAGTCCACAGGCGC-3'; 12/93.4) (SEQ ID NO: 260) and 5'-GCTGTTGGACATCACGGGCCAGG-3'; 9/93.28) (SEQ ID NO: 261) were used to synthesize an approximately 1400 base pair EcoRI to BclI fragment at the 5' end of the IBDV polymerase gene. cDNA and PCR primers (5'-ACCCGGAACATATGGTCAGCTCCAT-3'; 12/93.2) (SEQ ID NO: 262) and 5'-GGCGCGCCAGGCG AAGGCCGGGGATACGG-3'; 12/93.3) (SEQ ID NO: 263) were used to synthesize an approximately 1800 base pair BclI to AscI fragment at the 3' end of the IBDV polymerase gene. The two fragments were ligated at the BclI site to form the approximately 2700 base pair EcoRI to BclI fragment. Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 761-75.B18. The plasmid 761-75.B18 was constructed for the purpose of inserting foreign DNA into SPV. It incorporates an *E. coli* β-galactosidase (lac Z) marker gene and a feline immunodeficiency virus (FIV) protease (gag) gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a swinepox virus 01L gene promoter and the FIV gag gene is under the control of the late/early promoter (LP2EP2). The homology vector was constructed utilizing standard recombinant DNA techniques (22, 30), by joining restriction fragments from the following sources with the synthetic DNA sequences. The plasmid vector was derived from an approximately 2519 base pair HindIII to SphI restriction fragment of pSP65 (Promega). Fragment 1 is an approximately 855 base pair sub-fragment of the SPV HindIII restriction fragment M (23) synthesized by polymerase chain reaction using DNA primers 5' GAAGCATGCCCGTTCTTATCAATAGTTTA GTCGAAAAT-3' (SEQ ID NO: 185) and 5'-CATAAG ATCTGGCATTGTGTTATTATACTAACAAAAATAAG-3' (SEQ ID NO: 186) to produce an 855 base pair fragment with SphI and BglII ends. Fragment 2 is a 3002 base pair BamHI to PvuII fragment derived from plasmid pJF751 (49) containing the *E. coli* lacZ gene. Fragment 3 is an approximately 1878 base pair EcoRI to BglII restriction fragment synthesized by polymerase chain reaction (PCR) using cDNA from the FIV (PPR strain) (61). The primer (5' GCGT GAATTCGGGGAATGGACAGGGGCGAGAT-3'; 11/94.9) (SEQ ID NO: 264) synthesizes from the 5' end of the FIV gag gene, introduces an EcoRI site at the 5' end of the gene and an ATG start codon. The primer (5'-GAGCC AGATCTGCTCTTTTTACTTTCCC-3'; 11/94.10) (SEQ ID NO: 265) synthesizes from the 3' end of the FIV gag gene. The PCR product was digested with EcoRI and BglII to yield a fragment 1878 base pairs in length corresponding to the FIV gag gene. Fragment 4 is an approximately 1113 base pair subfragment of the SPV HindIII fragment M synthesized by polymerase chain reaction using DNA primers 5'-CCGTAGTCGACAAAGATCGACTTATTAATATGTA TGGGATT-3' (SEQ ID NO: 187) and 5' GCCTGAA GCTTCTAGTACAGTATTTACGACTTTTGAAAT-3' (SEQ ID NO: 188) to produce an 1113 base pair fragment with SalI and HindIII ends.

HOMOLOGY VECTOR 781-84.C11. The plasmid 781-84.C11 was used to insert foreign DNA into SPV. It incorporates an E. coli β-galactosidase (lacZ) marker gene and the feline immunodeficiency virus (FIV) envelope (env) gene flanked by SPV DNA. When this plasmid was used according to the HOMOLOGOUS RECOMBINATION PROCEDURE FOR GENERATING RECOMBINANT SPV a virus containing DNA coding for the foreign genes results. Note that the β galactosidase (lacZ) marker gene is under the control of a synthetic late pox promoter (LP1) and the FIV env gene is under the control of a synthetic late/early pox promoter (LP2EP2). The homology vector was constructed utilizing standard recombinant DNA techniques (22 and 30), by joining restriction fragments from the following sources with the appropriate synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII fragment M (23). Fragment 3 is an approximately 2564 base pair BamHI to BamHI fragment of the FIV env gene (61) synthesized by CLONING WITH THE POLYMERASE CHAIN REACTION. The template for the PCR reaction was FIV strain PPR genomic cDNA (61). The upstream primer 10/93.21 (51'-GCCCGGATCCTATGGCAGAA GGGTTTGCAGC-3'; SEQ ID NO. 266) was synthesized corresponding to the 5' end of the FIV env gene starting at nucleotide 6263 of FIV strain PPR genomic cDNA, and the procedure introduced a BamHI site at the 5' end. The BamHI site was destroyed during the cloning of the PCR fragment. The downstream primer 10/93.20 (5'-CCGTGG ATCCGGCACTCCATCATTCCTCCTC-3'; SEQ ID NO. 267) was synthesized corresponding to the 3' end of the FIV env gene starting at nucleotide 8827 of FIV PPR genomic cDNA, and the procedure introduced a BamHI site at the 3' end. Fragment 3 is an approximately 3010 base pair BamHI to PvuII restriction fragment of plasmid pJF751 (11). Fragment 4 is an approximately 2149 base pair AccI to HindIII restriction sub-fragment of the SPV HindIII restriction fragment M (23). The AccI site in the SPV homology vector was converted to a unique NotI site.

EXAMPLES

Example 1

Homology Vector 515-85.1. The homology vector 515-85.1 is a plasmid useful for the insertion of foreign DNA into SPV. Plasmid 515-85.1 contains a unique AccI restriction site into which foreign DNA may be cloned. A plasmid containing such a foreign DNA insert may be used according to the HOMOLOGOUS RECOMBINATION PROCEDURE FOR GENERATING RECOMBINANT SPV to generate a SPV containing the foreign DNA. For this procedure to be successful it is important that the insertion site (AccI) be in a region non-essential to the replication of the SPV and that the site be flanked with swinepox virus DNA appropriate for mediating homologous recombination between virus and plasmid DNAs. AccI site in homology vector 515-85.1 is used to insert foreign DNA into at least three recombinant SPV (see examples 2–4).

In order to define an appropriate insertion site, a library of SPV HindIII restriction fragments was generated. Several of these restriction fragments (HindIII fragments G, J, and M see FIG. 1A–1B) were subjected to restriction mapping analysis. Two restriction sites were identified in each fragment as potential insertion sites. These sites included HpaI and NruI in fragment G, BalI and XbaI in fragment J, and AccI and PstI in fragment M. A β-galactosidase (lacZ) marker gene was inserted in each of the potential sites. The resulting plasmids were utilized in the HOMOLOGOUS RECOMBINATION PROCEDURE FOR GENERATING RECOMBINANT SPV. The generation of recombinant virus was determined by the SCREEN FOR RECOMBINANT SPV EXPRESSING β-GALACTOSIDASE ASSAYS. Four of the six sites were found to generate recombinant virus, however the ability of each of these viruses to be purified away from the parental SPV varied greatly. In one case virus could not be purified above the level of 1%, in another case virus could not be purified above the level of 50%, and in a third case virus could not be purified above the level of 90%. The inability to purify these viruses indicates instability at the insertion site. This makes the corresponding sites inappropriate for insertion of foreign DNA. However the insertion at one site, the AccI site of Homology vector 515-85.1, resulted in a virus which was easily purified to 100% (see example 2), clearly defining an appropriate site for the insertion of foreign DNA.

The homology vector 515-85.1 was further characterized by DNA sequence analysis. Two regions of the homology vector were sequenced. The first region covers a 599 base pair sequence which flanks the unique AccI site (see FIGS. 2A and 2B). The second region covers the 899 base pairs upstream of the unique HindIII site (see FIGS. 2A and 2B). The sequence of the first region codes for an open reading frame (ORF) which shows homology to amino acids 1 to 115 of the vaccinia virus (VV) O1L open reading frame identified by Goebel et al, 1990 (see FIGS. 3A–3C). The sequence of the second region codes for an open reading frame which shows homology to amino acids 568 to 666 of the same vaccinia virus O1L open reading frame (see FIGS. 3A–3C). These data suggest that the AccI site interrupts the presumptive VV O1L-like ORF at approximately amino acid 41, suggesting that this ORF codes for a gene non-essential for SPV replication. Goebel et al. suggest that the VV O1L ORF contains a leucine zipper motif characteristic of certain eukaryotic transcriptional regulatory proteins, however they indicate that it is not known whether this gene is essential for virus replication.

The DNA sequence located upstream of the VV 01L-like ORF (see FIG. 2A) would be expected to contain a swinepox viral promoter. This swinepox viral promoter will be useful as the control element of foreign DNA introduced into the swinepox genome.

Example 2

S-SPV-003

S-SPV-003 is a swinepox virus that expresses a foreign gene. The gene for E.coli β-galactosidase (lacZ gene) was inserted into the SPV 515-85.1 ORF. The foreign gene (lacZ) is under the control of a synthetic early/late promoter (EP1LP2).

S-SPV-003 was derived from S-SPV-001 (Kasza strain). This was accomplished utilizing the homology vector 520-17.5 (see *Materials and Methods*) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-GALACTOSIDASE (BLUOGAL AND CPRG ASSAYS). The final result of red plaque purification was the recombinant virus designated S-SPV-003. This virus was assayed for β-galactosidase expression, purity, and insert stability by multiple passages monitored by the blue plaque assay as described in *Materials and Methods*. After the initial three rounds of purification, all plaques observed were blue indicating that the virus was pure, stable and expressing the foreign gene. The assays described here were carried out in VERO cells as well as EMSK cells, indicating that VERO cells would be a suitable substrate for the production of SPV recombinant vaccines. S-SPV-003 has been deposited with the ATCC under Accession No. VR 2335.

Example 3

S-SPV-008

S-SPV-008 is a swinepox virus that expresses at least two foreign genes. The gene for E. coli β-galactosidase (lacZ gene) and the gene for pseudorabies virus (PRV) g50 (gD) (26) were inserted into the SPV 515-85.1 ORF. The lacZ gene is under the control of a synthetic late promoter (LP1) and the g50 (gD) gene is under the control of a synthetic early/late promoter (EP1LP2).

S-SPV-008 was derived from S-SPV-001 (Kasza strain). This was accomplished utilizing the homology vector 538-46.16 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-GALACTOSIDASE (BLUOGAL AND CPRG ASSAYS). The final result of red plaque purification was the recombinant virus designated S-SPV-008. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable and expressing the marker gene.

S-SPV-008 was assayed for expression of PRV specific antigens using the BLACK PLAQUE SCREEN FOR FOREIGN GENE EXPRESSION IN RECOMBINANT SPV. Swine anti-PRV serum was shown to react specifically with S-SPV-008 plaques and not with S-SPV-009 negative control plaques. All S-SPV-008 observed plaques reacted with the swine antiserum indicating that the virus was stably expressing the PRV foreign gene. The black plaque assay was also performed on unfixed monolayers. The SPV plaques on the unfixed monolayers also exhibited specific reactivity with swine anti-PRV serum indicating that the PRV antigen is expressed on the infected cell surface.

Figure 6:
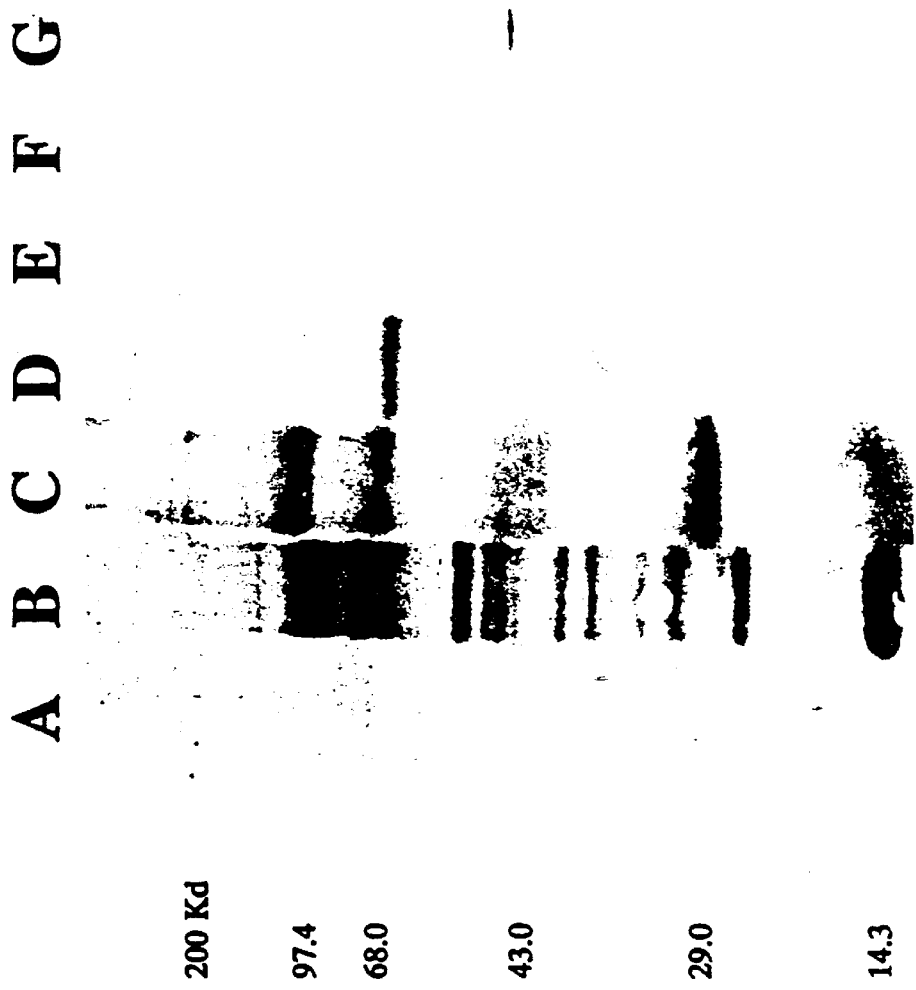

To confirm the expression of the PRV g50 (gD) gene product, cells were infected with SPV and samples of infected cell lysates were subjected to SDS-polyacrylamide gel electrophoresis. The gel was blotted and analyzed using the WESTERN BLOTTING PROCEDURE. The swine anti-PRV serum was used to detect expression of PRV specific proteins. As shown in FIG. 6, the lysate from S-SPV-008 infected cells exhibits a specific band of approximately 48 kd, the reported size of PRV g50 (gD) (35).

PRV g50 (gD) is the g50 (gD) homologue of HSV-1 (26). Several investigators have shown that VV expressing HSV-1 g50 (gD) will protect mice against challenge with HSV-1 (6 and 34). Therefore the S-SPV-008 should be valuable as a vaccine to protect swine against PRV disease.

It is anticipated that several other PRV glycoproteins will be useful in the creation of recombinant swinepox vaccines to protect against PRV disease. These PRV glycoproteins include gII (28), gIII (27), and gH (19). The PRV gIII coding region has been engineered behind several synthetic pox promoters. The techniques utilized for the creation of S-SPV-008 will be used to create recombinant swinepox viruses expressing all four of these PRV glycoprotein genes. Such recombinant swinepox viruses will be useful as vaccines against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals. S-SPV-008 has been deposited with the ATCC under Accession No. VR 2339.

Example 4

S-SPV-011

S-SPV-011 is a swinepox virus that expresses at least two foreign genes. The gene for E. coli β-galactosidase (lacZ) and the gene for pseudorabies virus gIII (gC) were inserted into the unique PstI restriction site (PstI linkers inserted into a unique AccI site) of the homology vector 570-33.32. The lac Z gene is under the control of the synthetic late promoter (LP1) and the PRV gIII (gC) gene is under the control of the synthetic early promoter (EP2).

S-SPV-011 was derived from S-SPV-001 (Kasza Strain). This was accomplished utilizing the homology vector 570-91.21 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-011. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-011 was assayed for expression of PRV specific antigens using the BLACK PLAQUE SCREEN FOR FOREIGN GENE EXPRESSION IN RECOMBINANT SPV. Polyclonal goat anti-PRV gIII (gC) antibody was shown to react specifically with S-SPV-011 plaques and not with S-SPV-001 negative control plaques. All S-SPV-011 observed plaques reacted with the swine anti-PRV serum indicating that the virus was stably expressing the PRV foreign gene. The assays described here were carried out in EMSK cells, indicating that EMSK cells would be a suitable substrate for the production of SPV recombinant vaccines.

To confirm the expression of the PRV gIII (gC) gene product, cells were infected with SPV and samples of infected cell lysates were subjected to SDS-polyacrylamide gel electrophoresis. The gel was blotted and analyzed using the WESTERN BLOTTING PROCEDURE. Polyclonal goat anti-PRV gIII (gC) antibody was used to detect expression of PRV specific proteins. As shown in FIG. 16, the lysate from S-SPV-011 infected cells exhibits a specific band of approximately 92 kd, the reported size of PRV gIII (gC) (37).

Recombinant-expressed PRV gIII (gC) has been shown to elicit a significant immune response in mice and swine (37, 38). Furthermore, when gIII (gC) is coexpressed with gII (gB) or g50 (gD), significant protection from challenge with virulent PRV is obtained (39). Therefore S-SPV-011 should be valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals.

Example 5

S-SPV-012

S-SPV-012 is a swinepox virus that expresses at least two foreign genes. The gene for E. coli β-galactosidase (lacZ)

and the gene for pseudorabies virus gIII (gC) were inserted into the unique PstI restriction site (PstI linkers inserted into a unique AccI site) of the homology vector 570-33.32. The lacZ gene is under the control of the synthetic late promoter (LP1) and the PRV gIII (gC) gene is under the control of the synthetic early late promoter (EP1LP2).

S-SPV-012 was derived from S-SPV-001 (Kasza Strain). This was accomplished utilizing the homology vector 570-91.41 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-012. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-012 was assayed for expression of PRV specific antigens using the BLACK PLAQUE SCREEN FOR FOREIGN GENE EXPRESSION IN RECOMBINANT SPV. Polyclonal goat anti-PRV gIII (gC) antibody was shown to react specifically with S-SPV-012 plaques and not with S-SPV-001 negative control plaques. All S-SPV-012 observed plaques reacted with the swine anti-PRV serum, indicating that the virus was stably expressing the PRV foreign gene. The assays described here were carried out in EMSK and VERO cells, indicating that EMSK cells would be a suitable substrate for the production of SPV recombinant vaccines.

To confirm the expression of the PRV gIII (gC) gene product, cells were infected with S-SPV-012 and samples of infected cell lysates were subjected to SDS-polyacrylamide gel electrophoresis. The gel was blotted and analyzed using the WESTERN BLOTTING PROCEDURE. Polyclonal goat anti-PRV gIII (gC) antibody was used to detect expression of PRV specific proteins. As shown in FIG. 16, the lysate from S-SPV-012 infected cells exhibits two specific bands which are the reported size of PRV gIII (gC) (37)—a 92 kd mature form and a 74 kd pre-golgi form.

Recombinant-expressed PRV gIII (gC) has been shown to elicit a significant immune response in mice and swine (37, 38). Furthermore, when gIII (gC) is coexpressed with gII (gB) or g50 (gD), significant protection from challenge with virulent PRV is obtained. (39) Therefore S-SPV-012 should be valuable as a vaccine to protect swine against PRV disease. Since the PRV vaccines described here do not express PRV gX or gI, they would be compatible with current PRV diagnostic tests (gx HerdChek®, gI HerdChek® and ClinEase®) which are utilized to distinguish vaccinated animals from infected animals.

Example 6

S-SPV-013

S-SPV-013 is a swinepox virus that expresses at least two foreign genes. The gene for E. coli β-galactosidase (lacZ) and the gene for pseudorabies virus gIII (gC) were inserted into the unique PstI restriction site (PstI linkers inserted into a unique AccI site) of the homology vector 570-33.32. The lacZ gene is under the control of the synthetic late promoter (LP1) and the PRV gIII (gC) gene is under the control of the synthetic late early promoter (LP2EP2).

S-SPV-013 was derived from S-SPV-001 (Kasza Strain). This was accomplished utilizing the homology vector 570-91.64 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-013. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-013 was assayed for expression of PRV specific antigens using the BLACK PLAQUE SCREEN FOR FOREIGN GENE EXPRESSION IN RECOMBINANT SPV. Polyclonal goat anti-PRV gIII (gC) antibody was shown to react specifically with S-SPV-013 plaques and not with S-SPV-001 negative control plaques. All S-SPV-013 observed plaques reacted with the swine anti-PRV serum indicating that the virus was stably expressing the PRV foreign gene. The assays described here were carried out in EMSK and VERO cells, indicating that EMSK cells would be a suitable substrate for the production of SPV recombinant vaccines.

To confirm the expression of the PRV gIII (gC) gene product, cells were infected with SPV and samples of infected cell lysates were subjected to SDS-polyacrylamide gel electrophoresis. The gel was blotted and analyzed using the WESTERN BLOTTING PROCEDURE. Polyclonal goat anti-PRV gIII (gC) antibody was used to detect expression of PRV specific proteins. As shown in FIG. 16, the lysate from S-SPV-013 infected cells exhibits two specific bands which are the reported size of PRV gIII (gC) (37)-a 92 kd mature form and a 74 kd pre-Golgi form.

Recombinant-expressed PRV gIII (gC) has been shown to elicit a significant immune response in mice and swine (37, 38). Furthermore, when gIII (gC) is coexpressed with gII (gB) or g50 (gD), significant protection from challenge with virulent PRV is obtained. (39) Therefore S-SPV-013 is valuable as a vaccine to protect swine against PRV disease. Since the PRV vaccines described here do not express PRV gX or gI, they would be compatible with current PRV diagnostic tests (gx HerdChek®, gI HerdChek® and ClinEask®) which are utilized to distinguish vaccinated animals from infected animals. S-SPV-013 has been deposited with the ATCC under Accession No. 2418.

Protection against Aujeszky's disease using recombinant swinepox virus vaccines S-SPV-008 and S-SPV-013.

A vaccine containing S-SPV-008 and S-SPV-013 ($1 \times 10^6$ PFU/ml) (2 ml of a 1:1 mixture of the two viruses) was given to two groups of pigs (5 pigs per group) by intradermal inoculation or by oral/pharyngeal spray. A control group of 5 pigs received S-SPV-001 by both intradermal and oral/pharyngeal inoculation. Pigs were challenged three weeks post-vaccination with virulent PRV, strain 4892, by intranasal inoculation. The table presents a summary of clinical responses. The data support an increase in protection against Aujeszky's disease in the S-SPV-008/S-SPV-013 vaccinates compared to the S-SPV-001 vaccinate controls.

| Vaccine | Route of inoculation | Post-challenge Respiratory Signs: (# with signs/ total number) | Post-challenge CNS signs: (# with signs/ total number) | Post-challenge Group average: (Days of clinical signs) |
|---|---|---|---|---|
| S-SPV-008 + S-SPV-013 | Intradermal | 3/5 | 0/5 | 2.6 |
| S-SPV-008 + S-SPV-013 | Oral/ pharyngeal | 3/5 | 0/5 | 2.2 |
| S-SPV-001 (Control) | Intradermal + Oral/ Pharyngeal | 5/5 | 2/5 | 7.8 |

Example 7

S-SPV-015

S-SPV-015 is a swinepox virus that expresses at least two foreign genes. The gene for E. coli β-galactosidase (lacZ) and the gene for pseudorabies virus (PRV) gII (gB) were inserted into the SPV 617-48.1 ORF (a unique NotI restriction site has replaced a unique ACCI restriction site). The lacZ gene is under the control of the synthetic late promoter (LP1), and the PRV gB gene is under the control of the synthetic late/early promoter (LP2EP2).

S-SPV-015 was derived from S-SPV-001 (Kasza Strain). This was accomplished utilizing the homology vector 727-54.60 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-015. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-015 was assayed for expression of PRV-specific antigens using the BLACK PLAQUE SCREEN FOR FOREIGN GENE EXPRESSION IN RECOMBINANT SPV. Polyclonal swine anti-PRV serum was shown to react specifically with S-SPV-015 plaques and not with S-SPV-001 negative control plaques. All S-SPV-015 observed plaques reacted with the antiserum indicating that the virus was stably expressing the PRV foreign gene. The assays described here were carried out in ESK-4 cells, indicating that ESK-4 cells would be a suitable substrate for the production of SPV recombinant vaccines.

To confirm the expression of the PRV gII gene product, cells were infected with SPV-015 and samples of infected cell lysates were subjected to SDS-polyacrylamide gel electrophoresis. The gel was blotted and analyzed using the WESTERN BLOTTING PROCEDURE. Polyclonal swine anti-PRV serum was used to detect expression of PRV specific proteins. The lysate from S-SPV-015 infected cells exhibited bands corresponding to 120 kd, 67 kd and 58 kd, which are the expected size of the PRV gII glycoprotein.

S-SPV-015 is useful as a vaccine in swine against pseudorabies virus. A superior vaccine is formulated by combining S-SPV-008 (PRV g50), S-SPV-013 (PRV gIII), and S-SPV-015 for protection against pseudorabies in swine.

Therefore S-SPV-015 should be valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals. S-SPV-015 has been deposited with the ATCC under Accession No. 2466.

Example 8

Recombinant swinepox virus expressing more than one pseudorabies virus (PRV) glycoproteins, which can elicit production of neutralizing antibodies against pseudorabies virus, is constructed in order to obtain a recombinant swinepox virus with enhanced ability to protect against PRV infection than that which can be obtained by using a recombinant swinepox virus expressing only one of those PRV glycoproteins.

There are several examples of such recombinant swinepox virus expressing more than one PRV glycoproteins: a recombinant swinepox virus expressing PRV g50 (gD) and gIII (gC), a recombinant swinepox virus expressing PRV g50 (gD) and gII (gB); a recombinant swinepox virus expressing PRV gII (gB) and gIII (gC); and a recombinant swinepox virus expressing PRV g50 (gD), gIII (gC) and gII (gB). Each of the viruses cited above is also engineered to contain and express E. coli β-galactosidase (lac Z) gene, which will facilitate the cloning of the recombinant swinepox virus.

Listed below are three examples of a recombinant swinepox virus expressing PRV g50 (gD), PRV gIII (gC), PRV gII (gB) and E. coli β-galactosidase (lacZ):

a) Recombinant swinepox virus containing and expressing PRV g50 (gD) gene, PRV gIII (gC) gene, PRV gII (gB) gene and lacZ gene. All four genes are inserted into the unique AccI restriction endonuclease site within the HindIII M fragment of the swinepox virus genome. PRV g50 (gD) gene is under the control of a synthetic early/late promoter (EP1LP2), PRV gIII (gC) gene is under the control of a synthetic early promoter (EP2), PRV gII (gB) gene is under the control of a synthetic late/early promoter (LP2EP2) and lacZ gene is under the control of a synthetic late promoter (LP1).

b) Recombinant swinepox virus containing and expressing PRV g50 (gD) gene, PRV gIII (gC) gene, PRV gII (gB) gene and lacZ gene. All four genes are inserted into the unique AccI restriction endonuclease site within the HindIII M fragment of the swinepox virus genome. PRV g50 (gD) gene is under the control of a synthetic early/late promoter (EP1LP2), PRV gIII (gC) gene is under the control of a synthetic early/late promoter (EP1LP2), PRV gII (gB) gene is under the control of a synthetic late/early promoter (LP2EP2) and lacZ gene is under the control of a synthetic late promoter (LP1).

c) Recombinant swinepox virus containing and expressing PRV gSO (gD) gene, PRV gIII (gC) gene, PRV gII (gB) gene and lacZ gene. All four genes are inserted into the unique AccI restriction endonuclease site within the HindIII M fragment of the swinepox virus genome. PRV g50 (gD) gene is under the control of a synthetic early/late promoter (EP1LP2), PRV gIII (gC) gene is under the control of a synthetic late/early promoter (LP2EP2), PRV gII (gB) gene is under the control of a synthetic late/early promoter (LP2EP2) and lacZ gene is under the control of a synthetic late promoter (LP1).

Protection against Aujeszky's disease using recombinant swinepox virus vaccines S-SPV-008, S-SPV-013 and S-SPV-015.

A vaccine containing S-SPV-008, S-SPV-013, or S-SPV-015 (2 ml of 1×10$^7$ PFU/ml of the virus) or a mixture of S-SPV-008, S-SPV-013, and S-SPV-015 (2ml of a 1:1:1 mixture of the three viruses; 1×10$^7$ PFU/ml) was given to four groups of pigs (5 pigs per group) by intramuscular inoculation. A control group of 5 pigs received S-SPV-001 by intramuscular inoculation. Pigs were challenged four weeks post-vaccination with virulent PRV, strain 4892, by intranasal inoculation. The pigs were observed daily for 14 days for clinical signs of pseudorabies, and the table presents a summary of clinical responses.The data show that pigs vaccinated with S-SPV-008, S-SPV-013, or S-SPV-015 had partial protection and pigs vacinated with the combination vaccine S-SPV-008/S-SPV-013/S-SPV-015 had complete protection against Aujeszky's disease caused by pseudorabies virus compared to the S-SPV-001 vaccinate controls.

| Vaccine | Route of inoculation | Post-challenge Respiratory Signs: (# with signs/ total number) | Post-challenge CNS signs: (# with signs/ total number) | Post-challenge Group average: (Days of clinical signs) |
|---|---|---|---|---|
| S-SPV-008 | Intramuscular | 2/5 | 2/5 | 2.0 |
| S-SPV-013 | Intramuscular | 1/5 | 0/5 | 0.4 |
| S-SPV-015 | Intramuscular | 3/5 | 0/5 | 1.0 |
| S-SPV-008 + S-SPV-013 + S-SPV-015 | Intramuscular | 0/5 | 0/5 | 0.0 |
| S-SPV-001 (Control) | Intramuscular | 5/5 | 2/5 | 3.6 |

Example 9

S-SPV-009

S-SPV-009 is a swinepox virus that expresses at least two foreign genes. The gene for *E. coli* β-galactosidase (lacZ gene) and the gene for Newcastle's Disease virus hemagglutinin (HN) gene were inserted into the SPV 515-85.1 ORF. The lacZ gene is under the control of a synthetic late promoter (LP1) and the HN gene is under the control of an synthetic early/late promoter (EP1LP2).

S-SPV-009 was derived from S-SPV-001 (Kasza strain). This was accomplished utilizing the homology vector 538-46.26 (see *Materials and Methods*) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-GALACTOSIDASE (BLUOGAL AND CPRG ASSAYS). The final result of red plaque purification was the recombinant virus designated S-SPV-009. This virus was assayed for β-galactosidase expression, purity, and insert stability by multiple passages monitored by the blue plaque assay as described in *Materials and Methods*. After the initial three rounds of purification, all plaques observed were blue indicating that the virus was pure, stable and expressing the marker gene.

S-SPV-009 was assayed for expression of PRV specific antigens using the BLACK PLAQUE SCREEN FOR FOREIGN GENE EXPRESSION IN RECOMBINANT SPV. Rabbit anti-NDV HN serum was shown to react specifically with S-SPV-009 plaques and not with S-SPV-008 negative control plaques. All S-SPV-009 observed plaques reacted with the swine antiserum indicating that the virus was stably expressing the NDV foreign gene. S-SPV-009 has been deposited with the ATCC under Accession No. VR 2344).

To confirm the expression of the NDV HN gene product, cells were infected with SPV and samples of infected cell lysates were subjected to SDS-polyacrylamide gel electrophoresis. The gel was blotted and analyzed using the WESTERN BLOTTING PROCEDURE. The rabbit anti-NDV HN serum was used to detect expression of the HN protein. The lysate from S-SPV-009 infected cells exhibited a specific band of approximately 74 kd, the reported size of NDV HN (29).

Example 10

S-SPV-014

S-SPV-014 is a swinepox virus that expresses at least two foreign genes. The gene for *E. coli* β-galactosidase (lacZ) and the gene for infectious laryngotracheitis virus glycoprotein G (ILT gG) were inserted into the SPV 570-33.32 ORF (a unique PstI site has replaced the unique AccI site). The lacZ gene is under the control of the synthetic late promoter (LP1), and the ILT gG gene is under the control of the synthetic early/late promoter (EP1LP2).

S-SPV-014 was derived from S-SPV-001 (Kasza Strain). This was accomplished utilizing the homology vector 599-65.25 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-014. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene. The assays described here were carried out in ESK-4 cells, indicating that ESK-4 cells would be a suitable substrate for the production of SPV recombinant vaccines.

To confirm the expression of the ILT gG gene product, cells were infected with SPV-014 and samples of infected cell lysates were subjected to SDS-polyacrylamide gel electrophoresis. The gel was blotted and analyzed using the WESTERN BLOTTING PROCEDURE. Peptide antisera to ILT gG was used to detect expression of ILT specific proteins. The lysate from S-SPV-014 infected cells exhibited a band at 43 kd which is the expected size of the ILT gG protein and additional bands of higher molecular weight which represent glycosylated forms of the protein which are absent in deletion mutants for ILT gG.

This virus is used as an expression vector for expressing ILT glycoprotein G (gG). Such ILT gG is used as an antigen to identify antibodies directed against the wild-type ILT virus as opposed to antibodies directed against gG deleted ILT viruses. This virus is also used as an antigen for the production of ILT gG specific monoclonal antibodies. Such antibodies are useful in the development of diagnostic tests specific for the ILT gG protein. Monoclonal antibodies are generated in mice utilizing this virus according to the PROCEDURE FOR PURIFICATION OF VIRAL GLYCOPROTEINS FOR USE AS DIAGNOSTICS (*Materials & Methods*).

Example 11

S-SPV-016

S-SPV-016 is a swinepox virus that expresses at least two foreign genes. The gene for *E. coli* β-galactosidase (lacZ) and the gene for infectious laryngotracheitis virus glycoprotein I (ILT gI) were inserted into the SPV 617-48.1 ORF (a unique NotI restriction site has replaced a unique AccI restriction site). The lacZ gene is under the control of the synthetic late promoter (LP1), and the ILT gI gene is under the control of the synthetic late/early promoter (LP2EP2).

S-SPV-016 was derived from S-SPV-001 (Kasza Strain). This was accomplished utilizing the homology vector 624-20.1C (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-016. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene. S-SPV-016 was assayed for expression of ILT gI- and β-galactosidase-specific antigens using the BLACK PLAQUE SCREEN FOR FOREIGN GENE EXPRESSION IN RECOMBINANT SPV. Polyclonal chicken anti-ILT antibody was shown to react specifically with S-SPV-016 plaques and not with S-SPV-017 negative control plaques. All S-SPV-016 observed plaques reacted with the chicken antiserum indicating that the virus was stably expressing the ILT foreign gene. The assays described here were carried out in ESK-4 cells, indicating that ESK-4 cells would be a suitable substrate for the production of SPV recombinant vaccines.

To confirm the expression of the ILT gI gene product, cells were infected with SPV-016 and samples of infected cell lysates were subjected to SDS-polyacrylamide gel electrophoresis. The gel was blotted and analyzed using the WESTERN BLOTTING PROCEDURE. Polyclonal chicken anti-ILT antibody was used to detect expression of ILT specific proteins. The lysate from S-SPV-016 infected cells exhibits a range of bands reactive to the anti-ILT antibody from 40 to 200 kd indicating that the ILT gI may be heavily modified.

This virus is used as an expression vector for expressing ILT glycoprotein I (gI). Such ILT gI is used as an antigen to identify antibodies directed against the wild-type ILT virus as opposed to antibodies directed against gI deleted ILT viruses. This virus is also used as an antigen for the production of ILT gI specific monoclonal antibodies. Such antibodies are useful in the development of diagnostic tests specific for the ILT gI protein. Monoclonal antibodies are generated in mice utilizing this virus according to the PROCEDURE FOR PURIFICATION OF VIRAL GLYCOPROTEINS FOR USE AS DIAGNOSTICS (*Materials & Methods*).

Example 12

S-SPV-017

S-SPV-017 is a swinepox virus that expresses at least two foreign genes. The gene for *E. coli* β-galactosidase (lacZ) and the gene for infectious bovine rhinotracheitis virus glycoprotein G (IBR gG) were inserted into the SPV 617-48.1 ORF (a unique NotI restriction site has replaced a unique AccI restriction site). The lacz gene is under the control of the synthetic late promoter (LP1), and the IBR gG gene is under the control of the synthetic late/early promoter (LP2EP2).

S-SPV-017 was derived from S-SPV-001 (Kasza Strain). This was accomplished utilizing the homology vector 614-83.18 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-017. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-017 was assayed for expression of IBR-specific antigens using the BLACK PLAQUE SCREEN FOR FOREIGN GENE EXPRESSION IN RECOMBINANT SPV. Monoclonal antibodies and peptide antisera to IBR gG were shown to react specifically with S-SPV-017 plaques and not with S-SPV-016 negative control plaques. All S-SPV-017 observed plaques reacted with the antiserum indicating that the virus was stably expressing the IBR foreign gene. The assays described here were carried out in ESK-4 cells, indicating that ESK-4 cells would be a suitable substrate for the production of SPV recombinant vaccines.

To confirm the expression of the IBR gG gene product, cells were infected with SPV-017 and samples of infected cell lysates were subjected to SDS-polyacrylamide gel electrophoresis. The gel was blotted and analyzed using the WESTERN BLOTTING PROCEDURE. Antisera to IBR gG was used to detect expression of IBR specific proteins. The lysate from S-SPV-017 infected cells exhibited a band at 43 kd which is the expected size of the IBR gG protein and additional bands of higher molecular weight which represent glycosylated forms of the protein which are absent in deletion mutants for IBR gG.

This virus is used as an expression vector for expressing IBR glycoprotein G (gG). Such IBR gG is used as an antigen to identify antibodies directed against the wild-type IBR virus as opposed to antibodies directed against gG deleted IBR viruses. This virus is also used as an antigen for the production of IBR gG specific monoclonal antibodies. Such antibodies are useful in the development of diagnostic tests specific for the IBR gG protein. Monoclonal antibodies are generated in mice utilizing this virus according to the PROCEDURE FOR PURIFICATION OF VIRAL GLYCOPROTEINS FOR USE AS DIAGNOSTICS (*Materials & Methods*).

Example 13

S-SPV-019

S-SPV-019 is a swinepox virus that expresses at least two foreign genes. The gene for *E. coli* β-galactosidase (lacZ) and the gene for infectious bovine rhinotracheitis virus (IBRV) gE were inserted into the SPV 617-48.1 ORF (a unique NotI restriction site has replaced a unique AccI restriction site). The lacZ gene is under the control of the synthetic late promoter (LP1), and the IBRV gE gene is under the control of the synthetic late/early promoter (LP2EP2).

S-SPV-019 was derived from S-SPV-001 (Kasza Strain). This was accomplished utilizing the homology vector 708-78.9 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-019. This virus was assayed for β-galactosidase expression, purity and insert stability by multiple passages monitored by the blue plaque assay as described in Materials and Methods.

Example 14
S-SPV-018

S-SPV-018 is a swinepox virus that expresses at least two foreign genes. The gene for E. coli β-galactosidase (lacZ) and the gene for pseudorabies virus glycoprotein E (PRV gE) are inserted into the SPV 570-33.32 ORF (a unique PstI site has replaced the unique AccI site). The lacZ gene is under the control of the synthetic late promoter (LP1), and the PRV gE gene is under the control of the synthetic early/late promoter (EP1LP2).

S-SPV-018 is derived from the S-SPV-001 (Kasza Strain). This is accomplished utilizing the final homology vector and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING β-galactosidase (BLUOGAL AND CPRG ASSAYS). Red plaque purification of the recombinant virus is designated S-SPV-018. This virus is assayed for β-galactosidase expression, purity, and insert stability by multiple passages monitored by the blue plaque assay described in Materials and Methods. After the initial three rounds of purification, all plaques observed are blue indicating that the virus is pure, stable, and expressing the foreign gene.

This virus is used as an expression vector for expressing PRV glycoprotein E (gE). Such PRV gE is used as an antigen to identify antibodies directed against the wild-type PRV virus as opposed to antibodies directed against gE deleted PRV viruses. This virus is also used as an antigen for the production of PRV gE specific monoclonal antibodies. Such antibodies are useful in the development of diagnostic tests specific for the PRV gE protein. Monoclonal antibodies are generated in mice utilizing this virus according to the PROCEDURE FOR PURIFICATION OF VIRAL GLYCOPROTEINS FOR USE AS DIAGNOSTICS (Materials & Methods).

Example 15
Homology Vector 520-90.15

The homology vector 520-90.15 is a plasmid useful for the insertion of foreign DNA into SPV. Plasmid 520-90.15 contains a unique NdeI restriction site into which foreign DNA may be cloned. A plasmid containing such a foreign DNA insert has been used according to the HOMOLOGOUS RECOMBINATION PROCEDURE FOR GENERATING RECOMBINANT SPV to generate a SPV containing the foreign DNA. For this procedure to be successful, it is important that the insertion site be in a region non-essential to the replication of the SPV and that the site be flanked with swinepox virus DNA appropriate for mediating homologous recombination between virus and plasmid DNAs. The unique NdeI restriction site in plasmid 520-90.15 is located within the coding region of the SPV thymidine kinase gene (32). Therefore, thymidine kinase gene of swinepox virus was shown to be non-essential for DNA replication and is an appropriate insertion site.

Example 16
S-PRV-010

S-SPV-010 is a swinepox virus that expresses a foreign gene. The E. coli β-galactosidase (lacZ) gene is inserted into a unique NdeI restriction site within the thymidine kinase gene. The foreign gene (lacZ) is under the control of the synthetic late promoter, LP1. Thus, swinepox virus thymidine kinase gene was shown to be non-essential for replication of the virus and is an appropriate insertion site.

A 1739 base pair HindIII-BamHI fragment subcloned from the HindIII G fragment contains the swinepox virus thymidine kinase gene and is designated homology vector 520-90.15. The homology vector 520-90.15 was digested with Nde I, and AscI linkers were inserted at this unique site within the thymidine kinase gene. The LP1 promoter-lac Z cassette with AscI linkers was ligated into the Asc I site within the thymidine kinase gene. The recombinant homology vector 561-36.26 was cotransfected with virus S-SPV-001 by the HOMOLOGOUS RECOMBINATION PROCEDURE FOR GENERATING RECOMBINANT SPV and virus plaques expressing β-galactosidase were selected by SCREEN FOR RECOMBINANT SPV EXPRESSING β-galactosidase (BLUOGAL AND CPRG ASSAY). The final result of blue and red plaque purification was the recombinant virus designated S-SPV-010. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable and expressing the foreign gene. The assays described here were carried out in ESK-4 cells, indicating that ESK-4 cells would be a suitable substrate for the production of SPV recombinant vaccines.

Example 17

The development of vaccines utilizing the swinepox virus to express antigens from various disease causing microorganisms can be engineered.

Transmissible Gastroenteritis Virus

The major neutralizing antigen of the transmissible gastroenteritis virus (TGE), glycoprotein 195, for use in the swinepox virus vector has been cloned. The clone of the neutralizing antigen is disclosed in U.S. Ser. No. 078,519, filed Jul. 27, 1987. It is contemplated that the procedures that have been used to express PRV g50 (gD) in SPV and are disclosed herein are applicable to TGE.

Porcine Parvovirus

The major capsid protein of the porcine (swine) parvovirus (PPV) was cloned for use in the swinepox virus vector. The clone of the capsid protein is disclosed in U.S. Pat. No. 5,068,192 issued Nov. 26, 1991. It is contemplated that the procedures that have been used to express PRV g50 (gD) in SPV and are disclosed herein are applicable to PPV.

Swine Rotavirus

The major neutralizing antigen of the swine rotavirus, glycoprotein 38, was cloned for use in the swinepox virus vector. The clone of glycoprotein 38 is disclosed in U.S. Pat. No. 5,068,192 issued Nov. 26, 1991. It is contemplated that the procedures that have been used to express PRV g50 (gD) in SPV and are disclosed herein are applicable to SRV.

Hog Cholera Virus

The major neutralizing antigen of the bovine viral diarrhea (BVD) virus was cloned as disclosed in U.S. Ser. No.

225,032, filed Jul. 27, 1988. Since the BVD and hog cholera viruses are cross protective (31), the BVD virus antigen has been targeted for use in the swinepox virus vector. It is contemplated that the procedures that have been used to express PRV g50 (gD) in SPV and are disclosed herein are applicable to BVD virus.

*Serpulina Hyodysenteriae*

A protective antigen of *Serpulina hyodysenteriae* (3), for use in the swinepox virus vector has been cloned. It is contemplated that the procedures that have been used to express PRV g50 in SPV and are disclosed herein are also applicable to *Serpulina hyodysenteriae*.

Antigens from the following microorganisms may also be utilized to develop animal vaccines: swine influenza virus, foot and mouth disease virus, African swine fever virus, hog cholera virus, *Mycoplasma hyopneumoniae,* porcine reproductive and respiratory syndrome/swine infertility and respiratory syndrome (PRRS/SIRS).

Antigens from the following microorganisms may also be utilized for animal vaccines: 1) canine—herpesvirus, canine distemper, canine adenovirus type 1 (hepatitis), adenovirus type 2 (respiratory disease), parainfluenza, *Leptospira canicola,* icterohemorragia, parvovirus, coronavirus, *Borrelia burgdorferi,* canine herpesvirus, *Bordetella bronchiseptica, Dirofilaria immitis* (heartworm) and rabies virus. 2) Feline—Fiv gag and env, feline leukemia virus, feline immunodeficiency virus, feline herpesvirus, feline infectious peritonitis virus, canine herpesvirus, canine coronavirus, canine parvovirus, parasitic diseases in animals (including *Dirofilaria immitis* in dogs and cats), equine infectious anemia, *Streptococcus equi,* coccidia, emeria, chicken anemia virus, *Borrelia bergdorferi,* bovine coronavirus, *Pasteurella haemolytica.*

Example 17A

Vaccines containing recombinant swinepox virus expressing antigens from hog cholera virus, swine influenza virus and (porcine reproducting and respiratory syndrome) PRRS virus.

Recombinant swinepox virus expressing genes for neutralizing antigens to hog cholera virus, swine influenza virus and PRRS virus is useful to prevent disease in swine. The genes expressed in the recombinant SPV include, but are not limited to hog cholera virus gE1 and gE2 genes, swine influenza virus hemagglutinin, neuraminidase, matrix and nucleoprotein, and PRRS virus ORF7.

Example 18

Recombinant swinepox viruses express equine influenza virus type A/Alaska 91, equine influenza virus type A/Prague 56, equine herpesvirus type 1 gB, or equine herpesvirus type 1 gD genes. S-SPV-033 and S-SPV-034 are useful as vaccines against equine influenza infection, and S-SPV-038 and S-SPV-039 are useful as a vaccine against equine herpesvirus infection which causes equine rhinotracheitis and equine abortion. These equine influenza and equine herpesvirus antigens are key to raising a protective immune response in the animal. The recombinant viruses are useful alone or in combination as an effective vaccine. The swinepox virus is useful for cloning other subtypes of equine influenza virus (including equine influenza virus type A/Miami/63 and equine influenza virus type A/Kentucky/81) to protect against rapidly evolving variants in this disease. S-SPV-033, S-SPV-034, S-SPV-038, and S-SPV-039 are also useful as an expression vector for expressing equine influenza or equine herpesvirus antigens. Such equine influenza or equine herpesvirus antigens are useful to identify antibodies directed against the wild-type equine influenza virus or equine herpesvirus. The viruses are also useful to in producing antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

Example 18A

S-SPV-033

S-SPV-033 is a recombinant swinepox virus that expresses at least two foreign genes. The gene for *E. coli* β-galactosidase (lacZ) and the gene for equine influenza virus type A/Alaska 91 neuraminidase were inserted into the SPV 617-48.1 ORF (a unique NotI restriction site has replaced a unique AccI restriction site). The lacZ gene is under the control of the synthetic late promoter (LP1), and the EIV AK/91 NA gene is under the control of the synthetic late/early promoter (LP2EP2).

S-SPV-033 was derived from S-SPV-001 (Kasza Strain). This was accomplished utilizing the homology vector 732-18.4 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-033. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

Example 18B

S-SPV-034

S-SPV-034 is a swinepox virus that expresses at least two foreign genes. The gene for *E. coli* β-galactosidase (lacZ) and the gene for equine influenza virus type A/Prague 56 neuraminidase were inserted into the SPV 617-48.1 ORF (a unique NotI restriction site has replaced a unique AccI restriction site). The lacZ gene is under the control of the synthetic late promoter (LP1), and the EIV PR/56 NA gene is under the control of the synthetic late/early promoter (LP2EP2).

S-SPV-034 was derived from S-SPV-001 (Kasza Strain). This was accomplished utilizing the homology vector 723-59A9.22 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-034. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-034 was assayed for expression of EIV-specific antigens using the BLACK PLAQUE SCREEN FOR FOREIGN GENE EXPRESSION IN RECOMBINANT SPV.

Monospecific polyclonal antibodies to EIV PR/56 NA were shown to react specifically with S-SPV-034 plaques and not with S-SPV-001 negative control plaques. All S-SPV-034 observed plaques reacted with the antiserum indicating that the virus was stably expressing the EIV PR/56 NA gene. The assays described here were carried out in ESK-4 cells, indicating that ESK-4 cells would be a suitable substrate for the production of SPV recombinant vaccines.

Example 18C
S-SPV-038

S-SPV-038 is a swinepox virus that expresses at least two foreign genes. The gene for E. coli β-galactosidase (lacZ) and the gene for equine herpesvirus type 1 glycoprotein B are inserted into the SPV 617-48.1 ORF (a unique NotI restriction site has replaced a unique AccI restriction site). The lacZ gene is under the control of the synthetic late promoter (LP1), and the EHV-1 gB gene is under the control of the synthetic late/early promoter (LP2EP2).

S-SPV-038 is derived from S-SPV-001 (Kasza Strain). This is accomplished utilizing the homology vector 744-34 (see Materials and Methods) and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING β-galactosidase (BLUOGAL AND CPRG ASSAYS). The final result of red plaque purification is the recombinant virus designated S-SPV-038. This virus is assayed for β-galactosidase expression, purity, and insert stability by multiple passages monitored by the blue plaque assay as described in Materials and Methods. After the initial three rounds of purification, all plaques observed are blue indicating that the virus is pure, stable, and expressing the foreign gene.

Example 18D
S-SPV-039

S-SPV-039 is a swinepox virus that expresses at least two foreign genes. The gene for E. coli β-galactosidase (lacZ) and the gene for equine herpesvirus type 1 glycoprotein D are inserted into the SPV 617-48.1 ORF (a unique NotI restriction site has replaced a unique AccI restriction site). The lacZ gene is under the control of the synthetic late promoter (LP1), and the EHV-1 gD gene is under the control of the synthetic late/early promoter (LP2EP2).

S-SPV-039 is derived from S-SPV-001 (Kasza Strain) This is accomplished utilizing the homology vector 744-38 (see Materials and Methods) and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING β-galactosidase (BLUOGAL AND CPRG ASSAYS). The final result of red plaque purification is the recombinant virus designated S-SPV-039. This virus is assayed for β-galactosidase expression, purity, and insert stability by multiple passages monitored by the blue plaque assay as described in Materials and Methods. After the initial three rounds of purification, all plaques observed are blue indicating that the virus is pure, stable, and expressing the foreign gene.

Example 19

Recombinant swinepox viruses express bovine respiratory syncytial virus attachment protein (BRSV G) , BRSV Fusion protein (BRSV F), BRSV nucleocapsid protein (BRSV N), bovine viral diarrhea virus (BVDV) g48, BVDV g53, bovine parainfluenza virus type 3 (BPI-3) F, or BPI-3 HN. S-SPV-020, S-SPV-029, S-SPV-030, and S-SPV-032, S-SPV-028 are useful as vaccines against bovine disease. These BRSV, BVDV, and BPI-3 antigens are key to raising a protective immune response in the animal. The recombinant viruses are useful alone or in combination as an effective vaccine. The swinepox virus is useful for cloning other subtypes of BRSV, BVDV, and BPI-3 to protect against rapidly evolving variants in this disease. S-SPV-020, S-SPV-029, S-SPV-030, and S-SPV-032, S-SPV-028 are also useful as an expression vector for expressing BRSV, BVDV, and BPI-3 antigens. Such BRSV, BVDV, and BPI-3 antigens are useful to identify antibodies directed against the wild-type BRSV, BVDV, and BPI-3. The viruses are also useful as antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

Example 19A
S-SPV-020

S-SPV-020 is a swinepox virus that expresses at least two foreign genes. The gene for E. coli β-galactosidase (lacZ) and the gene for bovine respiratory syncytial virus (BRSV) G were inserted into the SPV 617-48.1 ORF (a unique NotI restriction site has replaced a unique AccI restriction site). The lacZ gene is under the control of the synthetic late promoter (LP1), and the BRSV G gene is under the control of the synthetic late/early promoter (LP2EP2).

S-SPV-020 was derived from S-SPV-001 (Kasza Strain). This was accomplished utilizing the homology vector 727-20.5 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-020. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-020 was assayed for expression of BRSV-specific antigens using the BLACK PLAQUE SCREEN FOR FOREIGN GENE EXPRESSION IN RECOMBINANT SPV. Bovine anti-BRSV FITC (Accurate Chemicals) was shown to react specifically with S-SPV-020 plaques and not with S-SPV-003 negative control plaques. All S-SPV-020 observed plaques reacted with the antiserum indicating that the virus was stably expressing the BRSV foreign gene. The assays described here were carried out in ESK-4 cells, indicating that ESK-4 cells would be a suitable substrate for the production of SPV recombinant vaccines.

To confirm the expression of the BRSV G gene product, cells were infected with S-SPV-020 and samples of infected cell lysates were subjected to SDS-polyacrylamide gel electrophoresis. The gel was blotted and analyzed using the WESTERN BLOTTING PROCEDURE. Bovine anti-BRSV FITC (Accurate Chemicals) was used to detect expression of BRSV specific proteins. The lysate from S-SPV-020 infected cells exhibited a band at 36 kd which is the expected size of the non-glycosylated form of BRSV G protein and bands at 43 to 45 kd and 80 to 90 kd which are the expected size of glycosylated forms of the BRSV G protein.

Example 19B

S-SPV-029

S-SPV-029 is a swinepox virus that expresses at least two foreign genes. The gene for E. coli β-galactosidase (lacZ) and the gene for bovine respiratory syncytial virus (BRSV) F were inserted into the SPV 617-48.1 ORF (a unique NotI restriction site has replaced a unique AccI restriction site). The lacZ gene is under the control of the synthetic late promoter (LP1), and the BRSV F gene is under the control of the synthetic late/early promoter (LP2EP2).

S-SPV-029 was derived from S-SPV-001 (Kasza Strain). This was accomplished utilizing the homology vector 727-20.10 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-029. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-029 was assayed for expression of BRSV-specific antigens using the BLACK PLAQUE SCREEN FOR FOREIGN GENE EXPRESSION IN RECOMBINANT SPV. Bovine anti-BRSV FITC (Accurate Chemicals) was shown to react specifically with S-SPV-029 plaques and not with S-SPV-003 negative control plaques. All S-SPV-029 observed plaques reacted with the antiserum indicating that the virus was stably expressing the BRSV foreign gene. The assays described here were carried out in ESK-4 cells, indicating that ESK-4 cells would be a suitable substrate for the production of SPV recombinant vaccines.

Example 19C

S-SPV-030

S-SPV-030 is a swinepox virus that expresses at least two foreign genes. The gene for E. coli β-galactosidase (lacZ) and the gene for bovine respiratory syncytial virus (BRSV) N were inserted into the SPV 617-48.1 ORF (a unique NotI restriction site has replaced a unique AccI restriction site). The lacZ gene is under the control of the synthetic late promoter (LP1), and the BRSV N gene is under the control of the synthetic late/early promoter (LP2EP2).

S-SPV-030 was derived from S-SPV-001 (Kasza Strain). This was accomplished utilizing the homology vector 713-55.37 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-030. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-030 was assayed for expression of BRSV-specific antigens using the BLACK PLAQUE SCREEN FOR FOREIGN GENE EXPRESSION IN RECOMBINANT SPV. Bovine anti-BRSV FITC (Accurate Chemicals) was shown to react specifically with S-SPV-030 plaques and not with S-SPV-003 negative control plaques. All S-SPV-030 observed plaques reacted with the antiserum indicating that the virus was stably expressing the BRSV foreign gene. The assays described here were carried out in ESK-4 cells, indicating that ESK-4 cells would be a suitable substrate for the production of SPV recombinant vaccines.

To confirm the expression of the BRSV N gene product, cells were infected with SPV-030 and samples of infected cell lysates were subjected to SDS-polyacrylamide gel electrophoresis. The gel was blotted and analyzed using the WESTERN BLOTTING PROCEDURE. Bovine anti-BRSV FITC (Accurate Chemicals) was used to detect expression of BRSV specific proteins. The lysate from S-SPV-030 infected cells exhibited a band at 43 kd which is the expected size of the BRSV N protein.

Example 19D

S-SPV-028

S-SPV-028 is a swinepox virus that expresses at least two foreign genes. The gene for E. coli β-galactosidase (lacZ) and the gene for bovine parainfluenza virus type 3 (BPI-3) F were inserted into the SPV 617-48.1 ORF (a unique NotI restriction site has replaced a unique AccI restriction site). The lacZ gene is under the control of the synthetic late promoter (LP1), and the BPI-3 F gene is under the control of the synthetic late/early promoter (LP2EP2).

S-SPV-028 was derived from S-SPV-001 (Kasza Strain). This was accomplished utilizing the homology vector 713-55.10 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-028. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-028 was assayed for expression of BPI-3-specific antigens using the BLACK PLAQUE SCREEN FOR FOREIGN GENE EXPRESSION IN RECOMBINANT SPV. Bovine anti-BPI-3 FITC (Accurate Chemicals) was shown to react specifically with S-SPV-028 plaques and not with S-SPV-003 negative control plaques. All S-SPV-028 observed plaques reacted with the antiserum indicating that the virus was stably expressing the BPI-3 foreign gene. The assays described here were carried out in ESK-4 cells, indicating that ESK-4 cells would be a suitable substrate for the production of SPV recombinant vaccines.

To confirm the expression of the BPI-3 F gene product, cells were infected with SPV-028 and samples of infected cell lysates were subjected to SDS-polyacrylamide gel electrophoresis. The gel was blotted and analyzed using the WESTERN BLOTTING PROCEDURE. Bovine anti-BPI-3 FITC (Accurate Chemicals) was used to detect expression of BPI-3 specific proteins. The lysate from S-SPV-028 infected cells exhibited bands at 43, and 70 kd which is the expected size of the BPI-3 F protein.

Example 19E

S-SPV-032

S-SPV-032 is a swinepox virus that expresses at least two foreign genes. The gene for E. coli β-galactosidase (lacZ) and the gene for bovine viral diarrhea virus (BVDV) g48 were inserted into the SPV 617-48.1 ORF (a unique NotI restriction site has replaced a unique AccI restriction site).

The lacZ gene is under the control of the synthetic late promoter (LP1), and the BVDV g48 gene is under the control of the synthetic late/early promoter (LP2EP2).

S-SPV-032 was derived from S-SPV-001 (Kasza Strain). This was accomplished utilizing the homology vector 727-78.1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-032. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

Example 19F

S-SPV-040

S-SPV-040 is a swinepox virus that expresses at least two foreign genes. The gene for *E. coli* β-galactosidase (lacZ) and the gene for bovine viral diarrhea virus (BVDV) g53 were inserted into the SPV 617-48.1 ORF (a unique NotI restriction site has replaced a unique AccI restriction site). The lacZ gene is under the control of the synthetic late promoter (LP1), and the BVDV g53 gene is under the control of the synthetic late/early promoter (LP2EP2). p S-SPV-040 is derived from S-SPV-001 (Kasza Strain). This is accomplished utilizing the homology vector 738-96 (see Materials and Methods) and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING β-galactosidase (BLUOGAL AND CPRG ASSAYS). The final result of red plaque purification is the recombinant virus designated S-SPV-040. This virus is assayed for β-galactosidase expression, purity, and insert stability by multiple passages monitored by the blue plaque assay as described in Materials and Methods. After the initial three rounds of purification, all plaques observed are blue indicating that the virus is pure, stable, and expressing the foreign gene.

Example 19G

Shipping Fever Vaccine

Shipping fever or bovine respiratory disease (BRD) complex is manifested as the result of a combination of infectious diseases of cattle and additional stress related factors (52). Respiratory virus infections augmented by pathophysiological effects of stress, alter the susceptibility of cattle to Pasteurella organisms by a number of mechanisms. Control of the viral infections that initiate BRD is essential to preventing the disease syndrome (53).

The major infectious disease pathogens that contribute to BRD include but are not limited to infectious bovine rhinotracheitis virus (IBRV), parainfluenza virus type 3 (PI-3), bovine respiratory syncytial virus (BRSV), and *Pasteurella haemolytica* (53). Recombinant swinepox virus expressing protective antigens to organisms causing BRD is useful as a vaccine. S-SPV-020, S-SPV-029, S-SPV-030, S-SPV-032, and S-SPV-028 are useful components of such a vaccine.

Example 20

Recombinant swinepox viruses S-SPV-031 and S-SPV-035 are useful as a vaccine against human disease. S-SPV-031 expresses the core antigen of hepatitis B virus. S-SPV-031 is useful against hepatitis B infection in humans. S-SPV-035 expresses the cytokine, interleukin-2, and is useful as an immune modulator to enhance an immune response in humans. When S-SPV-031 and S-SPV-035 are combined, a superior vaccine against hepatitis B is produced.

Example 20A

S-SPV-031

S-SPV-031 is a swinepox virus that expresses at least two foreign genes. The gene for *E. coli* β-galactosidase (lacZ) and the gene for Hepatitis B Core antigen were inserted into the SPV 617-48.1 ORF (a unique NotI restriction site has replaced a unique AccI restriction site). The lacZ gene is under the control of the synthetic late promoter (LP1), and the Hepatitis B Core antigen gene is under the control of the synthetic early/late promoter (EP1LP2).

S-SPV-031 was derived from S-SPV-001 (Kasza Strain). This was accomplished utilizing the homology vector 727-67.18 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-031. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-031 was assayed for expression of Hepatitis B Core antigen-specific antigens using the BLACK PLAQUE SCREEN FOR FOREIGN GENE EXPRESSION IN RECOMBINANT SPV. Rabbit antisera to Hepatitis B Core antigen was shown to react specifically with S-SPV-031 plaques and not with S-SPV-001 negative control plaques. All S-SPV-031 observed plaques reacted with the antiserum indicating that the virus was stably expressing the Hepatitis B Core antigen gene. The assays described here were carried out in ESK-4 cells, indicating that ESK-4 cells would be a suitable substrate for the production of SPV recombinant vaccines.

To confirm the expression of the Hepatitis B Core antigen gene product, cells were infected with SPV-031 and samples of infected cell lysates were subjected to SDS-polyacrylamide gel electrophoresis. The gel was blotted and analyzed using the WESTERN BLOTTING PROCEDURE. Rabbit antisera to Hepatitis B Core antigen was used to detect expression of Hepatitis B specific proteins. The lysate from S-SPV-031 infected cells exhibited a band at 21 kd which is the expected size of the Hepatitis B Core antigen.

Example 20B

S-SPV-035

S-SPV-035 is a swinepox virus that expresses at least two foreign genes. The gene for *E. coli* β-galactosidase (lacZ) and the gene for human IL-2 were inserted into the SPV 617-48.1 ORF (a unique NotI restriction site has replaced a unique AccI restriction site). The lacZ gene is under the control of the synthetic late promoter (LP1), and the human IL-2 gene is under the control of the synthetic late/early promoter (LP2EP2).

S-SPV-035 was derived from S-SPV-001 (Kasza Strain). This was accomplished utilizing the homology vector 741-84.14 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-035. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

Example 21
Human Vaccines Using Recombinant Swinepox Virus as a Vector

Recombinant swinepox virus is useful as a vaccine against human diseases. For example, human influenza virus is a rapidly evolving virus whose neutralizing viral epitopes rapidly change. A useful recombinant swinepox vaccine is one in which the influenza virus neutralizing epitopes are quickly adapted by recombinant DNA techniques to protect against new strains of influenza virus. Human influenza virus hemagglutinin (HN) and neuraminidase (NA) genes are cloned into the swinepox virus as described in CLONING OF EQUINE INFLUENZA VIRUS HEMAGGLUTININ AND NEURAMINIDASE GENES (See Materials and Methods and Example 17).

Recombinant swinepox virus is useful as a vaccine against other human diseases when foreign antigens from the following diseases or disease organisms are expressed in the swinepox virus vector: hepatitis B virus surface and core antigens, hepatitis C virus, human immunodeficiency virus, human herpesviruses, herpes simplex virus-1, herpes simplex virus-2, human cytomegalovirus, Epstein-Barr virus, Varicella-Zoster virus, human herpesvirus-6, human herpesvirus-7, human influenza, measles virus, hantaan virus, pneumonia virus, rhinovirs, poliovirus, human respiratory syncytial virus, retrovirus, human T-cell leukemia virus, rabies virus, mumps virus, malaria (*Plasmodium falciparum*), *Bordetelia pertussis,* Diptheria, *Rickettsia prowazekii, Borrelia bergdorferi,* Tetanus toxoid, malignant tumor antigens.

Furthermore, S-SPV-035 (Example 20), when combined with swinepox virus interleukin-2 is useful in enhancing immune response in humans. Additional cytokines, including but not limited to, interleukin-2, interleukin-6, interleukin-12, interferons, granulocyte-macrophage colony stimulating factors, interleukin receptors from human and other animals when vectored into a non-essential site in the swinepox viral genome, and subsequently expressed, have immune stimulating effects.

Recombinant swinepox virus express foreign genes in a human cell line. S-SPV-003 (EP1LP2 promoter expressing the lacZ gene) expressed the lacZ gene in THP human monocyte cell lines by measuring β-galactosidase activity. Cytopathic effect of swinepox virus was observed on the THP human monocyte cells, indicating that recombinant swinepox virus can express foreign genes in a human cell line, but will not productively infect or replicated in the human cell line. Swinepox virus was demonstrated to replicate well in ESK-4 cells (embryonic swine kidney) indicating that ESK-4 cells would be a suitable substrate for the production of SPV recombinant vaccines.

Example 22

Avian vaccines using recombinant swinepox virus as a vector.

Example 22A
S-SPV-026

S-SPV-026 is a swinepox virus that expresses at least two foreign genes. The gene for *E. coli* β-galactosidase (lacZ) and the gene for infectious bursal disease virus (IBDV) polyprotein were inserted into the SPV 617-48.1 ORF (a unique NotI restriction site has replaced a unique AccI restriction site). The lacZ gene is under the control of the synthetic late promoter (LP1), and the IBDV polyprotein gene is under the control of the synthetic early/late promoter (EP1LP2).

S-SPV-026 was derived from S-SPV-001 (Kasza Strain). This was accomplished utilizing the homology vector 689-50.4 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-026. This virus was assayed for β-galactosidase expression, purity, and insert stability by multiple passages monitored by the blue plaque assay as described in Materials and Methods. After the initial three rounds of purification, all plaques observed were blue indication that the virus was pure, stable, and expressing the foreign gene.

S-SPV-026 was assayed for expression of IBDV polyprotein-specific antigens using the BLACK PLAQUE SCREEN FOR FOREIGN GENE EXPRESSION IN RECOMBINANT SPV. Rat antisera to IBDV polyprotein were shown to react specifically with S-SPV-026 plaques and not with S-SPV-001 negative control plaques. All S-SPV-026 observed plaques reacted with the antiserum indicating that the virus was stably expressing the IBDV polyprotein gene. The assays described here were carried out in ESK-4 cells, indicating that ESK-4 cells would be a suitable substrate for the production of SPV recombinant vaccines.

To confirm the expression of the IBDV polyprotein gene product, cells were infected with SPV-026 and samples of infected cell lysates were subjected to SDS-polyacrylamide gel electrophoresis. The gel was blotted and analyzed using the WESTERN BLOTTING PROCEDURE. Rat antisera to IBDV proteins VP2, VP3, and VP4 and monoclonal antibody R63 to IBDV VP2 were used to detect expression of IBDV proteins. The lysate from S-SPV-026 infected cells exhibited bands at 32 to 40 kd which is the expected size of the IBDV proteins.

Example 22B
S-SPV-027

S-SPV-027 is a swinepox virus that expresses at least two foreign genes. The gene for *E. coli* β-galactosidase (lacZ) and the gene for infectious bursal disease virus (IBDV) VP2 (40 kd) were inserted into the SPV 617-48.1 ORF (a unique NotI restriction site has replaced a unique AccI restriction site). The lacZ gene is under the control of the synthetic late promoter (LP1) and the IBDV VP2 gene is under the control of the synthetic early/late promoter (EP1LP2).

S-SPV-027 was derived from S-SPV-001 (Kasza Strain). This was accomplished utilizing the homology vector 689-50.7 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-027. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-027 was assayed for expression of IBDV VP2-specific antigens using the BLACK PLAQUE SCREEN FOR FOREIGN GENE EXPRESSION IN RECOMBINANT SPV. Rat antisera to IBDV protein was shown to react specifically with S-SPV-027 plaques and not with S-SPV-001 negative control plaques. All S-SPV-027 observed plaques reacted with the antiserum indicating that the virus was stably expressing the IBDV VP2 gene. The assays described here were carried out in ESK-4 cells, indicating that ESK-4 cells would be a suitable substrate for the production of SPV recombinant vaccines.

To confirm the expression of the IBDV VP2 gene product, cells were infected with S-SPV-027 and samples of infected cell lysates were subjected to SDS-polyacrylamide gel electrophoresis. The gel was blotted and analyzed using the WESTERN BLOTTING PROCEDURE. Rat antisera to IBDV protein and monoclonal antibody R63 to IBDV VP2 were used to detect expression of IBDV VP2 protein. The lysate from S-SPV-027 infected cells exhibited a band at 40 kd which is the expected size of the IBDV VP2 protein.

S-SPV-026 and S-SPV-027 are useful as vaccines against infectious bursal disease in chickens and also as expression vectors for IBDV proteins. Recombinant swinepox virus is useful as a vaccine against other avian disease when foreign antigens from the following diseases or disease organisms are expressed in the swinepox virus vector: Marek's disease virus, infectious laryngotracheitis virus, Newcastle disease virus, infectious bronchitis virus, and chicken anemia virus, Chick anemia virus, Avian encephalomyelitis virus, Avian reovirus, Avian paramyxoviruses, Avian influenza virus, Avian adenovirus, Fowl pox virus, Avian coronavirus, Avian rotavirus, Salmonella spp *E coli,* Pasteurella spp, Haemophilus spp, Chlamydia spp, Mycoplasma spp, Campylobacter spp, Bordetella spp, Poultry nematodes, cestodes, trematodes, Poultry mites/lice, Poultry protozoa (Eimeria spp, Histomonas spp, Trichomonas spp).

Example 23

SPV-036

S-SPV-036 is a swinepox virus that expresses at one foreign gene. The gene for *E. coli* β-galactosidase (lacZ) was inserted into the SPV 617-48.1 ORF (a unique NotI restriction site has replaced a unique AccI restriction site). The lacZ gene is under the control of the human cytomegalovirus immediate early (HCMV IE) promoter.

S-SPV-036 was derived from S-SPV-001 (Kasza Strain). This was accomplished utilizing the homology vector 741-80.3 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-036. This virus is assayed for β-galactosidase expression, purity, and insert stability by multiple passages monitored by the blue plaque assay as described in Materials and Methods. After the initial three rounds of purification, all plaques observed are blue indicating that the virus is pure, stable, and expressing the foreign gene.

The expression of lacZ from the HCMV IE promoter provides a strong promoter for expression of foreign genes in swinepox. S-SPV-036 is a novel and unexpected demonstration of a herpesvirus promoter driving expression of a foreign gene in a poxvirus. S-SPV-036 is useful in formulating human vaccines, and recombinant swinepox virus is useful for the expression of neutralizing antigens from human pathogens. Recombinant swinepox virus expressed foreign genes in a human cell line as demonstrated by S-SPV-003 (EP1LP2) promoter expressing the lacZ gene) expressed β-galactosidase in THP human monocyte cell lines. Cytopathic effects of swinepox virus on the THP human monocyte cells were not observed, indicating that recombinant swinepox virus can express foreign genes in a human cell line, but will not productively infect or replicated in the human cell line Example 24

Homology Vector 738-94.4

Figure 17:
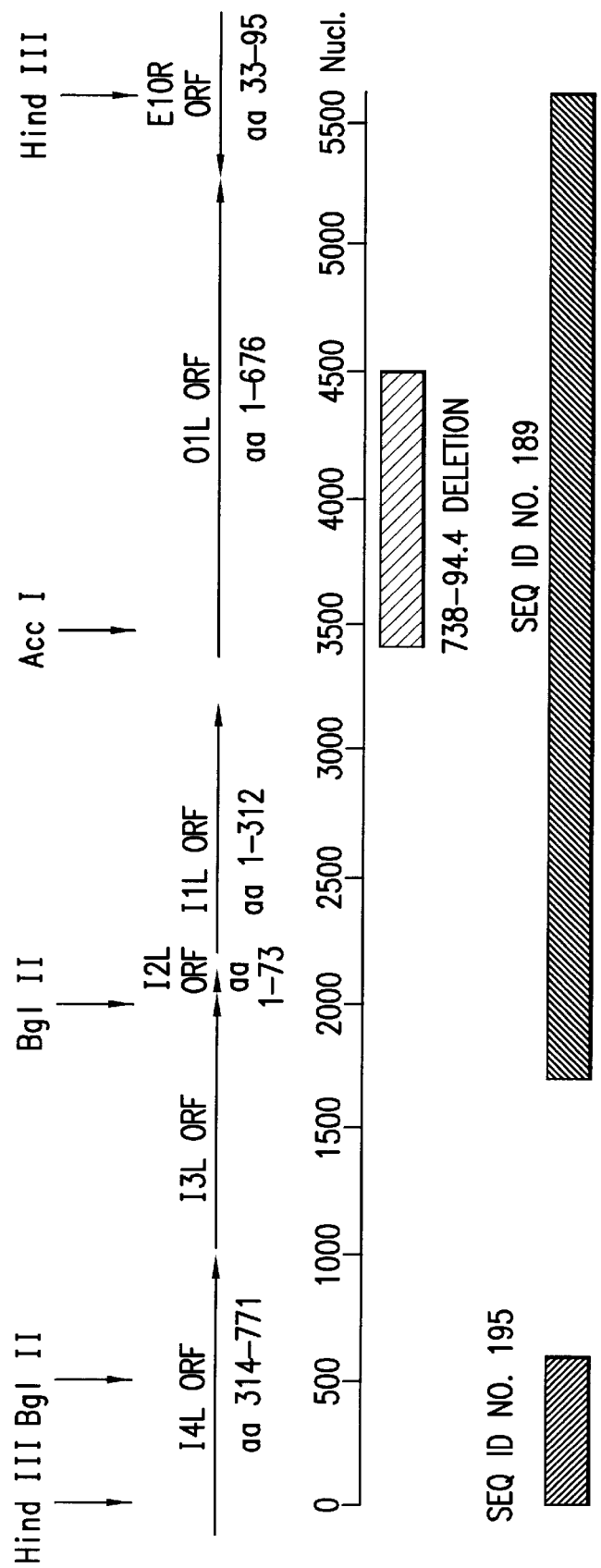

Homology Vector 738-94.4 is a swinepox virus vector that expresses one foreign gene. The gene for *E. coli* β-galactosidase (lacZ) was inserted into the the O1L open reading frame (SEQ ID NO: 115). The lacZ gene is under the control of the O1L promoter. The homology vector 738-94.4 contains a deletion of SPV DNA from nucleotides 1679 to 2452 (SEQ ID NO: 189; FIG. 17) which deletes part of the O1L ORF.

The upstream SPV sequences were synthesized by polymerase chain reaction using DNA primers 5'-GAAG CATGCCCGTTCTTATCAATAGTTTAGTCGAAAATA-3' (SEQ ID NO: 185) and 5'-CATAAGATCTGGCATT GTGTTATTATACTAACAAAAATAAG-3' (SEQ ID NO: 186) to produce an 855 base pair fragment with BglII and SphI ends. The O1L promoter is present on this fragment. The downstream SPV sequences were synthesized by polymerase chain reaction using DNA primers 5'-CCGTAGT CGACAAAGATCGACTTATTAATATGTATGGGATT-3' (SEQ ID NO: 187) and 5'-GCCTGAAGCTTCTAGT ACAGTATTTACGACTTTTGAAAT-3' (SEQ ID NO: 188) to produce an 1113 base pair fragment with SalI and HindIII ends. A recombinant swinepox virus was derived utilizing homology vector 738-94.4 and S-SPV-001 (Kasza strain) in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification is the recombinant virus. This virus is assayed for β-galactosidase expression, purity, and insert stability by multiple passages monitored by the blue plaque assay as described in Materials and Methods. After the initial three rounds of purification, all plaques observed are blue indicating that the virus is pure, stable, and expressing the foreign gene. Recombinant swinepox viruses derived from homology vector 738-94.4 are utilized as an expression vector to express foreign antigens and as a vaccine to raise a protective immune response in animals to foreign genes expressed by the recombinant swinepox virus. Other promoters in addition to the O1L promoter are inserted into the deleted region including LP1, EP1LP2, LP2EP2, HCMV immediate early, and one or more foreign genes are expressed from these promoters.

Example 24B

Homology Vector 752-22.1 is a swinepox virus vector that is utilized to express two foreign genes. The gene for *E. coli*

β-galactosidase (lacZ) was inserted into the the O1L open reading frame (SEQ ID NO: 115). The lacZ gene is under the control of the O1L promoter. A second foreign gene is expressed from the LP2EP2 promoter inserted into an EcoRI or BamHI site following the LP2EP2 promoter sequence. The homology vector 752-22.1 contains a deletion of SPV DNA from nucleotides 1679 to 2452 (SEQ ID NO: 189; FIG. 17) which deletes part of the O1L ORF. The homology vector 752-22.1 was derived from homology vector 738-94.4 by insertion of the LP2EP2 promoter fragment (see Materials and Methods). The homology vector 752-22.1 is further improved by placing the lacZ gene under the control of the synthetic LP1 promoter. The LP1 promoter results in higher levels of lacZ expression compared to the SPV O1L promoter Example 25

S-SPV-041

S-SPV-041 is a swinepox virus that expresses at least two foreign genes. The gene for *E. coli* β-galactosidase (lacZ) and the gene for equine herpesvirus type 1 glycoprotein B (gB) were inserted into the 738-94.4 ORF (a 773 base pair deletion of the SPV O1L ORF; Deletion of nucleotides 1679 to 2452, SEQ ID NO: 189). The lacZ gene is under the control of the swinepox O1L promoter, and the EHV-1 gB gene is under the control of the synthetic late/early promoter (LP2EP2).

S-SPV-041 was derived from S-SPV-001 (Kasza Strain). This was accomplished utilizing the homology vector 752-29.33 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-041. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-041 is useful as a vaccine in horses against EHV-1 infection and is useful for expression of EHV-1 glycoprotein B.

S-SPV-045

S-SPV-045 is a swinepox virus that expresses at least two foreign genes. The gene for *E. coli* β-galactosidase (lacZ) and the gene for infectious bovine rhinotracheitis virus glycoprotein E (gE) were inserted into the 738-94.4 ORF (a 773 base pair deletion of the SPV O1L ORF; Deletion of nucleotides 1679 to 2452, SEQ ID NO: 189). The lacZ gene is under the control of the swinepox O1L promoter, and the IBRV gE gene is under the control of the synthetic late/early promoter (LP2EP2).

S-SPV-045 was derived from S-SPV-001 (Kasza Strain). This was accomplished utilizing the homology vector 746-94.1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-045. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-045 is useful for expression of IBRV glycoprotein E.

S-SPV-049

S-SPV-049 is a swinepox virus that expresses at least two foreign genes. The gene for *E. coli* β-galactosidase (lacZ) and the gene for bovine viral diarrhea virus glycoprotein 48 (gp48) were inserted into the 738-94.4 ORF (a 773 base pair deletion of the SPV O1L ORF; Deletion of nucleotides 1679 to 2452, SEQ ID NO: 189). The lacZ gene is under the control of the swinepox O1L promoter, and the BVDV gp48 gene is under the control of the synthetic late/early promoter (LP2EP2).

S-SPV-049 was derived from S-SPV-001 (Kasza Strain). This was accomplished utilizing the homology vector 771-55.11 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-049. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-049 is useful as a vaccine in cattle against BVDV infection and is useful for expression of BVDV glycoprotein 48.

S-SPV-050

S-SPV-050 is a swinepox virus that expresses at least two foreign genes. The gene for *E. coli* β-galactosidase (lacz) and the gene for the bovine viral diarrhea virus glycoprotein 53 (gp53) were inserted into the 738-94.4 ORF (a 773 base pair deletion of the SPV O1L ORF; Deletion of nucleotides 1679 to 2452, SEQ ID NO: 189). The lacZ gene is under the control of the swinepox O1L promoter, and the IBRV gE gene is under the control of the synthetic late/early promoter (LP2EP2).

S-SPV-050 was derived from S-SPV-001 (Kasza Strain). This was accomplished utilizing the homology vector 767-67.3 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-050. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-050 is useful as a vaccine in cattle against BVDV infection and is useful for expression of BVDV glycoprotein 53.

Example 26

Recombinant swinepox virus, S-SPV-042 or S-SPV-043, expressing chicken interferon (cIFN) or chicken myelomonocytic growth factor (cMGF), respectively, are useful to enhance the immune response when added to vaccines against diseases of poultry. Chicken myelomonocytic growth factor (cMGF) is homologous to mammalian interleukin-6 protein, and chicken interferon (cIFN) is homologous to mammalian interferon. When used in combination with vaccines against specific avian diseases, S-SPV-042 and S-SPV-043 provide enhanced mucosal, humoral, or cell mediated immunity against avian disease-causing viruses including, but not limited to, Marek's disease virus, Newcastle disease virus, infectious laryngotracheitis virus, infectious bronchitis virus, infectious bursal disease virus.

Example 26A

S-SPV-042

S-SPV-042 is a swinepox virus that expresses at least two foreign genes. The gene for E. coli β-galactosidase (lacZ) and the gene for chicken interferon (cIFN) were inserted into the SPV 617-48.1 ORF (a unique NotI restriction site has replaced a unique AccI restriction site). The lacZ gene is under the control of the synthetic late promoter (LP1), and the cIFN gene is under the control of the synthetic late/early promoter (LP2EP2).

S-SPV-042 was derived from S-SPV-001 (Kasza Strain). This was accomplished utilizing the homology vector 751-07.A1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-042. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-042 has interferon activity in cell culture. Addition of S-SPV-042 conditioned media to chicken embryo fibroblast (CEF) cell culture inhibits infection of the CEF cells by vesicular stomatitis virus or by herpesvirus of turkeys. S-SPV-042 is useful to enhance the immune response when added to vaccines against diseases of poultry.

Example 26B

S-SPV-043

S-SPV-043 is a swinepox virus that expresses at least two foreign genes. The gene for E. coli β-galactosidase (lacZ) and the gene for chicken myelomonocytic growth factor (CMGF) were inserted into the SPV 617-48.1 ORF (a unique NotI restriction site has replaced a unique AccI restriction site). The lacZ gene is under the control of the synthetic late promoter (LP1), and the cMGF gene is under the control of the synthetic late/early promoter (LP2EP2).

S-SPV-043 was derived from S-SPV-001 (Kasza Strain). This was accomplished utilizing the homology vector 751-56.A1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-043. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-043 is useful to enhance the immune response when added to vaccines against diseases of poultry.

Example 27

Insertion Into a Non-essential Site in the 2.0 kb HindIII to BglII Region of the Swinepox Virus HindIII M Fragment A 2.0 kb HindIII to BglII region of the swinepox virus HindIII M fragment is useful for the insertion of foreign DNA into SPV. The foreign DNA is inserted into a unique BglII restriction site in the region (FIG. 17; Nucleotide 540 of SEQ ID NOs: 195). A plasmid containing a foreign DNA insert is used according to the HOMOLOGOUS RECOMBINATION PROCEDURE FOR GENERATING RECOMBINANT SPV to generate an SPV containing the foreign DNA. For this procedure to be successful, it is important that the insertion site be in a region non-essential to the replication of the SPV and that the site be flanked with swinepox virus DNA appropriate for mediating homologous recombination between virus and plasmid DNAs. The unique BglII restriction site in the 2.0 kb HindIII to BglII region of the swinepox virus HindIII M fragment is located within the coding region of the SPV I4L open reading frame. The I4L ORF has sequence similarity to the vaccinia virus and smallpox virus ribonucleotide reductase (large subunit) gene (56–58). The ribonucleotide reductase (large subunit) gene is non-essential for DNA replication of vaccinia virus and is an appropriate insertion site in swinepox virus.

Example 28

S-SPV-047

S-SPV-047 is a swinepox virus that expresses two foreign genes. The gene for E. coli β-galactosidase (lacZ) and the gene for pseudorabies virus gE (gII) were inserted into a unique HindIII site (HindIII linker inserted into the BglII restriction endonuclease site within the 2.0 kb BglII to HindIII subfragment of the HindIII M fragment.) The BglII insertion site is within the SPV I4L open reading frame which has significant homology to the vaccinia virus ribonucleoside-diphosphate reductase gene. The lacZ gene is under the control of the synthetic late promoter (LP1), and the PRV gB (gII) gene is under the control of the synthetic late/early promoter (LP2EP2).

S-SPV-047 was derived from S-SPV-001 (Kasza Strain). This was accomplished utilizing the homology vector 779-94.31 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-047. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-047 was assayed for expression of PRV specific antigens using the BLACK PLAQUE SCREEN FOR FOREIGN GENE EXPRESSION IN RECOMBINANT SPV. Polyclonal swine anti-PRV serum was shown to react specifically with S-SPV-047 plaques and not with S-SPV-001 negative control plaques. All S-SPV-047 observed plaques reacted with the swine anti-PRV serum indicating that the virus was stably expressing the PRV foreign gene. The assays described here were carried out in ESK-4 cells, indicating that ESK-4 cells would be a suitable substrate for the production of SPV recombinant vaccines.

To confirm the expression of the PRV gB gene product, cells were infected with S-SPV-047 and samples of infected cell lysates and culture supernatants were subjected to SDS polyacrylamide gel electrophoresis. The gel was blotted and analyzed using the WESTERN BLOTTING PROCEDURE. A polyclonal swine anti-PRV serum was used to detect expression of PRV specific proteins. The cell lysate and supernatants from S-SPV-047 infected cells exhibited bands corresponding to 120 kD, 67 kD and 58 kD, which are the expected size of the PRV glycoprotein B.

SPV recombinant-expressed PRV gB has been shown to elicit a significant immune response in swine (37, 38; See example 8). Furthermore, PRV gB is expressed in recombinant SPV, significant protection from challenge with virulent PRV is obtained. (See Examples 6 and 8) Therefore S-SPV-047 is valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals.

S-SPV-052

S-SPV-052 is a swinepox virus that expresses three foreign genes. The gene for *E. coli* β-galactosidase (lacz) and the gene for pseudorabies virus gB (gII) were inserted into the unique HindIII restriction site (HindIII linkers inserted into a unique NdeI site in the SPV O1L open reading frame; An approximately 545 base pair NdeI to NdeI subfragment (Nucleotides 1560 to 2104; SEQ ID NO.) of the SPV HindIII M fragment has been deleted). The gene for PRV gD (g50) was inserted into the unique PstI restriction site (PstI linkers inserted into a unique AccI site in the SPV O1L open reading frame). The lacZ gene is under the control of the synthetic late promoter (LP1), the PRV gB (gII) gene is under the control of the synthetic late/early promoter (LP2EP2), and the PRV gD (g50) gene is under the control of the synthetic early/late promoter (EP1LP2).

S-SPV-052 was derived from S-SPV-001 (Kasza Strain). This was accomplished utilizing the homology vector 789-41.7 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 052. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-052 was assayed for expression of PRV specific antigens using the BLACK PLAQUE SCREEN FOR FOREIGN GENE EXPRESSION IN RECOMBINANT SPV. Polyclonal swine anti-PRV serum was shown to react specifically with S-SPV-052 plaques and not with S-SPV-001 negative control plaques. All S-SPV-052 observed plaques reacted with the swine anti-PRV serum indicating that the virus was stably expressing the PRV foreign gene. The assays described here were carried out in ESK-4 cells, indicating that ESK-4 cells would be a suitable substrate for the production of SPV recombinant vaccines.

To confirm the expression of the PRV gB and gD gene products, cells were infected with S-SPV-052 and samples of infected cell lysates and culture supernatants were subjected to SDS polyacrylamide gel electrophoresis. The gel was blotted and analyzed using the WESTERN BLOTTING PROCEDURE. A polyclonal swine anti-PRV serum was used to detect expression of PRV specific proteins. The cell lysate and supernatants from S-SPV-052 infected cells exhibited bands corresponding to 120 kD, 67 kD and 58 kD, which are the expected size of the PRV glycoprotein B; and a 48 kD which is the expected size of the PRV glycoprotein D.

SPV recombinant-expressed PRV gB and gD has been shown to elicit a significant immune response in swine (37, 38; See example 8). Furthermore, PRV gB and gD are expressed in recombinant SPV, significant protection from challenge with virulent PRV is obtained. (See Examples 6 and 8) Therefore S-SPV-052 is valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals.

S-SPV-053

S-SPV-053 is a swinepox virus that expresses three foreign genes. The gene for *E. coli* β-galactosidase (lacZ) and the gene for pseudorabies virus gB (gII) were inserted into the unique HindIII restriction site (HindIII linkers inserted into a unique NdeI site in the SPV O1L open reading frame; An approximately 545 base pair NdeI to NdeI subfragment (Nucleotides 1560 to 2104 of the SPV HindIII M fragment has been deleted). The gene for PRV gC (gIII) was inserted into the unique PstI restriction site (PstI linkers inserted into a unique AccI site in the SPV O1L open reading frame). The lacZ gene is under the control of the synthetic late promoter (LP1), the PRV gB (gII) gene is under the control of the synthetic late/early promoter (LP2EP2), and the PRV gC (gIII) gene is under the control of the synthetic early/late promoter (EP1LP2).

S-SPV-053 was derived from S-SPV-001 (Kasza Strain). This was accomplished utilizing the homology vector 789-41.27 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 053. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-053 was assayed for expression of PRV specific antigens using the BLACK PLAQUE SCREEN FOR FOREIGN GENE EXPRESSION IN RECOMBINANT SPV. Polyclonal swine anti-PRV serum was shown to react specifically with S-SPV-053 plaques and not with S-SPV-001 negative control plaques. All S-SPV-053 observed plaques reacted with the swine anti-PRV serum indicating that the virus was stably expressing the PRV foreign gene. The assays described here were carried out in ESK-4 cells, indicating that ESK-4 cells would be a suitable substrate for the production of SPV recombinant vaccines.

To confirm the expression of the PRV gB and gC gene products, cells were infected with S-SPV-053 and samples of infected cell lysates and culture supernatants were subjected to SDS polyacrylamide gel electrophoresis. The gel was blotted and analyzed using the WESTERN BLOTTING PROCEDURE. A polyclonal swine anti-PRV serum was used to detect expression of PRV specific proteins. The cell lysate and supernatants from S-SPV-053 infected cells exhibited bands corresponding to 120 kD, 67 kD and 58 kD, which are the expected size of the PRV glycoprotein B; and a 92 kD which is the expected size of the PRV glycoprotein C.

SPV recombinant-expressed PRV gB and gC has been shown to elicit a significant immune response in swine (37, 38; See example 8). Furthermore, PRV gB and gC are expressed in recombinant SPV, significant protection from challenge with virulent PRV is obtained. (See Examples 6 and 8) Therefore S-SPV-053 is valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals.

S-SPV-054

S-SPV-054 is a swinepox virus that expresses three foreign genes. The gene for *E. coli* β-galactosidase (lacZ) and the gene for pseudorabies virus gC (gIII) were inserted into the unique HindIII restriction site (HindIII linkers inserted into a unique NdeI site in the SPV O1L open reading frame; An approximately 545 base pair NdeI to NdeI subfragment (Nucleotides 1560 to 2104 of the SPV HindIII M fragment has been deleted). The gene for PRV gD (g50) was inserted into the unique PstI restriction site (PstI linkers inserted into a unique AccI site in the SPV O1L open reading frame). The lacZ gene is under the control of the synthetic late promoter (LP1), the PRV gC (gIII) gene is under the control of the synthetic early/late promoter (EP1LP2), and the PRV gD (g50) gene is under the control of the synthetic early/late promoter (EP1LP2).

S-SPV-054 was derived from S-SPV-001 (Kasza Strain) This was accomplished utilizing the homology vector 789-41.47 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 054. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-054 was assayed for expression of PRV specific antigens using the BLACK PLAQUE SCREEN FOR FOREIGN GENE EXPRESSION IN RECOMBINANT SPV. Polyclonal swine anti-PRV serum was shown to react specifically with S-SPV-054 plaques and not with S-SPV-001 negative control plaques. All S-SPV-054 observed plaques reacted with the swine anti-PRV serum indicating that the virus was stably expressing the PRV foreign gene. The assays described here were carried out in ESK-4 cells, indicating that ESK-4 cells would be a suitable substrate for the production of SPV recombinant vaccines.

To confirm the expression of the PRV gC and gD gene products, cells were infected with S-SPV-054 and samples of infected cell lysates and culture supernatants were subjected to SDS polyacrylamide gel electrophoresis. The gel was blotted and analyzed using the WESTERN BLOTTING PROCEDURE. A polyclonal swine anti-PRV serum was used to detect expression of PRV specific proteins. The cell lysate and supernatants from S-SPV-054 infected cells exhibited a band corresponding to 92 kD which is the expected size of the PRV glycoprotein C and a 48 kD which is the expected size of the PRV glycoprotein D.

SPV recombinant-expressed PRV gC and gD has been shown to elicit a significant immune response in swine (37, 38; See example 8). Furthermore, PRV gC and gD are expressed in recombinant SPv, significant protection from challenge with virulent PRV is obtained. (See Examples 6 and 8) Therefore S-SPV-054 is valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals.

S-SPV-055

S-SPV-055 is a swinepox virus that expresses four foreign genes. The gene for *E. coli* β-galactosidase (lacZ) and the gene for pseudorabies virus gB (gII) were inserted into the unique HindIII restriction site (HindIII linkers inserted into a unique NdeI site in the SPV O1L open reading frame; An approximately 545 base pair NdeI to NdeI subfragment (Nucleotides 1560 to 2104 of the SPV HindIII M fragment has been deleted). The gene for PRV gD (g50) and PRV gC (gIII) were inserted into the unique PstI restriction site (PstI linkers inserted into a unique AccI site in the SPV O1L open reading frame). The lacZ gene is under the control of the synthetic late promoter (LP1), the PRV gB (gII) gene is under the control of the synthetic late/early promoter (LP2EP2), the PRV gD (g50) gene is under the control of the synthetic late/early promoter (LP2EP2), and the PRV gC (gIII) gene is under the control of the synthetic early/late promoter (EP1LP2).

S-SPV-055 was derived from S-SPV-001 (Kasza Strain). This was accomplished utilizing the homology vector 789-41.73 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 055. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-055 was assayed for expression of PRV specific antigens using the BLACK PLAQUE SCREEN FOR FOREIGN GENE EXPRESSION IN RECOMBINANT SPV. Polyclonal swine anti-PRV serum was shown to react specifically with S-SPV-055 plaques and not with S-SPV-001 negative control plaques. All S-SPV-055 observed plaques reacted with the swine anti-PRV serum indicating that the virus was stably expressing the PRV foreign gene. The assays described here were carried out in ESK-4 cells, indicating that ESK-4 cells would be a suitable substrate for the production of SPV recombinant vaccines.

To confirm the expression of the PRV gB, gC and gD gene products, cells were infected with S-SPV-055 and samples of infected cell lysates and culture supernatants were subjected to SDS polyacrylamide gel electrophoresis. The gel was blotted and analyzed using the WESTERN BLOTTING PROCEDURE. A polyclonal swine anti-PRV serum was used to detect expression of PRV specific proteins. The cell lysate and supernatants from S-SPV-055 infected cells exhibited a bands corresponding to 120 kD, 67 kD, and 58 kD which is the expected size of the PRV glycoprotein B; a 92 kD which is the expected size of the PRV glycoprotein C; and a 48 kD which is the expected size of the PRV glycoprotein D.

SPV recombinant-expressed PRV gB, gC and gD has been shown to elicit a significant immune response in swine (37, 38; See example 8). Furthermore, PRV gB, gC and gD are expressed in recombinant SPV, significant protection from challenge with virulent PRV is obtained. (See Examples 6 and 8) Therefore S-SPV-055 is valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals.

Example 29

SPV-059

S-SPV-059 is a swinepox virus that expresses one foreign gene. The gene for *E. coli* β-glucuronidase (uida) was inserted into the unique EcoRI restriction site in the SPV B18R open reading frame within the SPV HindIII K genomic fragment. The uidA gene is under the control of the synthetic late/early promoter (LP2EP2). Partial sequence from a 3.2 kb region of the SPV 6.5 kb HindIII K fragment indicates three potential open reading frames. The SPV B18R ORF shows sequence homology to the vaccinia virus B18R gene, 77.2K protein from rabbit fibroma virus, vaccinia virus C19L/B25R ORF and an ankyrin repeat region from a human brain variant. The B18R gene codes for a soluble interferon receptor with high affinity and broad specificty. The SPV B4R open reading frame shows sequence homology to the T5 protein of rabbit fibroma virus.

S-SPV-059 was derived from S-SPV-001 (Kasza Strain). This was accomplished utilizing the homology vector 796-50.31 and virus S-SPV-001 in the HOMOLOGOUS RECOMBINATION PROCEDURE FOR GENERATING RECOMBINANT SPV. Homology vector 796-50.31 was generated by insertion of a blunt ended NotI fragment containing the LP2EP2 promoter uida cassette from plasmid 551-47.23 (see Materials and Methods) into a unique EcoRI site (blunt ended) in the SPV 6.5 kb HindIII K fragment, (FIG. 29B). The transfection stock was screened by the SCREEN FOR RECOMBINANT HERPESVIRUS EXPRESSING ENZYMATIC MARKER GENES. The final result of blue plaque purification was the recombinant virus designated S-SPV-059. This virus was assayed for β-glucuronidase expression, purity, and insert stability by multiple passages monitored by the blue plaque assay as described in Materials and Methods. After the initial three rounds of purification, plaques observed were blue indicating that the virus was pure, stable, and expressing the foreign gene.

S-SPV-059 has been purified and expresses the foreign gene, *E. coli* uidA, indicating that the EcoRI site within the 6.5 kb HindIII K fragment is a stable insertion site for foreign genes. Recombinant swinepox virus utilizing this insertion site is useful for expression of foreign antigen genes, as a vaccine against disease or as an expression vector to raise antibodies to the expressed foreign gene.

SPV-060

S-SPV-060 is a swinepox virus that expresses one foreign gene. The gene for *E. coli* β-glucuronidase (uidA) was inserted into the unique EcoRV restriction site within the SPV HindIII N genomic fragment. The uida gene is under the control of the synthetic late/early promoter (LP2EP2). Partial sequence of the SPV 3.2 kb HindIII N fragment indicates two potential open reading frames. The SPV I7L ORF shows sequence homology to protein I7 of vaccinia virus. The SPV I4L open reading frame shows sequence homology to the ribonucleoside diphosphate reductase gene of vaccinia virus. Two potential open reading frames I5L and I6L, between I4L ORF and I7L ORF are of unknown function.

S-SPV-060 was derived from S-SPV-001 (Kasza Strain). This was accomplished utilizing the homology vector 796-71.31 and virus S-SPV-001 in the HOMOLOGOUS RECOMBINATION PROCEDURE FOR GENERATING RECOMBINANT SPV. Homology vector 796-71.31 was generated by insertion of a blunt ended NotI fragment containing the LP2EP2 promoter uida cassette from plasmid 551-47.23 (see Materials and Methods) into a unique EcoRV site in the SPV 3.2 kb HindIII N fragment (FIG. 29A). The transfection stock was screened by the SCREEN FOR RECOMBINANT HERPESVIRUS EXPRESSING ENZYMATIC MARKER GENES. The final result of blue plaque purification is the recombinant virus designated S-SPV-060. This virus is assayed for β-glucuronidase expression, purity, and insert stability by multiple passages monitored by the blue plaque assay as described in Materials and Methods. After the initial three rounds of purification, plaques observed are blue indicating that the virus is pure, stable, and expressing the foreign gene.

S-SPV-060 is purified and expresses the foreign gene, *E. coli* uidA, indicating that the EcoRI site within the 3.2 kb HindIII N fragment is a stable insertion site for foreign genes. Recombinant swinepox virus utilizing this insertion site is useful for expression of foreign antigen genes, as a vaccine against disease or as an expression vector to raise antibodies to the expressed foreign gene.

S-SPV-061

S-SPV-061 is a swinepox virus that expresses one foreign gene. The gene for *E. coli* β-glucuronidase (uidA) was inserted into the unique SnaBI restriction site within the SPV HindIII N genomic fragment. The uidA gene is under the control of the synthetic late/early promoter (LP2EP2). Partial sequence of the SPV 3.2 kb HindIII N fragment indicates two potential open reading frames. The SPV I7L ORF shows sequence homology to protein 17 of vaccinia virus. The SPV I4L open reading frame shows sequence homology to the ribonucleoside diphosphate reductase gene of vaccinia virus. Two potential open reading frames I5L and I6L, between I4L ORF and I7L ORF are of unknown function.

S-SPV-061 was derived from S-SPV-001 (Kasza Strain). This was accomplished utilizing the homology vector 796-71.41 and virus S-SPV-001 in the HOMOLOGOUS RECOMBINATION PROCEDURE FOR GENERATING RECOMBINANT SPV. Homology vector 796-71.41 was generated by insertion of a blunt ended NotI fragment containing the LP2EP2 promoter uidA cassette from plasmid 551-47.23 (see Materials and Methods) into a unique SnaBI site in the SPV 3.2 kb HindIII N fragment. The transfection stock was screened by the SCREEN FOR RECOMBINANT HERPESVIRUS EXPRESSING ENZYMATIC MARKER GENES. The final result of blue plaque purification is the recombinant virus designated S-SPV-061. This virus is assayed for β-glucuronidase expression, purity, and insert stability by multiple passages monitored by the blue plaque assay as described in Materials and Methods. After the initial three rounds of purification, plaques observed are blue indicating that the virus is pure, stable, and expressing the foreign gene.

S-SPV-061 is purified and expresses the foreign gene, *E. coli* uidA, indicating that the SnaBI site within the 3.2 kb HindIII N fragment is a stable insertion site for foreign genes. Recombinant swinepox virus utilizing this insertion site is useful for expression of foreign antigen genes, as a vaccine against disease or as an expression vector to raise antibodies to the expressed foreign gene.

S-SPV-062

S-SPV-062 is a swinepox virus that expresses one foreign gene. The gene for *E. coli* β-glucuronidase (uidA) was inserted into the unique BglII restriction site within the SPV HindIII N genomic fragment (FIG. 29A). The uidA gene is under the control of the synthetic late/early promoter (LP2EP2). Partial sequence of the SPV 3.2 kb HindIII N fragment indicates two potential open reading frames. The SPV I7L ORF shows sequence homology to protein 17 of vaccinia virus. The SPV I4L open reading frame shows sequence homology to the ribonucleoside diphosphate reductase gene of vaccinia virus. Two potential open reading frames I5L and I6L, between I4L ORF and I7L ORF are of unknown function.

S-SPV-062 was derived from S-SPV-001 (Kasza Strain). This was accomplished utilizing the homology vector 796-71.51 and virus S-SPV-001 in the HOMOLOGOUS RECOMBINATION PROCEDURE FOR GENERATING RECOMBINANT SPV. Homology vector 796-71.51 was generated by insertion of a blunt ended NotI fragment containing the LP2EP2 promoter uidA cassette from plasmid 551-47.23 (see Materials and Methods) into a unique BglII site in the SPV 3.2 kb HindIII N fragment. The transfection stock was screened by the SCREEN FOR RECOMBINANT HERPESVIRUS EXPRESSING ENZYMATIC MARKER GENES. The final result of blue plaque purification is the recombinant virus designated S-SPV-062. This virus is assayed for β-glucuronidase expression, purity, and insert stability by multiple passages monitored by the blue plaque assay as described in Materials and Methods. After the initial three rounds of purification, plaques observed are blue indicating that the virus is pure, stable, and expressing the foreign gene.

S-SPV-062 is purified and expresses the foreign gene, *E. coli* uidA, indicating that the BglII site within the 3.2 kb HindIII N fragment is a stable insertion site for foreign genes. Recombinant swinepox virus utilizing this insertion site is useful for expression of foreign antigen genes, as a vaccine against disease or as an expression vector to raise antibodies to the expressed foreign gene.

Example 30

Recombinant swinepox virus expressing *E coli* β-galactosidase (lacZ) under the control of a synthetic early or synthetic late pox promoter.

Three recombinant swinepox viruses, S-SPV-056, S-SPV-057, and S-SPV-058 expressing *E coli* β-galactosidase (lacZ) under the control of a synthetic pox promoter, LP1, LP2, and EP1, respectively, have been constructed.

S-SPV-056 was derived from S-SPV-001 (Kasza Strain). This was accomplished utilizing the homology vector 791-63.19 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). S-SPV-057 was derived from S-SPV-001 (Kasza Strain). This was accomplished utilizing the homology vector 791-63.41 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). S-SPV-058 was derived from S-SPV-001 (Kasza Strain). This was accomplished utilizing the homology vector 796-18.9 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification were the recombinant viruses designated S-SPV-056, S-SPV-057 and S-SPV-058. The viruses were assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

Recombinant swinepox virus expresses a foreign gene such as *E. coli* β-galactosidase in a human cell line but does not replicate in the human cell line. To optimize expression of the foreign gene, S-SPV-056, S-SPV-057 and S-SPV-058 are used to compare optimal expression levels of *E. coli* β-galactosidase under the control of early or late synthetic pox viral promoters. The human cell lines in which expression of recombinant swinepox virus has been detected include, but are not limited to 143B (osteosarcoma), A431 (epidermoid carcinoma), A549 (lung carcinoma), Capan-1 (liver carcinoma), CF500 (foreskin fibroblasts), Chang Liver (liver), Detroit (down's foreskin fibroblasts), HEL-199 (embryonic lung), HeLa (cervical carcinoma), HEp-2 (epidermal larynx carcinoma), HISM (intestinal smooth muscle), HNK (neonatal kidney), MRC-5 (embryonic lung), NCI-H292 (pulmonary mucoepidermoid carcinoma), OVCAR-3 (ovarian carcinoma), RD (rhabdosarcoma), THP (monocyte leukemia), WIL2-NS (B lymphocyte line, non-secreting), WISH (amnion).

Example 31

S-SPV-051

S-SPV-051 is a swinepox virus that expresses at least two foreign genes. The gene for *E. coli* β-galactosidase (lacZ) and the gene for the bovine viral diarrhea virus glycoprotein 53 (g53) were inserted into the SPV 617-48.1 ORF (a unique NotI restriction site has replaced a unique AccI restriction site). The lacZ gene is under the control of the synthetic late promoter (LP1), and the BVDV g53 gene is under the control of the synthetic late/early promoter (LP2EP2).

S-SPV-051 was derived from S-SPV-001 (Kasza Strain). This was accomplished utilizing the homology vector 783-39.2 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 051. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-051 was assayed for expression of BVDV specific antigens using the BLACK PLAQUE SCREEN FOR FOR- EIGN GENE EXPRESSION IN RECOMBINANT SPV. A mouse monoclonal antibody to BVDV g53 was shown to react specifically with S-SPV-051 plaques and not with S-SPV-001 negative control plaques. All S-SPV-051 observed plaques reacted with the monoclonal antibody to BVDV g53 indicating that the virus was stably expressing the BVDV foreign gene. The assays described here were carried out in ESK-4 cells, indicating that ESK-4 cells would be a suitable substrate for the production of SPV recombinant vaccines.

To confirm the expression of the BVDV g53 gene product, cells were infected with S-SPV-051 and samples of infected cell lysates and culture supernatants were subjected to SDS polyacrylamide gel electrophoresis. The gel was blotted and analyzed using the WESTERN BLOTTING PROCEDURE. A mouse monoclonal antibody to BVDV g53 was used to detect expression of BVDV specific proteins. The cell lysate and supernatant from S-SPV-051 infected cells exhibited bands at 53 kd and higher indicating glycosylated and unglycosylated forms of the BVDV g53 protein.

S-SPV-051 is useful as a vaccine in cattle against BVDV infection and is useful for expression of BVDV glycoprotein 53.

Example 32

S-SPV-044

S-SPV-044 is a swinepox virus that expresses at least two foreign genes. The gene for *E. coli* β-galactosidase (lacZ) and the gene for the infectious bursal disease virus (IBDV) polymerase protein were inserted into the 617-48.1 ORF (a unique NotI site has replaced a unique AccI restriction site). The lacZ gene is under the control of the synthetic late promoter (LP1), and the IBDV polymerase gene is under the control of the synthetic late/early promoter (LP2EP2).

S-SPV-044 was derived from S-SPV-001 (Kasza Strain). This was accomplished utilizing the homology vector 749-75.78 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-044. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-044 is useful for expression of IBDV polymerase protein. S-SPV-044 is useful in an in vitro approach to a recombinant IBDV attenuated vaccine. RNA strands from the attenuated IBDV strain are synthesized in a bacterial expression system using T3 or T7 promoters (pBlueScript plasmid; Stratagene, Inc.) to synthesize double stranded short and long segments of the IBDV genome. The IBDV double stranded RNA segments and S-SPV-044 are transfected into CEF cells. The swinepox virus expresses the IBDV polymerase but does not replicate in CEF cells. The IBDV polymerase produced from S-SPV-044 synthesizes infectious attenuated IBDV virus from the double stranded RNA genomic templates. The resulting attenuated IBDV virus is useful as a vaccine against infectious bursal disease in chickens.

Example 33

S-SPV-046

S-SPV-046 is a swinepox virus that expresses at least two foreign genes. The gene for *E. coli* β-galactosidase (lacZ) and the gene for the feline immunodeficiency virus (FIV) gag protease (gag) were inserted into the 738-94.4 ORF (a 773 base pair deletion of the SPV O1L ORF; Deletion of nucleotides 1669 to 2452, SEQ ID NO: 189). The lacZ gene is under the control of the swinepox O1L promoter, and the FIV gag gene is under the control of the synthetic late/early promoter (LP2EP2).

S-SPV-046 was derived from S-SPV-001 (Kasza Strain). This was accomplished utilizing the homology vector 761-75.B18 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 046. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

To confirm the expression of the FIV gag gene product, cells were infected with S-SPV-046 and samples of infected cell lysates and culture supernatants were subjected to SDS polyacrylamide gel electrophoresis. The gel was blotted and analyzed using the WESTERN BLOTTING PROCEDURE. Feline anti-FIV (PPR strain) sera was used to detect expression of FIV specific proteins. The cell lysate and supernatant from S-SPV-046 infected cells exhibited bands at 26 kd and 17 kd which are the expected sizes of the processed form of the FIV gag protein. The recombinant swinepox virus expressed FIV gag protein is processed properly and secreted into the culture media.

S-SPV-048

S-SPV-048 is a swinepox virus that expresses at least two foreign genes. The gene for *E. coli* β-galactosidase (lacZ) and the gene for feline immunodeficiency virus (FIV) envelope (env) were inserted into the SPV 617 48.1 ORF (a unique NotI restriction site has replaced a unique AccI restriction site). The lacZ gene is under the control of the synthetic late promoter (LP1), and the FIV env gene is under the control of the synthetic late/early promoter (LP2EP2).

S-SPV-048 was derived from S-SPV-001 (Kasza Strain). This was accomplished utilizing the homology vector 781-84.C11 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 048. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-046 and S-SPV-048 are useful alone or in combination as a vaccine in cats against FIV infection and are useful for expression of the FIV env and gag proteins. A recombinant swinepox virus expressing both the FIV env and gag proteins is useful as a vaccine in cats against FIV infection.

Recombinant swinepox virus expressing human respiratory synctial virus F and G proteins is useful as a vaccine against the human disease.

Example 34

In vitro Properties of Chicken IFN Expressed in Recombinant Pox Viruses

Growth properties of recombinant viruses in cell culture. Growth properties of recombinant S-SPV-042 were not effected in embryonic swine kidney cells (ESK-4) compared to wild-type swinepox virus.

Western blot analysis was performed on supernatants from cells infected with SPV/cIFN recombinant virus. Rabbit and mouse antisera were raised against cIFN from concentrated SPV/cIFN infected supernatants and pre-cleared against ESK-4 cells infected with wild-type SPV in preparation for western analysis. Rabbit and mouse anti-cIFN antisera were reacted with denatured proteins on nitrocellulose from recombinant SPV/cIFN and SPV wild type virus infected supernatants. A reactive band with an estimated molecular weight size range of 17-20 kilodaltons was present in the SPV/cIFN lanes, and absent in the SPV wild type control lanes.

Effect of cIFN Expressed in Supernatants from SPV/cIFN (S-SPV-042), FPV/cIFN, and FPV/cIFN/NDV Infected Cells on the Growth of Vesicular Stomatis Virus Virion cleared supernatants from SPV/cIFN, FPV/cIFN and FPV/cIFN/NDV infected cells were tested for the presence of viral inhibitory activity, results shown in Table 1. Briefly, CEF cells were incubated with serially diluted viral supernatants. Subsequently, 40,000 plaque forming units (pfu)/well of vesicular stomatitis virus (VSV) were added and 48 hours later, wells were scored for the presence of VSV cytopathic effect (CPE). Recombinant viral supernatants containing cIFN were shown to inhibit VSV induced CPE, whereas, control viral supernatants did not. VSV induced cytopathic effect could be reversed in the presence of rabbit anti-cIFN sera.

TABLE 1

| Recombinant Viral Supernatants. | cIFN Activity (units/ml)[a] |
|---|---|
| SPV/IFN | 2,500000 |
| SPV | <100 |
| FPV/IFN | 250,000 |
| FPV/cIFN/NDV | 250,000 |
| FPV | <100 |

[a]One unit of cIFN activity is defined as the dilution of pox virus supernatant at which 100% VSV CPE was inhibited.

Effect of cIFN Expressed from Supernatants of SPV/cIFN Infected Cells on Herpes Virus of Turkeys Supernatant containing recombinant cIFN from ESK-4 cells infected with SPV/cIFN virus, was tested for its ability to inhibit the growth of herpes virus of turkeys (HVT) in CEF cells, results shown in Table 2. Briefly, serially diluted supernatants were incubated with CEF cells, and then subsequently infected with 100 pfu/well of wild-type HVT. Plaques were counted in all wells after 48 hours. It was shown that 10–100 units of cIFN activity inhibited plaque formation of HVT(100 pfu/well). Supernatants from wild type SPV did not inhibit HVT plaque formation.

TABLE 2

| SPV/cIFN Supernatant (units/ml[a]) | Number of HVT plaques |
|---|---|
| 0 | 99 |
| 1000 | 0 |
| 100 | 0 |
| 10 | 45 |

[a]One unit of cIFN activity is defined as the dilution of pox virus supernatant at which 100% VSV CPE was inhibited.

Induction of NO by Chicken Macrophages After Treatment with cIFN Expressed in Supernatants from SPV/cIFN Infected Cells HD 11 cells or bone marrow adherent cells were incubated with 1000 unit/ml of cIFN from SPV/cIFN supernatants, lipopolysaccharide (L,PS) (6 ng/ml) or with both cIFN and LPS, results shown in Table 3. After 24 hours, supernatant fluids were collected and nitrite levels were measured. These data demonstrate that cIFN expressed from SPV/cIFN supernatants has the ability to activate chicken macrophages in the presence of LPS.

TABLE 3

| | Nitrite (micro/mol) levels following stimulation with : | | |
|---|---|---|---|
| Cell source | LPS | SPV/cIFN | LPS + SPV/cIFN |
| HD11 | 10.76 | 6.4 | 35.29 |
| BMAC | 13.1 | 5.8 | 35.10 |

Conclusions

1. Recombinant swinepox viruses express biologically active chicken interferon into the supernatants of infected cells, as measured by protection of CEF cells from VSV infection.
2. Chicken interferon expressed in supernatants from recombinant SPV/cIFN infected cells has been shown to protect CEF cells against infection with HVT in a dose dependent manner.
3. Chicken interferon expressed from SPV/cIFN acted synergistically with LPS to activate chicken macrophages as detected by nitric oxide induction.
4. The foregoing data indicate that recombinant swinepox viruses expressing chicken IFN may have beneficial applications as immune modulating agents in vitro, in vivo and in ovo.

Example 35

As an alternative to the construction of a IBD vaccine using a viral vectored delivery system and/or subunit approaches, IBD virus RNA is directly manipulated re-constructing the virus using full length RNA derived from cDNA clones representing both the large (segment A) and small (segment B) double-stranded RNA subunits. Generation of IBD virus is this manner offers several advantages over the first two approaches. First, if IBD virus is re-generated using RNA templates, one is able to manipulate the cloned cDNA copies of the viral genome prior to transcription (generation of RNA). Using this approach, it is possible to either attenuate a virulent IBD strain or replace the VP2 variable region of the attenuated vaccine backbone with that of virulent strains. In doing so, the present invention provides protection against the virulent IBDV strain while providing the safety and efficacy of the vaccine strain.

Furthermore, using this approach, the present invention constructs and tests temperature sensitive IBD viruses generated using the RNA polymerase derived from the related birnavirus infectious pancreatic necrosis virus (IPNV) and the polyprotein derived from IBDV. The IPNV polymerase has optimum activity at a temperature lower than that of IBDV. If the IPNV polymerase recognizes the regulatory signals present on IBDV, the hybrid virus is expected to be attenuated at the elevated temperature present in chickens. Alternatively, it is possible to construct and test IBD viruses generated using the RNA polymerase derived from IBDV serotype 2 virus and the polyprotein derived from IBDV-serotype 1 virus.

cDNA clones representing the complete genome of IBDV (double stranded RNA segments A and B) is constructed, initially using the BursaVac vaccine strain (Sterwin Labs). Once cDNA clones representing full length copies of segment A and B are constructed, template RNA is prepared. Since IBDV exists as a bisegmented double-stranded RNA virus, both the sense and anti-sense RNA strands of each segment are produced using the pBlueScript plasmid; Stratagene, Inc.). These vectors utilize the highly specific phage promoters SP6 or T7 to produce substrate amounts of RNA in vitro. A unique restriction endonuclease site is engineered into the 3' PCR primer to linearize the DNA for the generation of run-off transcripts during transcription.

The purified RNA transcripts (4 strands) are transfected into chick embryo fibroblasts (CEF) cells to determine whether the RNA is infectious. If IBD virus is generated, as determined by black plaque assays using IBDV specific Mabs, no further manipulations are required and engineering of the vaccine strain can commence. The advantage of this method is that engineered IBD viruses generated in this manner will be pure and require little/no purification, greatly decreasing the time required to generate new vaccines. If negative results are obtained using the purified RNA's, functional viral RNA polymerase is required by use of a helper virus. Birnaviruses replicate their nucleic acid by a strand displacement (semi-conservative) mechanism, with the RNA polymerase binding to the ends of the double-stranded RNA molecules forming circularized ring structures (Muller & Nitschke, Virology 159, 174–177, 1987). RNA polymerase open reading frame of about 878 amino acids in swinepox virus is expressed and this recombinant virus (S-SPV-044) is used to provide functional IBDV RNA polymerase in trans. Swinpox virus expressed immunologically recognizable foreign antigens in avian cells (CEF cells), where there are no signs of productive replication of the viral vector. In the present invention the IBDV polymerase protein is expressed in the same cells as the transfected RNA using the swinepox vector without contaminating the cells with SPV replication.

With the demonstration that IBD virus is generated in vitro using genomic RNA, an improved live attenuated virus vaccines against infectious bursal disease is developed. Using recombinant DNA technology along with the newly defined system of generating IBD virus, specific deletions within the viral genome, facilitating the construction of attenuated viruses are made. Using this technology, the region of IBDV responsible for virulence and generate attenuated, immunogenic IBDV vaccines are identified. The present invention provides a virulent IBD strain or replacement of the VP2 variable region of the attenuated vaccine backbone with that of a virulent strain, thus protecting against the virulent strain while providing the safety and efficacy of the vaccine strain.

Example 36
Effects of Rabbit Anti-chicken Interferon (cIFN) Antibody on the Growth of Herpes Virus of Turkeys Supernatants from SPV/cIFN (SPV 042) infected ESK-4 cells were harvested 48 hours after infection and then concentrated 5–10 times, by Centricon 10 columns (Amicon). One ml of concentrated supernatant was injected into a rabbit 3 times, at 3 week intervals, and then bled. This rabbit antisera was then used in culture to study the effect of interferon on the growth of HVT. It was shown that anti-cIFN reverses the block to HVT (1:200) and VSV(1:80) growth induced by the addition of cIFN in plaque assays. Furthermore, it was shown that the addition of anti-cIFN (1:100) in the media of CEFs transiently transfected with sub-plaqueing levels of HVT viral DNA, enhances the formation of HVT plaques (200 plaques/well). CEFs transfected with HVT DNA in the absence of anti-cIFN did not yield plaques.

HVT is highly susceptible to interferon produced from CEFs and that when cIFN is blocked, HVT growth is enhanced.

Applications include: (1) Use antibody to cIFN as an additive to increase HVT titers in vaccine stocks; (2) Use antibody to cIFN as an additive to facilitate the formation of new recombinant HVT viruses via cosmid reconstructions.

REFERENCES

1. C. Bertholet, et al., *EMBO Journal* 5, 1951–1957 (1986).
2. R. A. Bhat, et al., *Nucleic Acids Research* 17, 1159–1176 (1989).
3. D. A. Boyden, et al., *Infection and Immunity* 57, 3808–3815 (1989).
4. D. B. Boyle and B. E. H. Coupar, *Virus Research* 10, 343–356 (1988).
5. R. M. Buller, et al., *Nature* 317, 813–815 (1985).
6. K. J. Cremer, et al., *Science* 228, 737–739 (1985).
7. A. J. Davidson and B. Moss, *J. Mol. Biol.* 210, 749–769 (1989).
8. A. J. Davidson and B. Moss, *J. Mol. Biol.* 210, 771–784 (1989).
9. P. L. Earl, et al., *Journal of Virology* 64, 2448–2451 (1990).
10. C. J. Esposito, et al., *Virology* 165, 313 (1988).
11. F. A. Ferrari, et al., *J. of Bacteriology* 161, 556–562 (1985).
12. C. Flexner, et al., *Vaccine* 8, 17–21 (1990).
13. S. J. Goebel, et al., *Virology* 179, 247–266 (1990).
14. U. Gubler and B. J. Hoffman, *Gene* 25, 263–269 (1983).
15. M. A. Innis, et al., *PCR Protocols A Guide to Methods and Applications,* 84–91, Academic Press, Inc., San Diego (1990).
16. S. Joshi, et al., *Journal of Virology.* 65, 5524–5530 (1991).
17. L. Kasza, et al., *Am. J. Vet. Res.* 21, 269–273 (1960).
18. L. Kasza, *Diseases of Swine,* 254–260, Ed. A. D. Leman, et al., The Iowa State University Press, Ames, Iowa (1981).
19. B. G. Klupp and T. C. Mettenleiter, *Virology* 182, 732–741 (1991).
20. U. K. Laemnli, *Nature* 227, 680–685 (1970).
21. B. Lominiczi, et al., *Journal of Virology* 49, 970–979 (1984).
22. T. Maniatis, et al., *Molecular Cloning: A Laboratory Manual,* Cold Spring Harbor Press, Cold Spring Harbor, N.Y. (1982).
23. R. F. Massung, and R. W. Moyer, *Virology* 180, 347–354 (1991).

24. R. F. Massung, and R. W. Moyer, *Virology* 180, 355–364 (1991).
25. B. Moss, *Science* 252, 1662–1667 (1991).
26. E. A. Petrovskis, et al., *Journal of Virology* 59, 216–223 (1986).
27. A. K. Robbins et al., *Journal of Virology* 58, 339–347 (1986).
28. A. K. Robbins et al., *Journal of Virology* 61, 2691–2701 (1987).
29. A. C. R. Samson, *Journal of Virology* 67, 1199–1203 (1986).
30. J. Sambrook, et al., *Molecular Cloning A Laboratory Manual Second Edition,* Cold Spring Harbor Press, Cold Spring Harbor, N.Y. (1989).
31. Sheffy, et al., *Proceedings 65th Annual Meeting of the United States Livestock Association* 65, 347–353 (1961).
32. W. M. Schnitzlein and D. N. Tripathy, *Virology* 181, 727–732, (1991).
33. J. Taylor, et al., *Vaccine* 9, 190–193, (1991).
34. M. Wachsman, et al., *Journal of General Virology* 70, 2513–2520 (1989).
35. M. W. Wathen, et al., *Journal of Virology* 51, 57–62 (1984).
36. M. Weerasinge, *Journal of Virology* 65, 5531–5534 (1991).
37. T. Ben-Porat, et al., *Journal of Virology,* volume 154, 325–334 (1986).
38. F. Zuckerman, et al., *Vaccination and Control of Adjesky's Disease,* J. T. Van Oirchot (ed.). Kluwer Academic Publishers, London, pp. 107–117 (1989).
39. Paolette, et al., *Journal of Virology,* volume 66, pp. 3424–3434 (June, 1992).
40. M. W. Mellencamp, et al., *Journal of Clinical Microbiology,* volume 27, pp. 2208–2213 (1989).
41. L. A. Herzenberg, et al., *Selected Methods in Cellular Immunology,* Freeman Publ. Co., San Francisco, 351–372 (1980).
42. Katz et al., *Journal of Virology* 64, 1808–1811 (1990).
43. Taniguchi, T., et al., *Biochem. Biophys. Res. Commun.* 115 1040–1047 (1983).
44. Cochran, M. D. and Macdonald, R. D., WO 93/02104, published Feb. 4, 1993.
45. Galibert, F., et al., *Nature* 281, 646–650 (1979).
46. Thomsen, D. R., et al., *Proc. Natl. Acad. Sci. USA* 81, 659–663 (1984).
47. Catalog Number 267402, Beckman Instruments, Inc., Fullerton Calif.
48. Whalley, J. M., et al., *Journal of General Virology* 57 307–323 (1981).
49. Collett, M. S., et al., *Virology* 165 200–208 (1988).
50. Schodel, F. et al., *Journal of Virology* 66, 106–114 (1992).
51. Cochran, M. D., WO 93/25665, published Dec. 23, 1993.
52. C. A. Hjerpe, *The bovine Respiratory Disease Complex.* Ed. by J. L. Howard, Philadelphia, W. B. Saunders Co., 670–680 (1986).
53. F. Fenner, et al., *Veterinary Virology.* Academic Press, Inc., Orlando Fla., 183–202 (1987).
54. A. Leutz, et al., EMBO Journal 8: 175–182 (1989).
55. M. J. Sekellick, et al., Journal of Interferon Research 14: 71–79 (1994).
56. S. J. Child, et al., Virology 174: 625–629 (1990).
57. G. P. Johnson, et al. Virology 196: 381–401 (1993).
58. R. F Massung, et al. Virology 201: 215–240 (1994).
60. Child, S. J. et al., Virology 174, 625–629 (1990).
61. T. R. Phillips, et al., J. Virology 64, 4605–4613 (1990).

What is claimed is:

1. A recombinant swinepox virus comprising a foreign DNA inserted into a swinepox virus genome, wherein the foreign DNA is inserted within a region corresponding to a 3.2 kB subfragment which contains a HindIII site and an EcoRI site within the HindIII K fragment of the swinepox virus genome and is capable of being expressed in a host cell into which the virus is introduced.

2. The recombinant swinepox virus of claim 1, wherein the foreign DNA is inserted into an open reading frame within the region corresponding to the 3.2 kB subfragment.

3. The recombinant swinepox virus of claim 2, wherein the foreign DNA is inserted into a B18R gene.

4. The recombinant swinepox virus of claim 2, wherein the foreign DNA is inserted into a B4R gene.

5. The recombinant swinepox virus of claim 1, wherein the foreign DNA encodes a polypeptide.

6. The recombinant swinepox virus of claim 5, wherein the polypeptide is antigenic.

7. The recombinant swinepox virus of claim 5, wherein the polypeptide is derived from a virus which is selected from the group consisting of: human herpesvirus, herpes simplex virus-1, herpes simplex virus-2, human cytomegalovirus, Epstein-Barr virus, varicella-zoster virus, human herpesvirus-6, human herpesvirus-7, human influenza, human immunodeficiency virus, rabies virus, measles virus, hepatitis B virus, and hepatitis C virus.

8. The recombinant swinepox virus of claim 5, wherein the polypeptide is hepatitis B virus core protein or hepatitis B virus surface protein.

9. The recombinant swinepox virus of claim 5, wherein the polypeptide is equine influenza virus neuraminidase or equine influenza virus hemagglutinin.

10. The recombinant swinepox virus of claim 5, wherein the polypeptide is selected from the group consisting of: equine influenza virus type A/Alaska 91 neuraminidase, equine influenza virus type A/Kentucky 92 neuraminidase, equine influenza virus type A/Prague 56 neuraminidase, equine influenza virus type A/Miami 63 neuraminidase, equine influenza virus type A/Kentucky 81 neuraminidase, equine herpesvirus type 1 glycoprotein B, and equine herpesvirus type 1 glycoprotein D.

11. The recombinant swinepox virus of claim 5, wherein the polypeptide is selected from the group consisting of: hog cholera virus glycoprotein E1, hog cholera virus glycoprotein E2, swine influenza virus hemagglutinin, swine influenza virus neuraminidase, swine influenza virus matrix, swine influenza virus nucleoprotein, pseudorabies virus glycoprotein B, pseudorabies virus glycoprotein C, pseudorabies virus glycoprotein D, and PRRS virus ORF7.

12. The recombinant swinepox virus of claim 5, wherein the polypeptide is selected from the group consisting of: Infectious bovine rhinotracheitis virus gE, bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase.

13. The recombinant swinepox virus of claim 5, wherein the polypeptide is bovine viral diarrhea virus (BVDV) glycoprotein 48 or bovine viral diarrhea virus glycoprotein 53.

14. The recombinant swinepox virus of claim 5, wherein the polypeptide is selected from the group consisting of: feline immunodeficiency virus gag, feline immunodeficiency virus env, infectious laryngotracheitis virus glycoprotein B, infectious laryngotracheitis virus glycoprotein I, infectious laryngotracheitis virus glycoprotein D, infectious bovine rhinotracheitis virus glycoprotein G, infectious bovine rhinotracheitis virus glycoprotein E, pseudorabies virus glycoprotein 50, pseudorabies virus II glycoprotein B, pseudorabies virus III glycoprotein C, pseudorabies virus glycoprotein E, pseudorabies virus glycoprotein H, Marek's disease virus glycoprotein A, Marek's disease virus glycoprotein B, Marek's disease virus glycoprotein D, Newcastle disease virus hemagglutinin, Newcastle disease virus neuraminidase, Newcastle disease virus fusion, infectious bursal disease virus VP2, infectious bursal disease virus VP3, infectious bursal disease virus VP4, infectious bursal disease virus polyprotein, infectious bronchitis virus spike, and infectious bronchitis virus matrix.

15. The recombinant swinepox virus of claim 5, wherein the polypeptide is derived from an organism selected from the group consisting of *Streptococcus equi,* equine infectious anemia virus, equine encephalitis virus, equine rhinovirus and equine rotavirus.

16. The recombinant swinepox virus of claim 5, wherein the polypeptide is derived from an organism selected from the group consisting of avian encephalomyelitis virus, avian reovirus, avian paramyxovirus, avian influenza virus, avian adenovirus, fowlpox virus, avian coronavirus, avian rotavirus, chick anemia virus, Salmonella spp., *E. coli,* Pasteurella spp., Bordetella spp., Eimeria spp., Histomonas spp., Trichomonas spp., poultry. nematodes, cestodes, trematodes, poultry mites, poultry lice and poultry protozoa.

17. The recombinant swinepox virus of claim 5, wherein the polypeptide is derived from an organism selected from the group consisting of canine herpesvirus, canine distemper virus, canine adenovirus type 1, canine adenovirus type 2, parainfluenza virus, *Leptospira canicola,* parvovirus, coronavirus, *Borrelia burgdorferi,* canine herpesvirus, *Bordetella bronchiseptica, Dirofilaria immitis* and rabies virus.

18. The recombinant swinepox virus of claim 5, wherein the polypeptide is derived from a virus selected from the group consisting of feline leukemia virus, feline immunodeficiency virus, feline herpesvirus and feline infectious peritonitis virus.

19. The recombinant swinepox virus of claim 1, further comprising a foreign DNA which encodes a detectable marker.

20. The recombinant swinepox virus of claim 19, wherein the detectable marker is *E. coli* beta-galactosidase.

21. The recombinant swinepox virus of claim 19, wherein the detectable marker is *E. coli* beta-glucuronidase.

22. The recombinant swinepox virus of claim 1, wherein the foreign DNA encodes a cytokine.

23. The recombinant swinepox virus of claim 22, wherein the cytokine is chicken myelomonocytic growth factor (cMGF) or chicken interferon (cIFN).

24. The recombinant swinepox virus of claim 22, wherein the cytokine is selected from the group consisting of interleukin-2, interleukin-6, interleukin-12, interferons, and granulocyte-macrophage colony stimulating factor.

25. The recombinant swinepox virus of claim 1, wherein the foreign DNA is under the control of an endogenous poxvirus promoter.

26. The recombinant swinepox virus of claim 1, wherein the foreign DNA is under the control of a heterologous promoter.

27. The recombinant swinepox virus of claim 1, wherein the promoter is: pox synthetic late promoter 1, pox synthetic late promoter 2 early promoter 2, pox O1L promoter, pox I4L promoter, pox I3L promoter, pox I2L promoter, pox I1L promoter, or pox E10R promoter.

28. A vaccine which comprises an effective immunizing amount of the recombinant swinepox virus of claim 1, and a suitable carrier.

29. A method of immunizing an animal against an animal pathogen which comprises administering to the animal an effective immunizing dose of the vaccine of claim 28.

30. A homology vector for producing a recombinant swinepox virus by inserting foreign DNA into a swinepox virus genome which comprises a double-stranded DNA consisting essentially of:

a) double stranded foreign DNA not usually present within the swinepox virus genome;

b) at one end the foreign DNA, double-stranded swinepox virus DNA homologous to the virus genome located at one side of the HindIII K fragment of the coding region of the swinepox virus genome; and c) at the other end of the foreign DNA, double-stranded swinepox virus DNA homologous to the virus genome located at the other side of the HindIII K fragment of the coding region of the swinepox virus genome.

31. The homology vector of claim 30, wherein the foreign DNA encodes a cytokine.

32. The homology vector of claim 31, wherein the cytokine is chicken myelomonocytic growth factor (cMGF) or chicken interferon (cIFN).

33. The homology vector of claim 30, wherein the foreign DNA encodes a polypeptide.

34. A homology vector of claim 33, wherein the polypeptide is antigenic.

35. The homology vector of claim 30, wherein the foreign DNA is under control of a promoter.

\* \* \* \* \*